(12) United States Patent
Zollers et al.

(10) Patent No.: US 11,090,292 B2
(45) Date of Patent: *Aug. 17, 2021

(54) COMPOSITIONS AND METHODS OF USE OF AN INAPPETANCE-CONTROLLING COMPOUND

(71) Applicant: Aratana Therapeutics, Inc., Kansas City, KS (US)

(72) Inventors: Bill Zollers, Kansas City, KS (US); Linda Rhodes, Kansas City, KS (US); Ernst Heinen, Kansas City, KS (US); Gopinath Devaraj, Auckland (NZ)

(73) Assignee: Aratana Therapeutics, Inc., Kansas City, KS (US)

( * ) Notice: Subject to any disclaimer, the term of this patent is extended or adjusted under 35 U.S.C. 154(b) by 712 days.

This patent is subject to a terminal disclaimer.

(21) Appl. No.: 14/039,114

(22) Filed: Sep. 27, 2013

(65) Prior Publication Data

US 2014/0088139 A1    Mar. 27, 2014

Related U.S. Application Data

(60) Provisional application No. 61/706,164, filed on Sep. 27, 2012.

(51) Int. Cl.
| | |
|---|---|
| *A61K 31/437* | (2006.01) |
| *A61K 45/06* | (2006.01) |
| *A23K 20/132* | (2016.01) |
| *A23K 20/111* | (2016.01) |
| *A23K 50/10* | (2016.01) |
| *A23K 50/40* | (2016.01) |
| *A61K 9/00* | (2006.01) |
| *A61K 9/08* | (2006.01) |

(52) U.S. Cl.
CPC .......... *A61K 31/437* (2013.01); *A23K 20/111* (2016.05); *A23K 20/132* (2016.05); *A23K 50/10* (2016.05); *A23K 50/40* (2016.05); *A61K 9/0095* (2013.01); *A61K 45/06* (2013.01); *A61K 9/08* (2013.01)

(58) Field of Classification Search
CPC ................................ A61K 31/437; A61P 1/14
See application file for complete search history.

(56) References Cited

U.S. PATENT DOCUMENTS

| | | |
|---|---|---|
| 2002/0086865 A1 | 7/2002 | Friedman et al. |
| 2008/0300194 A1 | 12/2008 | Mann et al. |
| 2009/0170757 A1* | 7/2009 | Fraser ................. A61K 31/395 514/1.1 |
| 2009/0221689 A1 | 9/2009 | Marsault et al. |
| 2010/0249228 A1 | 9/2010 | Dalton et al. |
| 2012/0095057 A1 | 4/2012 | Nishida et al. |
| 2012/0202759 A1 | 8/2012 | Pan |
| 2012/0322821 A1 | 12/2012 | Shimada et al. |

FOREIGN PATENT DOCUMENTS

| | | |
|---|---|---|
| CA | 2095786 A1 | 11/1993 |
| RU | C2-2459831 | 11/2010 |
| WO | WO/1997/024369 | 7/1997 |
| WO | WO2008/1039415 | 4/2008 |
| WO | WO2009/030755 | 3/2009 |
| WO | WO2014/052780 | 4/2014 |

OTHER PUBLICATIONS

Pan et al.; "Preclinical Pharmacology of CP-424,391, an Orally Active Pyrazolinone-Piperidine Growth Hormone Secretagogue"; 2001; Endocrine; 14(1): 121-132.*
SciFinder; CAS Registry No. 193273-66-4; accessed Mar. 7, 2016.*
International Search Report and Written Opinion, Int'l Appl. No. PCT/US2013/062227, dated May 5, 2014, 17 pages.
Carpino et al., Pyrazolinone-piperidine Dipeptide Growth Hormone Secretagogues (GHSs): Discovery of Capromorelin, Bioorganic & Medicinal Chemistry 11, 581-590 (2003).
Hersch et al., Growth hormone (GH) "releasing hormone and GH secretagogues in normal aging: Fountain of Youth or Pool of Tantalus" Clinical Interventions in Aging 3(1), 121-129 (2008).
White, HK et al., (2009), "Effects of an Oral Growth Hormone Secretagogue in Older Adults," *J Clin Endocrinol Metab.*, 94: 1198-1206.
Riviere et al., (2009), Veterinary Pharmacology and Therapeutics, Ninth Edition, Chapter 2, Absorption, Distribution, Metabolism, and Elimination, pp. 11-46.
Riviere et al., (2009), Veterinary Pharmacology and Therapeutics, Ninth Edition, Chapter 3, Pharmacokinetics, pp. 47-73.
Martinez et al., (2002), "Applying the biopharmaceutics classification system to veterinary pharmaceutical products Part II. Physiological considerations," *Advanced Drug Delivery Reviews*, 54: 825-850.
Sharma et al., (2009), "To scale or not to scale: the principles of dose extrapolation," *British Journal of Pharmacology*, 157: 907-921.
West et al., (1962), "Lysergic Acid Diethylamide: Its Effects on a Male Asiatic Elephant," *Science*, New Series, 138: 1100-1103.
Patent Examination Report No. 1, AU Appl. No. 2013323349, dated Mar. 22, 2016, 7 pages.
First Office Action, CN Appl. No. 201380061931.6, dated May 18, 2016, 7 pages.
Patent Examination Report No. 2, AU Appl. No. 2013323349, dated Jul. 29, 2016, 5 pages.
Communication pursuant to Rule 164(1) EPC, EP Appl. No. 13841455. 2, dated Jun. 23, 2016, 7 pages.
Notice of Allowance and Fee(s) Due, related to U.S. Appl. No. 15/007,525, dated Apr. 19, 2017, 15 pages.
Response to Non-Final Office Action, related to U.S. Appl. No. 15/007,525, dated Mar. 24, 2017, 19 pages.

(Continued)

*Primary Examiner* — Timothy P Thomas
(74) *Attorney, Agent, or Firm* — Polsinelli PC

(57) ABSTRACT

The invention provides for a method of treating inappetance-induced weight loss in one or more companion animals or livestock. The method provides for administering a therapeutically effective amount of a capromorelin-containing composition to the companion animal or livestock. Optionally, one or more flavoring agents or flavor-masking agents can be added to the capromorelin-containing composition to enhance or mask the flavoring of the composition for the companion animal or livestock.

46 Claims, 119 Drawing Sheets

(56) References Cited

OTHER PUBLICATIONS

European Search Report from related European Patent Application No. 13841455.2 dated Jun. 23, 2016, 7 pages.
Heidi et al., "Effects of an Oral Growth Hormone Secretagogue in Older Adults," Journal of Clinical Endocrinology and Metabolism, 2009, pp. 1198-1206, vol. 94, No. 4.
Chinese Office Action related to Application No. 201380061931.6, dated Jan. 3, 2017, 12 pages.
International Search Report and Written Opinion related to PCT/EP2008/061783, dated Mar. 12, 2009, 36 pages.
International Search Report and Written Opinion related to PCT/US2013062227, dated Sep. 27, 2013, 19 pages.
International Search Report and Written Opinion related to PCT/US2007/020595, dated Sep. 16, 2008, 7 pages.
Office Action related to U.S. Appl. No. 15/007,525, dated Dec. 13, 2016, 15 pages.
Quiroga, "Anti-Aging Medicine as it Relates to Dermatology," Cosmetic Dermatology, 2005, Chapter 1, 177 pages.
Russian Office Action related to Application No. 2015114996/13(023450), dated Feb. 17, 2017, 18 pages.
Australian Examination Report related to Application No. 2016216741, dated Mar. 23, 2017, 4 pages.
Jan. 23, 2019 English translation from Uthoff, Gomez, Vega, and & Uthoff, S.C. for Jan. 8, 2019 Office Action for corresponding MX Application No. MX/a/2015/003564.
Jul. 23, 2018 English translation from Uthoff, Gomez, Vega, and & Uthoff, S.C. for Jul. 19, 2018 Office Action for corresponding MX Application No. MX/a/2015/003564.
MacAndrew, Joseph T., et al., "Efficacy of a growth hormone-releasing peptide mimetic in cardiac ischemia/reperfusion injury". European journal of pharmacology, 2001, vol. 432, No. 2-3, p. 195-202.
Zollers et al., "Capromorelin oral solution (ENTYCE®) increases food consumption and body weight when administered for 4 consecutive days to healthy adult Beagle dogs in a randomized, masked, placebo controlled study", BMC Veterinary Research, 2017 13:10, DOI 10.1186/s12917-016-0925-z, Published online: Jan. 5, 2017 in 5 pages.

* cited by examiner

Group 1 (4 mg/kg PRT2-81):

| Parameter | Criteria | Number of Animals with Observation | | | | |
|---|---|---|---|---|---|---|
| | | Day 1 | Day 2 | Day 3 | Day 4 | Day 5 |
| Immediate response to taste | Well accepted | 4/5 | 0/5 | 3/5 | 4/5 | 0/5 |
| | Accepted | 1/5 | 4/5 | 2/5 | 0/5 | 3/5 |
| | Poor | 0/5 | 1/5 | 0/5 | 1/5 | 2/5 |
| Head shaking | None | 5/5 | 4/5 | 5/5 | 5/5 | 4/5 |
| | Some | 0/5 | 1/5 | 0/5 | 0/5 | 1/5 |
| | Profuse | 0/5 | 0/5 | 0/5 | 0/5 | 0/5 |
| Resistance to administration | None | 3/5 | 3/5 | 4/5 | 5/5 | 2/5 |
| | Some | 2/5 | 0/5 | 0/5 | 0/5 | 3/5 |
| | Strong | 0/5 | 2/5 | 1/5 | 0/5 | 0/5 |
| Clinical observations | No Observations | 4/5 | 0/5 | 1/5 | 1/5 | 2/5 |
| | Licking | 0/5 | 3/5 | 2/5 | 2/5 | 1/5 |
| | Smacking of the mouth / lips | 0/5 | 0/5 | 0/5 | 1/5 | 0/5 |
| | Moderate salivation | 0/5 | 0/5 | 1/5 | 0/5 | 2/5 |
| | Excessive salivation | 0/5 | 1/5 | 1/5 | 0/5 | 0/5 |
| | Grimace | 1/5 | 1/5 | 0/5 | 1/5 | 0/5 |

FIGURE 79

Group 2 (4 mg/kg New formulation #2 [0.05% preservative]):

| Parameter | Criteria | Number of Animals with Observation | | | | |
|---|---|---|---|---|---|---|
| | | Day 1 | Day 2 | Day 3 | Day 4 | Day 5 |
| Immediate response to taste | Well accepted | 5/5 | 1/5 | 1/5 | 3/5 | 0/5 |
| | Accepted | 0/5 | 1/5 | 3/5 | 2/5 | 5/5 |
| | Poor | 0/5 | 3/5 | 1/5 | 0/5 | 0/5 |
| Head shaking | None | 3/5 | 4/5 | 4/5 | 4/5 | 4/5 |
| | Some | 2/5 | 0/5 | 1/5 | 1/5 | 1/5 |
| | Profuse | 0/5 | 1/5 | 0/5 | 0/5 | 0/5 |
| Resistance to administration | None | 4/5 | 1/5 | 1/5 | 3/5 | 2/5 |
| | Some | 1/5 | 0/5 | 1/5 | 1/5 | 3/5 |
| | Strong | 0/5 | 4/5 | 3/5 | 1/5 | 0/5 |
| Clinical observations | No Observations | 3/5 | 0/5 | 1/5 | 1/5 | 0/5 |
| | Licking | 1/5 | 0/5 | 0/5 | 0/5 | 3/5 |
| | Smacking of the mouth / lips | 0/5 | 1/5 | 0/5 | 1/5 | 0/5 |
| | Moderate salivation | 1/5 | 1/5 | 3/5 | 1/5 | 2/5 |
| | Excessive salivation | 0/5 | 3/5 | 1/5 | 1/5 | 0/5 |
| | Grimace | 0/5 | 0/5 | 0/5 | 1/5 | 0/5 |

FIGURE 80

Group 3 (4 mg/kg PERT2-86):

| Parameter | Criteria | Number of Animals with Observation | | | | |
|---|---|---|---|---|---|---|
| | | Day 1 | Day 2 | Day 3 | Day 4 | Day 5 |
| Immediate response to taste | Well accepted | 4/5 | 2/5 | 3/5 | 1/5 | 0/5 |
| | Accepted | 1/5 | 0/5 | 1/5 | 4/5 | 2/5 |
| | Poor | 0/5 | 3/5 | 1/5 | 0/5 | 3/5 |
| Head shaking | None | 4/5 | 2/5 | 4/5 | 4/5 | 2/5 |
| | Some | 1/5 | 3/5 | 1/5 | 1/5 | 3/5 |
| | Profuse | 0/5 | 0/5 | 0/5 | 0/5 | 0/5 |
| Resistance to administration | None | 3/5 | 0/5 | 3/5 | 3/5 | 3/5 |
| | Some | 2/5 | 1/5 | 0/5 | 0/5 | 2/5 |
| | Strong | 0/5 | 4/5 | 2/5 | 2/5 | 0/5 |
| Clinical observations | No Observations | 2/5 | 1/5 | 2/5 | 1/5 | 0/5 |
| | Licking | 0/5 | 0/5 | 1/5 | 0/5 | 2/5 |
| | Smacking of the mouth / lips | 1/5 | 1/5 | 0/5 | 1/5 | 0/5 |
| | Moderate salivation | 1/5 | 1/5 | 2/5 | 1/5 | 3/5 |
| | Excessive salivation | 0/5 | 2/5 | 0/5 | 1/5 | 0/5 |
| | Grimace | 1/5 | 0/5 | 0/5 | 1/5 | 0/5 |

FIGURE 81

Group 4 (4 mg/kg PRT3-99I):

| Parameter | Criteria | Number of Animals with Observation ||||| 
| --- | --- | --- | --- | --- | --- | --- |
| | | Day 1 | Day 2 | Day 3 | Day 4 | Day 5 |
| Immediate response to taste | Well accepted | 1/5 | 0/5 | 1/5 | 1/5 | 0/5 |
| | Accepted | 3/5 | 2/5 | 3/5 | 1/5 | 3/5 |
| | Poor | 1/5 | 3/5 | 1/5 | 3/5 | 2/5 |
| Head shaking | None | 2/5 | 2/5 | 2/5 | 3/5 | 3/5 |
| | Some | 3/5 | 1/5 | 2/5 | 1/5 | 1/5 |
| | Profuse | 0/5 | 2/5 | 1/5 | 1/5 | 1/5 |
| Resistance to administration | None | 3/5 | 1/5 | 1/5 | 4/5 | 2/5 |
| | Some | 2/5 | 2/5 | 4/5 | 0/5 | 3/5 |
| | Strong | 0/5 | 2/5 | 0/5 | 1/5 | 0/5 |
| Clinical observations | No Observations | 0/5 | 0/5 | 0/5 | 0/5 | 0/5 |
| | Licking | 2/5 | 0/5 | 1/5 | 1/5 | 2/5 |
| | Smacking of the mouth / lips | 1/5 | 1/5 | 0/5 | 0/5 | 1/5 |
| | Moderate salivation | 1/5 | 0/5 | 1/5 | 1/5 | 1/5 |
| | Excessive salivation | 0/5 | 3/5 | 3/5 | 0/5 | 1/5 |
| | Grimace | 1/5 | 1/5 | 0/5 | 3/5 | 0/5 |

FIGURE 82

| Group ID (Gender) | Acclim. Mean (g) | Post-Dose Mean (g) | Mean Difference (g) | Acclim. Mean (g/kg) | Post-Dose Mean (g/kg) | Mean Difference (g/kg) |
|---|---|---|---|---|---|---|
| 1 (Males) | 40 | 73 | 33 | 6.5 | 11.9 | 5.3 |
| 1 (Females) | 30 | 59 | 29 | 8.3 | 16.2 | 7.9 |
| 2 (Males) | 42 | 78 | 36 | 5.4 | 10.3 | 4.9 |
| 2 (Females) | 34 | 75 | 41 | 10.9 | 23.3 | 12.4 |
| 3 (Males) | 46 | 78 | 32 | 7.5 | 13.2 | 5.6 |
| 3 (Females) | 45 | 57 | 12 | 13.0 | 16.5 | 3.6 |
| 4 (Males) | 44 | 69 | 25 | 6.1 | 9.7 | 3.6 |
| 4 (Females) | 45 | 60 | 15 | 13.2 | 17.7 | 4.5 |

FIGURE 84

| Group | Day -3 | Day -2 | Day -1 | Day 1 | Day 2 | Day 3 | Day 4 | Day 5 | Day 6 |
|---|---|---|---|---|---|---|---|---|---|
| 1 | 35.0 ± 11.5 | 36.2 ± 23.7 | 37.4 ± 18.0 | 70.4 ± 36.1 | 62.0 ± 26.5 | 64.4 ± 30.7 | 73.0 ± 32.4 | 75.4 ± 27.8 | 58.2 ± 21.2 |
| 2 | 24.2 ± 8.2 | 48.5 ± 7.0 | 44.0 ± 12.3 | 67.6 ± 13.2 | 72.4 ± 7.3 | 76.0 ± 6.0 | 83.2 ± 7.9 | 87.2 ± 8.3 | 69.2 ± 12.9 |
| 3 | 43.8 ± 7.4 | 44.6 ± 13.1 | 47.6 ± 14.3 | 75.8 ± 33.3 | 69.4 ± 21.7 | 75.0 ± 28.1 | 70.0 ± 21.9 | 78.8 ± 22.1 | 49.4 ± 34.6 |
| 4 | 37.0 ± 9.8 | 49.4 ± 12.8 | 46.0 ± 5.8 | 65.0 ± 12.4 | 63.2 ± 8.7 | 67.0 ± 9.8 | 65.2 ± 11.5 | 72.0 ± 9.6 | 47.6 ± 27.1 |

FIGURE 85

| Parameter | Units | Mean | SD | SE | Min | Median | Max | Geometric c mean | Harmonic c mean | Pseudo SD |
|---|---|---|---|---|---|---|---|---|---|---|
| AUC Extrapolated | % | 8.2 | 6.6 | 2.7 | 1.7 | 7.1 | 18.6 | 5.8 | 3.9 | 4.2 |
| AUC 0-INF | hr*ng/mL | 3494 | 1281 | 523 | 1934 | 3823 | 5032 | 3290 | 3112 | 1215 |
| C0 | ng/mL | 1096.0 | 610.0 | 249.0 | 595.8 | 801.8 | 2040.7 | 976.3 | 886.3 | 372.1 |
| CL | mL/min/kg | 31.1 | 11.6 | 4.7 | 17.8 | 30.0 | 49.8 | 29.3 | 27.7 | 10.5 |
| T1/2 λz | hr | 0.90 | 0.18 | 0.07 | 0.68 | 0.85 | 1.12 | 0.89 | 0.87 | 0.16 |
| λz | 1/hr | 0.793 | 0.145 | 0.059 | 0.619 | 0.814 | 1.019 | 0.782 | 0.771 | 0.143 |
| MRT 0-INF | hr | 0.84 | 0.23 | 0.09 | 0.60 | 0.75 | 1.21 | 0.82 | 0.79 | 0.19 |
| Vss | L/kg | 1.57 | 0.67 | 0.27 | 0.77 | 1.66 | 2.34 | 1.43 | 1.30 | 0.70 |
| Vz | L/kg | 2.39 | 0.91 | 0.37 | 1.30 | 2.22 | 3.82 | 2.23 | 2.11 | 0.87 |

FIGURE 108

| Parameter | Units | Mean | SD | SE | Min | Median | Max | Geometric mean | Harmonic mean | Pseudo SD |
|---|---|---|---|---|---|---|---|---|---|---|
| AUC Extrapolated | % | 2.9 | 0.8 | 0.4 | 2.0 | 2.5 | 3.9 | 2.8 | 2.7 | 0.7 |
| AUC0-INF | hr*ng/mL | 4701 | 2226 | 996 | 2670 | 3718 | 8016 | 4317 | 3996 | 1653 |
| Cl/F | mL/min/kg | 989 | 394 | 176 | 478 | 1031 | 1433 | 908 | 813 | 423 |
| Cmax | ng/mL | 1483 | 902 | 363 | 248 | 1415 | 2930 | 1187 | 821 | 1584 |
| T1/2λz | hr | 1.04 | 0.20 | 0.09 | 0.87 | 1.04 | 1.36 | 1.03 | 1.01 | 0.17 |
| λz | 1/hr | 0.683 | 0.118 | 0.053 | 0.510 | 0.667 | 0.801 | 0.672 | 0.665 | 0.132 |
| MRT0-INF | hr | 2.37 | 0.23 | 0.11 | 2.09 | 2.34 | 2.74 | 2.36 | 2.36 | 0.23 |
| Tmax | hr | 2.00 | 0.00 | 0.00 | 2.00 | 2.00 | 2.00 | 2.00 | 2.00 | 0.00 |
| Vz/F | L/kg | 8.38 | 2.98 | 1.32 | 5.63 | 7.87 | 12.91 | 7.96 | 7.57 | 2.36 |
| Estimated F | % | 33 |  |  |  |  |  | 33 | 32 |  |
| Estimated MAT | hr | 1.55 |  |  |  |  |  | 1.55 | 1.55 |  |

FIGURE 109

| Parameter | Units | Mean | SD | SE | Min | Median | Max | Geometric mean | Harmonic mean | Pseudo SD |
|---|---|---|---|---|---|---|---|---|---|---|
| AUC_%Extrap_obs | % | 4.9 | 6.7 | 2.7 | 1.4 | 1.9 | 18.2 | 2.7 | 2.1 | 1.9 |
| AUClast | hr*ng/mL | 458.7 | 233.0 | 95.1 | 213.7 | 383.5 | 874.4 | 415.6 | 379.1 | 185.6 |
| AUCINF_obs | hr*ng/mL | 475.7 | 232.3 | 94.8 | 261.4 | 380.5 | 900.6 | 436.8 | 406.1 | 158.3 |
| C0 | ng/mL | 486 | 131 | 53 | 280 | 445 | 740 | 470 | 464 | 93 |
| Cl_obs | mL/min/kg | 23.8 | 9.2 | 3.7 | 10.7 | 25.0 | 37.0 | 22.1 | 20.3 | 11.2 |
| HL_Lambda_z | hr | 0.74 | 0.08 | 0.04 | 0.67 | 0.71 | 0.90 | 0.74 | 0.73 | 0.08 |
| MRTINF_obs | hr | 1.01 | 0.13 | 0.06 | 0.87 | 0.95 | 1.23 | 1.00 | 1.00 | 0.12 |
| Vss_obs | L/kg | 1.43 | 0.61 | 0.24 | 0.72 | 1.37 | 2.40 | 1.33 | 1.25 | 1.09 |
| Vz_obs | L/kg | 1.55 | 0.75 | 0.31 | 0.72 | 1.46 | 2.88 | 1.41 | 1.28 | 1.09 |

FIGURE 117

| Parameter | Units | Mean | SD | SE | Min | Median | Max | Geometric mean | Harmonic mean | Pseudo SD |
|---|---|---|---|---|---|---|---|---|---|---|
| AUC_%Extrap_obs | % | 0.7 | 0.4 | 0.2 | 0.4 | 0.6 | 1.5 | 0.6 | 0.6 | 0.3 |
| AUClast | hr*ng/mL | 1588.9 | 292.6 | 119.5 | 1165.6 | 1588.9 | 2017.4 | 1575.9 | 1552.3 | 310.3 |
| AUCINF_obs | hr*ng/mL | 1610.3 | 292.2 | 119.3 | 1171.5 | 1606.5 | 2024.6 | 1597.4 | 1583.8 | 313.0 |
| CL_F_obs | mL/min/kg | 16.4 | 3.2 | 1.3 | 12.7 | 16.0 | 21.9 | 16.2 | 15.9 | 2.9 |
| Cmax | ng/mL | 905 | 147 | 60 | 626 | 979 | 1000 | 885 | 880 | 193 |
| HL_Lambda_z | hr | 0.83 | 0.14 | 0.06 | 0.64 | 0.81 | 1.03 | 0.82 | 0.81 | 0.14 |
| MRTINF_obs | hr | 1.41 | 0.18 | 0.07 | 1.14 | 1.39 | 1.63 | 1.40 | 1.39 | 0.19 |
| Tmax | hr | 0.46 | 0.19 | 0.08 | 0.25 | 0.50 | 0.75 | 0.42 | 0.39 | 0.19 |
| Vz_F_obs | L/kg | 1.18 | 0.17 | 0.07 | 0.92 | 1.15 | 1.38 | 1.16 | 1.13 | 0.18 |
| F | | 1.27 | | | | | | 1.37 | 1.35 | |
| MAT | hr | 0.40 | | | | | | 0.40 | 0.39 | |

FIGURE 118

COMPOSITIONS AND METHODS OF USE OF AN INAPPETANCE-CONTROLLING COMPOUND

CROSS-REFERENCE TO RELATED APPLICATIONS

The present application claims priority under 35 U.S.C. § 119(e) to U.S. Provisional Application No. 61/706,164 filed on Sep. 27, 2012, the entire contents and disclosure of which are herein incorporated by reference.

FIELD OF THE INVENTION

The present invention relates to an inappetance-controlling compound and methods of use thereof to control inappetance in animals. In particular, the current invention is directed to a novel use of an inappetance-controlling compound to potentially induce increased food intake and lean muscle growth in animals suffering from inappetance or other maladies or disorders that induce weight loss, frailty, and/or wasting.

BACKGROUND OF THE INVENTION

Like humans, companion animals and livestock can suffer from inappetance and other disorders that can result in loss of lean muscle, an inability to participate in physical activity, and other undesirable outcomes for the companion animal and the owner. For instance, companion animals undergoing chemotherapy or afflicted with cancer, heart disease, or chronic kidney disease can suffer from inappetance, weight loss, general frailty, and/or cachexia. Moreover, the conditions or afflictions inducing the inappetance, weight loss, general frailty and/or cachexia can be at least partially exacerbated by the fact that the diets of these animals consist of fewer calories, vitamins, minerals, protein, and other necessary nutritional components, due to the decrease in food intake. As a result, these animals can exhibit a decrease in lean muscle, general weakness including a weakened immune system, possibly making the animals susceptible to infections.

Furthermore, although a general increase in food consumption could be helpful to animals, it is important that these animals do not experience a significant increase in deposition of adipose tissue. Accordingly, it would be desirable to have a composition and a method of using the composition to control inappetance while not inducing a significant increase in adipose tissue. To date, there are no approved veterinary active pharmaceutical ingredients for the treatment of inappetance, unwanted weight loss, general frailty, wasting, and other related afflictions, complications, and maladies. As such, it is desired to have a compound or treatment for use in treating inappetance in animals, including companion animals.

It is also desirable to have a compound that increases lean muscle mass in companion animals, but this is especially desirable in livestock. Increasing lean muscle mass is important for the overall health of companion animals and livestock. A compound for controlling inappetance while building lean muscle mass has not been previous provided in the art. Thus, there is a need for a compound capable of decreasing inappetance while building lean muscle mass.

SUMMARY OF THE INVENTION

The present invention relates to compositions and methods of use of an inappetance-controlling compound which can also increase lean muscle mass. For example, the inappetance-controlling compound preferably comprises a ghrelin agonist, such as a capromorelin and is administered to one or more companion animals (e.g., canines or felines) or livestock (e.g., animals used as a food source). The composition comprising a ghrelin agonist is preferably provided in a therapeutically effective amount to treat inappetance-induced weight loss or to promote the addition of lean muscle mass. In some embodiments, the capromorelin-containing composition is administered to the companion animals or livestock through a variety of different pathways, including the oral cavity or intravenously, and can be administered at least once or twice per day during the treatment regimen. By way of example only, in one embodiment, the capromorelin-containing composition preferably includes a concentration of between about 0.2 and 6 milligrams of capromorelin per kilogram of body weight of the animal. The compound can be a pill or a liquid and can be flavored to mask any unpleasant or bitter taste. Moreover, in some embodiments, the capromorelin-containing composition is administered to the companion animal in conjunction with a chemotherapeutic regimen to at least partially prevent, inhibit, control, and/or alleviate inappetance associated with chemotherapy treatment. In another embodiment, the capromorelin-containing composition is administered as a part of food product, a treat, and/or a chew. For example, in a preferred embodiment the food product, treat, or chew is manufactured such that the capromorelin-containing composition is integrated into the product prior to reaching the consumer. Alternatively, the capromorelin-containing composition can be formulated as a liquid and sprayed on an animal food product, such as feed for livestock. In an alternate embodiment, the capromorelin-containing composition is added to a preformed food product, treat, or chew prior to feeding the companion animals.

Specifically, a method for increasing lean muscle mass in a non-human animal is provided. Preferably, this method comprises the step of administering a capromorelin composition to a non-human animal. The method preferably also alleviates weight loss. The capromorelin composition is preferably orally administered. The dose of the capromorelin composition is preferably a therapeutically effective dose of a capromorelin composition. The capromorelin composition may optionally include one or more flavoring agents or flavor-masking agents, however this is not required. In a preferred embodiment, the therapeutically effective dose of the capromorelin composition induces the non-human animal or livestock to consume greater amounts of food relative to those animals experiencing inappetance but not receiving the capromorelin composition or when compared to no food consumption by the animal. Further, the therapeutically effective dose of the capromorelin composition preferably increases lean muscle mass relative to those animals not receiving the capromorelin composition. Preferably, lean muscle mass is increased by 1% to 100%, where increases such as, 2%, 5%, 10%, 15%, 20%, 25%, 30%, 35%, 40%, 45%, 50%, 55%, 60%, 65%, 70%, 75%, 80%, 85%, 90%, and 95% increase in lean muscle mass are envisioned. In a further embodiment, the capromorelin composition includes a concentration of between about 0.2 and 6 milligrams of capromorelin per kilogram of body weight of the non-human animal. Further, the concentration of capromorelin in the composition may be provided as 0.5 mg, 0.8 mg, 1.0 mg, 2.0 mg. 3.0 mg. 4.0 mg, 5.0 mg, 6.0 mg or values in-between, where the amount of capromorelin is per kilogram body weight of the animal. In a preferred embodiment, the capromorelin composition of the present invention wherein the capromorelin-containing composition comprises a sufficient amount of capromorelin to achieve a Cmax of around 150 nanograms of capromorelin or a metabolite thereof per milliliter of plasma at a Tmax of around two hours. Moreover, in some embodiments, the capromorelin composition is be administered to the non-human animal in conjunction with a chemotherapeutic regimen to at least partially prevent, inhibit, control, and/or alleviate inappetance associated with the chemotherapy. Preferably, lean muscle mass is also increased.

The present invention provides for a method of treating a non-human animal experiencing inappetance-induced weight loss. The method preferably comprises the steps of determining that the non-human animal is experiencing inappetance-induced weight loss and administering at least one dose of a capromorelin-containing composition to the non-human animal. In another embodiment, the method further includes the step of observing an indicator (e.g., food consumption, body weight, leans muscle mass, levels of insulin-like growth factor, growth hormone, etc.) or obtaining a sample from the non-human animal and measuring an amount of the plasma marker (e.g., levels of insulin-like growth factor, growth hormone, etc.) in the sample. In some embodiments, the dose of the capromorelin-containing composition can be adjusted in light of the amount of the plasma marker in the sample. In other embodiments, the composition can be administered to the non-human animal until the animal gains a sufficient amount of weight. In some embodiments, the plasma marker can be at least one of insulin-like growth factor-1, cortisol, capromorelin, and combinations thereof. For example, in certain embodiments, the dose of the capromorelin-containing composition is increased to a level that induces an increase in the amount insulin-like growth factor-1 in the sample. In some embodiments, the dose of the capromorelin-containing composition can be decreased to correspondingly decrease the amount of cortisol in the sample. In another embodiment, the method further comprises the step of obtaining a serum sample from the non-human animal, where the serum sample optionally can be analyzed for the level of certain plasma markers or changes in the level of certain plasma markers over time.

The present invention additionally provides for a pharmaceutical composition for treatment of inappetance in non-human animals. The pharmaceutical composition preferably comprises a therapeutically effective amount of capromorelin and at least one carrier. Optionally, the pharmaceutical composition also includes at least one of a flavoring agent or a flavor-masking agent (e.g., a sweetening agent, a savory agent, a bittering agent, a souring agent, etc.). Moreover, in certain embodiments, the pharmaceutical composition includes either an emulsifying agent or a viscosifying agent, or combinations thereof. For example, the pharmaceutical composition preferably comprises about 0.01% to about 10% weight per volume of the emulsifying agent and/or the viscosifying agent, where values such as 0.03%, 0.2%, 0.4%, 0.6%, 0.8%, 1.0%, 2%, 3%, 4%, 5%, 6%, 7%, 8%, 9%, and 10% weight per volume of the emulsifying agent and/or the viscosifying agent are envisioned. The therapeutically effective amount of capromorelin preferably includes a concentration of between about 0.2 and 6 milligrams of capromorelin per kilogram of body weight of the non-human animal. Further, the concentration of capromorelin in the composition may be provided as 0.5 mg, 0.8 mg, 1.0 mg, 2.0 mg. 3.0 mg. 4.0 mg, 5.0 mg, 6.0 mg or values in-between, where the amount of capromorelin is per kilogram body weight of the animal. In an additional embodiment of the present invention, the pharmaceutical composition includes a carrier and the volume of the dose can be contained within a syringe for oral administration. In a preferred embodiment the capromorelin-containing composition, wherein the capromorelin-containing composition comprises a sufficient amount of capromorelin to achieve a Cmax of around 150 nanograms of capromorelin or a metabolite thereof per milliliter of plasma at a Tmax of around two hours. The pharmaceutical composition of the present invention can be formulated for oral, intravenous, intramuscular, and/or subcutaneous administration. In embodiments comprising a carrier, the carrier may comprise a salt or buffer solution that can be mixed with the capromorelin. Preferably, an embodiment comprising a salt or buffer solution can be administered via intravenous or subcutaneous administration. The preferred dose of the pharmaceutical composition of the present invention is provided in a dose of about 1, about 3, about 4.5, and/or about 6 milligrams of capromorelin per kilogram of body weight. The dose of the pharmaceutical composition of the present invention is preferably administered to the non-human animal at least once a day or at least twice per day for a predetermined time period, while further subsequent dose are envisioned. In one embodiment, the predetermined time period for administration is about seven days.

A further method for treating weight loss in a companion animal is provided by the present invention. Preferably, a method of building lean muscle mass in an animal or livestock is also provided. The method preferably includes the steps of determining that the companion animal is experiencing weight loss and administering at least one dose of a capromorelin-containing composition to the animal. In a further embodiment, the method includes the step of administering the composition to the animal using a syringe. The method optionally includes a further step of assessing one or more plasma markers of the animal that are associated with weight loss. Preferably, the dose of the capromorelin-containing composition is adjusted in view of the assessment of the one or more plasma markers. The plasma markers preferably include, but are not limited to, insulin like growth factor-1, cortisol, capromorelin, and combinations thereof. For example, the dose of the capromorelin-containing composition can be increased or decreased depending on the level of the plasma marker present in the animal. Preferably, the pharmaceutical composition of the present invention is administered to the companion animal at least once or twice per day. The preferred dose of the composition includes a concentration of between about 0.2 to about 6 milligrams of capromorelin per kilogram of body weight of the companion animal or livestock. Further, the concentration of capromorelin in the composition may be provided as 0.5 mg, 0.8 mg, 1.0 mg, 2.0 mg. 3.0 mg. 4.0 mg, 5.0 mg, 6.0 mg or values in-between, where the amount of capromorelin is per kilogram body weight of the animal. In one embodiment, the capromorelin-containing composition comprises a sufficient amount of capromorelin to achieve a Cmax of around 150 nanograms of capromorelin or a metabolite thereof per milliliter of plasma at a Tmax of around two hours. Preferably, the composition is administered to the companion animal by oral, intravenous, intramuscular, subcutaneous, or intraperitoneal administration. In an additional embodiment, an indicator is assessed in order to determine if the animal requires subsequent doses or an increased amount of the capromorelin-containing composition. The indicators include, but are not limited to, change in weight, weight gain, weight loss, change in food intake, and increase or decrease in lean muscle mass.

A kit for treating inappetance-induced weight loss in a non-human animal is also provided by the present invention. The kit preferably includes a syringe and a vessel comprising a pharmaceutical composition that includes capromorelin. The kit also preferably includes directions to instruct the user to withdraw a dose of the composition from the vessel and administer the dose to the non-human animal. The directions preferably instruct a user to withdraw about one dose of the pharmaceutical composition from the vessel using the syringe and administering the about one dose of the pharmaceutical composition to the non-human animal with a syringe. The pharmaceutical composition included in the kit is preferably formulated for oral, intravenous, intramuscular, and/or subcutaneous administration.

A further method of the present invention provides for treating non-human animals (e.g., livestock) with a pharmaceutical composition that can induce a healthy weight gain in the non-human animals, where non-human animals include, but are not limited to, companion animals and livestock. For example, efficient and/or improved weight gain is preferably induced after the pharmaceutical composition of the present invention is administered to non-human animal. In an embodiment where the pharmaceutical composition is administered to livestock, the livestock preferably build lean muscle mass. The pharmaceutical composition of the present invention can be administered to the non-human animals via one or more routes of administration. The route of administration is preferably selected from the group consisting of, but not limited to, oral, intravenous, or as an implant disposed within the cutaneous or muscle tissue of the livestock. Alternatively, the pharmaceutical composition of the present invention can be mixed with feed provided to the non-human animals for sustenance. In a further alternate embodiment, the composition can be administered as a pill, a tablet, an implant, a patch, a film, an injection, a suppository, transdermally, spray for food products, liquid filled syringe, etc., or combinations thereof. In some embodiments, the composition can be administered to the livestock as a portion of a food product (e.g., livestock feed) such that the normal feeding process results in administration of the composition to the livestock. In addition, the composition can be administered to the livestock at a dose of between 0.2 milligrams to 6.0 milligrams of capromorelin per kilogram of body weight of the livestock. Further, the concentration of capromorelin in the composition may be provided as 0.5 mg, 0.8 mg, 1.0 mg, 2.0 mg. 3.0 mg. 4.0 mg, 5.0 mg, 6.0 mg or values in-between, where the amount of capromorelin is per kilogram body weight of the animal. Preferably, non-human animals (e.g., livestock exhibit increased lean muscle mass after administration of the pharmaceutical composition of the present invention. Preferably, building lean muscle mass results in improved meat production for sale to downstream consumers.

In a further embodiment the pharmaceutical composition of the present invention is provided as an oral pharmaceutical composition suitable for the treatment of inappetance in dogs or cats. Preferably, the oral pharmaceutical composition includes a therapeutically effective amount of capromorelin. The therapeutically effective amount of capromorelin preferably comprises a concentration of about 0.2 milligrams to about 4 milligrams of capromorelin per kilogram of body weight of the dogs or cats. However, the concentration of capromorelin may also comprise amounts of about 0.5 mg, 0.8 mg, 1.0 mg, 1.5 mg, 2.0 mg, 2.5 mg, 3.0 mg, and about 4.0 mg of capromorelin per kilogram of body weight of the dogs or cats.

A method of treating or preventing hepatic lipidosis in companion animals is also provided by the present invention. Preferably the companion animal is a cat, however, the invention is not so limited and may include other companion animal such as, but not limited to dogs. The method preferably includes the steps of administering a therapeutically effective amount of a capromorelin-containing composition to the companion animal. The composition can be orally administered using a mode of administration selected from, but not limited to, a syringe, a spray, a pill, or a tablet or the composition can be parenterally administered. The preferred dose of the composition includes a concentration about 2 milligrams to about 4 milligrams of capromorelin per kilogram of body weight of the companion animals. However, the concentration of capromorelin may also comprise amounts of about 0.5 mg, 0.8 mg, 1.0 mg, 1.5 mg, 2.0 mg, 2.5 mg, 3.0 mg, and about 4.0 mg of capromorelin per kilogram of body weight of the dogs or cats. In preferred embodiment, the capromorelin-containing composition comprises a sufficient amount of capromorelin to achieve a Cmax of around 150 nanograms of capromorelin or a metabolite thereof per milliliter of plasma at a Tmax of around two hours.

A method for treating inappetance in a non-human animal is also provided by the present invention. The method preferably includes the steps of administering a pharmaceutical composition to the non-human animal at least once per day until sufficient weight gain occurs. In some aspects, sufficient weight gain includes a 5%, 10%, or 20% increase in body weight relative to the body weight of the non-human animal prior to receiving the pharmaceutical composition. Preferably, the pharmaceutical composition includes approximately 3 milligrams of capromorelin per kilogram of body weight of the non-human animal.

In addition, a method of maintaining a body weight in a companion animal is also provided by the present invention. The method preferably includes the steps of administering an amount of a capromorelin-containing composition to the companion animal and monitoring the weight of the companion animal to determine that the body weight of the animal is being maintained. In one embodiment, the composition is administered to the companion animal at least once every two days for a period of about one month. The preferred dose of the pharmaceutical composition includes a concentration of 0.2 milligrams of capromorelin per kilogram of body weight of the companion animal. In a further embodiment, the composition may be orally administered or administered as a part of a chew, a treat, or a food product.

A method for achieving desired pharmacokinetic values by administration of a pharmaceutical composition and a carrier is also provided. The composition administered as part of the method preferably includes a sufficient amount of capromorelin to achieve a $C_{max}$ of around 150 nanograms of capromorelin or a metabolite thereof per milliliter of plasma at a $T_{max}$ of around 2 hours. Alternatively, the composition includes a sufficient amount of capromorelin to achieve a $C_{max}$ of around 905 nanograms of capromorelin or a metabolite thereof per milliliter of plasma at a $T_{max}$ of around 25 minutes. Preferably, the Tmax is from about twenty-five minutes to 2 hours, where the Tmax may be 25 minutes, 30 minutes, 1 hour, or 2 hours. The Cmax preferably ranges from about 100 ng/mL to about 1000 ng/mL.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

BRIEF DESCRIPTION OF THE DRAWINGS

FIG. 79 is a chart depicting acceptability observations over a six-day period in cats that received an oral administration of a capromorelin-containing composition.

FIG. 80 is a chart depicting acceptability observations over a six-day period in cats that received an oral administration of a capromorelin-containing composition.

FIG. 81 is a chart depicting acceptability observations over a six-day period in cats that received an oral administration of a capromorelin-containing composition.

FIG. 82 is a chart depicting acceptability observations over a six-day period in cats that received an oral administration of a capromorelin-containing composition.

FIG. 84 is a chart depicting measurements of food intake prior to and during over a six-day period in cats that received an oral administration of a capromorelin-containing composition.

FIG. 85 is a chart depicting measurements of food intake (in grams) prior to and during over a six-day period in cats that received an oral administration of a capromorelin-containing composition.

FIG. 108 is a table depicting pharmacokinetic data in cats that received an intravenous administration of a capromorelin composition.

FIG. 109 is a table depicting pharmacokinetic data in cats that received an oral administration of a capromorelin composition.

FIG. 117 is a table depicting pharmacokinetic data in cats that received an intravenous administration of a capromorelin composition.

FIG. 118 is a table depicting pharmacokinetic data in cats that received a subcutaneous administration of a capromorelin composition.

DETAILED DESCRIPTION OF THE INVENTION

Figure 1:
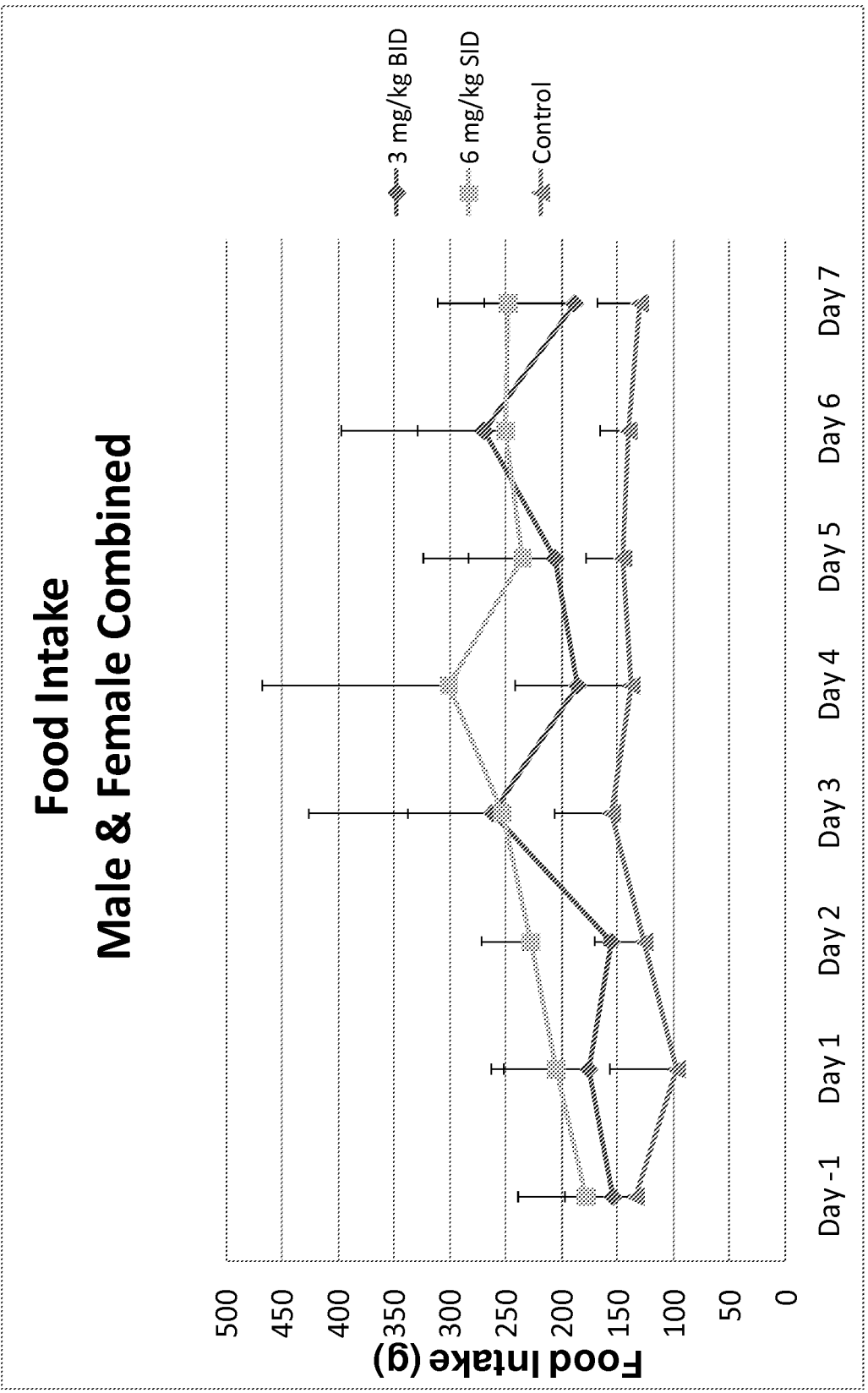
FIG. 1 is a line graph depicting a comparison between a first capromorelin treatment regimen (3 milligrams of capromorelin per kilogram of body weight administered twice per day), a second capromorelin treatment regimen (6 milligrams of capromorelin per kilogram of body weight administered once per day), and a negative control.

The compositions provided herein can be used for treatment, prevention, alleviation, and/or control of inappetance-induced weight loss in animals, including companion animals, as well as use in equines, livestock, a variety of mammals, and avian species. For example, livestock includes any non-human animals that can be used in food production, which includes, but is not limited to, bovine species, ovine species, porcine species, and other animals whose products (e.g., meat derived from muscle) can be consumed by humans. Preferably, upon administration of the pharmaceutical composition of the present invention to a non-human animal the composition induces the production of one or more molecules that can cause the non-human animal to experience a hunger sensation. In one embodiment, a method of increasing the production of one or more molecules that cause the animal to experience a hunger sensation is provided. The method preferably includes the step of administering a composition comprising capromorelin to an animal exhibiting inappetance.

A method for increasing lean muscle mass is also provided. The method preferably includes the step of administering a composition comprising capromorelin. Preferably, administration of the capromorelin-containing composition to a non-human animal induces one or more molecules that increase lean muscle mass. In one embodiment, the food consumed as a result of the increased hunger sensation, resulting from administration of the capromorelin-containing composition, is used in building lean muscle in lieu of a significant amount of adipose deposition. The composition of the present invention preferably increases lean muscle mass by at least 5%, at least 10% or at least 15%. In an embodiment where the animal is livestock, it is preferred that the capromorelin-containing composition is sprayed on or integrated into the livestock's feed. The pharmaceutical composition of the present invention preferably comprises a ghrelin agonist, such as, but not limited to, capromorelin. Preferably, the pharmaceutical composition of the present invention includes at least one flavoring agent or a flavor-masking agent. As described in greater detail below, one embodiment of the present invention provides for pharmaceutical compositions intended for non-oral administration, and as such, these pharmaceutical compositions do not include a flavoring agent or a flavor-masking agent. The present invention is based on, at least in part, the finding that treatment of companion animals and livestock afflicted with inappetance-induced weight loss that receive one or more doses of the pharmaceutical composition of the present invention exhibit increased body weights, increased food consumption, and increased serum levels of one or more relevant proteins and/or other molecules, such as, but not limited to, insulin-like growth factor-1 (hereinafter "IGF-1"), growth hormone (hereinafter "GH"), and/or cortisol. Accordingly, the present invention provides for a method of increasing body weight of an animal comprising the steps of administering a composition comprising capromorelin to an animal in need thereof. A method of increasing food consumption in an animal comprising the steps of administering a composition comprising capromorelin to an animal in need thereof is also provided.

Further, a method of increasing serum levels of one or more relevant proteins and/or other molecules, used as plasma markers, such as, but not limited to insulin-like growth factor-1 (hereinafter "IGF-1"), growth hormone (hereinafter "GH"), and/or cortisol, comprising the step of administering a composition comprising capromorelin to an animal in need thereof. In one embodiment, the method further comprises the step of determining the concentration of the plasma marker in the blood of the animal and monitoring the concentration of the plasma marker in the blood stream of the animal over time. Preferably, the method further includes the step of administering the capromorelin composition to the animal until a point where the concentration of the plasma markers in the blood increase relative to the initial concentration of the plasma marker in the animal.

The compositions of the present invention provide for the management of inappetance-induced weight loss preferably include capromorelin, which includes any racemates, polymorphs, enantiomers, salts, and any other suitable pharmaceutically acceptable derivative of capromorelin. For example, in some aspects, the composition can include any active ingredient disclosed in U.S. Pat. Nos. 6,482,825, 6,852,722, or 6,306,875, all of which are incorporated herein by reference in their entirety. In particular, capromorelin is also known as 2-amino-N-[2-(3aR-benzyl-2-methyl-3-oxo-2,3,3a,4,6,7-hexahydro-pyrazolo[4,3-c]pyridine-5-yl-1R-benzyloxymethyl-2-oxo-ethyl]-isobutyramid-L-tartrate. In addition, capromorelin has the following chemical structure.

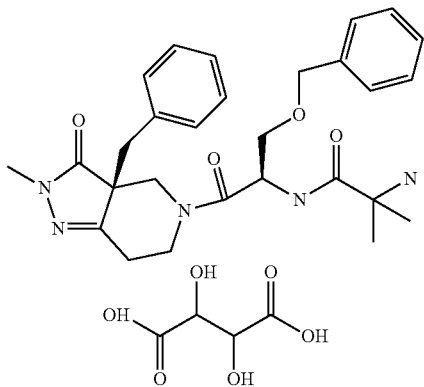

In some companion animals and livestock, ghrelin is a hormone that is produced predominantly in the stomach and other portions of the alimentary canal and is the endogenous ligand of the ghrelin receptor, which is also known as the growth hormone secretagogue receptor (GHS-R). GHS-Rs can be expressed in multiple tissues, including neurological tissues, such as, but not limited to the pituitary gland and the hypothalamus. Ghrelin exhibits a relatively short half-life (e.g., approximately ten minutes) in the blood of animals, including companion animals and livestock, and begins accumulating in the blood shortly after completion of a meal. Accordingly, the longer the period of time since the last meal of the animal, the greater the concentration of ghrelin will be in the animal's blood. Moreover, once sufficient amounts of ghrelin bind the GHS-Rs in the hypothalamus, the animals begin feeling hunger, which stimulates food intake.

In addition to binding GHS-Rs in the hypothalamus, circulating ghrelin can also bind GHS-Rs in the pituitary gland to stimulate the release of GH. Furthermore, in addition to the release of GH originating from ghrelin binding the GHS-Rs in the pituitary gland, animals naturally secrete GH throughout the circadian rhythm cycle. Although this natural release remains constant throughout the life of the animal, the magnitude of the releases of GH diminishes over the course of the life of the animal. The released GH can circulate through the companion animal, which can induce the production and secretion of IGF-1 into circulation. The increase in circulating IGF-1 levels can induce lean muscle growth, which can be correlated with increased strength, stamina, and well-being. Moreover, in addition to inducing GH production, ghrelin can also induce production of cortisol, which has been shown to increase the likelihood of adipose deposition of adipose tissue.

When administered to an animal, such as a companion animal or livestock, capromorelin can function as a GHS-R agonist to control inappetance, weight loss, anorexia, and/or cachexia. Specifically, the administration of capromorelin can induce appetite stimulation and secretion of GH. Unlike endogenous ghrelin, capromorelin typically exhibits a longer half-life in circulation and unlike exogenous ghrelin, capromorelin can be orally administered. In some embodiments of the present invention, capromorelin compositions are preferably orally administered to the animals. However, as discussed in greater detail below, capromorelin compositions can also be administered via other routes, including, but not limited to, (e.g., intravenous, intraperitoneal, intramuscular, intrathecal, subcutaneous, and any other suitable route of administration).

Moreover, in some embodiments, the pharmaceutical compositions of the present invention comprise ghrelin-like compounds (e.g., agonists of GHS-R) other than capromorelin. These compositions are effective to treat and/or at least partially alleviate inappetance-induced weight loss. For example, at least some of the non-capromorelin ghrelin-like compounds can similarly bind to GHS-Rs to induce a hunger sensation and stimulate food intake in the animals that receive these compounds. For purposes of the present invention any suitable agonist of GHS-R can be used in the pharmaceutical composition of the present invention.

The pharmacologic mechanism of action of capromorelin operates similar to the mechanism of ghrelin. For example, after administration, capromorelin binds to GHS-R, a G-protein-coupled receptor that can activate protein kinase C and stimulate GH release from the pituitary gland, which can result in the elevation of circulating GH. GH can then cause the release of IGF-1, which may induce negative feedback to the pituitary gland, thereby reducing or inhibiting GH release. As previously mentioned, IGF-1 also acts to increase lean body mass. Moreover, the administration of capromorelin can supplement the diminishing natural release of GH over the life of the animal. In addition, the negative feedback arising from the circulating IGF-1 can also reduce levels of circulating cortisol, thereby at least partially reducing the likelihood of increased adipose deposition.

Similarly, the same pharmacologic mechanism of action of capromorelin applies to the use of the composition for non-inappetance-based treatments. For example, the same process can occur in healthy or relatively healthy livestock that are administered the composition. In particular, it may be desirable to induce healthy, efficient, and improved muscle-mass growth in healthy livestock, which can lead to greater retail value of the livestock-derived products (e.g., meat). Specifically, individuals selling livestock-derived products can administer one or more doses of the composition to induce increased muscle mass, which corresponds to a greater quantity of livestock-derived products available for resale. Moreover, as described in greater detail below, the composition can be administered to the livestock as a part of their daily intake of food to require little effort to provide the livestock with the composition.

In some embodiments, capromorelin is included within the inappetance-controlling composition in one or more concentrations. In some of the following embodiments, the capromorelin is at least partially dissolved in an aqueous solvent (e.g., deionized and/or purified water). For example, in some embodiments, the concentration of capromorelin within the inappetance-controlling composition is preferably within the range of about 0.01 milligrams of capromorelin per kilogram of animal body weight (hereinafter "mg/kg") to about 75 mg/kg. For example, in some embodiments, the capromorelin concentration is preferably within the range of about 0.1 mg/kg to about 7.5 mg/kg. In one embodiment, the range of capromorelin concentration is preferably between about 0.75 mg/kg to about 6 mg/kg. By way of further example, in some embodiments, the concentration of capromorelin is preferably at least one of 0.75 mg/kg, 1.0 mg/kg, 2.0 mg/kg, 3.0 mg/kg, 4.0 mg/kg, 5.0 mg/kg, 6.0 mg/kg, and any concentrations there between. In addition, in some embodiments, as described in further detail below, capromorelin can be at least partially dissolved in an aqueous solvent and the pharmaceutical composition can comprise other non-active ingredients, such as preservatives, emulsifying and/or viscosifying agents, sweeteners, flavoring agents, flavor-masking agents, and/or other carrier materials.

Moreover, in some embodiments, the concentration of capromorelin within the inappetance-controlling composition is at least partially dependent upon the route of administration and/or the number of times in a pre-determined time period the composition is administered to companion animals or livestock. For example, one or more formulations of the composition are designed for injectable administration. As a result, the capromorelin within the composition can be delivered directly to the circulatory system (e.g., via intravenous administration), thereby circumventing the need for absorption in the alimentary canal. Accordingly, greater amounts of capromorelin can reach the desired targets (e.g., GHS-Rs) relative to oral formulations, leading to a lower necessary concentration of capromorelin in a sterile injectable version. In other embodiments, the inappetance-controlling composition is orally administered one or more times per day. For example, the composition can be administered as a solution, a solid, or a preferred viscous liquid formulation. Correspondingly, the greater number of times per day the composition is administered to the companion animals, the lesser the amount of capromorelin is needed to produce desired results.

By way of example only, in some embodiments, dosing of the animals can be divided into multiple treatment regimens, depending on severity of the indications of the animal. In some embodiments, an animal may receive a 0.1 mg/kg, 0.2 mg/kg, 0.3 mg/kg, 0.33 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, or 6 mg/kg dosing regimen. Moreover, some of these dosing regimens may be in the form of solid or liquid formulations. For example, some animals (e.g., dogs) can receive one or more solid oral formulations, such as inappetance-controlling composition formulated for administration via capsules, gel caps, gel-like liquids (i.e., viscous liquids), pills, caplets, tablets, or other solid, liquid, or nebulized forms. For example, the capsules or other forms can include different concentrations of capromorelin to enable dosing of animals of a plurality of weights (i.e., because the capromorelin dosing is at least partially dependent on the weight of the animal). By way of example only, in some embodiments, capsules can be manufactured with a capromorelin concentration of 20 mg per capsule, 35 mg per capsule, and 75 mg per capsule. As a result, different combinations of capsules can be administered to the animals in need of treatment to provide the necessary dose of capromorelin to the animal. By way of example only, an animal weighing approximately 15 kg and placed on a 3 mg/kg treatment regimen would require about 45 mg of capromorelin per dose. Accordingly, the animal can receive two 20 mg capsules to provide a dose of capromorelin that is close to 45 mg (i.e., with between 5 and 10 milligrams of the desired dose based on animal weight or within a dosing band). Other animals of other sizes and placed on other treatment regimens can be similarly treated to provide an efficacious amount of capromorelin.

In a preferred embodiment, the dose of capromorelin comprises a sufficient amount to achieve a Cmax of around 150 nanograms of capromorelin or a metabolite thereof per milliliter of plasma at a Tmax of around 2 hours. In an alternate embodiment, the dose of capromorelin comprises a sufficient amount to achieve a Cmax of around 905 nanograms of capromorelin or a metabolite thereof per milliliter of plasma at a Tmax of around twenty-five minutes. The Tmax can occur in individual animals preferably at a 30 minute, 1 hour or 2 hour time interval, with the range being from about 30 minutes to 2 hours to reach Tmax. Preferably, the Cmax is between 100 ng/mL to 1000 ng/, however, this varies in different animals, therefore the Cmax could be even higher. Preferably, the Cmax is about 100 ng/mL, about 200 ng/mL, about 300 ng/mL, about 400 ng/mL, about 500 ng/mL, about 600 ng/mL, about 700 ng/mL, about 800 ng/mL, about 900 ng/mL, and about 100 ng/mL.

In some embodiments, the dosing regimen chosen can be at least partially correlated with the treatment goals. For example, under some circumstances, it may be desirous to provide doses to animals that are either experiencing significant side effects of inappetance or are being treated to more efficiently and effectively develop lean muscle. In addition, under some circumstances, it may be desirous to provide doses to animals that function to maintain current weight and muscle mass. As such, these maintenance doses can be given on a regular basis (e.g., once per week, per month, bi-monthly, every other day for a month, etc.) and can comprise a lesser dosage of capromorelin (e.g., 0.2 mg/kg) such that the administration yields the benefits of reduced inappetance and/or increased lean muscle mass, but not to the same extent as greater doses.

In addition, some embodiments of the inappetance-controlling composition comprise liquid oral formulations that can be used in a manner similar to the above solid oral formulation. Additionally, the liquid formulations can be administered in a syringe or sprayed on animal food, treats, or chews. In an embodiment where the animal is livestock, the inappetance-controlling composition is preferably sprayed on or incorporated into feed. For example, the liquid formulations can be prepared to comprise the following concentrations of capromorelin within the liquid formulation: 20 mg/mL, 30 mg/mL, 40 mg/mL, or 60 mg/mL. Similar to the solid formulations discussed above, the different concentrations of the liquid formulation can be used to enable dosing of animals of a plurality of weights (i.e., because the capromorelin dosing is at least partially dependent on the weight of the animal). As a result, different volumes of the different solutions can be administered to the animals to provide the required dose of capromorelin. By way of example only, an animal weighing approximately 15 kg and placed on a 3 mg/kg treatment regimen would require about 45 mg of capromorelin per dose. Accordingly, the animal can receive about 2.3 mL of the 20 mg/mL solution or 1.1 mL of the 40 mg/mL solution to provide a dose of capromorelin that is close to 45 mg. Similarly, if the same animal was placed on a 4.5 mg/kg treatment regimen, the animal could receive 2.3 mL of the 30 mg/mL solution or 1.1 mL of the 60 mg/mL solution to provide a dose of capromorelin close to 67.5 mg (i.e., the dose a 15 kg animal should receive on this treatment regimen). Other animals of other sizes and placed on other treatment regimens can be similarly treated to provide an efficacious amount of capromorelin.

In some embodiments, the inappetance-controlling composition can be administered using any one of a plurality of routes of administration. The inappetance-controlling composition can be orally, parenterally, and/or topically administered. For example, in some embodiments, the inappetance-controlling composition can be orally formulated in a liquid and/or a solid formulation so that the composition can be administered using at least one of a spray, a syringe, a pill, a tablet, a caplet, a gel-cap, or an otherwise liquid-based administration scheme. In other embodiments, the composition can be formulated for administration via subcutaneous, intradermal, intravenous, intramuscular, intracranial, intraperitoneal, or intrathecal administration (e.g., via an injection or composition-dispensing pump). For example, in some embodiments, the composition can be formulated as a parenterally administered depot formulation that can be configured for extended release of the capromorelin (e.g., release over the period of multiple days to multiple months). Moreover, the composition can be administered as a gel that contacts the skin or other tissue of the animals and is accordingly absorbed there through. Alternatively, the composition can be administered using an electrophoresis system to drive the composition into circulation of the animal.

In yet other embodiments, the composition can be formulated for transdermal and/or transmucosal administration (e.g., via a buccal film or patch that is applied to the epidermis of the animal). In addition, in some embodiments, the inappetance-controlling composition can be administered intranasally or in the form of one or more suppositories. In some embodiments, the composition can be formulated as an implant that can be disposed within the soft tissue of the animals. For example, the composition-containing implant can be implanted into the cutaneous, subcutaneous, and/or muscle tissue of the animals for extended release. Moreover, the composition can also be formulated to be administered to the skin of the animal in a "spot-on" manner. In yet other embodiments, the inappetance-controlling composition can be formulated for any other suitable route of administration known in the art.

In some embodiments, the composition can be administered to the animal as a part of a daily feeding regimen. For example, the composition can be formulated to be mixed with the feed or other food product intended to be consumed by the animal such that, as the animal consumes its daily food intake (e.g., kibble or soft food), the animal is also consuming the composition. In particular, the composition can be formulated as a liquid or a powder so that prior to feeding the animal, the formulation can be applied (e.g., sprayed) to the food for consumption by the animal. Moreover, in some embodiments, the food provided to the animals (e.g., companion animals or livestock) can be provided with the pharmaceutical composition already ad-mixed with the food product such that the animal's caretaker need only provide the medicated food to the animal.

In some embodiments, other food products provided to the animal (e.g., companion animals or livestock) can be supplemented with the capromorelin composition. For example, soft or hard treats or chews (e.g., rawhide or other animal-based products given to animals for enjoyment and/or enrichment) can be supplemented with the capromorelin composition, where the capromorelin composition is either incorporated into the treat or chew or sprayed onto the treat or chew. In some aspects, the treats or chews can be purchased in a form that already includes the capromorelin composition. In other aspects, the capromorelin composition can be later added to the treats or chews by the individual feeding the animal.

Moreover, in some embodiments, the kibble, treats, and/or chews is mixed with a maintenance level dosage of the capromorelin-containing composition. Preferably, an animal receiving the maintenance level dosage is able to maintain a certain level of food consumption. For example, as discussed above, a maintenance dose (e.g., 0.2 mg/kg) can be provided to the animals on a regular or irregular basis to provide lower doses of the active ingredient to continue to prevent inappetance, to treat minor occurrences of inappetance, or to provide low doses to continually stimulate lean muscle growth. By providing these maintenance doses with the food products (e.g., kibble), treats, and/or chews, the animals can relatively enjoy the experience of receiving the maintenance doses such that little to no active ingredient is lost in the administration process.

In some embodiments, the composition is produced and delivered in the form of a kit. The kit preferably includes a syringe, one or more vessels, and directions that instruct the user to withdraw about one done from the vessels and administer the dose to the animals. By way of example only, in some embodiments, the composition can be stored in one or more vessels (e.g., a sterile bottle) from which an individual (e.g., a veterinarian and/or a caretaker/owner of the animal) can access the inappetance-controlling composition. For instance, using a syringe, the individual can withdraw about one dose of the composition (e.g., about five milliliters) from the vessel for administration to the animal. In some embodiments, the individual can secure the animal and place the syringe within the mouth of the animal (e.g., a back corner of the mouth near the back of the tongue. Once prepared, the individual can depress the plunger of the syringe to release the composition into the mouth/oral cavity of the animal so that the animal swallows the composition. As a result of placing the syringe near the rear of the mouth, the animal will nearly involuntarily swallow the composition so that some or all of the composition is received within the alimentary canal of the animal. In other embodiments, prior to and/or after withdrawing the dose of the inappetance-controlling composition from the vessel, a needle can be affixed to the syringe and the dose can be administered to the animal through any of the previously mentioned routes of administration. In yet other embodiments, the inappetance-controlling can comprise a solid-dosage formulation so that the composition can be given in other forms (e.g., pills, caplets, tablets, etc.) with or without food.

In some embodiments, the inappetance-controlling composition is provided to the individual in a "ready-to-use" formulation. For example, the composition can be provided in the vessel so that the individual is not required to make any further additions to the vessel or treat the composition in any way to prepare the composition for administration to the animal. In other embodiments, the inappetance-controlling composition can be provided in an emulsified liquid formulation or suspension so that one or more additional compounds, excipients, other materials or preparatory steps may need to be added or carried out to ready the composition for administration to the animal.

In some embodiments, the composition includes one or more pharmaceutically acceptable excipients or carriers. For example, some examples of possible excipients or carriers include, but are not limited to, diluents, binders, fillers, buffering agents, pH modifying agents, disintegrants, dispersing agents, stabilizers, preservatives, salt solutions, and/or coloring agents. The amount and types of excipients may be selected according to known principles of pharmaceutical science.

In some embodiments, the composition includes one or more flavoring agents and/or flavor-masking agents. Particularly, the composition may have an unpleasant or undesirable flavor so that one or more additional compounds may be added to increase palatability. In some embodiments, the flavoring agents and/or flavor masking agents may comprise one or more of a sweetening agent, a savory agent (i.e., an agent that imbues the composition with a salty flavor), a bittering agent, and a souring agent. In some embodiments, the inappetance-controlling composition that may be formulated for oral administration can include one or more of the following flavoring agents and/or flavor-masking agents (e.g., sweetening agents): sucralose, MagnaSweet®, Di-Pac® compressible sugar (i.e., a 97%:3% mixture of sucrose and maltodextrin), Thaumatin T200X, Talin-Pure, OptisweetSD, stevia extract rebaudioside A, and/or neotame. In particular, some sugar-containing sweeteners (e.g., saccharose-containing materials) may at least partially degrade the capromorelin within the composition. Accordingly, large concentrations of some sugar-containing sweeteners should be avoided. In addition, in some embodiments, the flavoring agents and/or flavor-masking agents can comprise a vanilla-comprising composition, such as, but not limited to ethyl vanillin, vanillin-RHD, vanillin-Merck, vanilla-TG-old and suitable solvents (e.g., ethanol and/or water). In other aspects, other flavoring agents and/or flavor-masking agents can be added that confer other flavors on the composition, such as banana, pork liver, beef, etc.

In some embodiments, the flavoring agents and/or flavor-masking agents preferably comprise a percent weight per final volume of the inappetance-controlling composition of between about 50% to about 0.001%, depending on the agent selected. Preferably, the flavoring agents and/or flavor-masking agents can comprise a percent weight per final volume of the inappetance-controlling composition of between about 40% to about 0.01%, depending on the agent selected. More preferably, the flavoring agents and/or flavor-masking agents can comprise a percent weight per final volume of the inappetance-controlling composition of between about 30% to about 0.01%, depending on the agent selected. As previously mentioned, in some embodiments, the inappetance-controlling composition can include more than one flavoring agent and/or flavor-masking agent.

In some embodiments, the inappetance-controlling composition includes one or more inactive ingredients (i.e., carriers) that can function to stabilize or buffer the composition, function as an emulsifier or viscosifying agent for at least one or more of the constituents of the composition, function as a vehicle, function as a replacement material for sucrose, function as a solvent, and can function to serve any other desirable role. For example, the inappetance-controlling composition can include one or more of the following substances: citric acid, sodium citrate, sodium chloride, methyl 4-hydroxybenzoate salt, propyl 4-hydroxybenzoate salt, neosorb sorbitol, maltitol, propylene glycol, vegetable glycerin, Kollidon 90F, xanthan gum, Pluriol-E3350®, polyvinylpyrrolidone, polyethylene glycol and/or purified/deionized water. In some embodiments, the inactive ingredients can comprise a percent weight per final volume of the inappetance-controlling composition of between about 80% to about 0.001%, depending on the agent selected. Preferably, the inactive ingredients can comprise a percent weight per final volume or weight of the inappetance-controlling composition of between about 40% to about 0.01%, depending on the agent selected. More preferably, the inactive ingredients can comprise a percent weight per final volume of the inappetance-controlling composition of between about 25% to about 0.01%, depending on the agent selected. As previously mentioned, in some embodiments, the inappetance-controlling composition can include more than one inactive ingredient.

In some embodiments, the composition can be alternatively formulated. For example, as previously mentioned, the composition can be formulated for intravenous injection, in which the formulation can include capromorelin dissolved in a physiologically acceptable sterile solution (i.e., a carrier), such as water or a salt-based solution (e.g., a phosphate-buffered saline solution). In other embodiments, the composition can be formulated for subcutaneous administration. As such, the formulation can include physiologically acceptable carriers such as benzyl alcohol and buffer (e.g., a citrate buffer).

In some embodiments, the inappetance-controlling composition can include the following base formulation in a solution:

| Ingredient | % weight per volume |
| --- | --- |
| Capromorelin | 2.10, 3.10, or 4.10 |
| Methyl 4-Hydroxybenzoate S. Salt | 0.045-0.115 |
| Propyl 4-Hydroxybenzoate S. Salt | 0.005-0.015 |
| Citric Acid (Anhydrous) | 0.5-0.7 |
| Sodium Citrate | 0.5 |
| Sodium Chloride | 0.7-1.0 |
| Neosorb sorbitol 70% | 30-31 |
| Maltitol Solution | 25 |
| Vegetable-based Glycerin | 17-21 |
| Purified Water | q.s. |

However, this formulation is exemplary, with the amounts of each components and combination of ingredients is subject to variation.

Moreover, the following combinations of materials, solutions, compositions, and/or compounds can be added to the base formulation disclosed above to form one or more inappetance-controlling compositions for administration to treat inappetance-induced weight loss. In a preferred embodiment, the composition of the present invention comprises capromorelin, a viscosifying agent, and a flavoring agent and/or flavor-masking agent. The flavoring agent and/or flavor-masking agent is preferably a sweetener. In addition, one or more of the constituents can be omitted from the base formulation when preparing the inappetance-controlling compositions. The formulations shown below are exemplary and are not intended to be limiting.

| Formulation Number | Concentration of Capromorelin Composition (in mg/mL) | Viscosifying Agent (in % weight per volume) | Sweetener | Flavoring Agent and/or Flavor-Masking Agent |
|---|---|---|---|---|
| 1 | 21 | Kollidon 90F (1.5%) | Thaumatin T200X (0.4%); Stevia Rebaudioside A (0.4%); and MagnaSweet ® (0.5%) | Ethyl Vanillin (0.1%) and Ethanol (0.25%) |
| 2 | 21 | Kollidon 90F (1.4%-1.5%) | Sucralose (0.7%) and MagnaSweet ® (0.5%) | Vanillin (0.1%) and optionally Ethanol (0.25%) |
| 3 | 21 | Kollidon 90F (1.5%) | Talin-Pure (0.3%) and MagnaSweet ® (0.5%) | Ethyl Vanillin (0.1%) and Ethanol (0.25%) |
| 4 | 21 | Kollidon 90F (1.5%) | OptisweetSD (0.5%) and MagnaSweet ® (0.5%) | Ethyl Vanillin (0.1%) and Ethanol (0.25%) |
| 5 | 21 | Xanthan-Gum (0.05%) | Thaumatin T200X (0.4%); Stevia Rebaudioside A (0.4%); and MagnaSweet ® (0.5%) | Vanillin-RHD (0.1%) and water |
| 6 | 21 | Pluriol-E3350 ® (7.5%) | Thaumatin T200X (0.4%); Stevia Rebaudioside A (0.4%); and MagnaSweet ® (0.5%) | Ethyl Vanillin (0.13%) and Ethanol (0.3%) |
| 7 | 21 | None | Thaumatin T200X (0.4%); Stevia Rebaudioside A (0.4%); and MagnaSweet ® (0.5%) | Vanillin-Merck (0.13%) and Ethanol (0.3%) |
| 8 | 21 | Kollidon 90F (1.5%) | Thaumatin T200X (0.10-0.4%); Stevia Rebaudioside A (0.1-0.4%); and MagnaSweet ® (0.3-0.5%) | Vanillin-Merck (0.13%) and Ethanol (0.3%) |
| 9 | 31 | Kollidon 90F (1.5%) | Thaumatin T200X (0.6%-0.7%); Stevia Rebaudioside A (0.7%); and MagnaSweet ® (0.5%) | Vanillin (0.10-0.20%) and Ethanol (0.3-0.5%) |
| 10 | 41 | Kollidon 90F (1.5%) | Thaumatin T200X (0.7%); Stevia Rebaudioside A (0.7%); and MagnaSweet ® (0.5%) | Ethyl Vanillin (0.13%) and Ethanol (0.3%) |
| 11 | 21 | Polyvinylpyrrolidone K-90 (1.5%) | Thaumatin T200X (0.4%); Stevia Rebaudioside A (0.4%); and MagnaSweet ® (0.5%) | Vanilla-TG-Old (0.4%) and water |
| 12 | 21 | Polyvinylpyrrolidone K-90 (1.5%) | Sucralose (0.5%) and MagnaSweet ® (0.3%) | Vanilla-TG-old (0.25%) and water |

In some embodiments, the compositions can be used in conjunction with another treatment regimen that may induce inappetance. For example, in some embodiments, the compositions can be administered to animals (e.g., companion animals and/or livestock) as a part of a chemotherapeutic or radiation treatment regimen. Those skilled in the art will recognize that chemotherapeutic or radiation treatment regimens may cause significant weight loss, wasting, muscle loss, cachexia, or other negative side effects that can be at least partially improved or abrogated by additional food consumption and/or increases in lean muscle mass. Accordingly, administration of therapeutically effective amounts of the compositions comprising capromorelin can induce food intake, thereby leading to weight gain and increased lean muscle mass. As a result, the animals can have more energy for activities and coping with the treatment regimens.

Moreover, in some embodiments, the compositions are administered to animals suffering from other conditions requiring unappetizing food. For example, some animals diagnosed with chronic kidney disease are placed on a specialized diet to improve this condition. However, some animals do not find the specialized diet food to be appetizing, and, as a result, do not consume enough of the specialized diet food for treatment of the chronic kidney disease or for sustenance. Accordingly, some animals can receive therapeutically effective amounts of the inappetance-controlling composition comprising capromorelin to stimulate hunger and induce consumption of the specialized diet food. As a result, the chronic kidney disease can be better controlled by the specialized diet food and the animal can consume sufficient calories for a pleasant existence.

In some embodiments, the compositions can be used to treat a general state of inappetance-induced weight loss. For example, some animals, for unknown reasons, experience inappetance, which, as previously mentioned, can lead to weigh loss, wasting, cachexia, lethargy, and other unpleasant results. After diagnosis of inappetance-induced weight loss by one skilled in the art, such as a veterinarian, the animals can receive one or more therapeutically effective doses of the composition comprising capromorelin to increase food consumption and lean muscle mass. As result, the companion animals can experience healthy weight gain leading to an improved quality of life.

In some embodiments, the composition can be used to increase lean muscle mass. For example, it can be desirous to increase the lean muscle mass in some animals (e.g., livestock such as bovine or porcine animals), as previously mentioned. Accordingly, the composition can be administered in a therapeutically effective amount in one or more doses to increase lean muscle mass without the need to treat inappetance-induced weight loss. In a preferred embodiment, the capromorelin-containing composition comprises a sufficient amount of capromorelin to achieve a Cmax of around 150 nanograms of capromorelin or a metabolite thereof per milliliter of plasma at a Tmax of around two hours. However, the Tmax is preferably from about twenty-five minutes to 2 hours, where intervals are envisioned at about 30 minutes, about an hour, and about 2 hours. Additionally, the Tmax is preferably from about 100 ng/mL to about 1,000 ng/mL.

In some embodiments, the composition can be administered to companion animals for the treatment or prevention of other maladies, illnesses, afflictions, or other indications. For example, in some embodiments, the capromorelin-containing composition can be administered to cats to treat and/or prevent feline hepatic lipidosis (i.e., feline fatty liver disease). Under some conditions, feline hepatic lipidosis can result from excess fatty deposits in the liver, which results in the disruption of normal hepatocyte functioning. Although the mechanism leading to the onset of feline hepatic lipidosis is not completely understood, feline inappetance is believed to be a trigger of this condition. In particular, after a cat has stopped eating or greatly reduces its daily food intake (e.g., due to stress), the feline liver begins to attempt to process excess body fat for upkeep of the metabolism. The transport of body fat to the liver results in excess fat being stored in the liver, which leads to the onset of hepatic lipidosis.

In some embodiments, the present invention provides for a method of treating hepatic lipidosis in cats or dogs. The method preferably comprises the step of administering a capromorelin-containing composition to an animal in need thereof. For example, a cat that is suffering from inappetance or has already been diagnosed with feline hepatic lipidosis can be administered between about 2 mg/kg to about 4 mg/kg of capromorelin in either an oral solution formulation or an injectable formulation one or more times per day for between about 4 days to about a week. In some aspects, the capromorelin-containing composition can be administered as a preventative measure when the cat is expected to have a reduced appetite (e.g., chemotherapy, hospitalization, boarding, etc.). Furthermore, the capromorelin-containing composition can be administered when the cat has already started to develop feline hepatic lipidosis or might reasonably be expected to do so (e.g., after a prolonged period of inappetance). As a result of the administration of the administration of the capromorelin-containing composition, the cat may experience an increase in appetite, which will likely result in increased food consumption after the first dose through the treatment period. For example, the owner of the cat can generally observe the amount of food consumed by the cat to be certain that the treatment is effective. As the cat consumes greater amounts of food because of treatment with the composition, the hepatic lipidosis will be treated or will be prevented from occurring. In some embodiments, the treatment for hepatic lipidosis can be repeated as many times as necessary.

The treatment regimen of the inappetance-controlling composition of the present invention can be at least partially adjusted during the course of treatment. For example, after the animal is diagnosed as experiencing inappetance-induced weight loss (e.g., regardless of cause), an amount of the composition believed to be therapeutically effective can be administered to the animal (e.g., orally, intravenously, etc.). After a pre-determined time period, (e.g., about eight hours after the first administration of the composition and about seven days later), a technician, a veterinarian, or any other suitable individual can extract a sample (e.g., a serum sample) from the animal to measure amounts of one or more plasma markers within the sample. In other embodiments, the samples can be taken at any other suitable time points known to those skilled in the art that would be appropriate for measuring the one or more plasma markers. For example, the plasma markers are preferably selected from the group consisting of, but not limited to, IGF-1, cortisol, capromorelin, and combinations thereof. In an alternate embodiment, an indicator is used. The indicator is preferably selected from, but not limited to, weight gain, weight loss, an increase in food consumption, a decrease in food consumption, an increase in muscle mass, a decrease in muscle mass, and combinations thereof. As a result of knowing the amounts of one or more of these plasma markers and/or indictors, the dose of the composition can be adjusted in light of the amounts of the plasma markers or indicators within the sample. In one embodiment, a minimum concentration of one or more of the plasma markers is determined at a first time point, a minimum concentration of one or more of the plasma markers is determined at a second time point, and so on. Preferably, the minimum concentration of one or more of the plasma markers is determined at a first time point, a first and a second time point, or a first, a second, and a third time point. Preferably, the concentration of the plasma markers can be compared to determine if the plasma marker is increasing or decreasing over time. Further, in one embodiment the concentration of the plasma markers can be compared to a predetermined value such that the dose of the pharmaceutical composition can be increased or decreased depending on the concentration of the plasma marker. A method of determining the effectiveness of the composition can be determined using the steps above and is preferably adjusted during the course of treatment. For example, if the amount or concentration of IGF-1 within the sample is low, the dose of the composition is increased in either concentration of capromorelin or amount of capromorelin administered to the companion animal. Conversely, if the amount of cortisol within the sample is too great, which can lead to increased adipose deposition, the dose of the composition can be decreased in either concentration of capromorelin or amount of capromorelin administered to the companion animal.

In a further embodiment, a method is provided for determining the effectiveness of the pharmaceutical composition. The method preferably comprises the steps of determining that an animal is experiencing inappetance, measuring one or more plasma markers, administering a composition comprising capromorelin to the animal, taking a further measurement of one or more plasma markers, and determining if the dose is appropriate or needs to be adjusted. The plasma markers are preferably selected from the group consisting of, but not limited to, IGF-1, cortisol, capromorelin, and combinations thereof In some embodiments, the above treatment regimen can be carried out without extracting a sample. For example, after administering one or more the therapeutically effective doses to the animal, other indicators of weight loss can be measured to assess the effectiveness of the treatment regimen. These indicators can include a change in weight (e.g., continued weight loss, weigh gain, weight loss stabilization), a change in food intake (e.g., increase in food intake relative to the pre-treatment time period), and/or a measurement of a change in lean muscle (e.g., scoring a value of the lean muscle index of the animal to assess lean muscle growth). As a result, the animal does not experience the invasive extraction of a serum sample and the individuals monitoring the treatment regimen can accordingly adjust the dose of the treatment regimen.

In some embodiments, one or more of the above-described treatment regimens can be carried out until a satisfactory result is achieved. In particular, the capromorelin composition can be administered to an animal in need thereof until the animal is no longer in need thereof. For example, the capromorelin composition can be administered to an animal suffering from inappetance-induced weight loss until the animal regains a sufficient amount of weight. Specifically, the veterinarian or caretaker can continue to administer the composition (e.g., daily, every other day, etc.) until the weight of the animal increases a sufficient amount. For example, the sufficient amount of weight gain may be a 5% increase in body weight compared to the body weight of the animal prior to receiving the initial dose of the composition. In other embodiments, the sufficient amount of weight gain may be more than 5% (e.g., 10%, 20%, 25%, etc.), as determined by the needs of the animal.

The present invention provides for a method of treating inappetance comprising the steps of determining that an animal has inappetance, administering at least one dose of a capromorelin-containing composition, assessing a plasma marker or indicator value in the animal, and continuing to administer the capromorelin-containing composition until the value of the plasma marker or indicator is appropriate for the animal.

Although the invention described herein is susceptible to various modifications and alternative iterations, specific embodiments thereof have been described in greater detail above. It should be understood, however, that the detailed description of the composition is not intended to limit the invention to the specific embodiments disclosed. Rather, it should be understood that the invention is intended to cover all modifications, equivalents, and alternatives falling within the spirit and scope of the invention as defined by the claim language.

DEFINITIONS

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "animal" designates non-human animals, such as "livestock" and "companion animals."

As used herein, the term "livestock" includes cattle, sheep, pigs, poultry (e.g., chickens, turkeys, quail, etc.) goats, llamas, and other similar animals.

As used herein, the term "h" designates hours.

As used herein, the term "composition" applies to any solid object, semi-solid, or liquid composition designed to contain a specific pre-determined amount (dose) of a certain ingredient, for example, an active pharmaceutical ingredient, as previously mentioned and as discussed below. Suitable compositions may be pharmaceutical drug delivery systems, including those for oral administration, buccal administration, rectal administration, topical or mucosal administration, or subcutaneous implants, or other implanted drug delivery systems; or compositions for delivery minerals, vitamins and other nutraceuticals, oral care agents, flavorants, flavor-masking agents, and the like. In one embodiment of the invention, the compositions are generally liquid, however they may contain solid or semi-solid components. Generally, the dosage form is an orally administered system for delivering a pharmaceutical active ingredient to the alimentary canal of a companion animal.

As used herein, the term "mg/kg" designates milligrams of composition per kilogram of body weight.

As used herein, the term "treatment" or "treating" of a condition, such as inappetance, includes inhibiting an existing condition or arresting its development; or ameliorating or causing regression of the condition. The term "preventing" or "prevention" of a condition, such as inappetance, weight loss, or cachexia, includes substantially blocking or inhibiting the development or growth of a condition before it starts.

As used herein, the term "animal" refers to a mammal, specifically a companion animal, including but not limited to dogs, cats, rabbits, ferrets, horses, and hamsters.

As used herein, the phrase "therapeutically effective amount" refers to an amount effective, at dosages and for periods of time necessary, to achieve the desired therapeutic result. A therapeutically effective amount of capromorelin may be determined by a person skilled in the art (e.g., a veterinarian) and may vary according to factors such as the clinical state, age, sex, and weight of the companion animal, bioavailability of capromorelin, and the ability of the active agent(s) to elicit a desired response in the companion animal. A therapeutically effective amount is also one in which any toxic or detrimental effects of the active agent(s), are outweighed by the therapeutically beneficial effects. A therapeutically effective amount also encompasses an amount that is effective, at dosages and for periods of time necessary, to achieve the desired result (e.g., weight gain through the addition of lean muscle mass).

As used herein, the term "q.s." means to add a quantity (e.g., volume or mass) of an ingredient until the final amount (e.g., volume or mass) is reached.

As used herein, the term "w/v" designates a concentration of a substance as measured in weight of the substance per volume of a solution or composition.

The following examples are intended to further illustrate and explain the present invention. The invention, therefore, should not be limited to any of the details in these examples.

EXAMPLE 1

Defining a Dosing Regimen of an Inappetance-Controlling Compound Containing Capromorelin for Inducing Food Intake and Lean Muscle Increases in Companion Animals A controlled, seven-day study was performed to assess the impact of different capromorelin-dosing regimens on the production of insulin-like growth factor 1 (hereinafter "IGF-1"), growth hormone (hereinafter "GH"), and cortisol. The different capromorelin-dosing regimens were also assessed for the impact on food intake and changes in body mass.

Eighteen adult non-naïve Beagle dogs (nine males and nine females) were divided into one of three treatment groups. Each of the three treatment groups included three males and three females. Group A, which was the control group, was dosed twice per day, via oral gavage, with a vehicle (deionized water alone) and was used as a baseline data point for comparison against the active treatment regimens. Group B comprised an active treatment group that received two treatments per day, via oral gavage, with a capromorelin-containing composition with a concentration of 3 mg/kg capromorelin per treatment. Finally, Group C comprised an active treatment group that received one treatment per day, via oral gavage, with a capromorelin-containing composition with a concentration of 6 mg/kg capromorelin per treatment.

During the ten day study period, on an at least once-daily basis, each of the dogs was monitored for clinical observations, mortality, morbidity, body mass, and food consumption. Serum samples were taken to measure capromorelin concentration, GH concentration, IGF-1 concentration, and cortisol concentration. Serum samples were taken on days 1, 2, 4, and 7 at −15 minutes (pre-dose), immediately prior to dosing (0 minutes) and 30, 45, 60, 90, 120, 240, 360, and/or 480 minutes post dosing. Additional blood samples were taken at 8 AM on Day 10 of the study to assess long-term impact of the active treatments.

Figure 2:
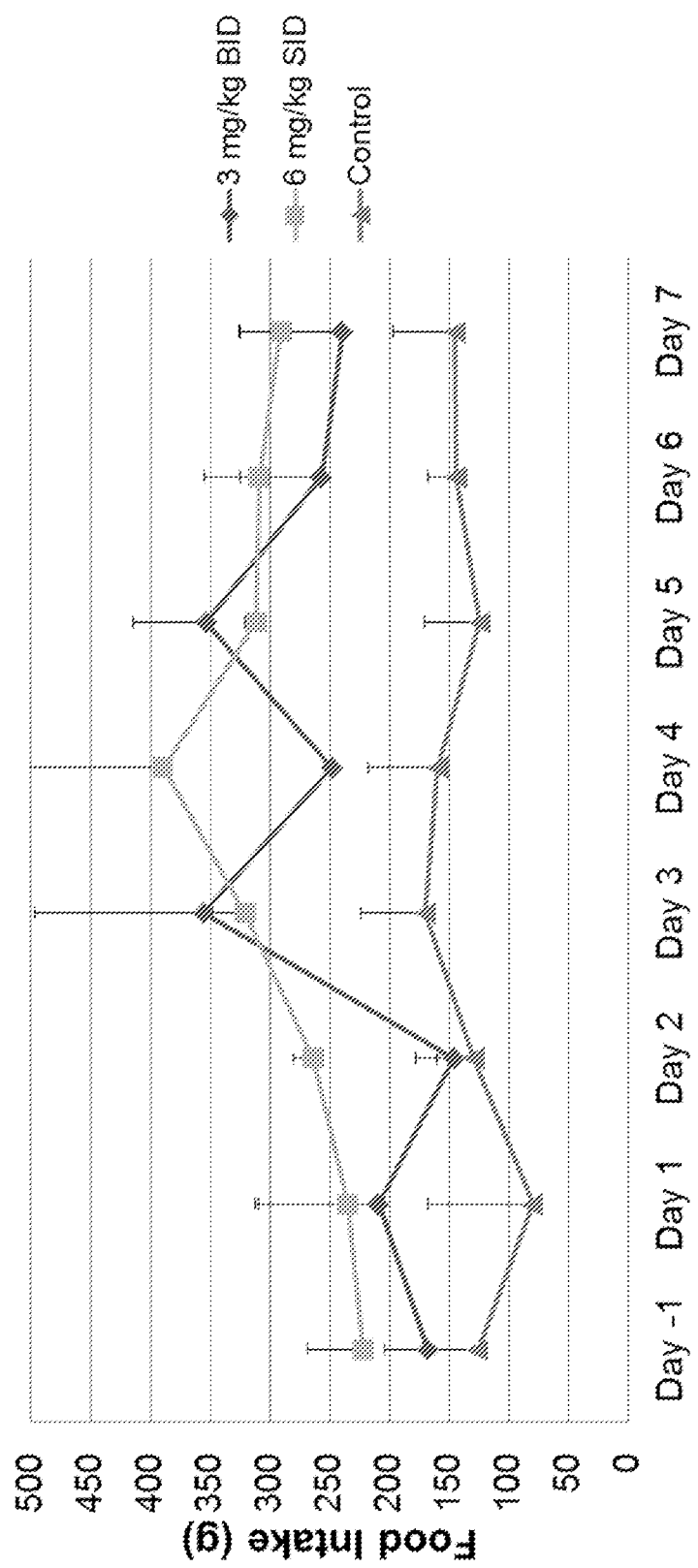
FIG. 2 is a line graph depicting the food intake data of FIG. 1 from only male beagles.
Figure 3:
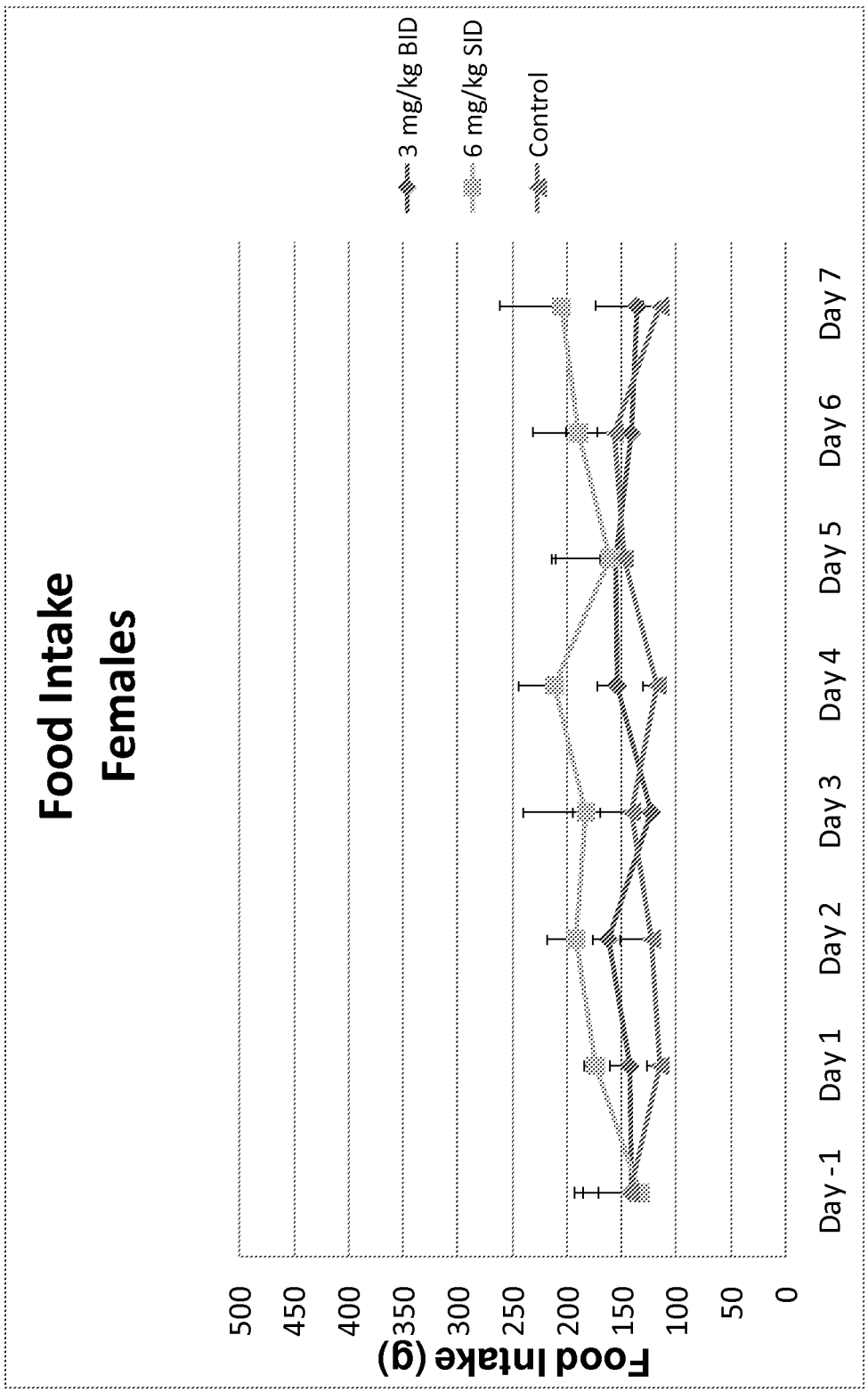
FIG. 3 is a line graph depicting the food intake data of FIG. 1 from only female beagles.
Figure 4:
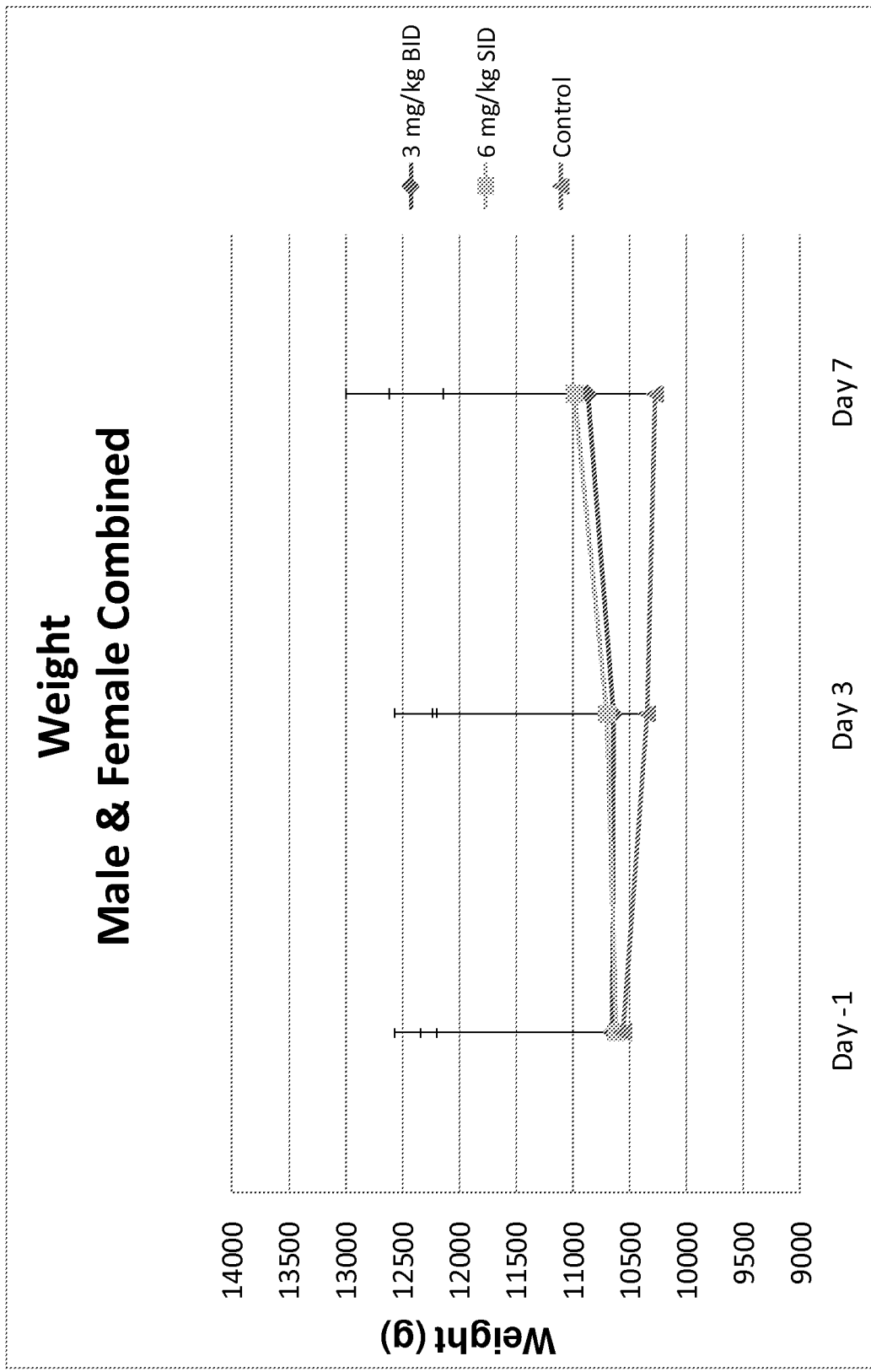
FIG. 4 is a line graph depicting a comparison between the first capromorelin treatment regimen, the second capromorelin treatment regimen, and the negative control.
Figure 5:
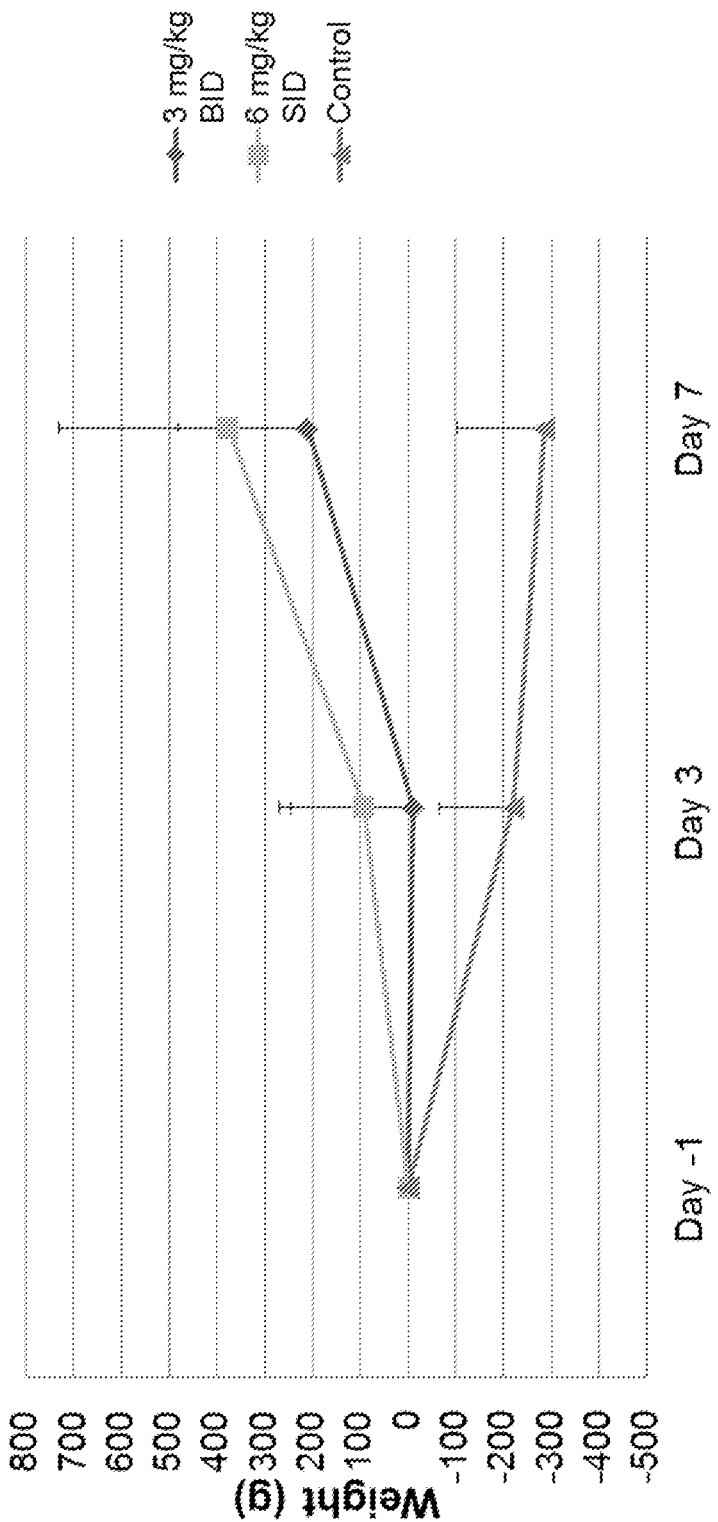
FIG. 5 is a line graph depicting a comparison between the first capromorelin treatment regimen, the second capromorelin treatment regimen, and the negative control.

As indicated in FIGS. 1-7, dogs in the active treatment groups (i.e., Groups B and C) consumed greater amounts of food and put on more weight compared to dogs in the control group (i.e., Group A). As shown in FIGS. 1-3, overall, dogs treated with a once-daily 6 mg/kg or a twice-daily 3 mg/kg dose of capromorelin consumed more food relative to dogs receiving deionized water only. Furthermore, referring to FIGS. 2 and 3, although males treated with the once-daily 6 mg/kg or the twice-daily 3 mg/kg dose of capromorelin tended to consume more food, females treated with the once-daily 6 mg/kg tended to consume more food relative to females in the other groups.

Figure 6:
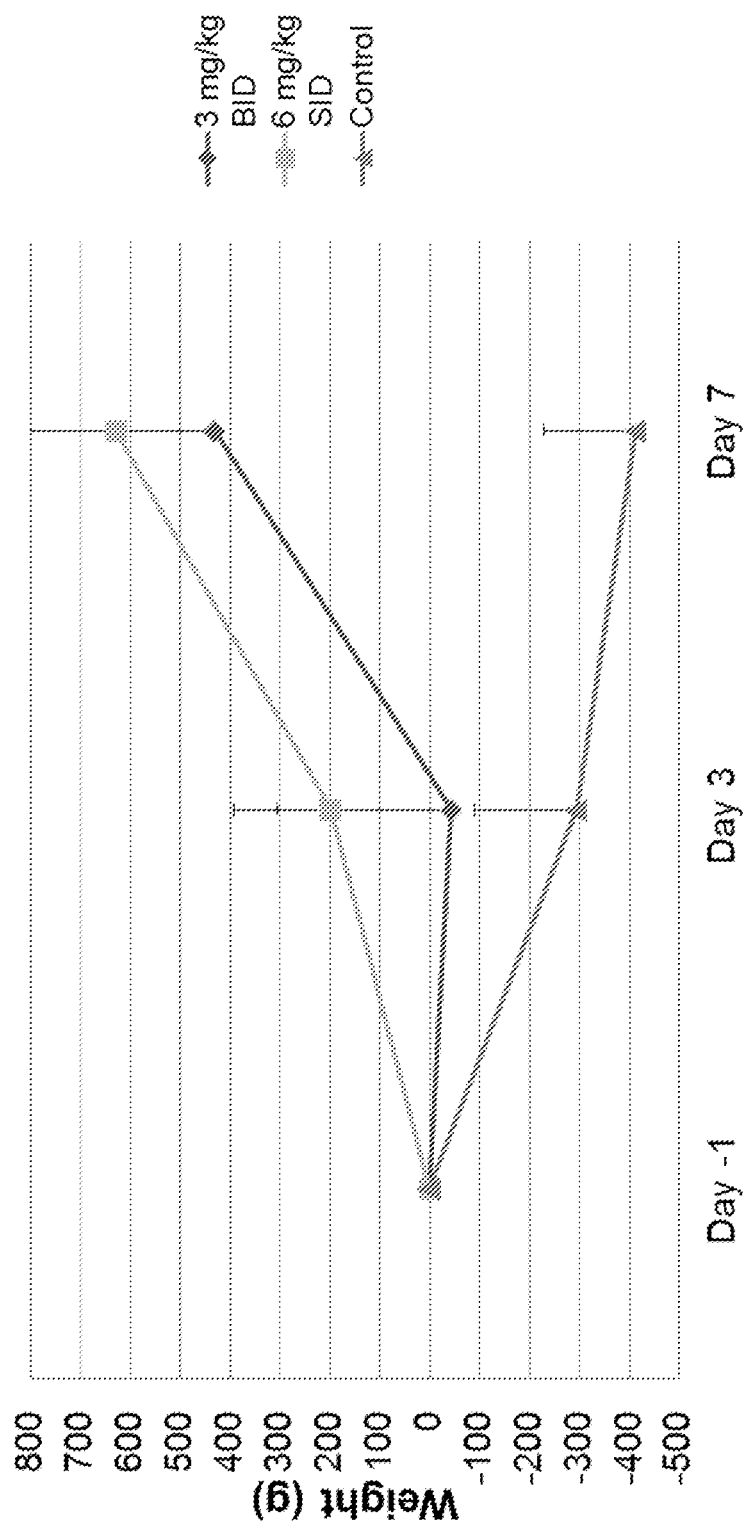
FIG. 6 is a line graph depicting the weight gain from baseline data depicted in FIG. 5 from only male beagles.
Figure 7:
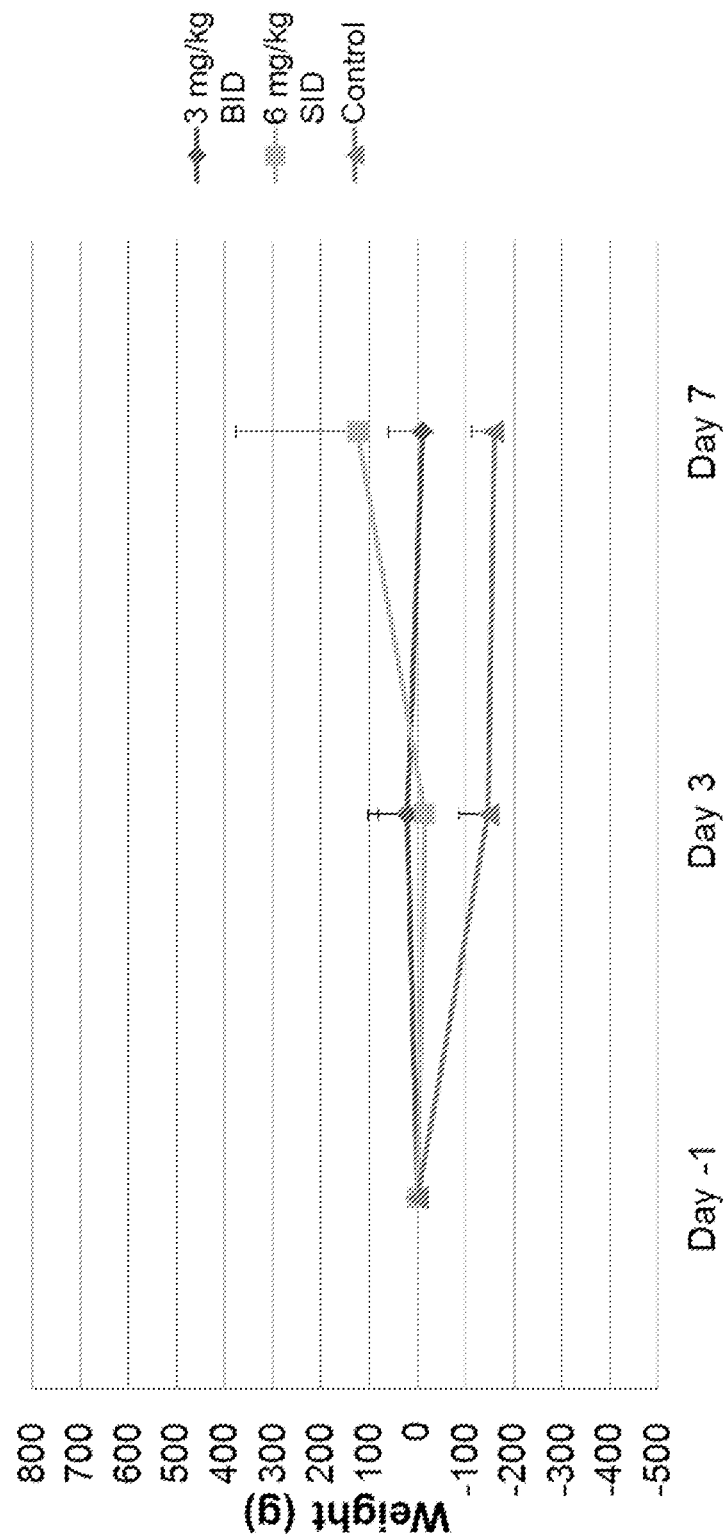
FIG. 7 is a line graph depicting the weight gain from baseline data depicted in FIG. 5 from only female beagles.

Similarly, as shown in FIGS. 4-7, dogs treated with the once-daily 6 mg/kg or the twice-daily 3 mg/kg dose of capromorelin gained more weight relative to dogs receiving deionized water only. The male dogs in these treatment groups experienced a 4-5% increase in weight over the course of the seven day treatment period (FIG. 6); however body weight changes in female dogs (FIG. 7) were not as clearly defined. The increase in body weight appears to be correlated with the increase in food consumption. More specifically, as discussed above, male dogs tended to consume more food (FIG. 2), and, correspondingly, male dogs also gained more body weight (FIG. 6).

Figure 8:
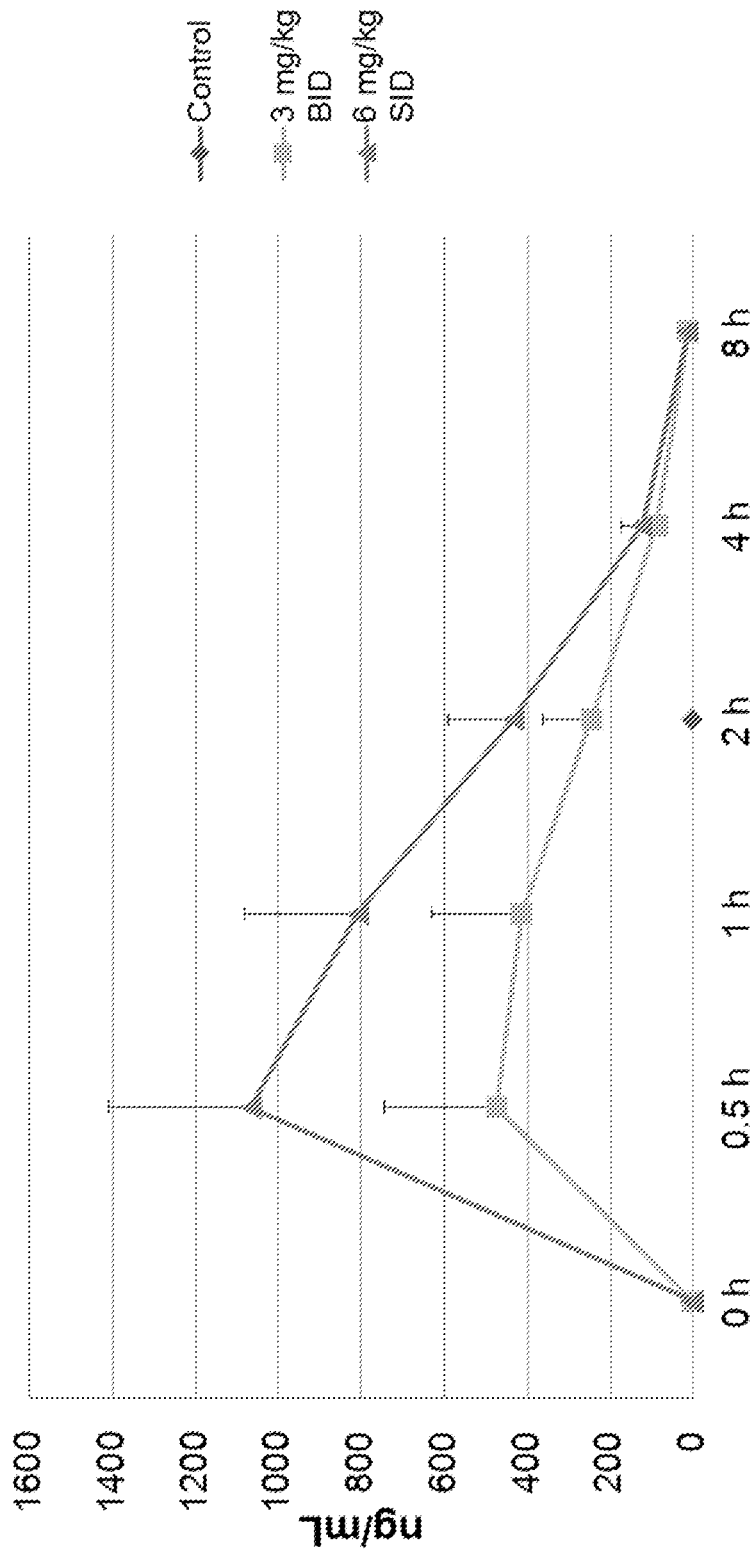
FIG. 8 is a line graph depicting measurements of capromorelin concentration in the serum in male and female dogs treated with the first treatment regimen, the second treatment regimen, and the negative control.
Figure 9:
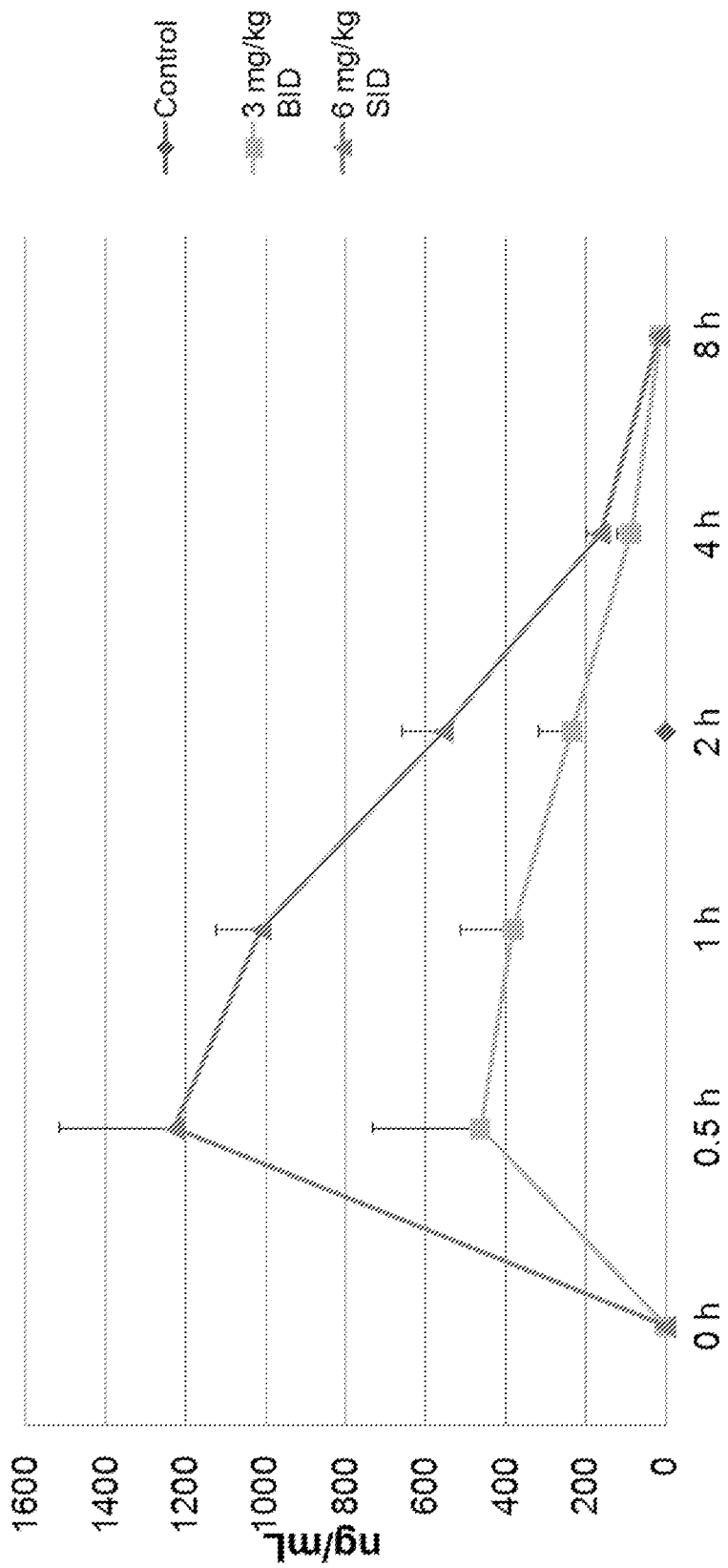
FIG. 9 is a line graph depicting the serum concentration of capromorelin depicted in FIG. 8 from only male beagles.
Figure 10:
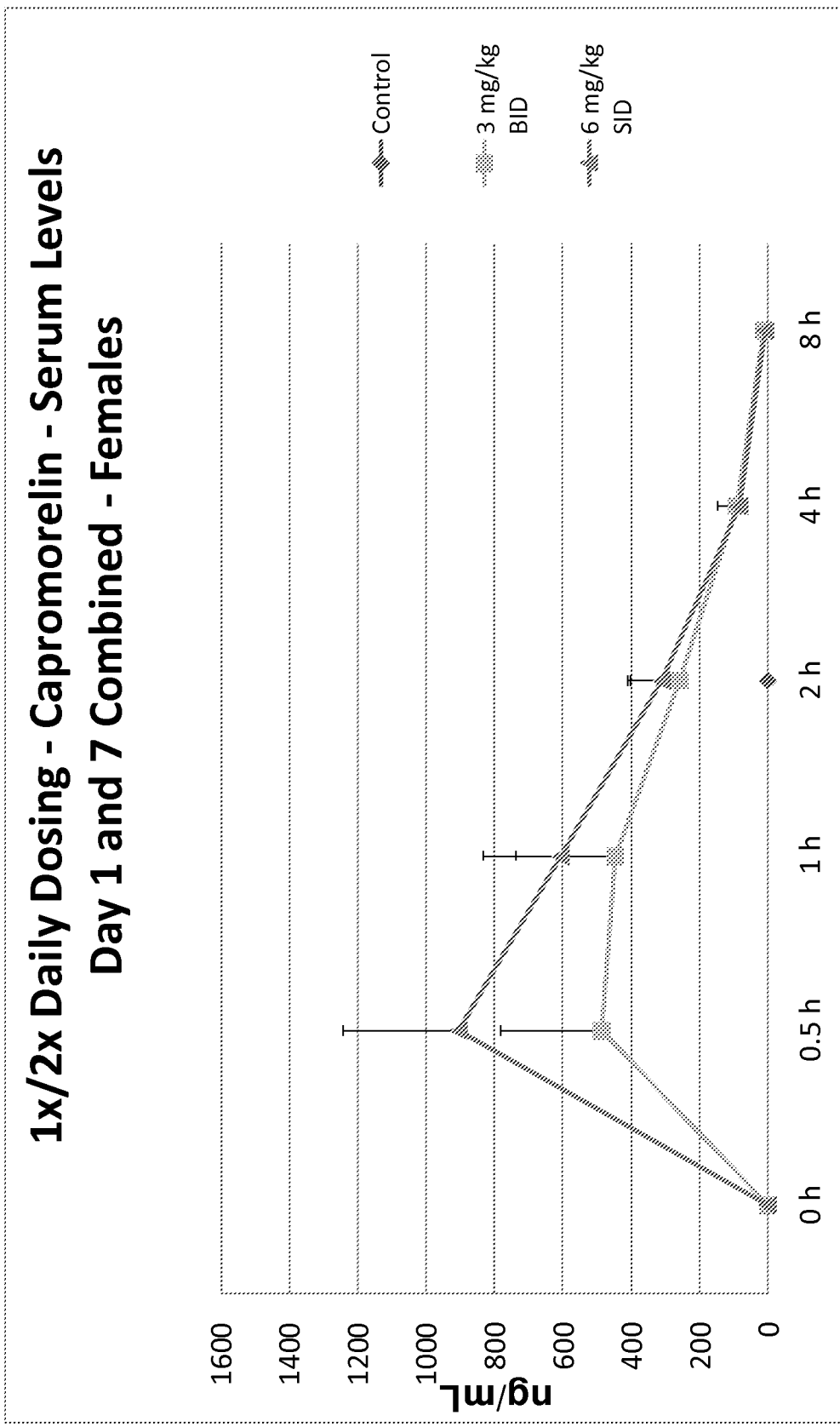
FIG. 10 is a line graph depicting the serum concentration of capromorelin depicted in FIG. 8 from only female beagles.

Referring now to FIGS. 8-10, dogs in both Groups B and C exhibited elevated concentrations of capromorelin in their serum. Using data from serum samples taken on Days 1 and 7 of the study, capromorelin concentrations tended to spike at approximately 0.5 h after dosing and, in general, decreased to near undetectable levels by eight hours after dosing (i.e., 480 minutes). The amount of capromorelin detected in the serum of the dogs correlates with the dosing regimen. Particularly, dogs receiving a 6 mg/kg dose exhibited higher capromorelin concentrations in their serum (about 2.3-fold higher) relative to dogs receiving the twice-daily 3 mg/kg dose, as shown in FIGS. 8-10. In addition, as shown in FIGS. 9 and 10, female dogs receiving with a 3 mg/kg dose exhibited a slightly higher capromorelin concentration in the serum relative to male dogs receiving the same dose.

As reflected in FIGS. 11-24, dogs in Groups B and C both experienced changes in serum concentrations of IGF-1, GH, and cortisol, which are likely attributable to the capromorelin administration.

Figure 11:
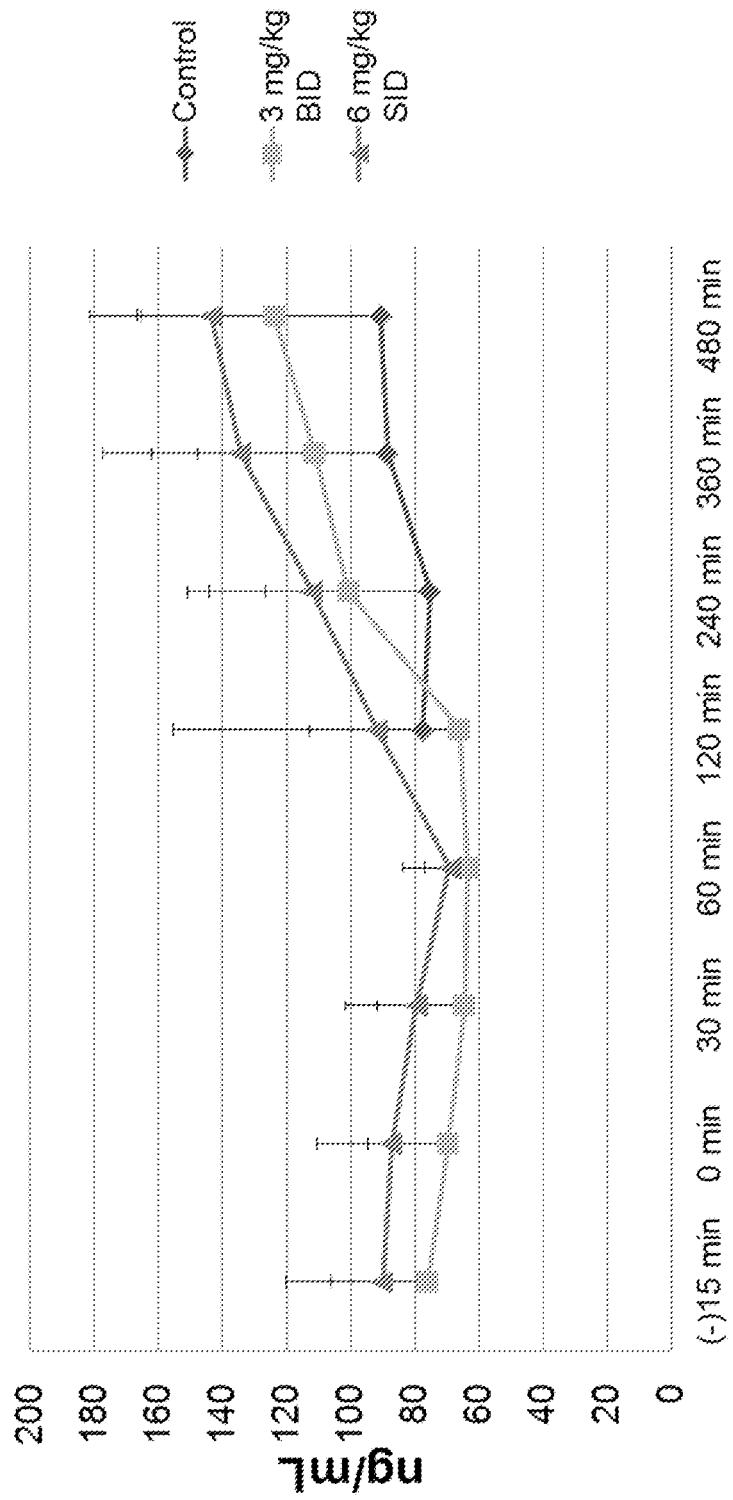
FIG. 11 is a line graph depicting measurements of insulin-like growth factor-1 concentration in the serum in male and female dogs treated with the first treatment regimen, the second treatment regimen, and the negative control on a first day of treatment.
Figure 12:
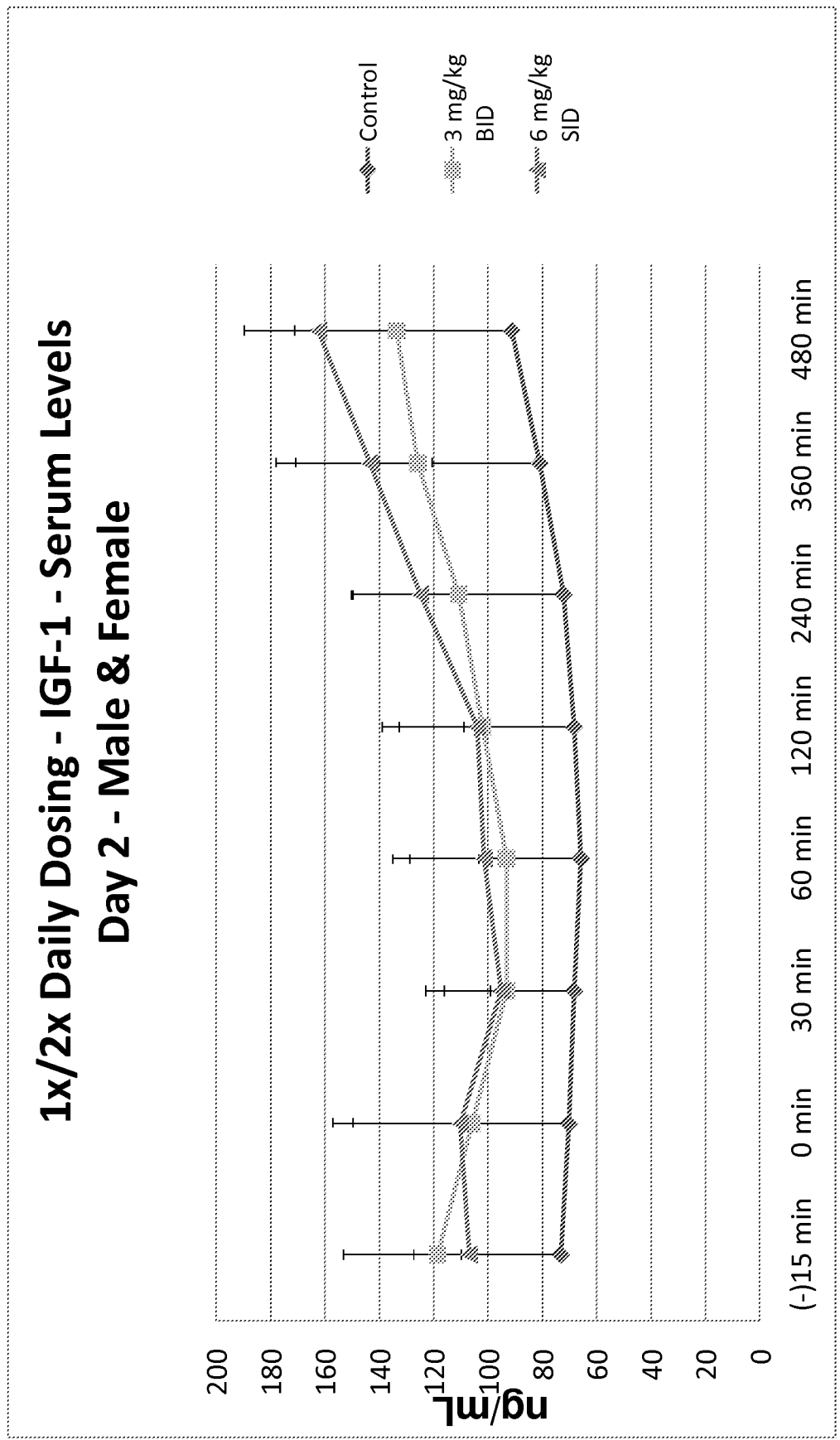
FIG. 12 is a line graph depicting measurements of insulin-like growth factor-1 concentration in the serum in male and female dogs treated with the first treatment regimen, the second treatment regimen, and the negative control on a second day of treatment.
Figure 13:
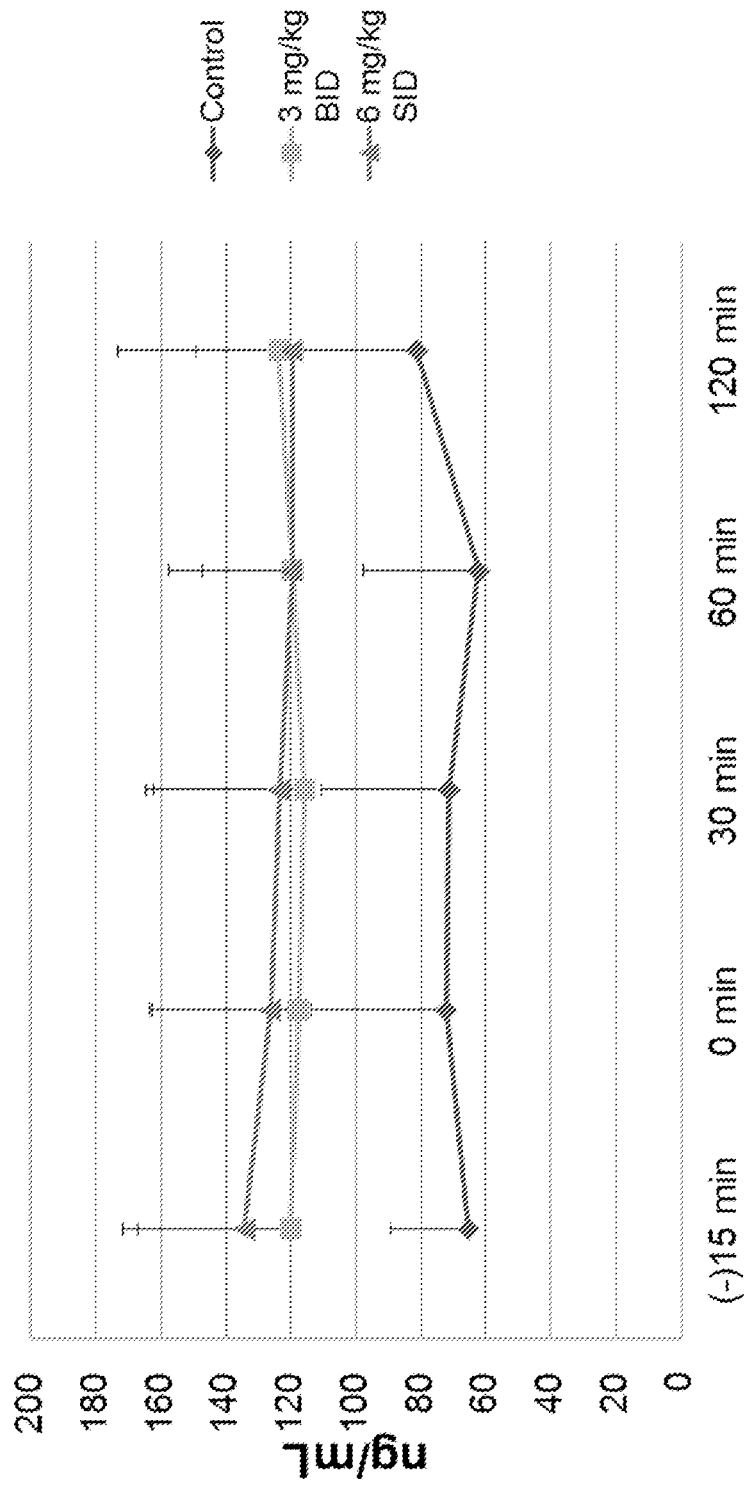
FIG. 13 is a line graph depicting measurements of insulin-like growth factor-1 concentration in the serum in male and female dogs treated with the first treatment regimen, the second treatment regimen, and the negative control on a fourth day of treatment.
Figure 14:
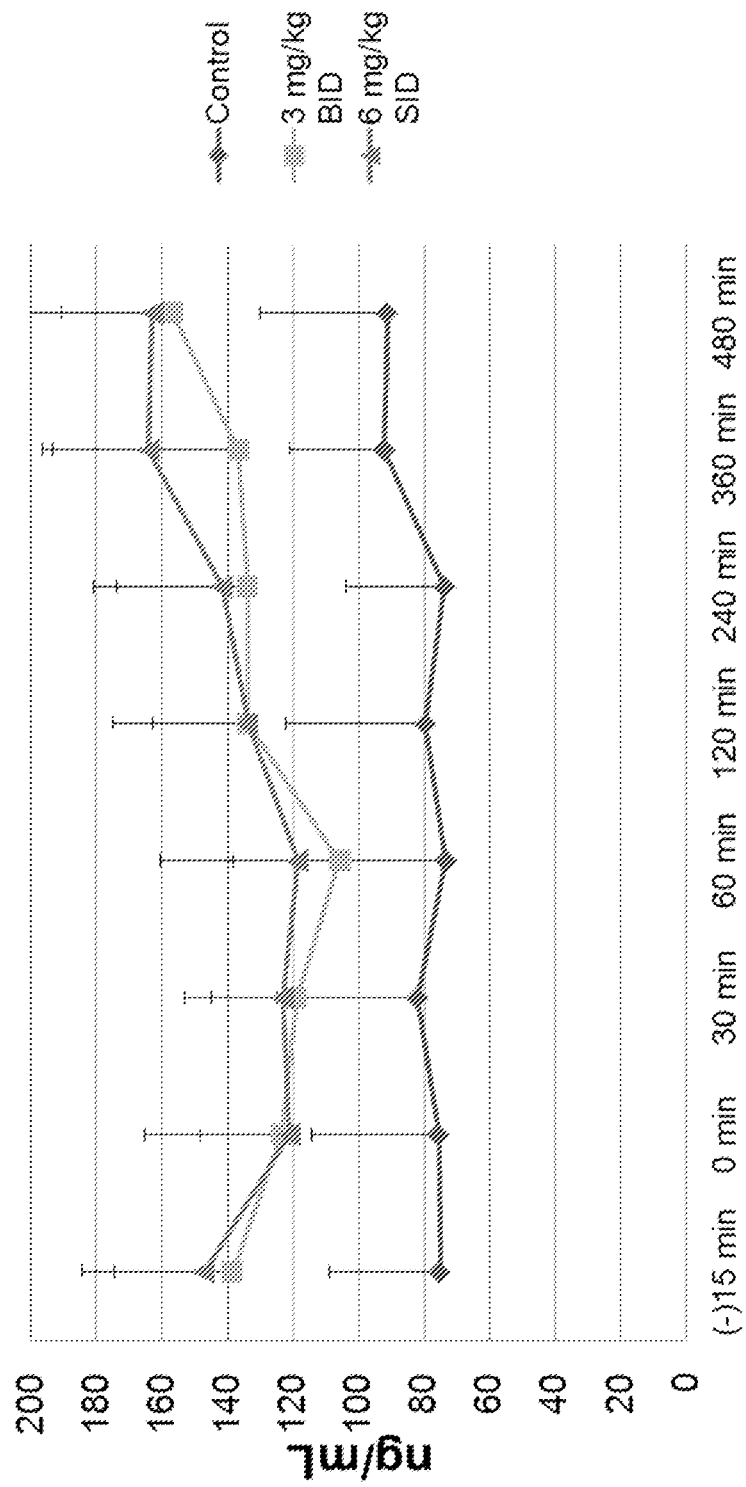
FIG. 14 is a line graph depicting measurements of insulin-like growth factor-1 concentration in the serum in male and female dogs treated with the first treatment regimen, the second treatment regimen, and the negative control on a seventh day of treatment.
Figure 15:
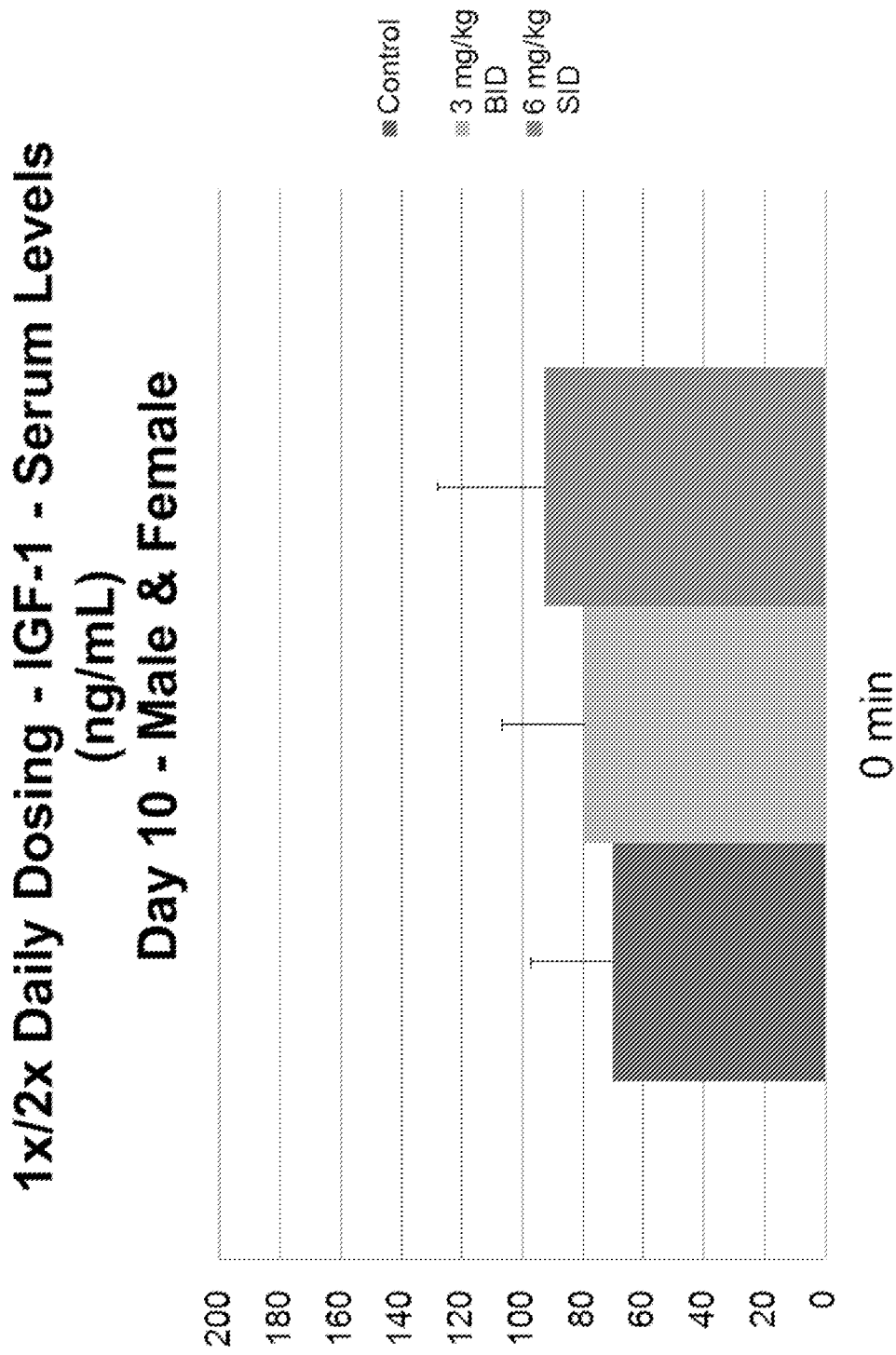
FIG. 15 is a bar graph depicting measurements of insulin-like growth factor-1 concentration in the serum in male and female dogs treated with the first treatment regimen, the second treatment regimen, and the negative control three days after completion of the treatment regimens.
Figure 16:
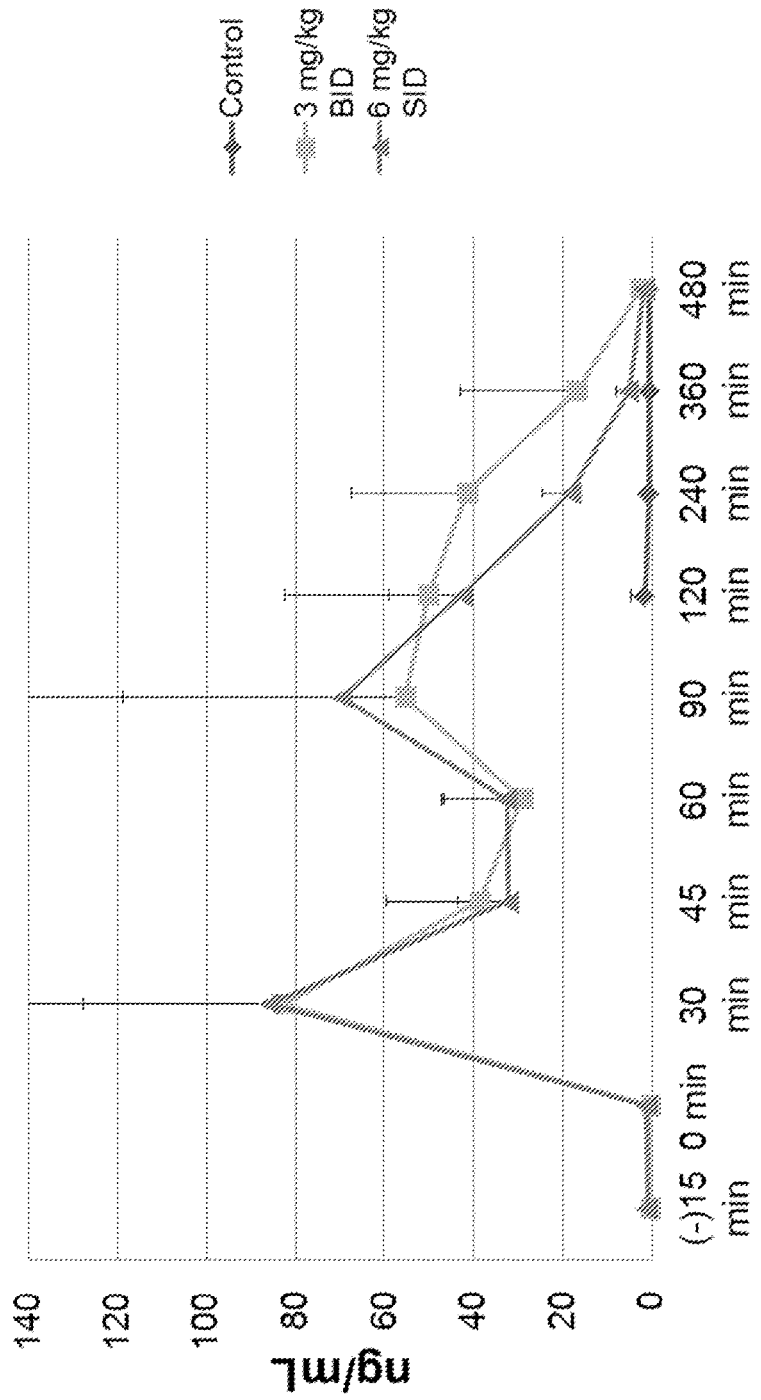
FIG. 16 is a line graph depicting measurements of growth hormone concentration in the serum in male and female dogs treated with the first treatment regimen, the second treatment regimen, and the negative control on a first day of treatment.
Figure 17:
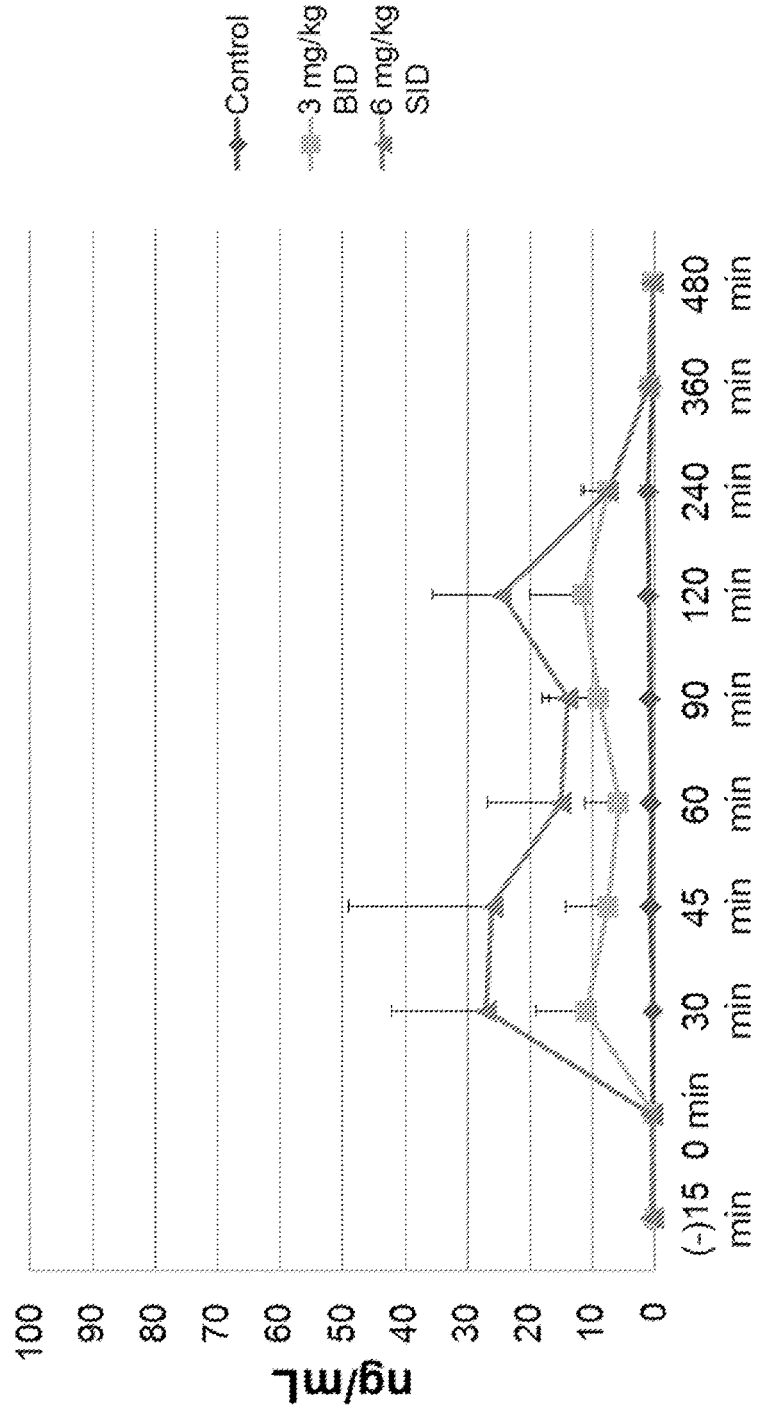
FIG. 17 is a line graph depicting measurements of growth hormone concentration in the serum in male and female dogs treated with the first treatment regimen, the second treatment regimen, and the negative control on a second day of treatment.
Figure 18:
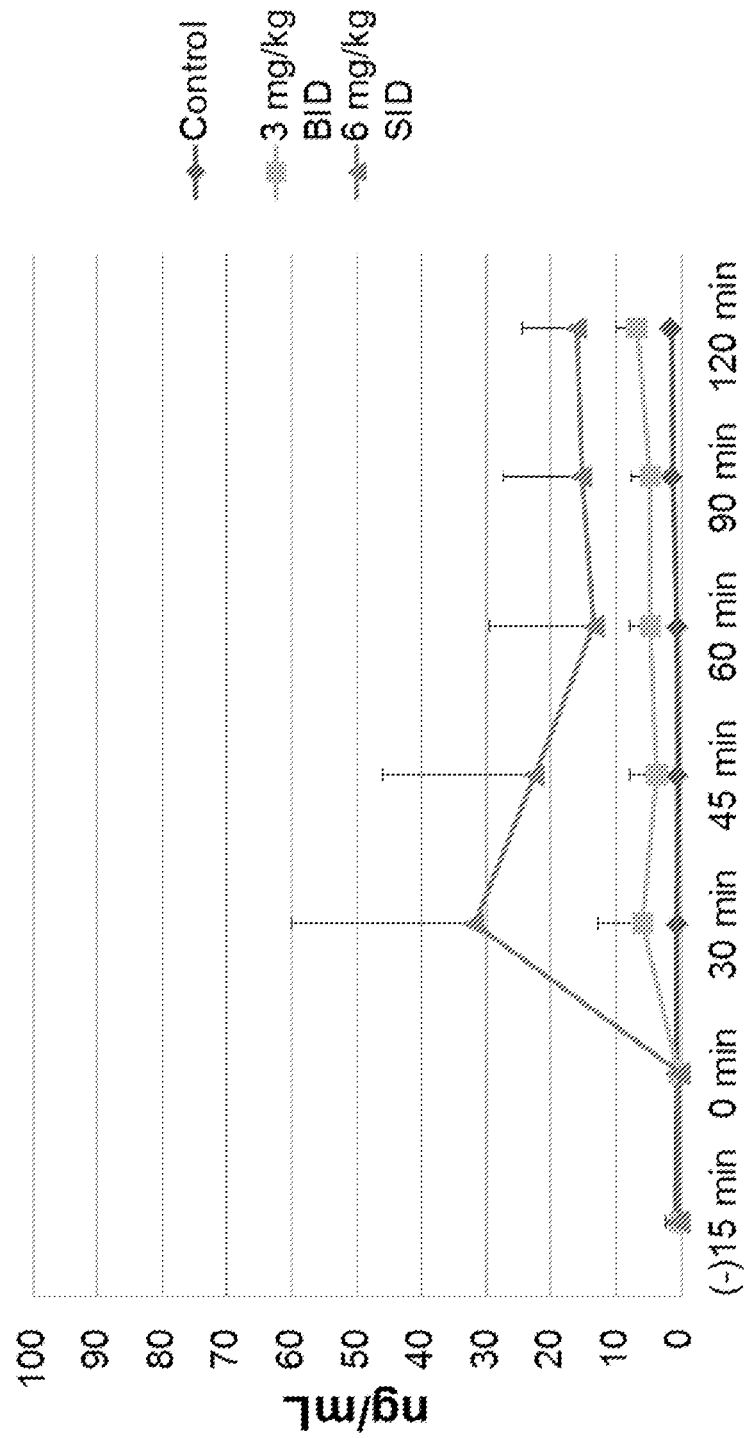
FIG. 18 is a line graph depicting measurements of growth hormone concentration in the serum in male and female dogs treated with the first treatment regimen, the second treatment regimen, and the negative control on a fourth day of treatment.
Figure 19:
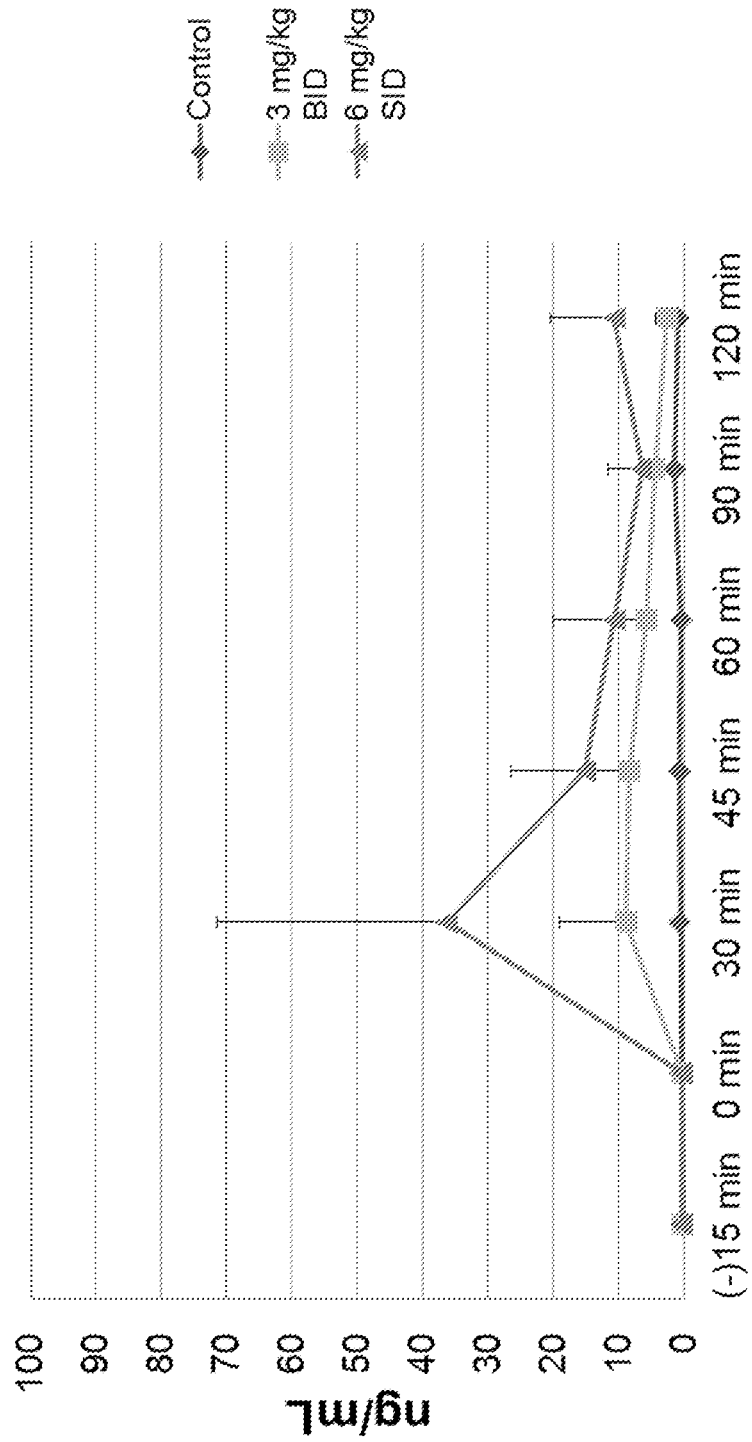
FIG. 19 is a line graph depicting measurements of growth hormone concentration in the serum in male and female dogs treated with the first treatment regimen, the second treatment regimen, and the negative control on a seventh day of treatment.

First, as shown in FIGS. 11-15, treatment with capromorelin induced IGF-1 levels within the serum of the dogs. Specifically, as shown in FIG. 11, approximately one to four hours after initially dosing the dogs with capromorelin, IGF-1 levels exhibited an increase in the serum, relative to the dogs receiving only deionized water. Moreover, as shown in FIGS. 12-14, on days 2, 4, and 7 of the treatment course, serum IGF-1 levels remained consistently higher in dogs receiving both doses of capromorelin. As shown in FIG. 15, three days after terminating treatment (Day 10), levels of serum IGF-1 in the dogs receiving capromorelin treatment were not significantly different than the levels of serum IGF-1 in the dogs receiving deionized water alone. In addition, the general elevation of IGF-1 during the treatment regimen was similarly observed dogs treated with the once-daily 6 mg/kg or the twice-daily 3 mg/kg dose of capromorelin.

Figure 20:
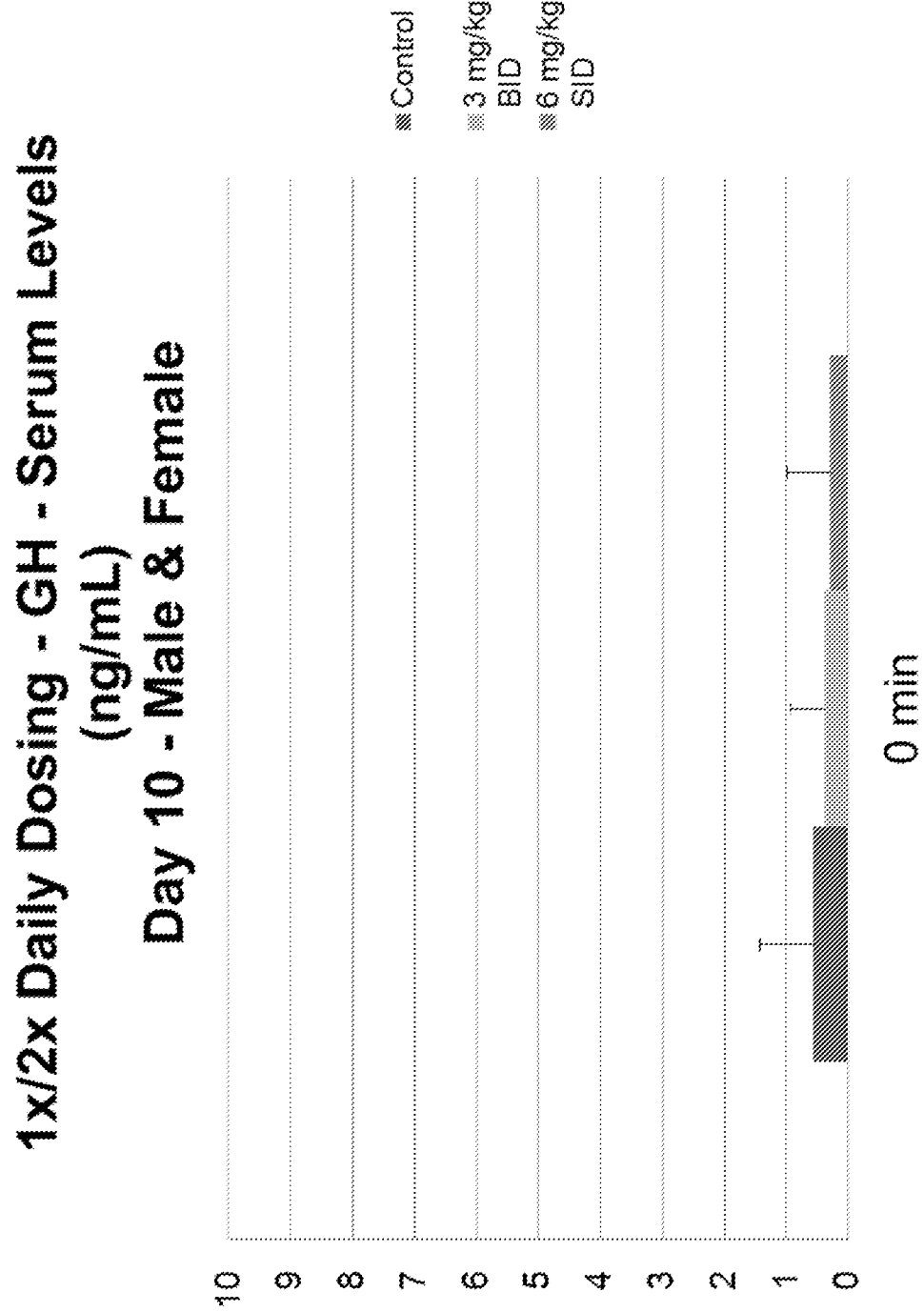
FIG. 20 is a bar graph depicting measurements of growth hormone concentration in the serum in male and female dogs treated with the first treatment regimen, the second treatment regimen, and the negative control three days after completion of the treatment regimens.
Figure 21:
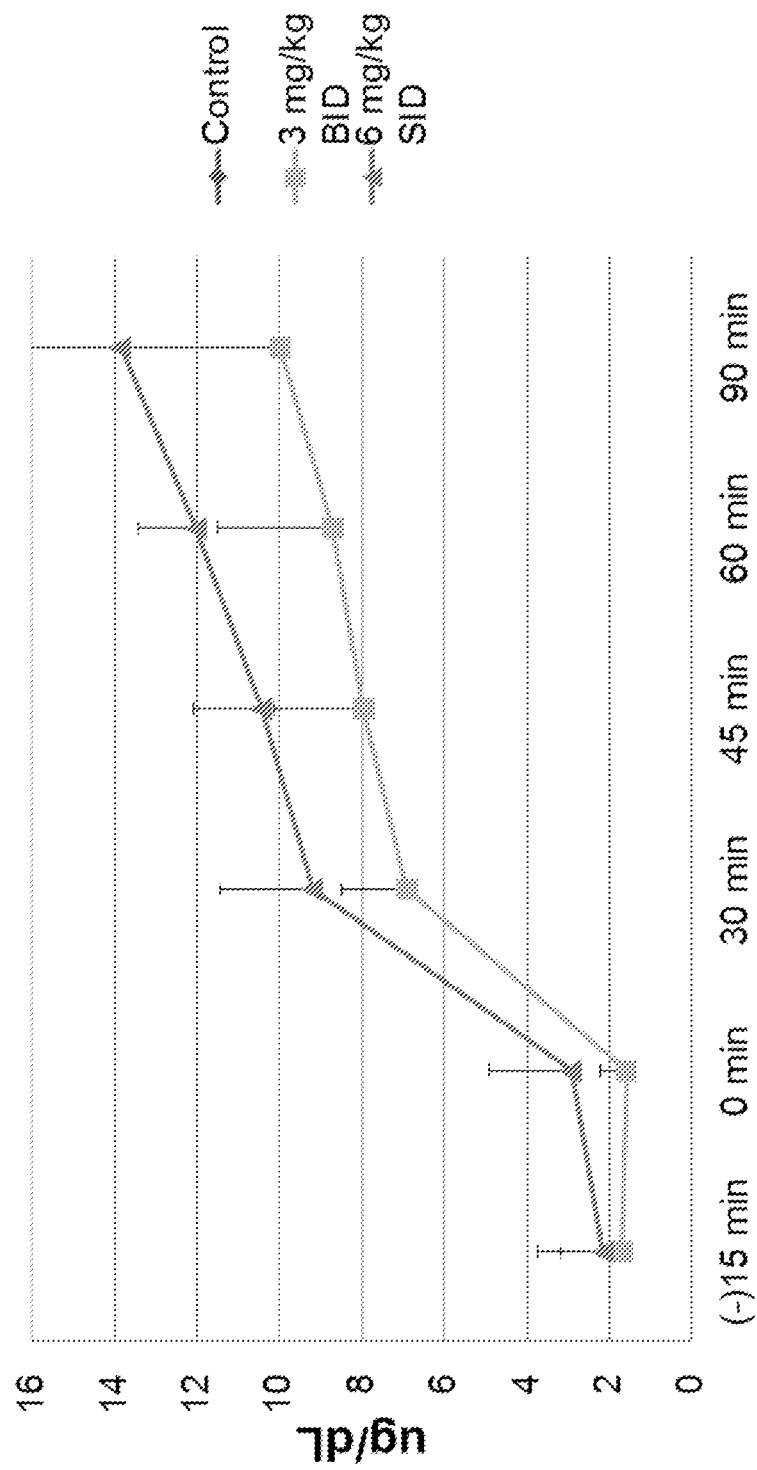
FIG. 21 is a line graph depicting measurements of cortisol concentration in the serum in male and female dogs treated with the first treatment regimen, the second treatment regimen, and the negative control on a first day of treatment.
Figure 22:
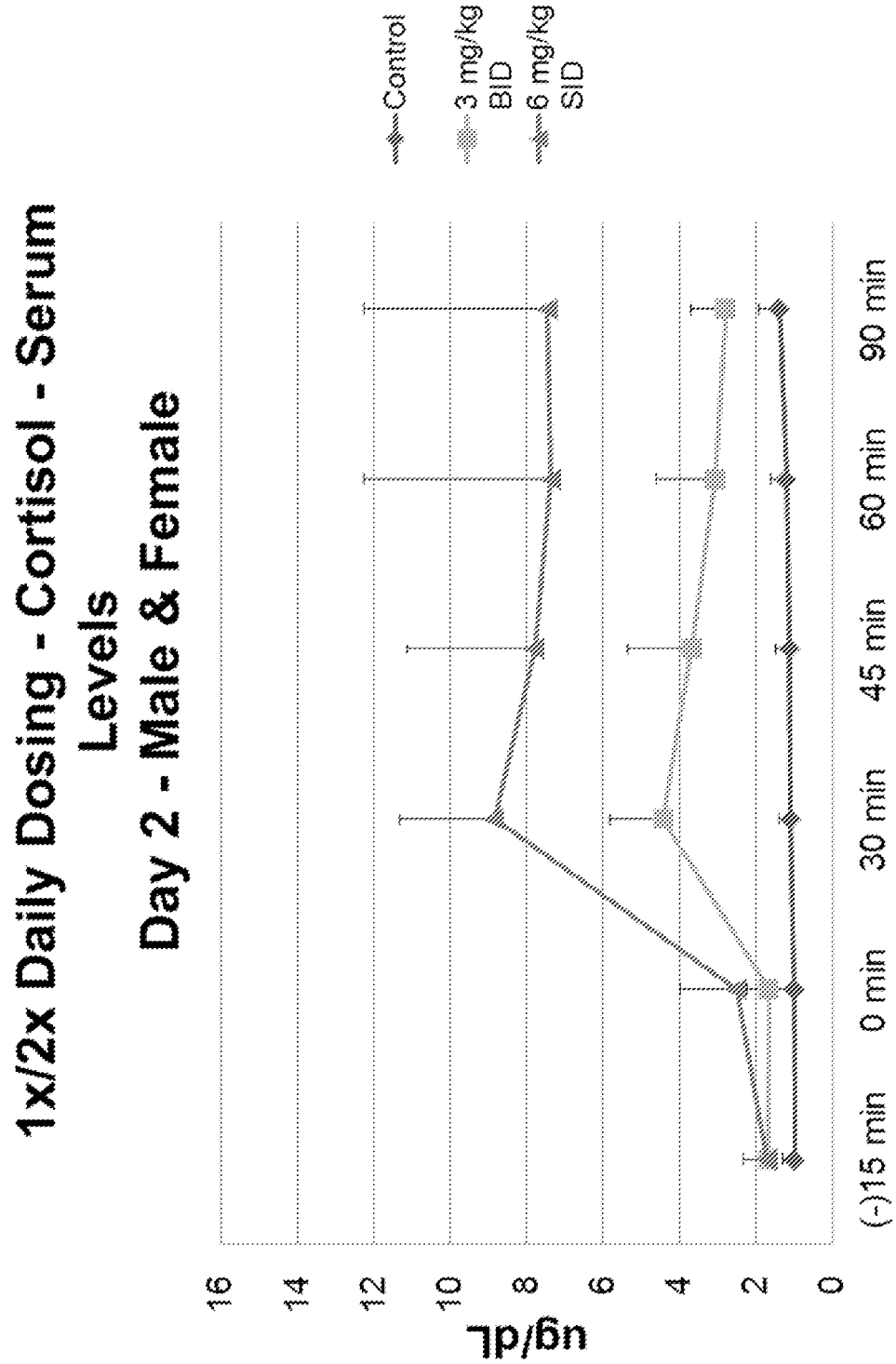
FIG. 22 is a line graph depicting measurements of cortisol concentration in the serum in male and female dogs treated with the first treatment regimen, the second treatment regimen, and the negative control on a second day of treatment.
Figure 23:
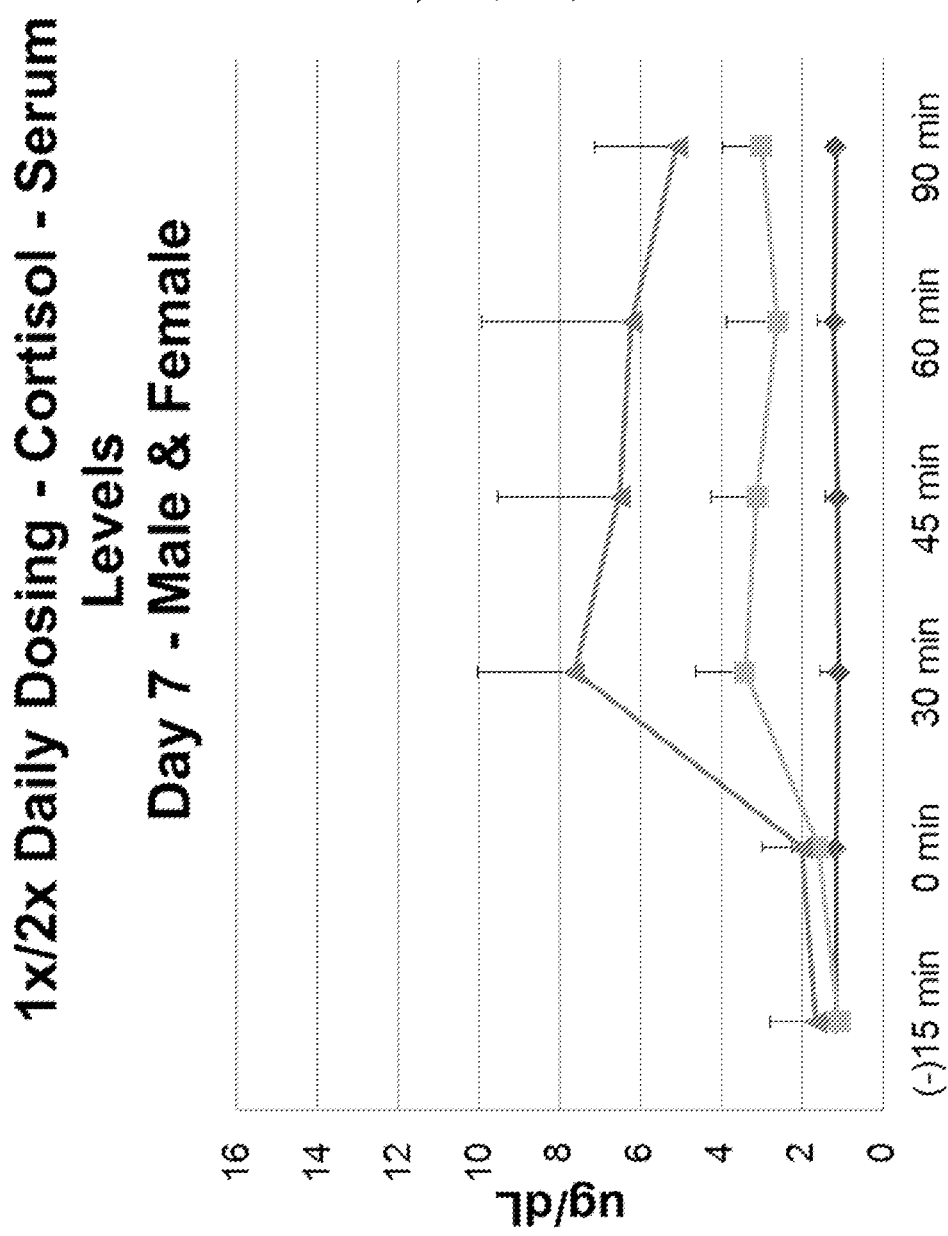
FIG. 23 is a line graph depicting measurements of cortisol concentration in the serum in male and female dogs treated with the first treatment regimen, the second treatment regimen, and the negative control on a seventh day of treatment.

Like serum IGF-1 levels, during the study, serum levels of GH appeared to be dependent upon capromorelin administration, as shown in FIGS. 16-20. Specifically, on days 1, 2, 4, and 7, GH levels increased approximately 0.5 h after the dogs received their capromorelin dosing. Prior to treatment, all dogs exhibited nearly undetectable levels of GH in the serum; however, after receiving either the once-daily 6 mg/kg or the twice-daily 3 mg/kg dose of capromorelin, dogs in Groups B and C exhibited a marked increase in GH levels in the serum that continued to be elevated relative to the dogs in Group A, which received only deionized water. As shown in FIG. 20, three days after terminating treatment (Day 10), levels of GH in the serum in the dogs receiving capromorelin treatment were not significantly different than the levels of GH in the serum in the dogs receiving deionized water alone. In addition, with the exception of Day 1 (FIG. 11), the levels of GH in the serum appear to correlated with the dose received by the dogs. Specifically, as shown in FIGS. 12-14, on days 2, 4, and 7, dogs receiving the once-daily 6 mg/kg dose exhibit greater concentrations of GH in the serum relative to dogs receiving the twice-daily 3 mg/kg dose.

Figure 24:
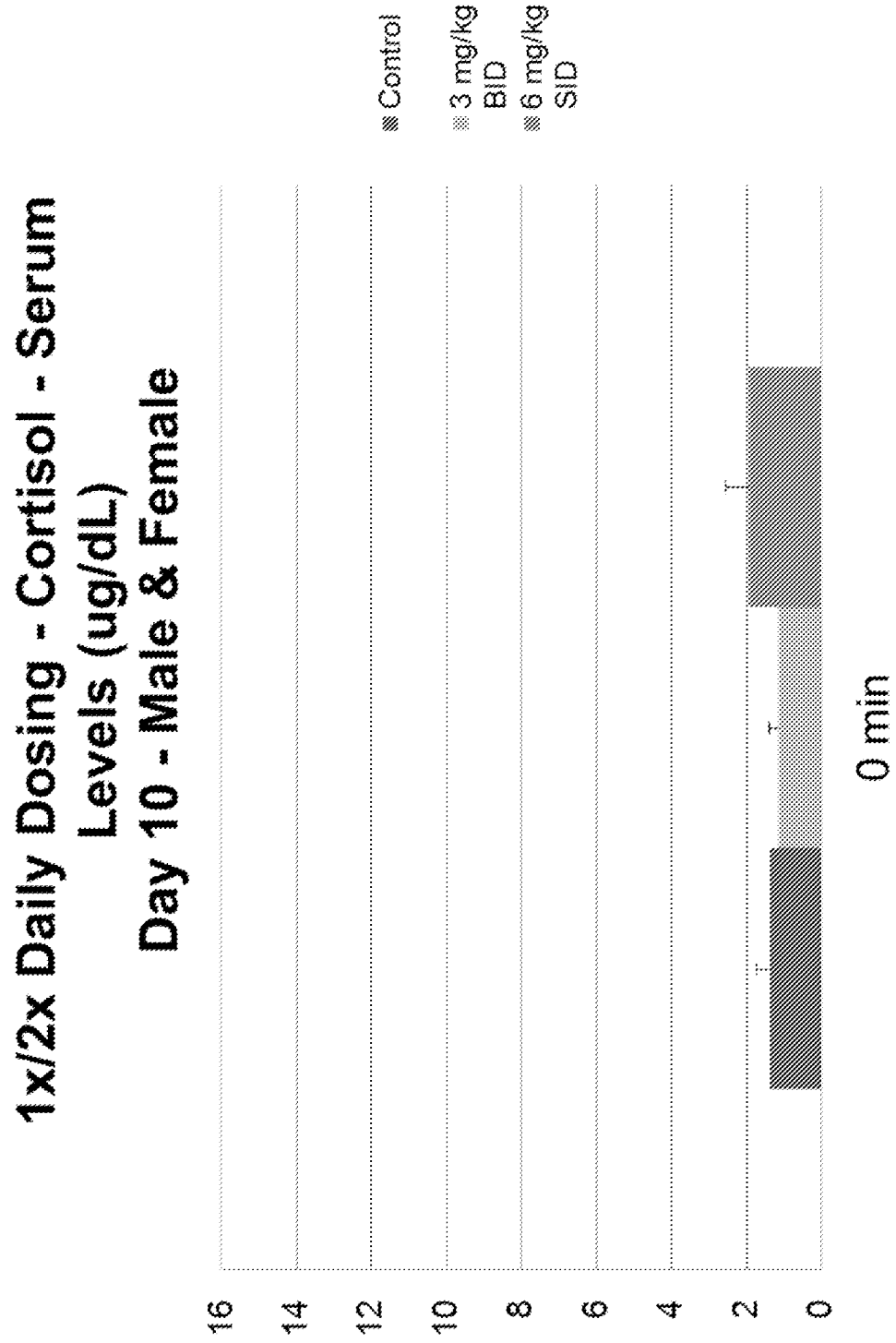
FIG. 24 is a bar graph depicting measurements of cortisol concentration in the serum in male and female dogs treated with the first treatment regimen, the second treatment regimen, and the negative control three days after completion of the treatment regimens.

Referring now to FIGS. 21-24, similar to GH, cortisol concentrations in the serum appear to correlate with administration of capromorelin. Specifically, on days 1, 2, and 7 (FIGS. 21-23, respectively), after approximately 0.5 h post treatment, cortisol concentrations in the serum of dogs treated with capromorelin increased relative to dogs receiving only deionized water. Moreover, the amount of increase in cortisol concentration in the serum correlates with the dosing regimen used. Particularly, dogs that received the once-daily 6 mg/kg dose exhibited greater concentrations of cortisol in the serum relative to dogs that received the twice-daily 3 mg/kg dose of capromorelin. Moreover, as shown in FIG. 24, three days after terminating treatment (Day 10), levels of cortisol in the serum in the dogs receiving capromorelin treatment were not significantly different than the levels of cortisol in the serum in the dogs receiving deionized water alone.

Overall, both dosing regimens produced discernible impacts on the dogs of Groups B and C, relative to the negative control dogs of Group A. Moreover, no toxicological responses were noted. Pharmacological effects were noted, including increased body weight and food consumption, as well as increased levels of serum GH, IGF-1, cortisol, and capromorelin. In general, the increases in serum concentrations of GH, IGF-1, and cortisol were more pronounced in animals receiving the once-daily 6 mg/kg dosing regimen. Moreover, although both dosing regimens induced GH, IGF-1, and cortisol, the twice-daily 3 mg/kg dosing regimen induced sufficient amounts of IGF-1 to promote lean muscle growth within the dogs, but also did not induce increases in GH and cortisol concentrations to the same extent as the once-daily 6 mg/kg dosing regimen. As a result of the lower concentrations of GH and cortisol, the dogs are less likely experience an increase in adipose deposition, meaning that the increase in body weight is more likely to be lean muscle.

EXAMPLE 2

Assessing the Pharmacokinetic Profile of Capromorelin and Dog Acceptability/Palatability After selecting the 3 mg/kg dosing regimen, a controlled, eight-hour study was performed to assess the pharmacokinetic profile and acceptability/palatability of different capromorelin formulations. Briefly, twelve Beagle dogs (six males and six females) were randomized into three groups, with four dogs per group (two males and two females). Each of the dogs received a test formulation of capromorelin via a single oral gavage or intravenous ("IV") administration. This testing included two iterations with the same three groups of dogs with a seven-day washout period between iterations. Serum was collected prior to administration (time 0) and 0.5 h and 1, 2, 4, and 8 hours after capromorelin administration. Serum was tested for capromorelin and IGF-1 concentrations and dogs were observed for clinical changes.

In addition, the same dogs were used to assess acceptability/palatability. The acceptability/palatability testing was conducted the first two days after the pharmacokinetic analysis. Briefly, at the same time on Days 1 and 2 after the pharmacokinetic analysis, dogs were orally dosed in the corner of the mouth with the capromorelin formulations used in the pharmacokinetic analysis. The dogs' responses to the different formulations were recorded.

Figure 25:
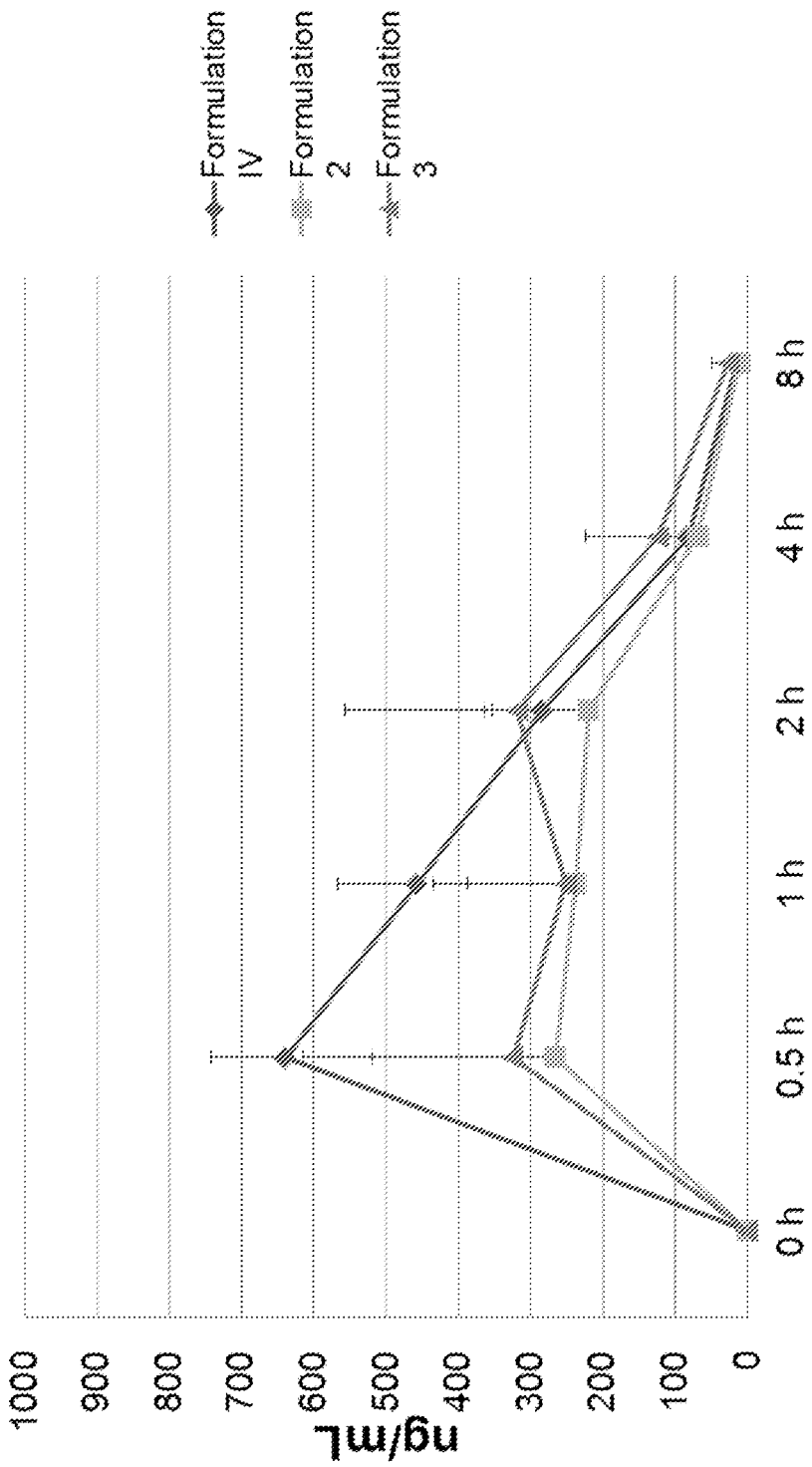
FIG. 25 is a line graph depicting the results of experiments testing the first capromorelin treatment regimen in combination with a positive control (i.e., intravenous administration) and two flavoring formulations as measured by capromorelin concentration in the serum of male and female beagles over eight hours.
Figure 26:
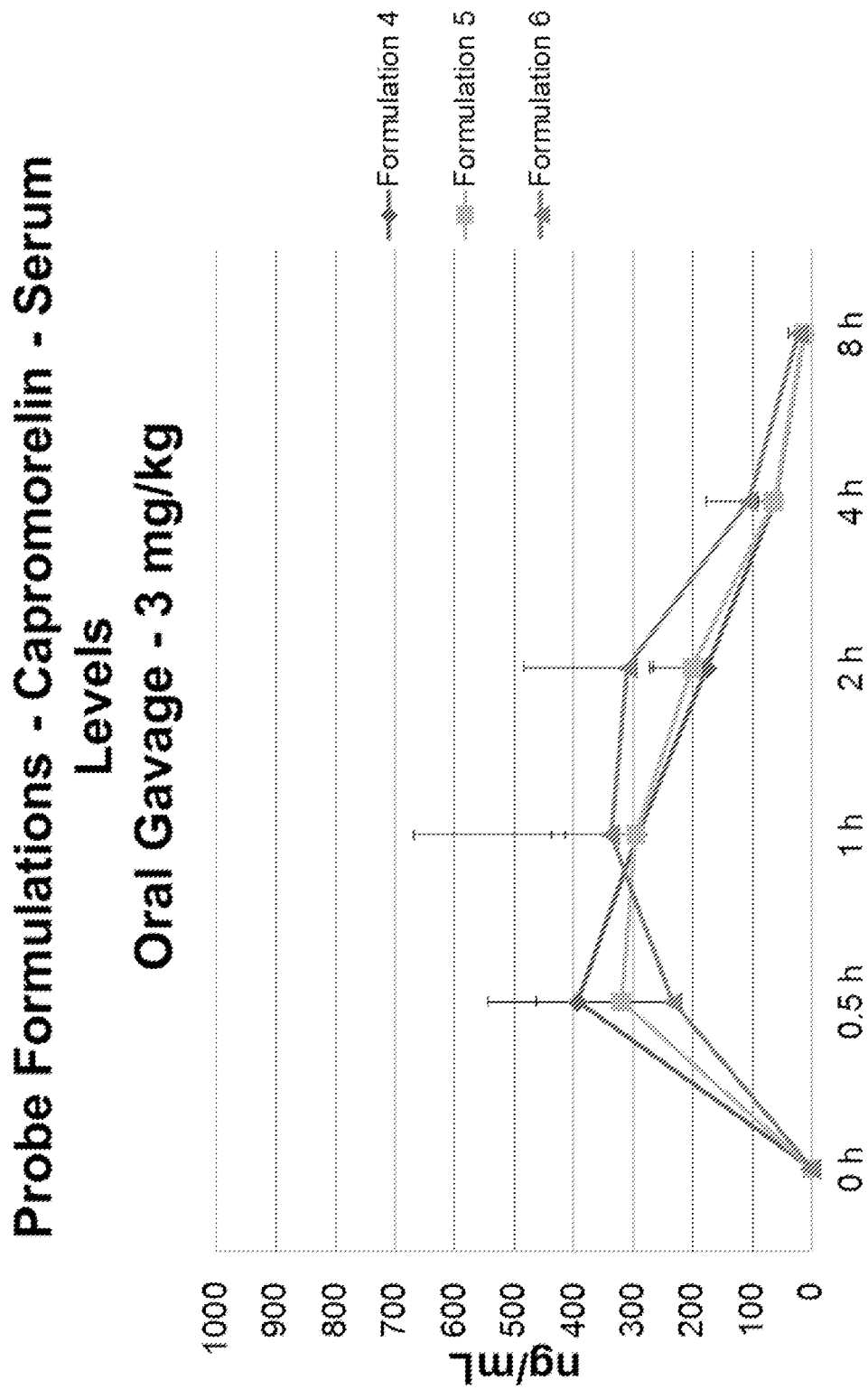
FIG. 26 is a line graph depicting the results of experiments testing the first capromorelin treatment regimen in combination with an additional three flavoring formulations as measured by capromorelin concentration in the serum of male and female beagles over eight hours.
Figure 27:
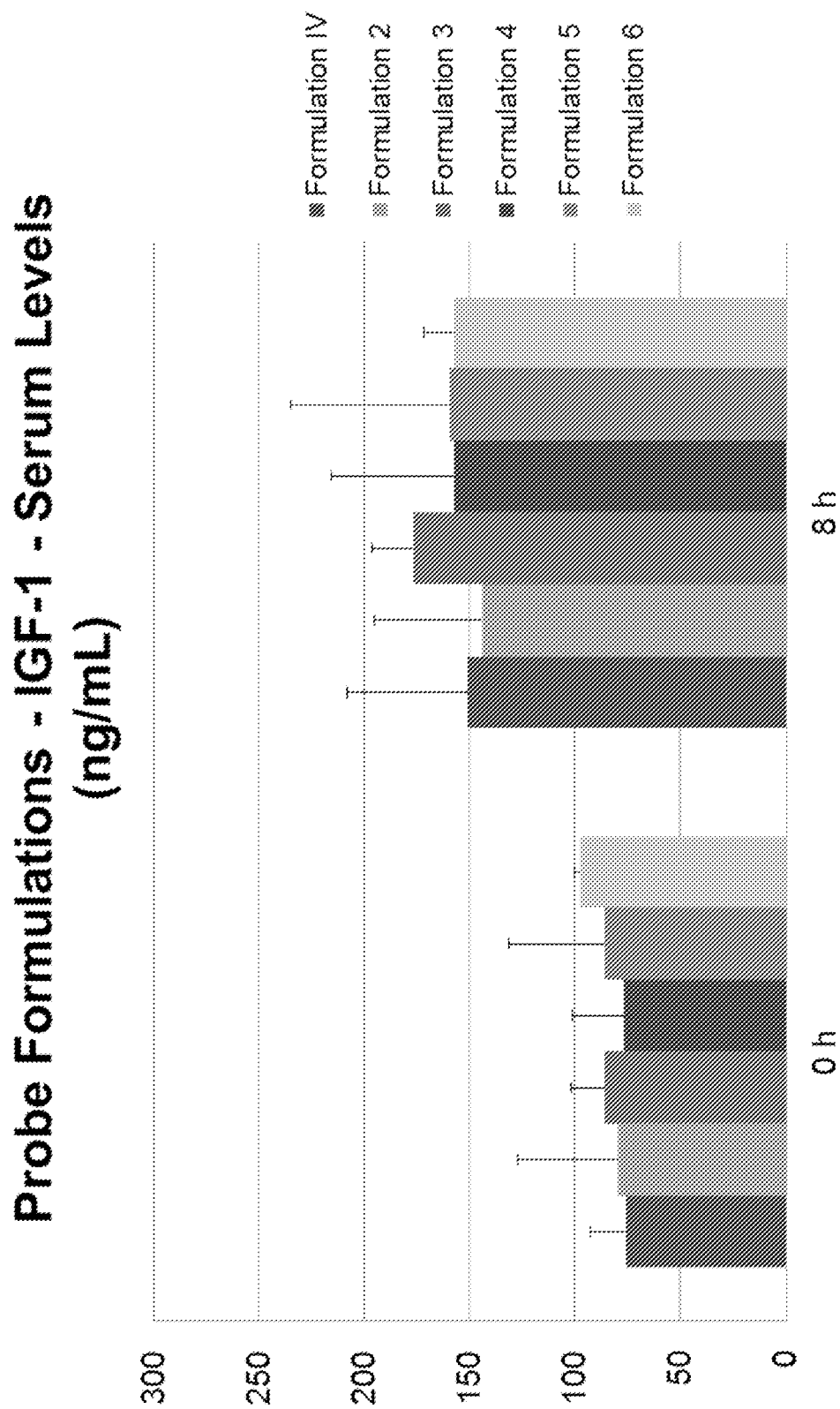
FIG. 27 is a bar graph depicting serum concentrations of insulin-like growth factor-1 in the male and female beagles from the experiments with results depicted in FIGS. 25 and 26.

As shown in FIGS. 25-27, all formulations tested in the pharmacokinetic analysis produced detectable levels of capromorelin and increased levels of IGF-1 in the serum of the dogs over an eight-hour period. Specifically, in the first iteration (FIG. 25), which includes the IV formulation and test formulations 2 and 3, all three formulations produced an increase in capromorelin concentration in the serum within 0.5 h of administration, which dropped over the course of the eight-hour study. Similarly, in the second iteration, which includes formulations 4, 5, and 6, all three formulations produced an increased capromorelin serum concentration, with peak concentrations occurring between 0.5 h and 2 h post administration. As shown in FIG. 27, IGF-1 levels at eight hours post administration were also increased by all formulations administered to the dogs. In general, no adverse clinical side effects were detected in any of the dogs during the trial, with the exception of excessive salivation in the dogs receiving the IV formulation.

Although no data is shown for the acceptability/palatability analysis, formulation administration in the corner of the mouth via syringe was accepted by the dogs, but not well accepted. It did not appear that the dogs liked the taste of the formulations, with formulation 5 being the most accepted and formulation 1 being the least accepted.

Overall, each of the tested formulations produced adequate serum concentrations of capromorelin. Moreover, the administration of all of the formulations produced increased levels of IGF-1 in the serum. However, formulation 4 will be used in future experimentation because it produced the most consistent capromorelin serum profile. As discussed in greater detail below, further refinement of formulation four will be needed in order to improve the palatability, which can improve the ease with which owners of the companion animals can administer the composition.

Specifically, formulation 4 includes the following constituents at the following concentrations, as measured in weight of the constituent per total volume of the solution:

| Ingredient | % weight per volume |
| --- | --- |
| Capromorelin | 2.10 |
| Methyl 4-Hydroxybenzoate Salt | 0.14 |
| Propyl 4-Hydroxybenzoate Salt | 0.02 |
| Ethyl Vanillin | 0.32 |
| Sucralose | 1.27 |
| Purified Water | 36.00 |
| Propylene Glycol | q.s. |

EXAMPLE 3

Refining Dog Acceptability/Palatability of the Capromorelin Composition

After selecting formulation 4, a controlled, eight-hour study was performed to refine formulation 4 to improve acceptability/palatability of this capromorelin formulation. Particularly, formulation 4 (as shown above) was mixed with a plurality of different sweeteners, flavors, and/or masking agents to improve dog acceptability/palatability of this formulation. Briefly, twenty Beagle dogs (ten males and ten females) were randomized into five groups, with four dogs per group (two males and two females). Each of the dogs received a test formulation of capromorelin via a single oral dose in the corner of the mouth. This testing included two iterations with the same groups of dogs on consecutive days. However, on the second day, only four groups were necessary because a total of nine formulations were tested (i.e., five formulations tested on the first day and four formulations tested on the second day).

During testing, nine new formulations of formulation 4 were tested at the 3 mg/kg dose. Moreover, during administration of the test formulations, dogs were observed to determine whether the test formulations were "well-accepted" by assessing a lack of clinical observations and an apparent acceptance or willingness to orally receive the formulations. Moreover, during testing, if at least three of the four dogs in a test group displayed a "well-accepted" response to a test formulation (as determined by testing personal), serum samples were collected a times 0, 0.5 h, 1 h, 2 h, 4 h, and 8 h post administration. Serum samples were tested for capromorelin and IGF-1 concentrations.

Figure 28:
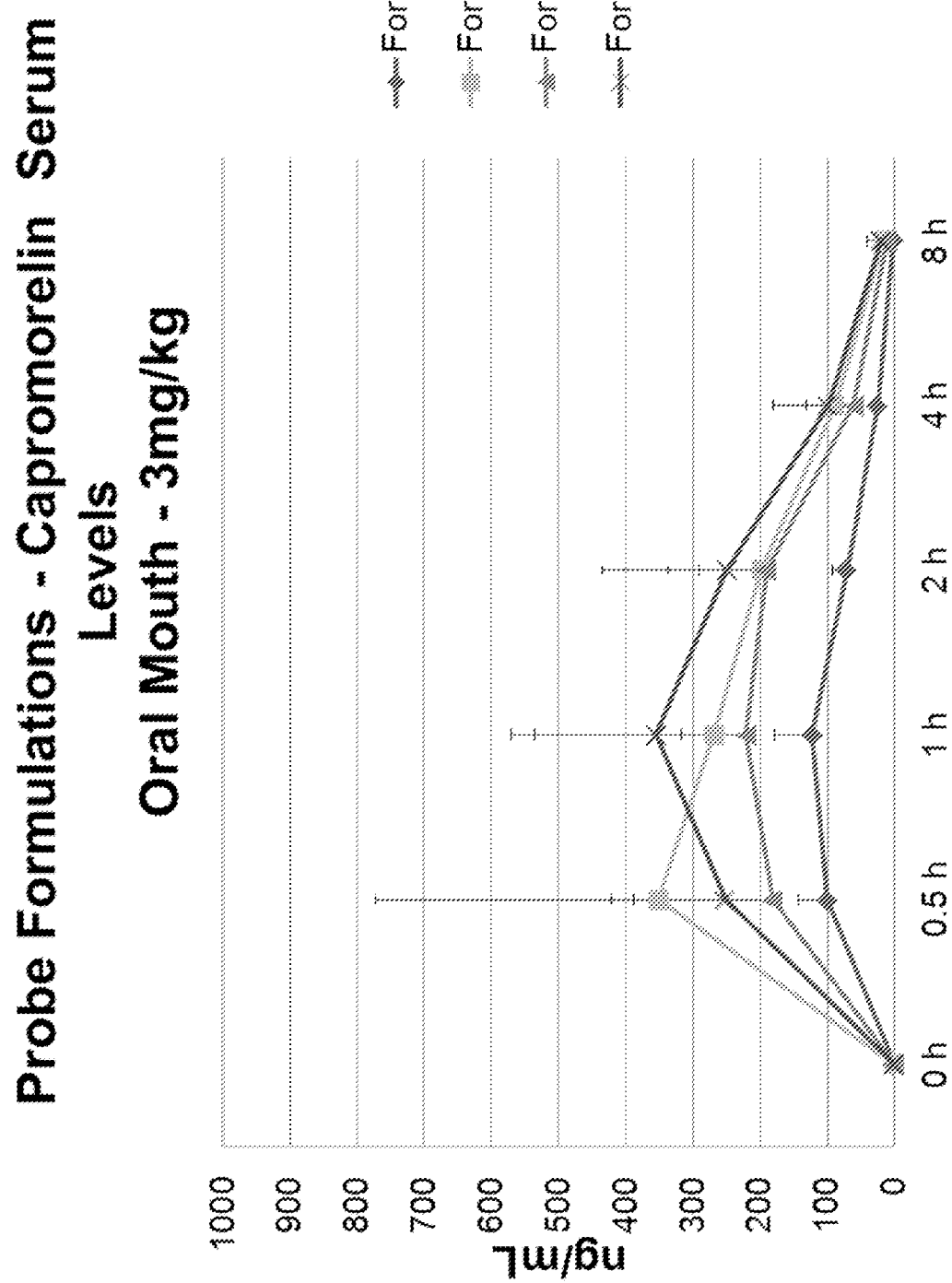
FIG. 28 is a line graph depicting the results of experiments testing the first capromorelin treatment regimen in combination with four flavoring formulations as measured by capromorelin concentration in the serum of male and female beagles over eight hours.
Figure 29:
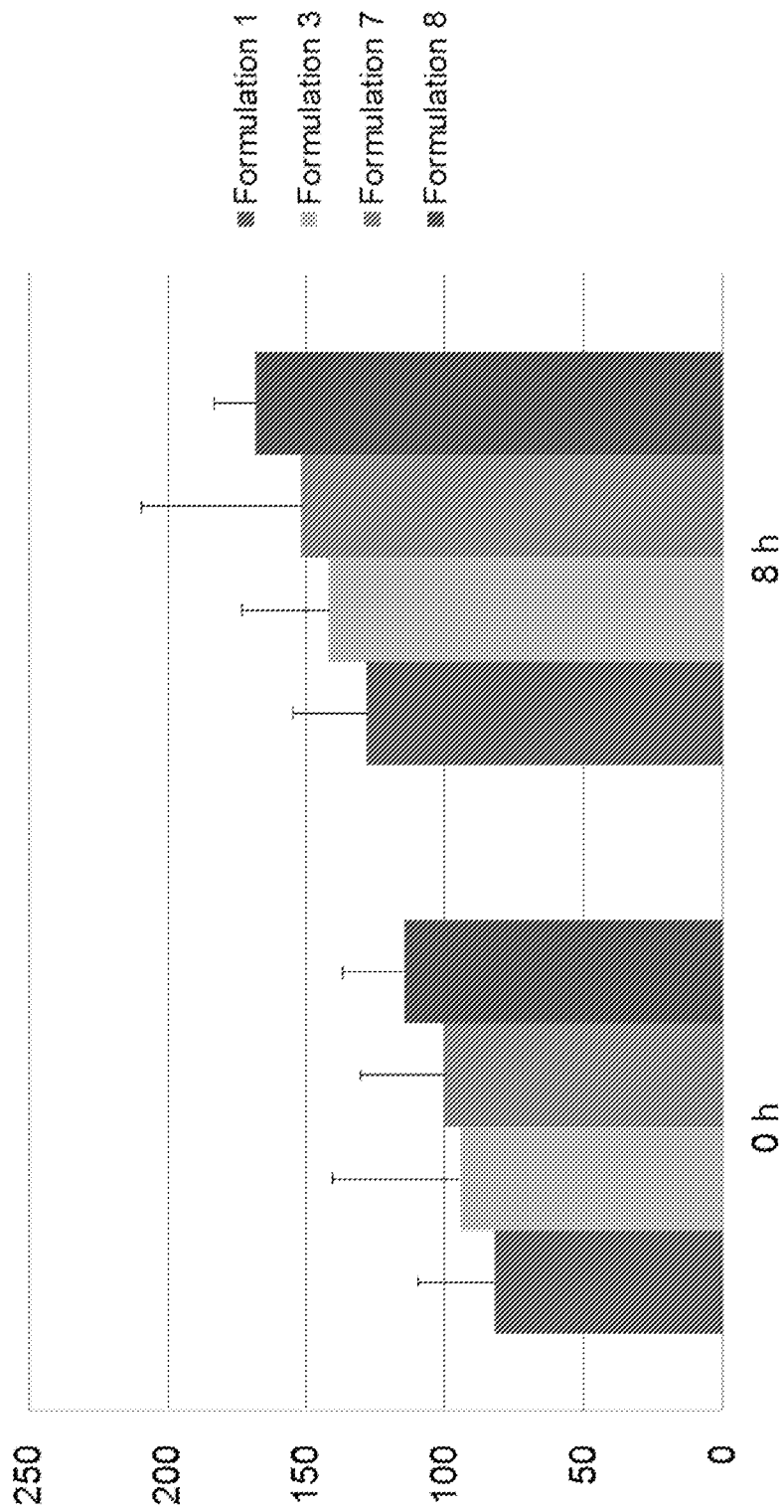
FIG. 29 is a bar graph depicting serum concentrations of insulin-like growth factor-1 in the male and female beagles from the experiments with results depicted in FIG. 28.

Data reflecting "well-accepted" formulations is shown in FIGS. 28 and 29. Specifically, of the nine test formulations, formulations 1, 3, 7, and 8 were determined to be "well-accepted" by the dogs. In addition to being "well-accepted," each of these formulations resulted in detectable levels of capromorelin in the serum and increases in IGF-1 at eight hours after administration. It was determined that formulation 8 produced the most consistent capromorelin serum profile, however, the present invention is not limited to the embodiment of formulation 8.

Specifically, the "well-accepted" formulations include the following constituents at the following concentrations, as measured in weight of the constituent per total volume of the solution:

| Formulation 1 | |
| --- | --- |
| Ingredient | % weight per volume |
| Capromorelin | 2.10 |
| Citric Acid | 0.50 |
| Sodium Citrate | 0.50 |
| Sodium Chloride | 1.00 |
| Methyl 4-Hydroxybenzoate Salt | 0.11 |
| Propyl 4-Hydroxybenzoate Salt | 0.01 |
| Sucralose | 0.50 |
| MagnaSweet | 0.50 |
| Natural Vanilla Flavor | 0.40 |
| Di-Pac ® Compressible sugar (97% Sucrose and 3% Maltodextrin) | 30.00 |
| Propylene Glycol | 25.00 |
| Vegetable Glycerin | 17.00 |
| Purified Water | q.s. |

| Formulation 3 | |
| --- | --- |
| Ingredient | % weight per volume |
| Capromorelin | 2.10 |
| Citric Acid | 0.50 |
| Sodium Citrate | 0.50 |
| Sodium Chloride | 1.00 |
| Methyl 4-Hydroxybenzoate Salt | 0.11 |
| Propyl 4-Hydroxybenzoate Salt | 0.01 |
| Sucralose | 0.50 |
| MagnaSweet | 0.50 |
| Macorogolglycerol Hydroxysterarate | 0.16 |
| Natural Vanilla Flavor | 0.40 |
| Di-Pac ® Compressible sugar (97% Sucrose and 3% Maltodextrin) | 30.00 |
| Propylene Glycol | 25.00 |
| Vegetable Glycerin | 17.00 |
| Purified Water | q.s. |

| Formulation 7 | |
| --- | --- |
| Ingredient | % weight per volume |
| Capromorelin | 2.10 |
| Citric Acid | 0.50 |
| Sodium Citrate | 0.50 |
| Sodium Chloride | 1.00 |
| Methyl 4-Hydroxybenzoate Salt | 0.11 |
| Propyl 4-Hydroxybenzoate Salt | 0.01 |
| Neotame | 0.15 |
| MagnaSweet | 0.35 |
| Natural Vanilla Flavor | 0.40 |
| Di-Pac ® Compressible sugar (97% Sucrose and 3% Maltodextrin) | 30.00 |
| Propylene Glycol | 25.00 |
| Vegetable Glycerin | 17.00 |
| Purified Water | q.s. |

| Formulation 8 | |
| --- | --- |
| Ingredient | % weight per volume |
| Capromorelin | 2.10 |
| Citric Acid | 0.50 |
| Sodium Citrate | 0.50 |
| Sodium Chloride | 1.00 |
| Methyl 4-Hydroxybenzoate Salt | 0.11 |
| Propyl 4-Hydroxybenzoate Salt | 0.01 |
| Thaumatin | 0.18 |
| *Stevia* Extract Rebaudioside A | 0.13 |
| MagnaSweet | 0.30 |
| Natural Vanilla Flavor | 0.40 |
| Di-Pac ® Compressible sugar (97% Sucrose and 3% Maltodextrin) | 30.00 |
| Propylene Glycol | 25.00 |
| Vegetable Glycerin | 17.00 |
| Purified Water | q.s. |

EXAMPLE 4

Refining the Dosing Regimen of the Inappetance-Controlling Compound Containing Capromorelin Although the twice-daily 3 mg/kg dosing regimen was previously selected for further formulation analysis, an additional analysis of the dosing regimen was conducted to refine the concentrations and numbers of daily administrations of the capromorelin composition. Specifically, an analysis was conducted to determine if a less frequent dosing regimen of the capromorelin composition was a viable alternative to the twice-daily 3 mg/kg dosing regimen.

A controlled, seven-day study was performed to assess the impact of different capromorelin-dosing regimens on the production of IGF-1, GH, and cortisol. The different capromorelin-dosing regimens were also assessed for the impact on food intake and changes in body mass.

Twenty-four adult non-naïve Beagle dogs (twelve males and twelve females) were divided into one of three treatment groups, with one negative control group and two active treatment groups. Each of the three treatment groups included three males and three females. The first group received a placebo formulation (i.e., deionized water) twice per day, via oral gavage. The second group received a once-daily dose of the capromorelin composition at a concentration of 3 mg/kg, via oral gavage. The third group received a twice-daily dose of the capromorelin composition at a concentration of 3 mg/kg, via oral gavage.

During the ten day study period, on an at least once-daily basis, each of the dogs was monitored for clinical observations, mortality, moribundity, body mass, acceptability/palatability, and food consumption. Serum samples were taken to measure capromorelin concentration, GH concentration, IGF-1 concentration, and cortisol concentration. Serum samples were taken on days 1, 2, 4, and 7 at −15 minutes (pre-dose), immediately prior to dosing (0 minutes) and 30, 45, 60, 90, 120, 240, 360, and/or 480 minutes post dosing. Additional serum samples were taken at 8 AM on Day 10 of the study to assess long-term impact of the active treatments.

Figure 30:
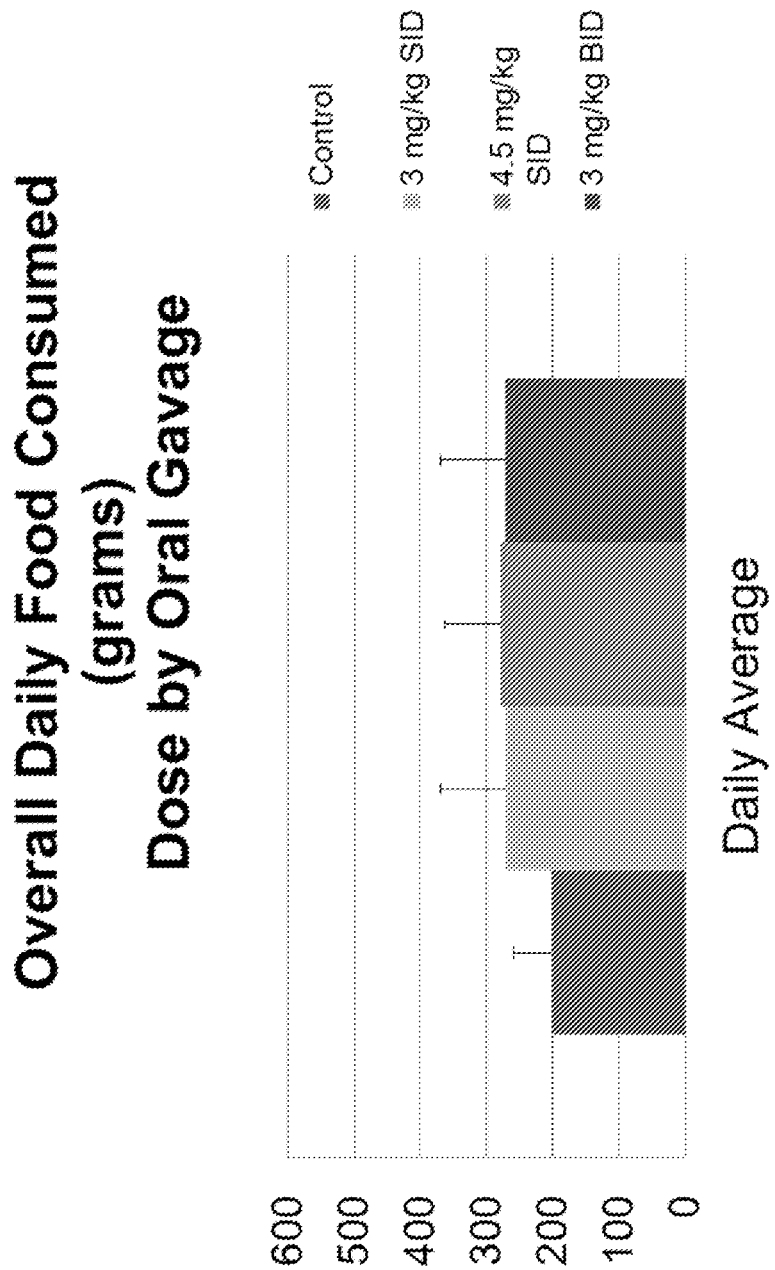
FIG. 30 is a bar graph depicting the overall food consumed by beagles in response to receiving different concentrations and treatment regimens of a capromorelin composition.
Figure 31:
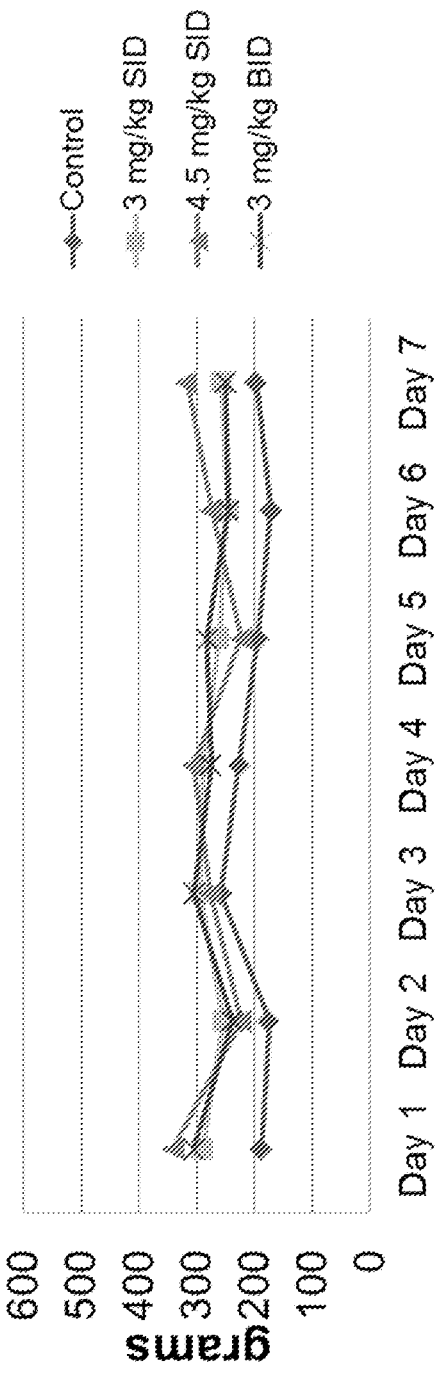
FIG. 31 is a line graph depicting the daily average food consumption by beagles in response to receiving different concentrations and treatment regimens of a capromorelin composition.
Figure 32:
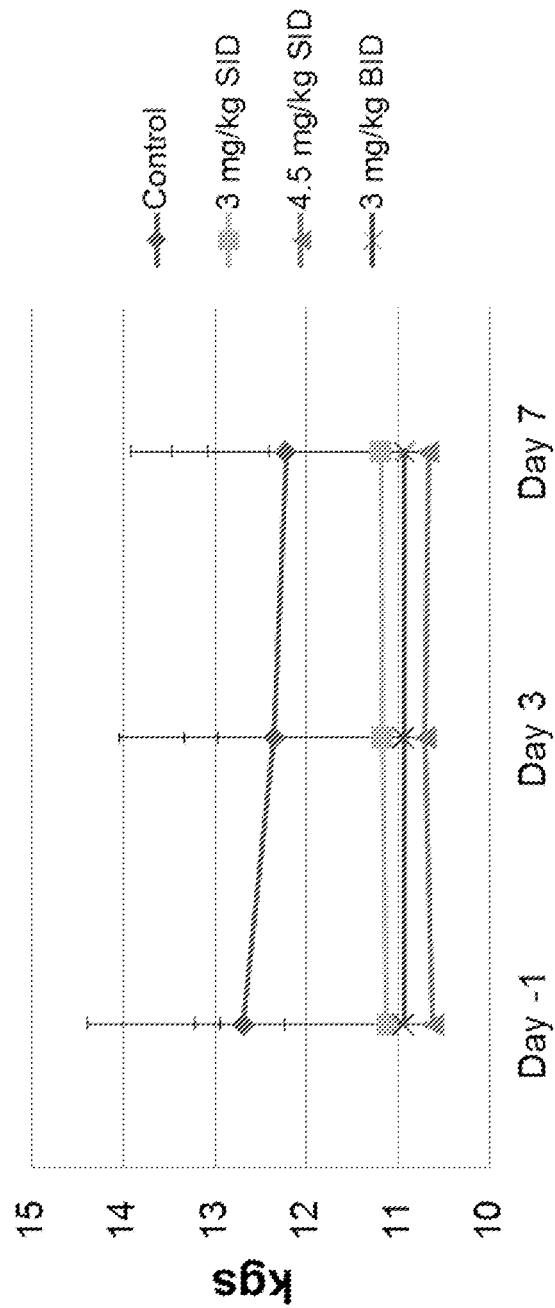
FIG. 32 is a line graph depicting the average body weight of beagles that have received different concentrations and treatment regimens of a capromorelin composition.

As indicated in FIGS. 30-32, dogs in the active treatment groups (i.e., the second and third treatment groups) consumed greater amounts of food and did not lose weight during the experiment, compared to dogs in the control group (i.e., the first group). Specifically, as shown in FIGS. 30 and 31, dogs receiving the active treatment, regardless of dose, consumed more food than did dogs in the negative control group. For example, dogs receiving the once-daily and the twice-daily 3 mg/kg dose of capromorelin consumed an average of approximately 34% more food consumed daily, relative to the negative control. Correspondingly, as shown in FIG. 32, the dogs receiving the active treatments did not experience the same weight loss exhibited by the dogs in the negative treatment group. Although the dogs in the active treatment groups did not experience significant weight gain, over the course of the experiment, the dogs receiving only deionized water exhibited an average weight loss of 3.73% body weight. Conversely, the dogs receiving the once-daily administration of capromorelin did not experience weight loss or did not experience as great a weight loss as the negative control.

Figure 33:
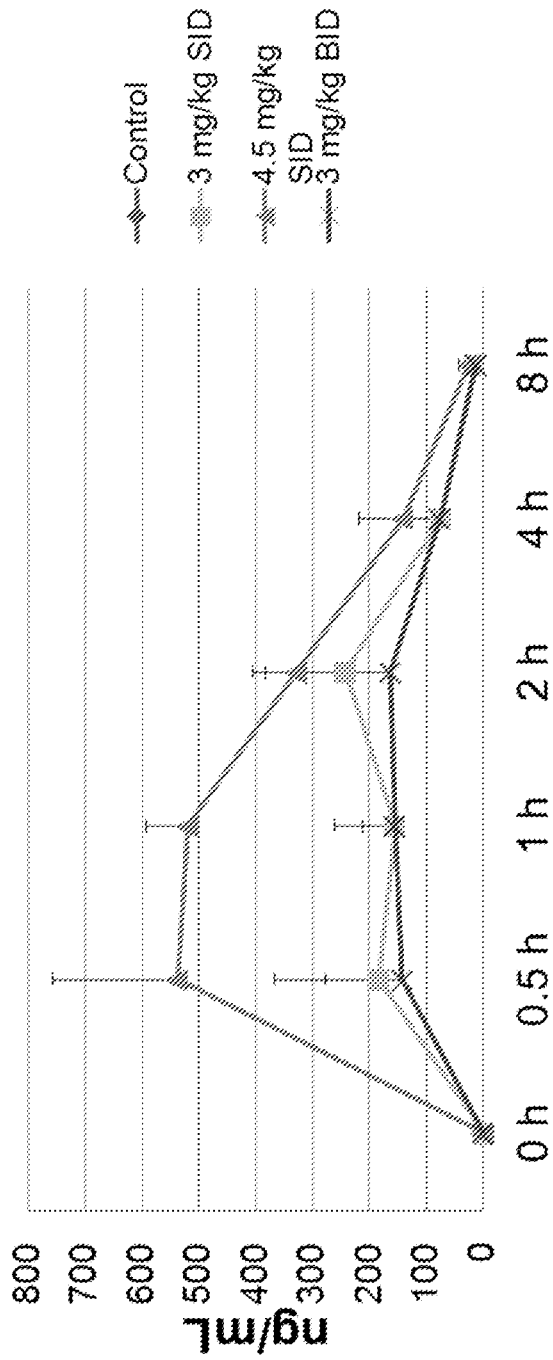
FIG. 33 is a line graph depicting measurements of capromorelin concentration in the serum of beagles on day 1 after being treated with different concentrations and treatment regimens of a capromorelin composition.
Figure 34:
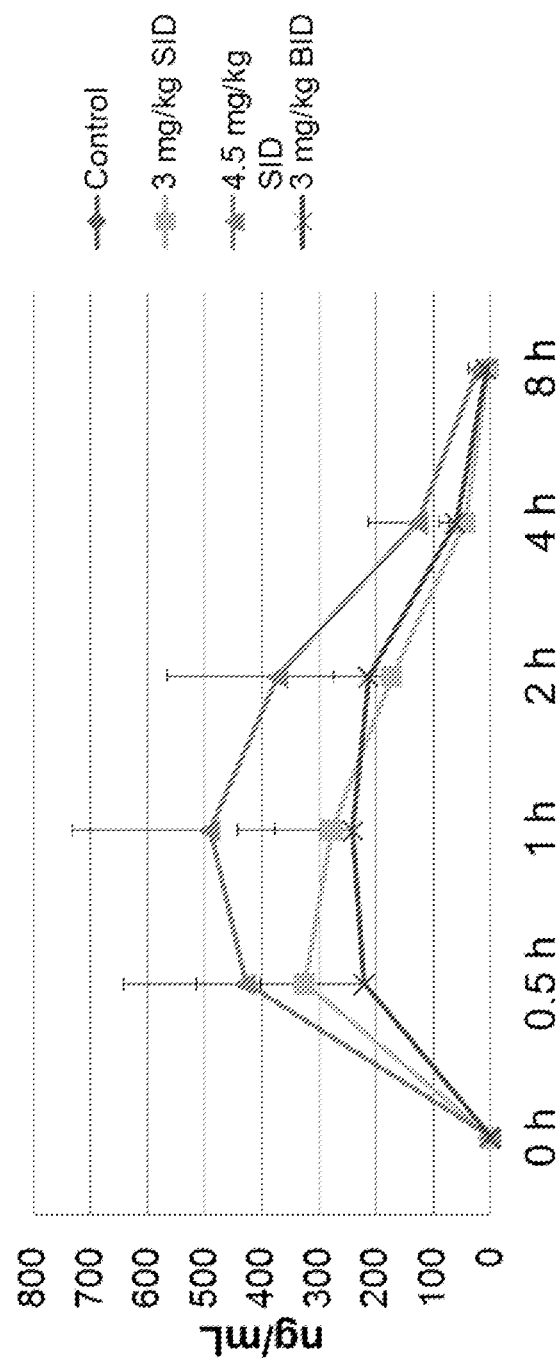
FIG. 34 is a line graph depicting measurements of capromorelin concentration in the serum of beagles on day 7 after being treated with different concentrations and treatment regimens of a capromorelin composition.

Referring now to FIGS. 33 and 34, dogs in the active treatment groups exhibited elevated concentrations of capromorelin in their serum. Using data from serum samples taken on Days 1 and 7 of the study, capromorelin concentrations tended to begin rising at approximately 0.5 h after dosing and, in general, decreased to near undetectable levels by eight hours after administration. The results confirmed that the capromorelin composition was correctly administered.

As reflected in FIGS. 35-46, dogs in the active treatment groups experienced changes in serum concentrations of IGF-1, GH, and cortisol, which are likely attributable to the capromorelin administration.

Figure 35:
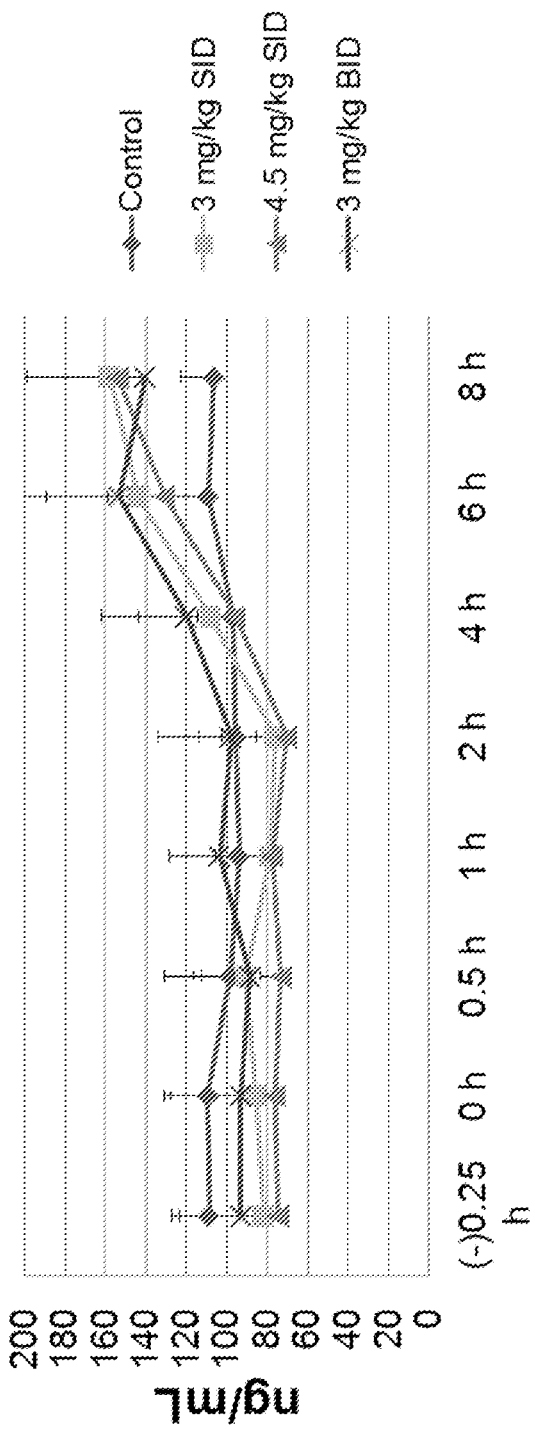
FIG. 35 is a line graph depicting measurements of insulin-like growth factor-1 concentration in the serum of beagles on day 1 after being treated with different concentrations and treatment regimens of a capromorelin composition.
Figure 36:
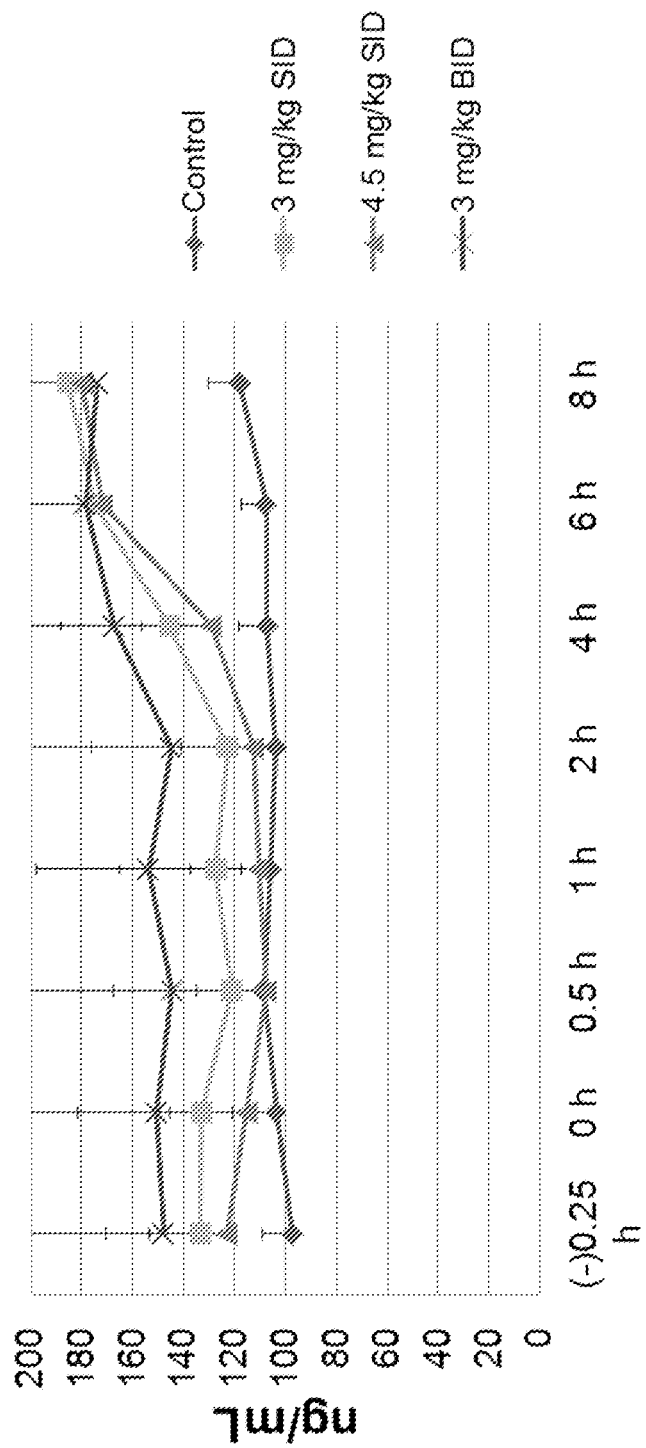
FIG. 36 is a line graph depicting measurements of insulin-like growth factor-1 concentration in the serum of beagles on day 4 after being treated with different concentrations and treatment regimens of a capromorelin composition.
Figure 37:
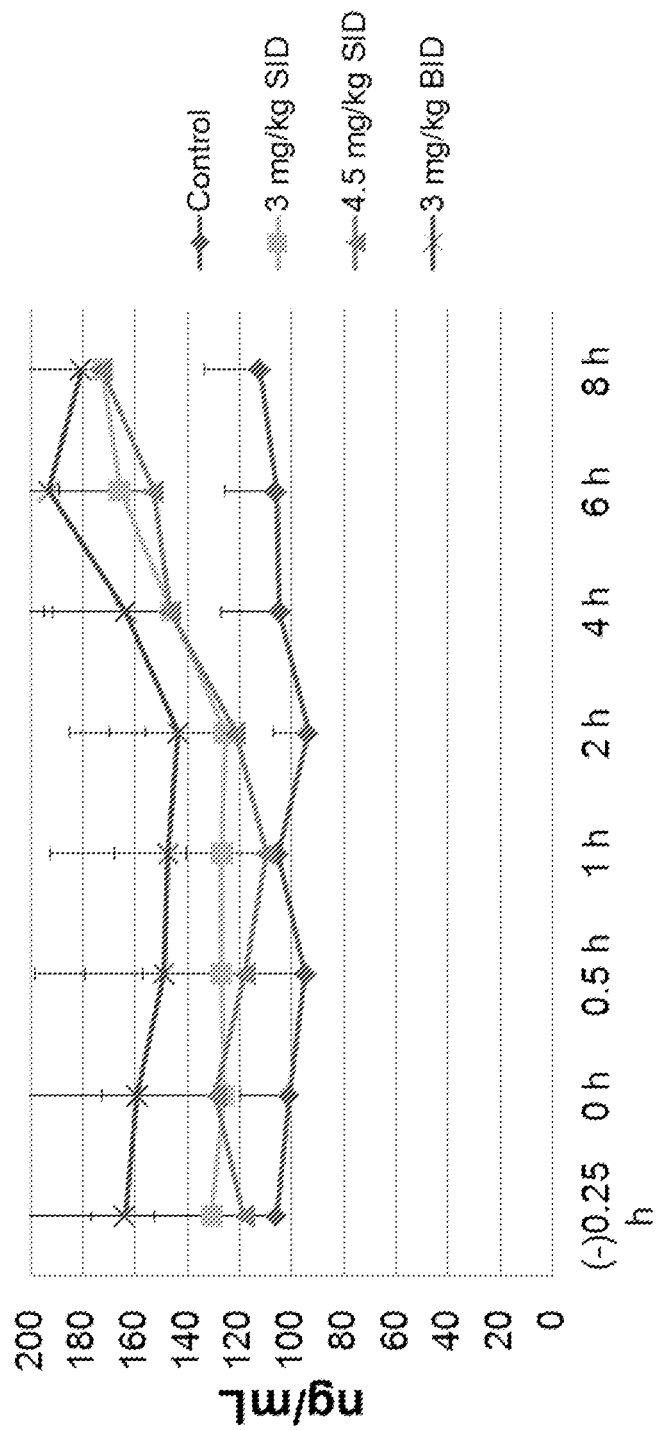
FIG. 37 is a line graph depicting measurements of insulin-like growth factor-1 concentration in the serum of beagles on day 7 after being treated with different concentrations and treatment regimens of a capromorelin composition.
Figure 38:
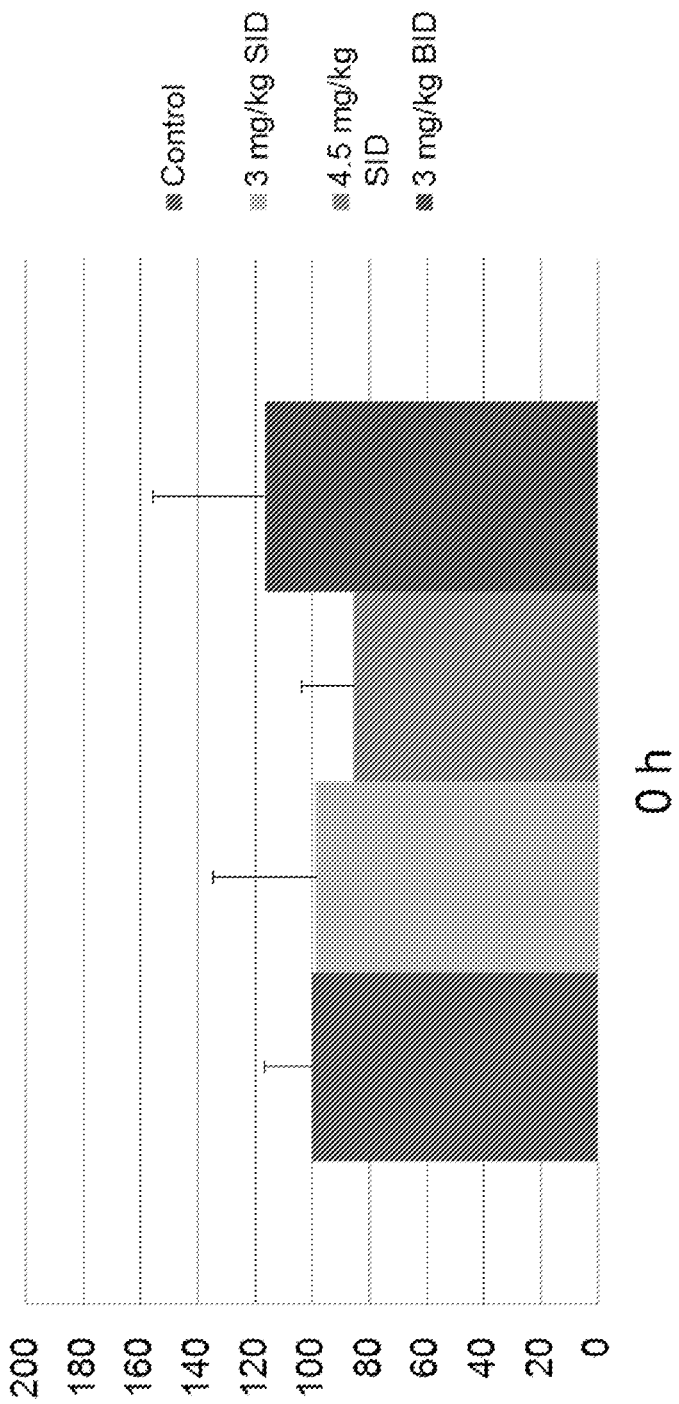
FIG. 38 is a bar graph depicting measurements of insulin-like growth factor-1 concentration in the serum of beagles after seven days of treatment with different concentrations and treatment regimens of a capromorelin composition and three days without treatment (i.e., Day 10).
Figure 39:
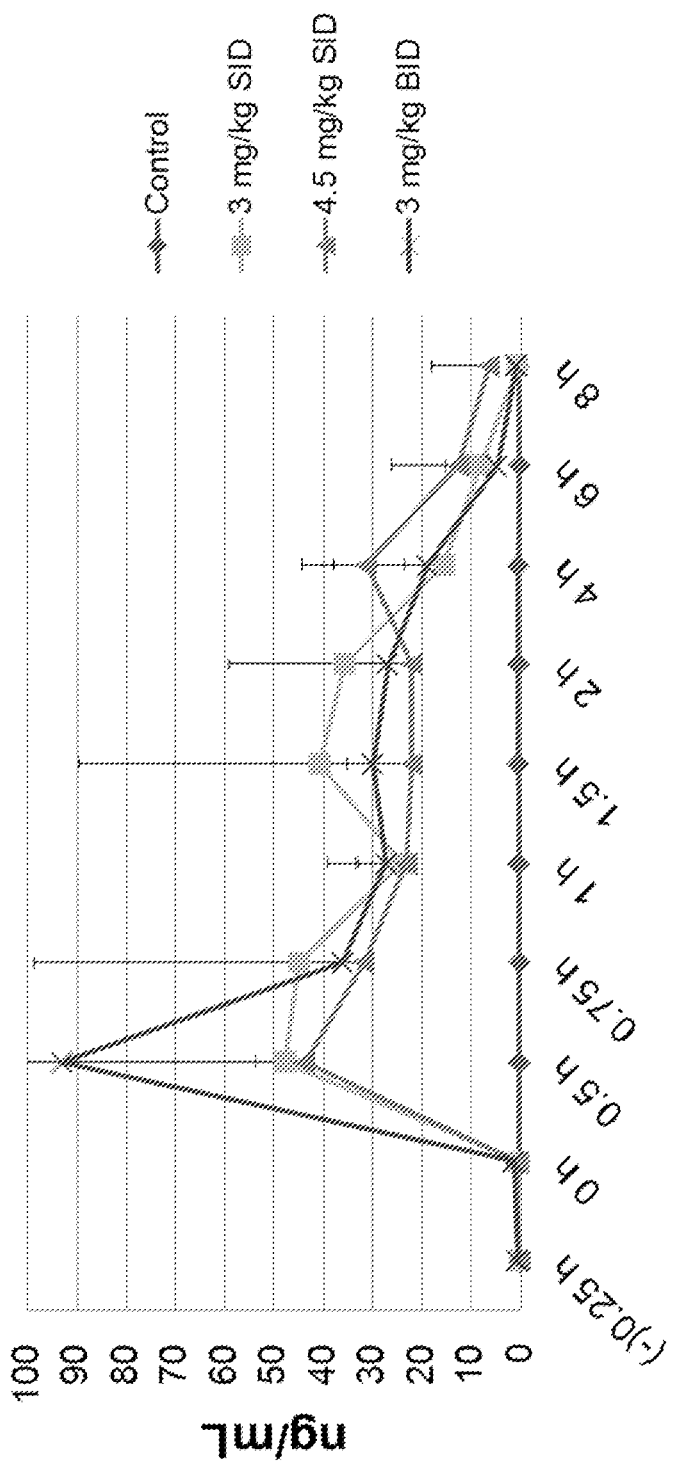
FIG. 39 is a line graph depicting measurements of growth hormone concentration in the serum of beagles on day 1 after being treated with different concentrations and treatment regimens of a capromorelin composition.
Figure 40:
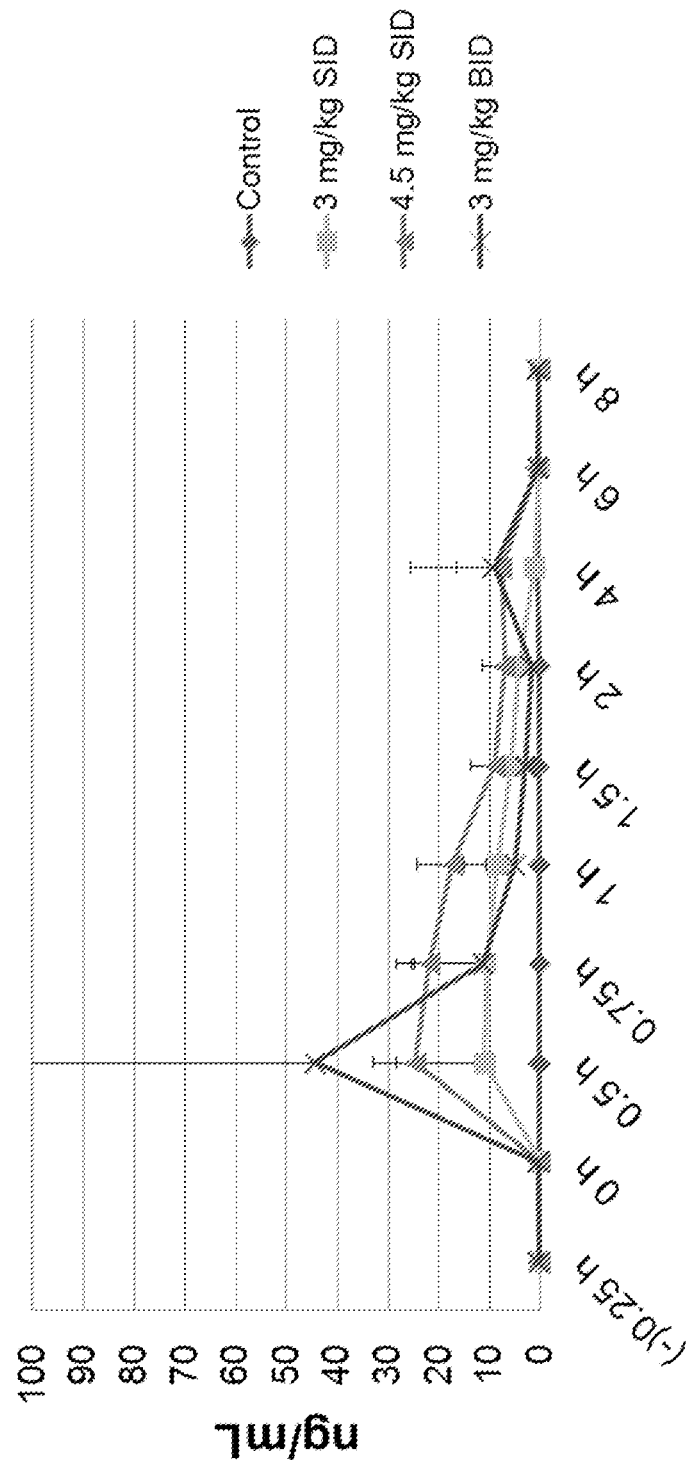
FIG. 40 is a line graph depicting measurements of growth hormone concentration in the serum of beagles on day 4 after being treated with different concentrations and treatment regimens of a capromorelin composition.
Figure 41:
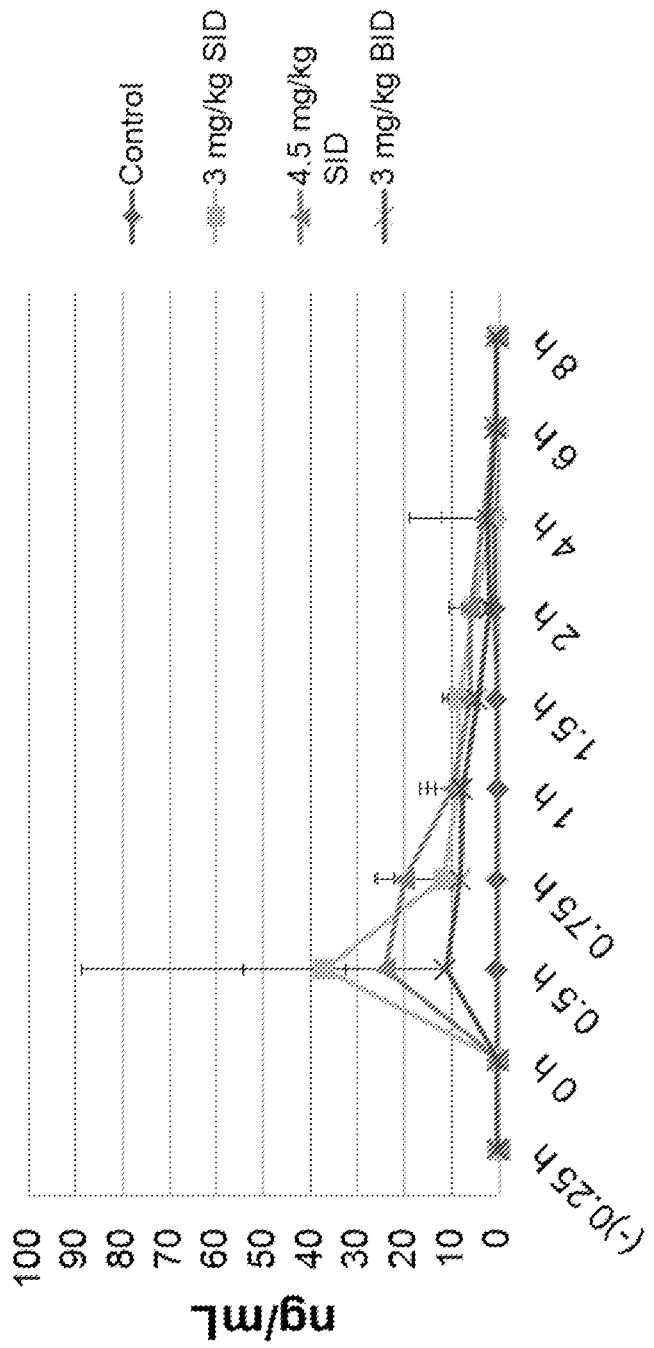
FIG. 41 is a line graph depicting measurements of growth hormone concentration in the serum of beagles on day 7 after being treated with different concentrations and treatment regimens of a capromorelin composition.

First, as shown in FIGS. 35-38, treatment with capromorelin induced IGF-1 levels within the serum of the dogs. Specifically, as shown in FIG. 35, approximately one to four hours after initially dosing the dogs with capromorelin, IGF-1 levels exhibited an increase in the serum, relative to the dogs receiving only deionized water. Moreover, as shown in FIGS. 36 and 37, on days 4 and 7 of the treatment experiment, serum IGF-1 levels remained consistently higher in dogs receiving capromorelin. As shown in FIG. 38, three days after terminating treatment (Day 10), levels of serum IGF-1 in the dogs receiving capromorelin treatment were not significantly different than the levels of serum IGF-1 in the dogs receiving deionized water alone.

In an additional analysis of the same data discussed above, relative to time 0 (i.e., prior to administration of the capromorelin composition), the dogs in the active treatment group exhibit increased IGF-1 levels in the serum. For example, on day 1, at eight hours post administration, the dogs receiving the once-daily treatment exhibit an approximately 83.9% increase in serum IGF-1 concentration, relative to time 0 on day 1. The dogs receiving the twice-daily treatment exhibit an approximately 50.6% increase in serum IGF-1 concentration, relative to time 0 on day 1. On days 4 and 7, at eight hours post administration, the once-daily treatment induces approximately 39.5% and 36.8% increases in serum IGF-1 concentration, relatively to time 0 on days 4 and 7, respectively. Similarly, on days 4 and 7, at eight hours post administration, the twice-daily treatment induces approximately 15.4% and 13.3% increases in serum IGF-1 concentration, relatively to time 0 on days 4 and 7, respectively. It is possible that the dogs receiving the twice-daily administration of the capromorelin composition exhibit increases of a lesser magnitude because serum concentrations of IGF-1 are already at higher concentrations than are IGF-1 levels in dogs receiving the once-daily administration of capromorelin.

Figure 42:
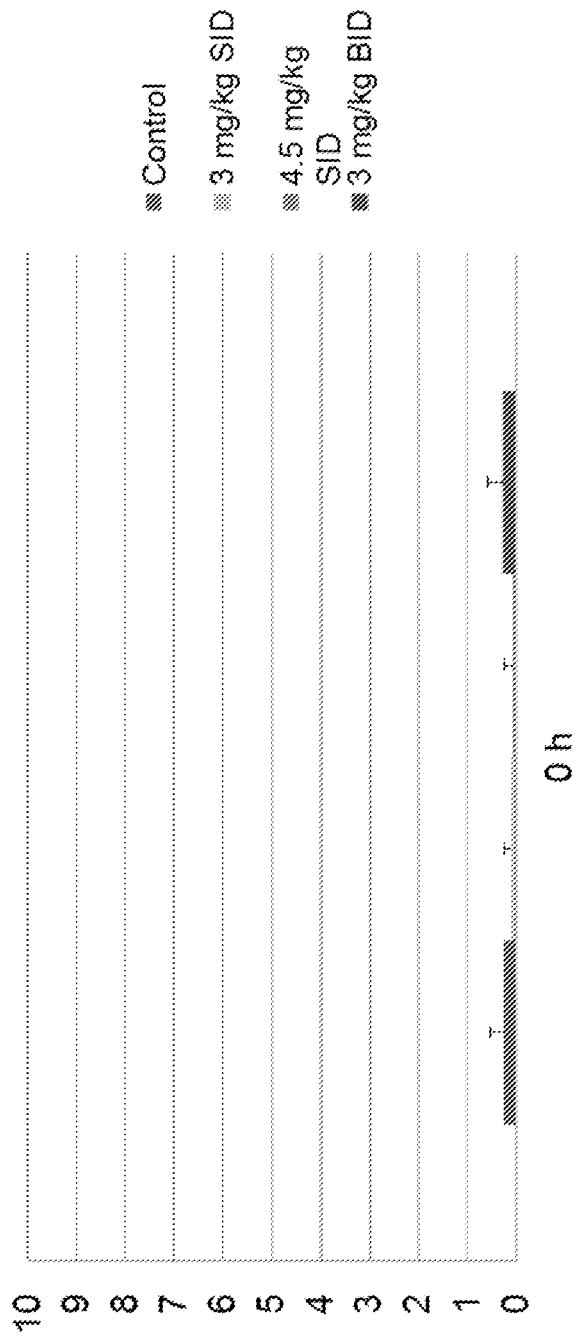
FIG. 42 is a bar graph depicting measurements of growth hormone concentration in the serum in beagles after seven days of treatment with different concentrations and treatment regimens of a capromorelin composition and three days without treatment (i.e., day 10).
Figure 43:
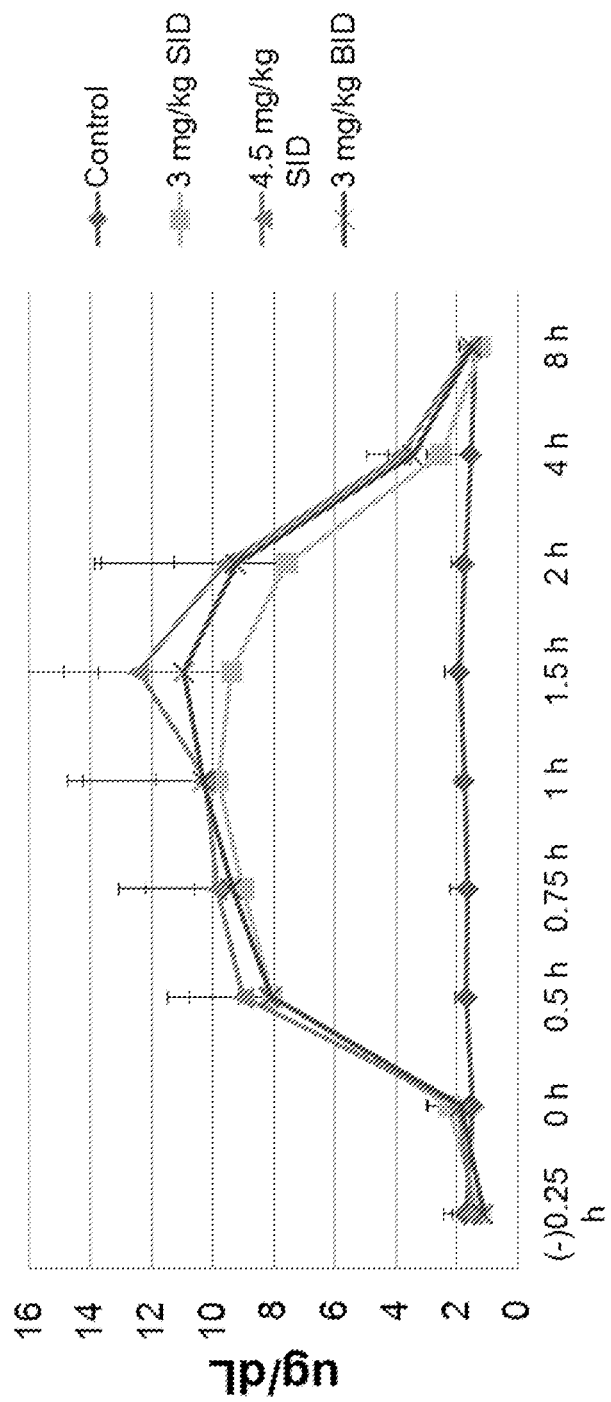
FIG. 43 is a line graph depicting measurements of cortisol concentration in the serum of beagles on day 1 after being treated with different concentrations and treatment regimens of a capromorelin composition.
Figure 44:
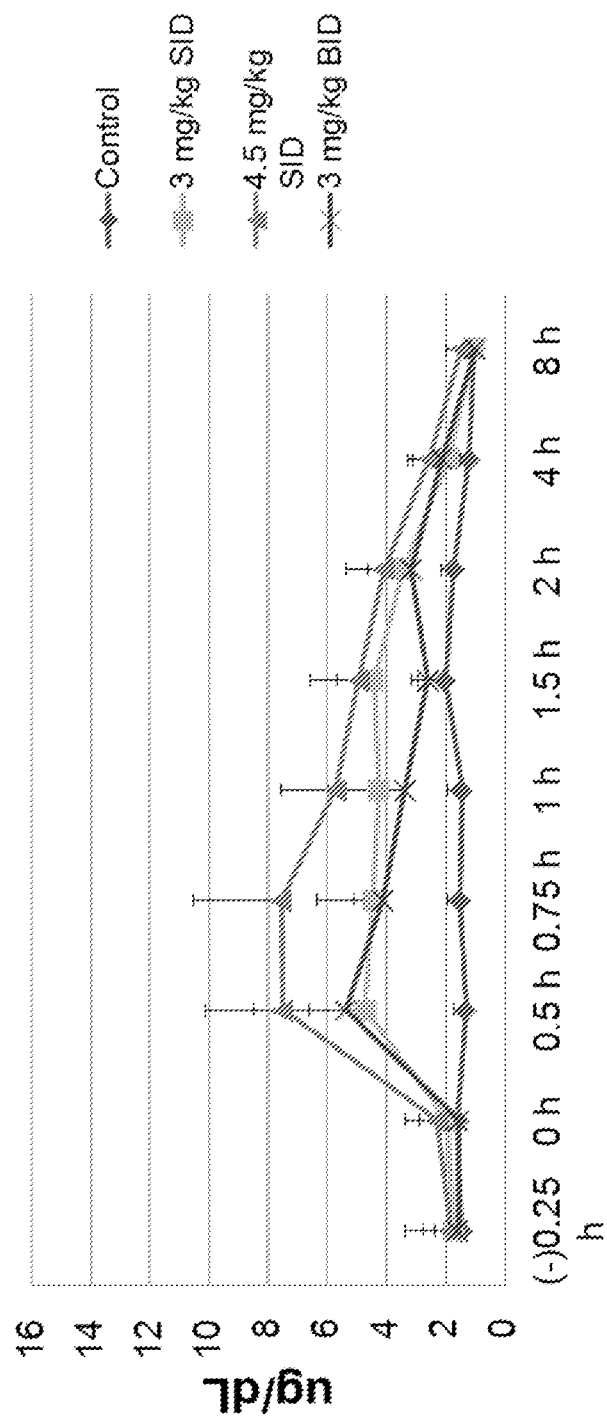
FIG. 44 is a line graph depicting measurements of cortisol concentration in the serum of beagles on day 4 after being treated with different concentrations and treatment regimens of a capromorelin composition.
Figure 45:
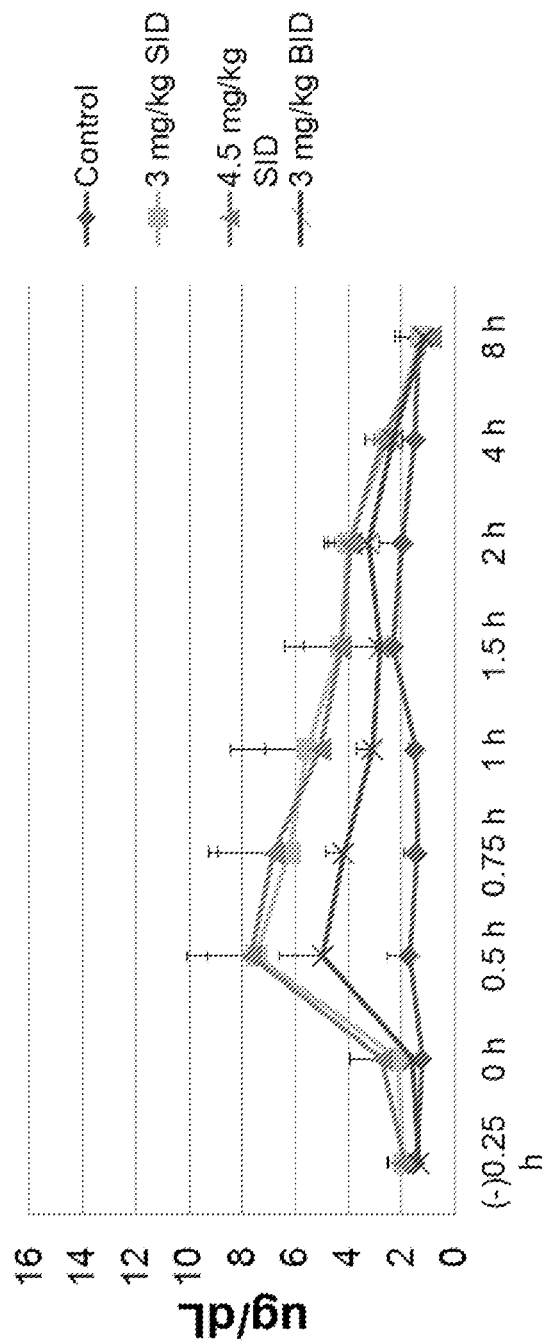
FIG. 45 is a line graph depicting measurements of cortisol concentration in the serum of beagles on day 7 after being treated with different concentrations and treatment regimens of a capromorelin composition.

Like serum IGF-1 levels, during the study, serum levels of GH appeared to be dependent upon capromorelin administration, as shown in FIGS. 39-42. Specifically, on days 1, 4, and 7, GH levels increased at approximately 0.5 h after the dogs received the capromorelin composition. Prior to treatment, all dogs exhibited nearly undetectable levels of GH in the serum; however, after receiving either the once-daily 3 mg/kg or the twice-daily 3 mg/kg dose of capromorelin, dogs in active treatment groups exhibited a marked increase in GH levels in the serum that continued to be elevated relative to the dogs in negative control group, which received only deionized water. As shown in FIG. 42, three days after terminating treatment (Day 10), levels of GH in the serum in the dogs receiving capromorelin treatment were not significantly different than the levels of GH in the serum in the dogs receiving deionized water alone.

Figure 46:
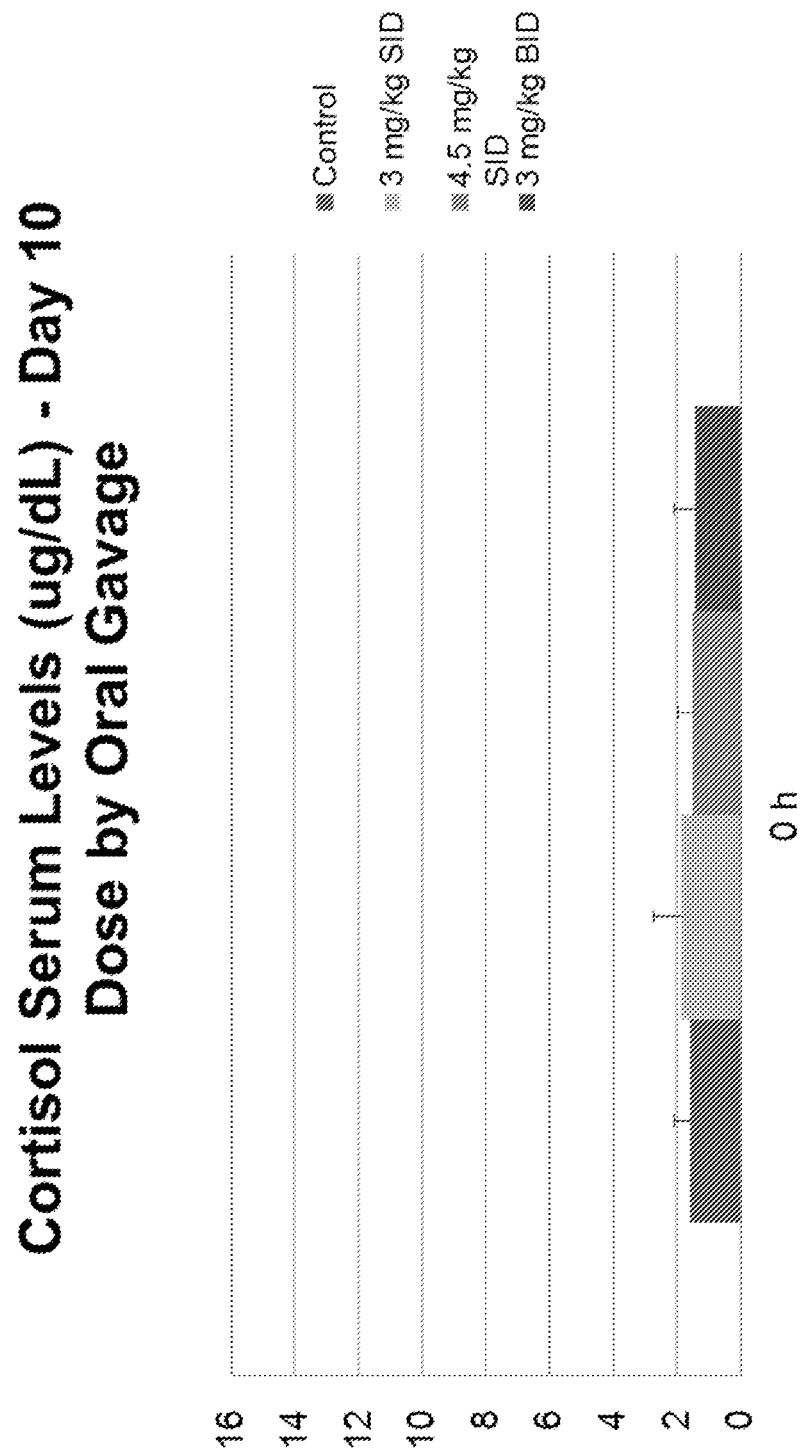
FIG. 46 is a bar graph depicting measurements of cortisol concentration in the serum in beagles after seven days of treatment with different concentrations and treatment regimens of a capromorelin composition and three days without treatment (i.e., Day 10).

Referring now to FIGS. 43-46, similar to GH, cortisol concentrations in the serum appear to correlate with administration of capromorelin. Specifically, on days 1, 4, and 7 (FIGS. 43-45, respectively), at approximately 0.5 h post treatment, cortisol concentrations in the serum of dogs treated with capromorelin increased relative to dogs receiving only deionized water. In addition, increases in cortisol serum levels were mitigated on days 4 and 7, and even more so with the twice-daily treatment of capromorelin. Moreover, as shown in FIG. 46, three days after terminating treatment (Day 10), levels of cortisol in the serum in the dogs receiving capromorelin treatment were not significantly different than the levels of cortisol in the serum in the dogs receiving deionized water alone.

Overall, both dosing regimens produced discernible impacts on the dogs of the active treatment groups, relative to the negative control dogs. Moreover, no toxicological responses were noted. Pharmacological effects were noted, including no significant decreases in body weight and increased food consumption, as well as increased levels of serum GH, IGF-1, cortisol, and capromorelin. In general, the more pronounced increases in serum concentrations of IGF-1 and mitigated expression of cortisol was noted in the dogs receiving the twice-daily administrations. Because of this noted benefit, the twice-daily administration of the capromorelin composition (at a concentration of 3 mg/kg) will be further explored, along with other dosing regimens to determine the most efficacious dose in an optimal volume.

EXAMPLE 5

Further Refinements of the Dosing Regimen of the Inappetance-Controlling Compound Containing Capromorelin In order to further refine the dosing regimen that would provide an appropriate blood profile of capromorelin and desired results from the perspective of increased food intake and weight gain, an additional series of experiments were conducted. In these experiments, twenty-four adult (male and female) Beagle dogs weighing approximately 9 to 13 kilograms were randomly divided into four groups. Group 1 received a placebo formulation, without any active compound, two times per day; Group 2 received a composition comprising 3 mg/kg of body weight of capromorelin one time per day; Group 3 received a composition comprising 4.5 mg/kg of body weight of capromorelin one time per day; and Group 4 received a composition comprising 3 mg/kg of body weight of capromorelin two times per day.

In particular, on the first day of dosing, Day 1, through the last day of dosing, Day 7, the compositions were orally administered (i.e., using a syringe) to the animals in a flavored formulation of the following composition:

| Formulation 9 | |
|---|---|
| Ingredient | % weight per volume |
| Capromorelin (not present in Group 1 composition) | 3.10 |
| Citric Acid | 0.70 |
| Sodium Citrate | 0.50 |
| Sodium Chloride | 0.70 |
| Methyl 4-Hydroxybenzoate Salt | 0.045 |
| Propyl 4-Hydroxybenzoate Salt | 0.005 |
| Thaumatin T200X | 0.60 |
| *Stevia* Extract Rebaudioside A 99% | 0.70 |
| MagnaSweet | 0.50 |
| Vanillin | 0.20 |
| Neosorb Sorbitol 70% | 30.30 |
| Maltitol Solution (Lycasin 80/55) | 25.00 |
| Glycerol Anhydrous | 20.20 |
| Kollidon 90F (PVP) | 1.5 |
| Ethanol (ABS) | 0.50 |
| Purified Water | q.s. |

In these experiments, the animals were orally administered the flavored formulation at approximately 8:00 AM and, for Group 4 only, again at 6:00 PM. The animals were fed at 10:00 AM beginning seven days prior to Day 1 and continuing for the duration of the study. The animals were offered twice the normal amount of food. Approximately two hours after the food offering, the remainder was removed and weighed to assess food intake. This restricted feeding regime was started at Day −7 to allow the animals to transition to a normal feed intake before the study was initiated. Food consumption was calculated and recorded on Days −7 through Day 7. Baseline food consumption was calculated for each individual dog as the average number of grams of food consumed on Days −3, −2, and −1. The study period food consumption was calculated for each individual dog as the average of Days 1 through 7. Body weights were collected on Days −1, 3, and 7. Blood was collected for measurements of capromorelin, growth hormone, cortisol, and IGF-1 concentrations on Days 1, 4, and 7 at about 15 minutes pre-administration, immediately prior to dosing (0 minutes), 30, 45, 60, 90, 120, 240, 360, and/or 480 minutes post dosing via the jugular or other accessible vessel. As reflected by the data in FIGS. 61-74, the animals' response to the capromorelin-containing composition is largely in accord with the results discussed above.

Figure 61:
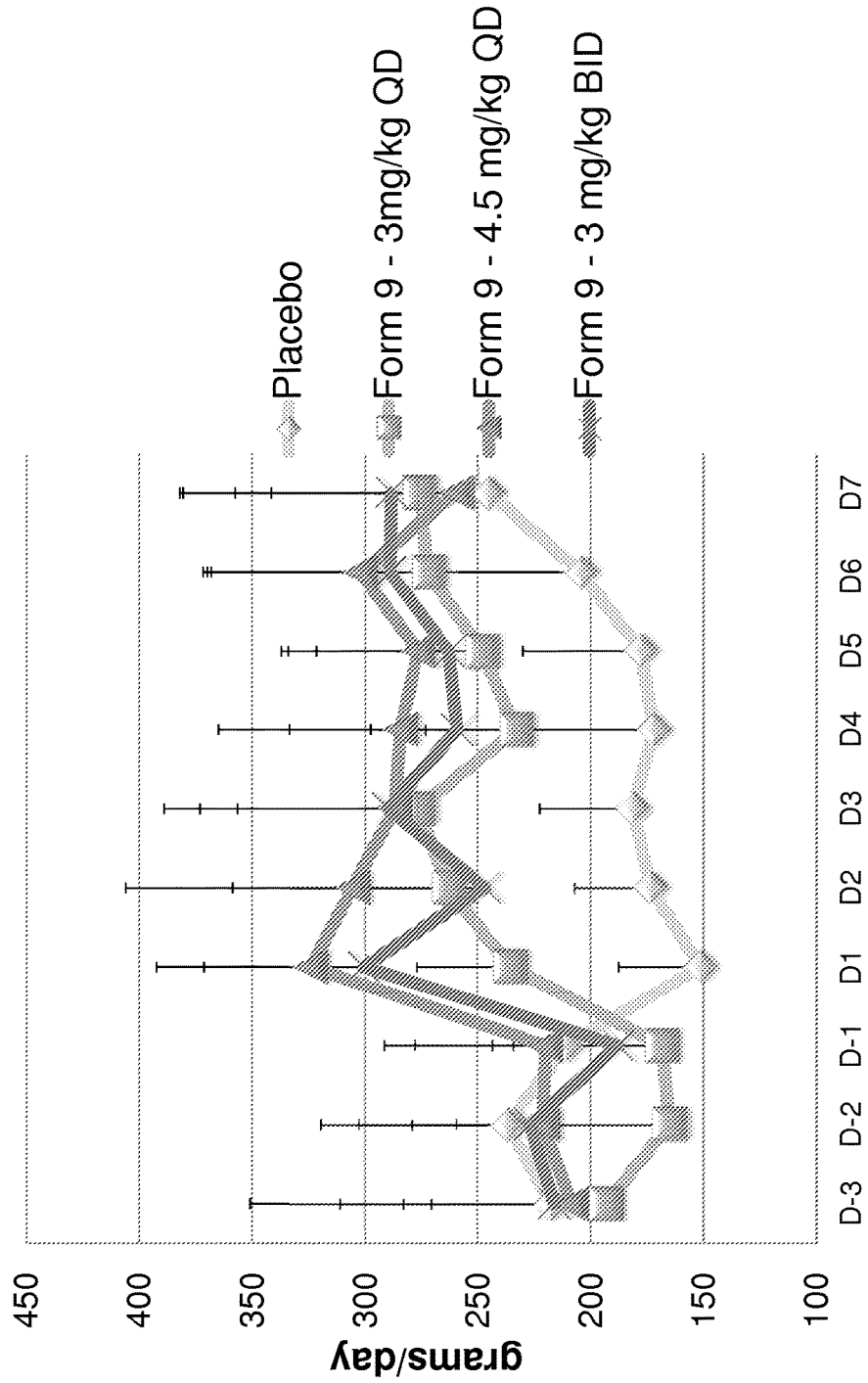
FIG. 61 is a line graph depicting measurements of food consumed by animals over the course of an experiment in which the animals were treated with different concentrations and treatment regiments of a capromorelin composition.

First, as shown in FIG. 61 and in Table 1 below, the animals that received the experimental compositions consumed greater amounts of food and gained more weight than the animals in Group 1 (i.e., the placebo group). In particular, as shown in FIG. 61, the animals of Groups 2-4, (i.e., those that received the capromorelin-containing composition), consumed greater amounts of food relative to the animals in the control group. Specifically, when comparing the food consumed on Days −1 and Day 7, the control animals consumed nearly 16% less food, with the Group 2 animals consuming 42.7% more food, the Group 3 animals consuming 34.5% more food, and the Group 4 animals consuming 31.5% more food. Moreover, as shown in Table 1 below, the increased food consumption corresponded to an increase in body weight.

TABLE 1

Weight Change

| Group | Treatment | Comparison of Weight on Day −1 to Weight on Day 7 (X ± SD, %) |
|---|---|---|
| 1 | Placebo - 2x per day | −1.17 ± 1.51% |
| 2 | Capromorelin - 3 mg/kg 1x per day | 4.52 ± 1.67% |
| 3 | Capromorelin - 4.5 mg/kg 1x per day | 3.78 ± 2.93% |
| 4 | Capromorelin - 3 mg/kg 2x per day | 4.17 ± 1.35% |

Figure 62:
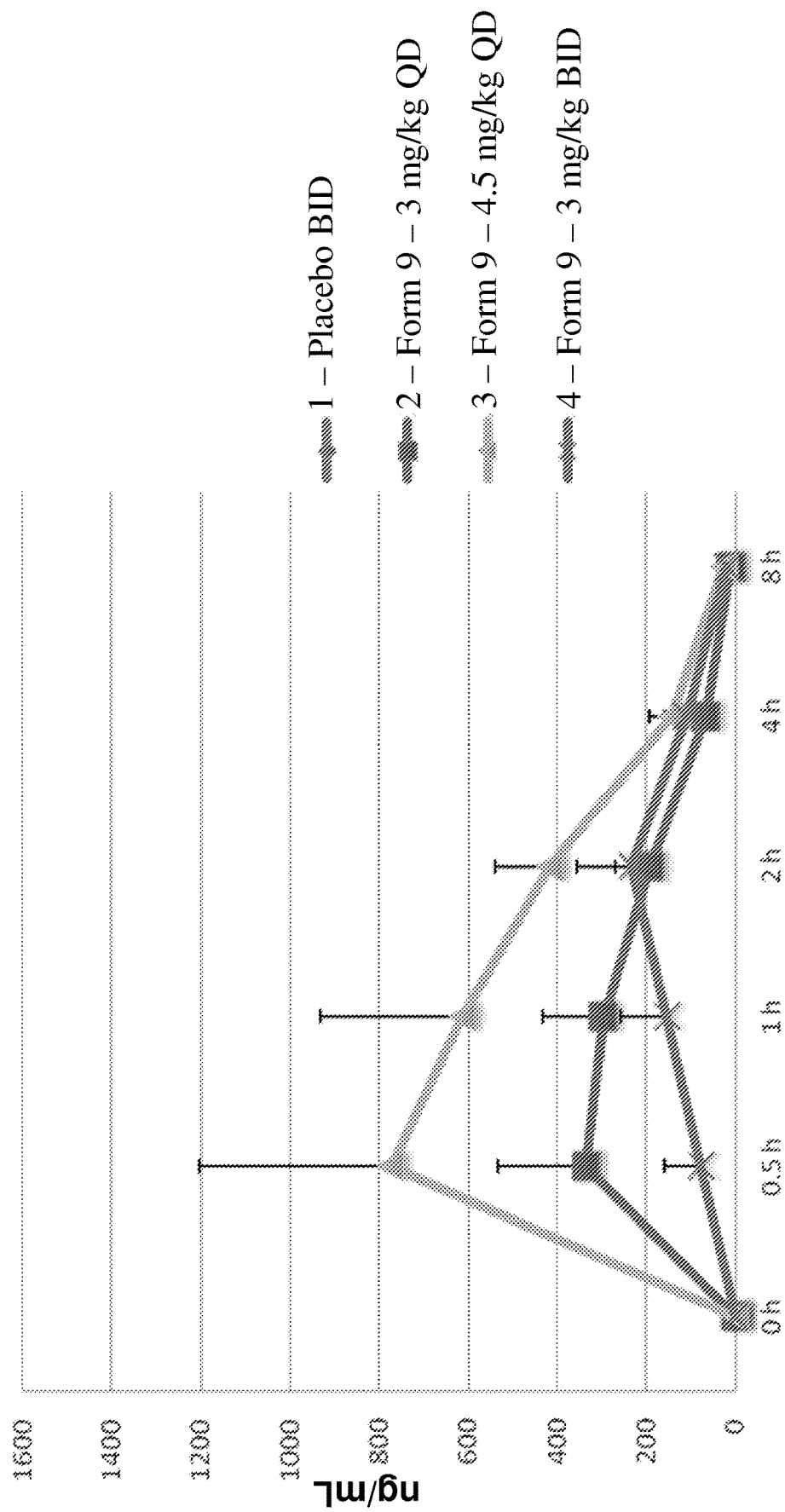
FIG. 62 is a line graph depicting serum concentrations of capromorelin in animals on Day 1 after being treated with different concentrations and treatment regimens of a capromorelin composition.
Figure 63:
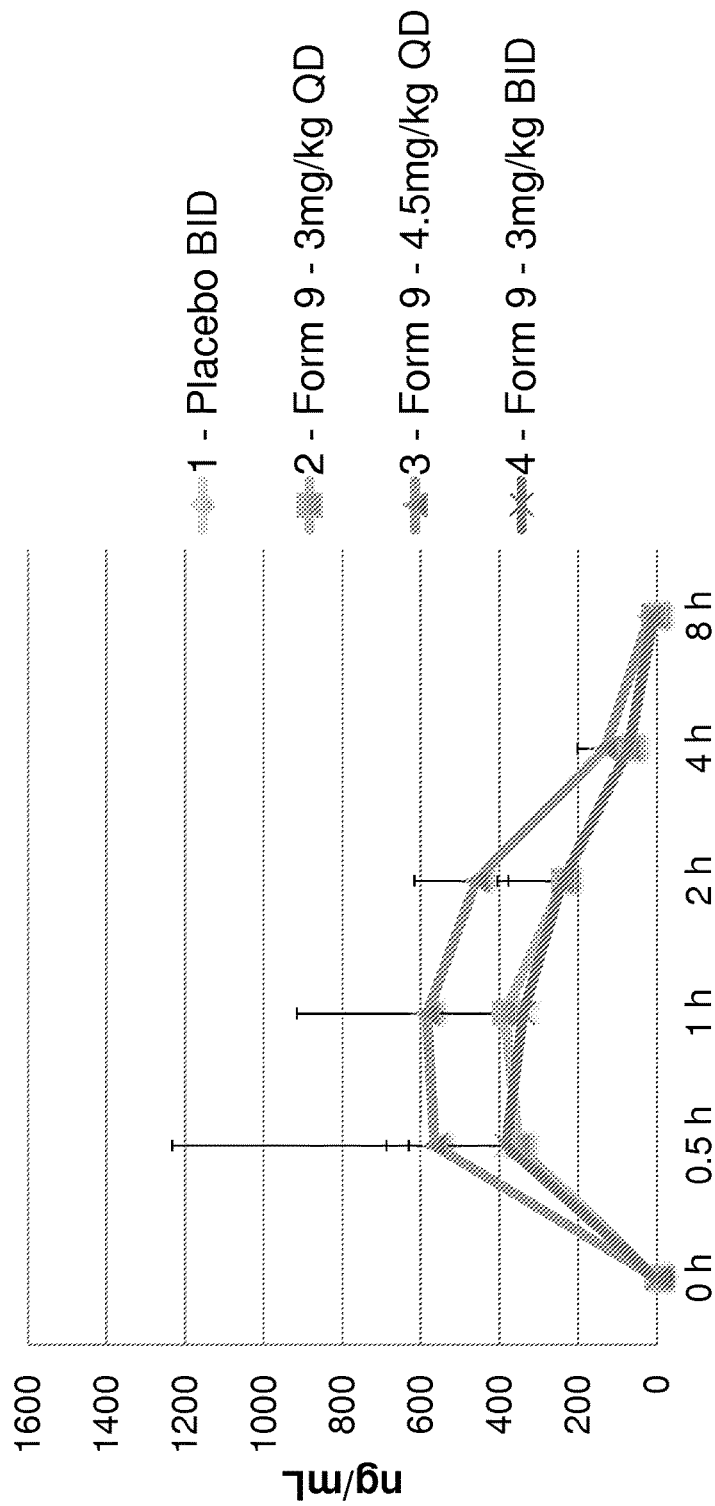
FIG. 63 is a line graph depicting serum concentrations of capromorelin in animals on Day 7 after being treated with different concentrations and treatment regimens of a capromorelin composition.
Figure 64A:
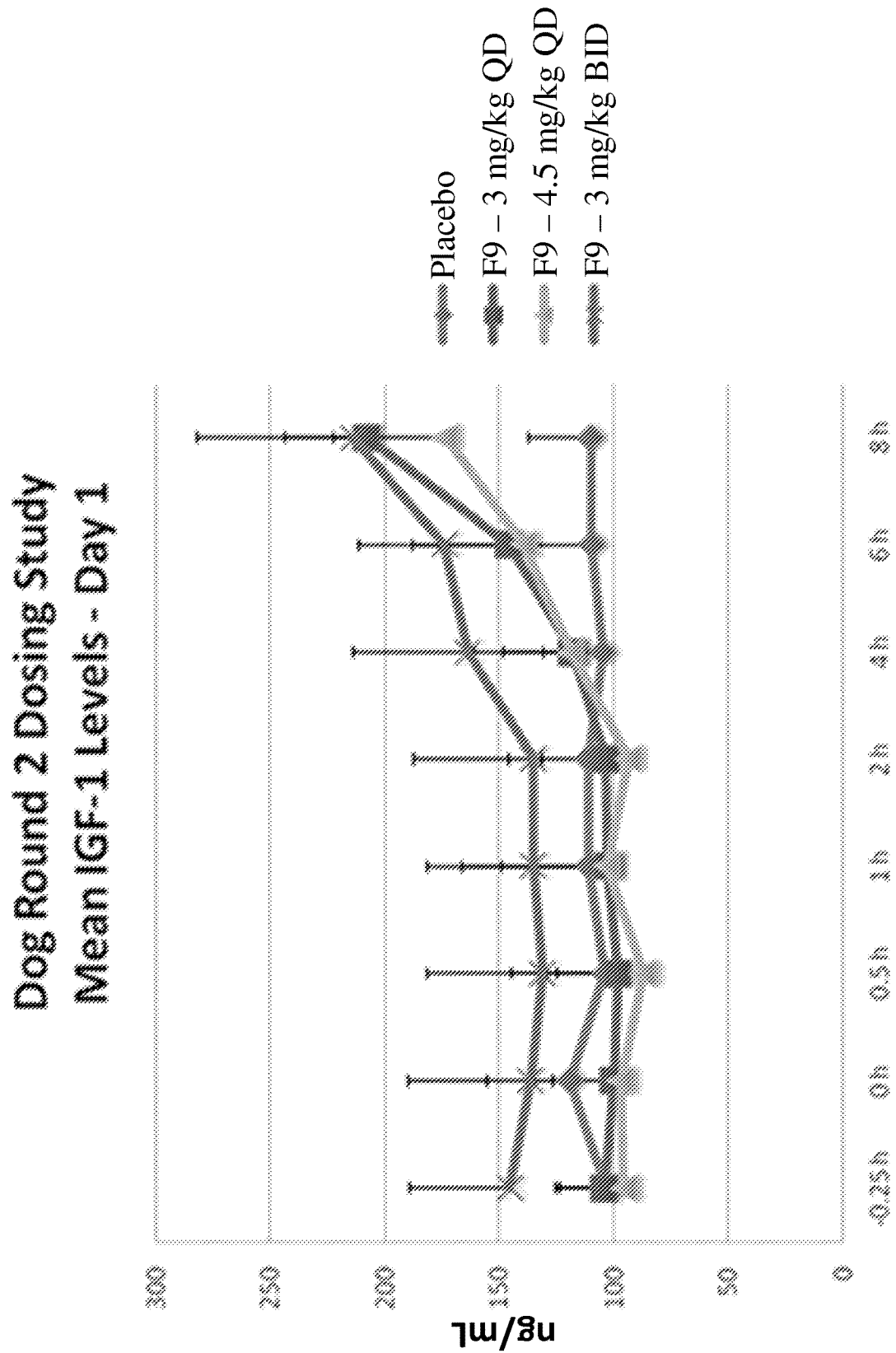
FIG. 64A is a line graph depicting serum concentrations of IGF-1 in animals on Day 1 after being treated with different concentrations and treatment regimens of a capromorelin composition.
Figure 64B:
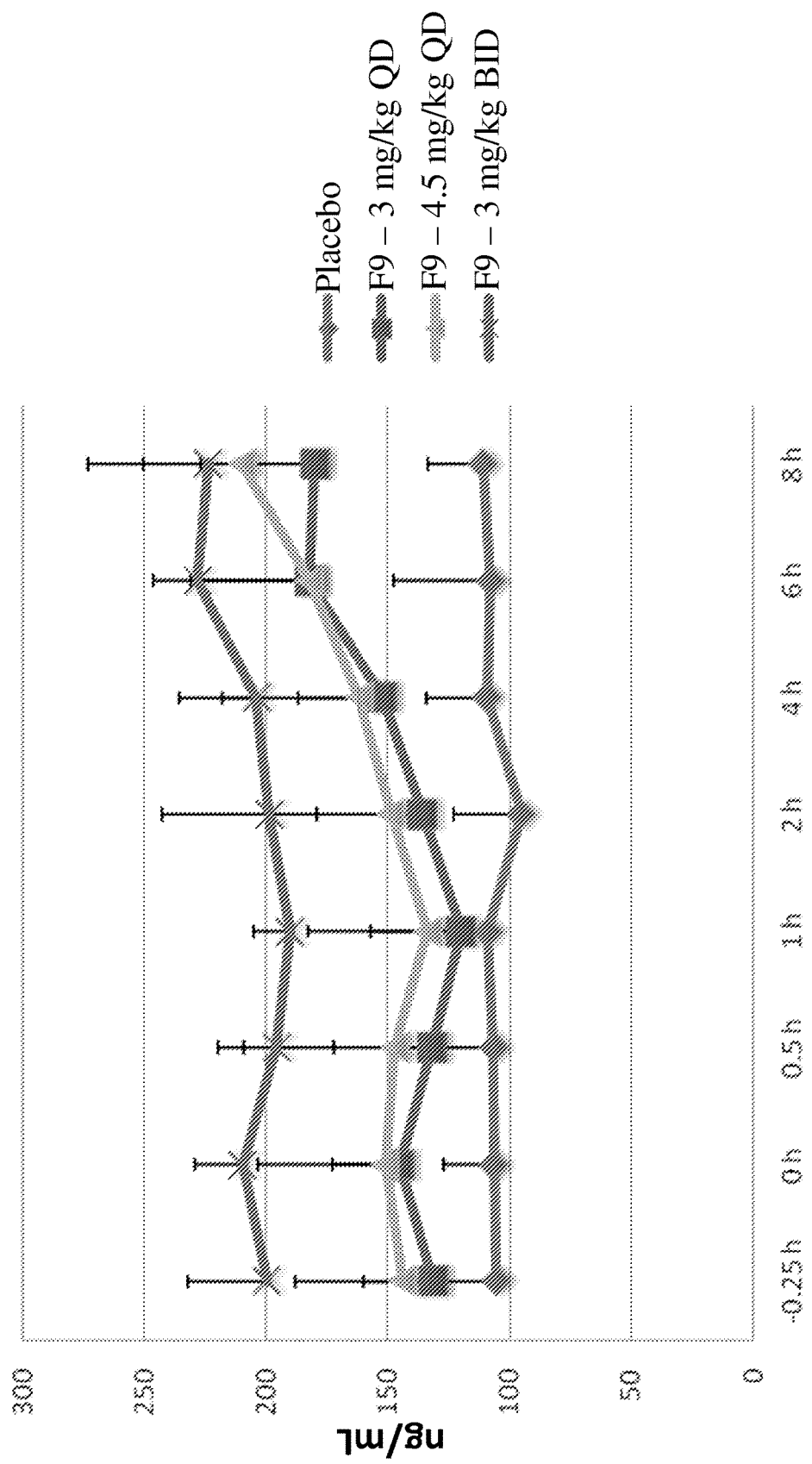
FIG. 64B is a line graph depicting serum concentrations of IGF-1 in animals on Day 4 after being treated with different concentrations and treatment regimens of a capromorelin composition.
Figure 65:
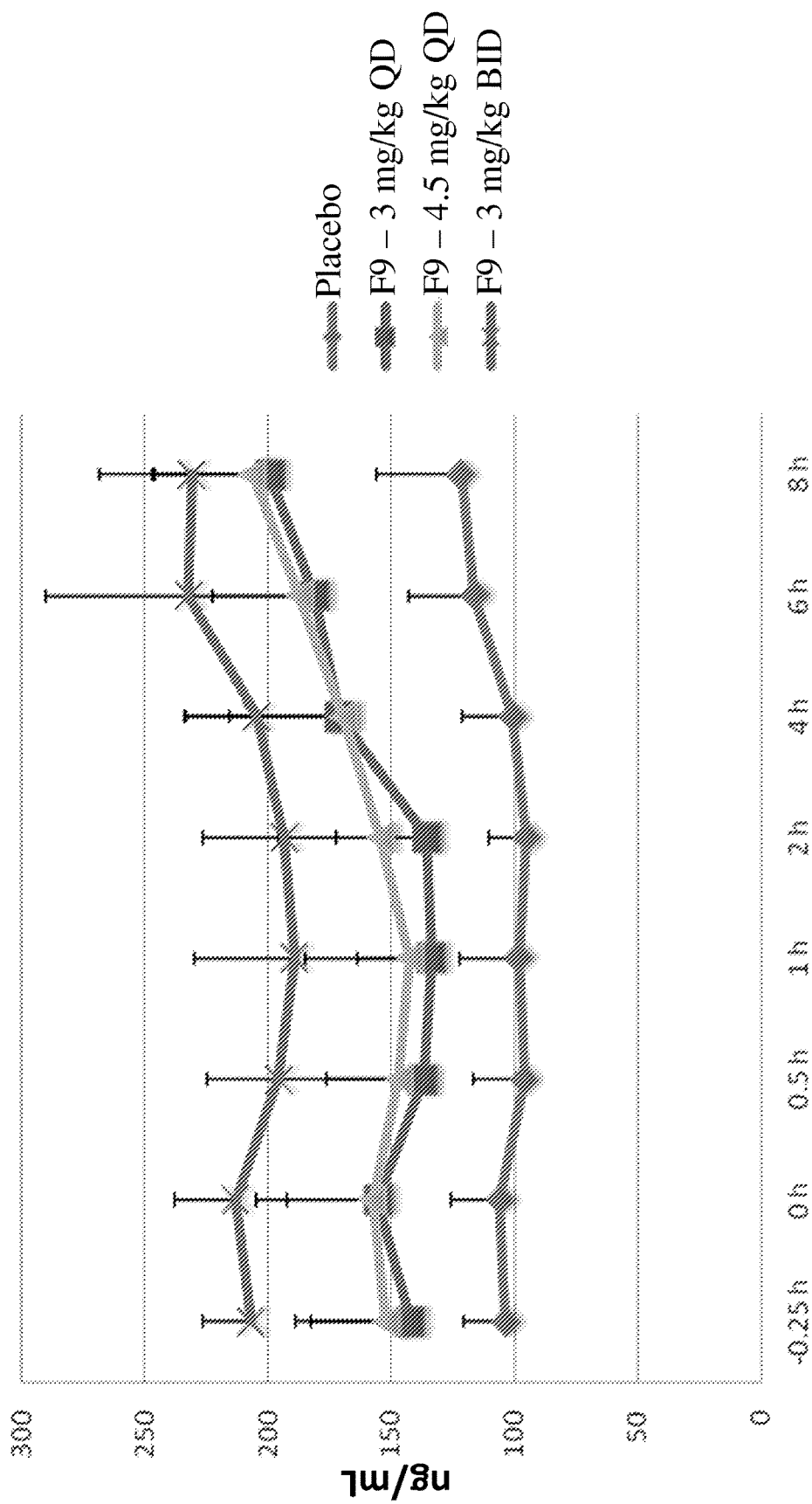
FIG. 65 is a line graph depicting serum concentrations of IGF-1 in animals on Day 7 after being treated with different concentrations and treatment regimens of a capromorelin composition.

Correspondingly, as shown in FIGS. 62 and 63, the concentrations of capromorelin within the serum were as expected. In particular, the serum concentration of capromorelin initially spiked at 30 minutes post administration and, by 8 hours was back to baseline levels. Moreover, as expected, the animals in Group 3, which received the highest dose of capromorelin, exhibited greater serum concentrations of capromorelin. In addition, this data also shows that there was no evidence of capromorelin accumulation in these animals, as the concentration dropped to below detectable levels by 8 hours post administration.

Figure 66:
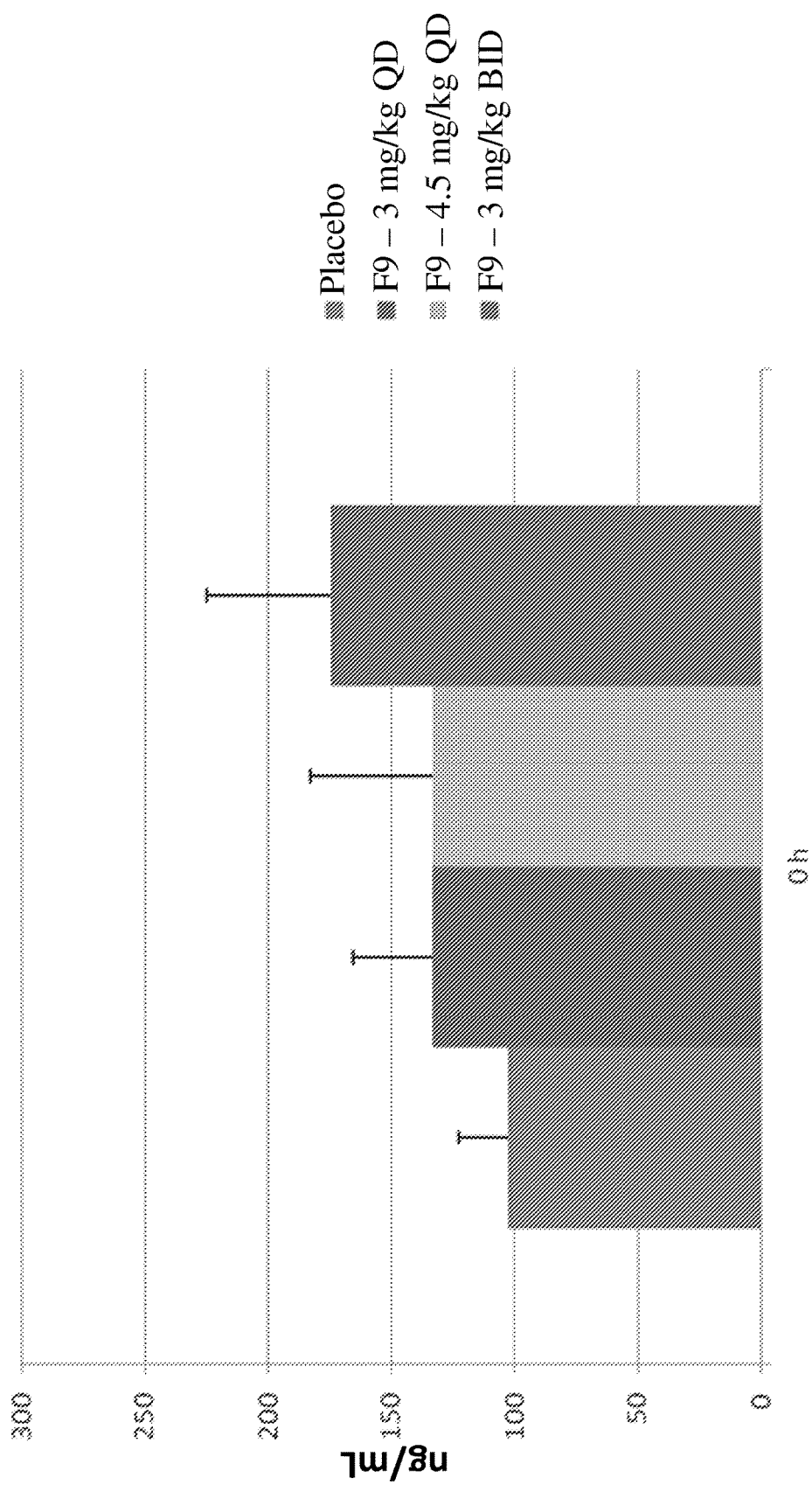
FIG. 66 is a bar graph depicting serum concentrations of IGF-1 in animals after seven days of treatment with a capromorelin composition and two days without treatment (i.e., day 9).
Figure 67:
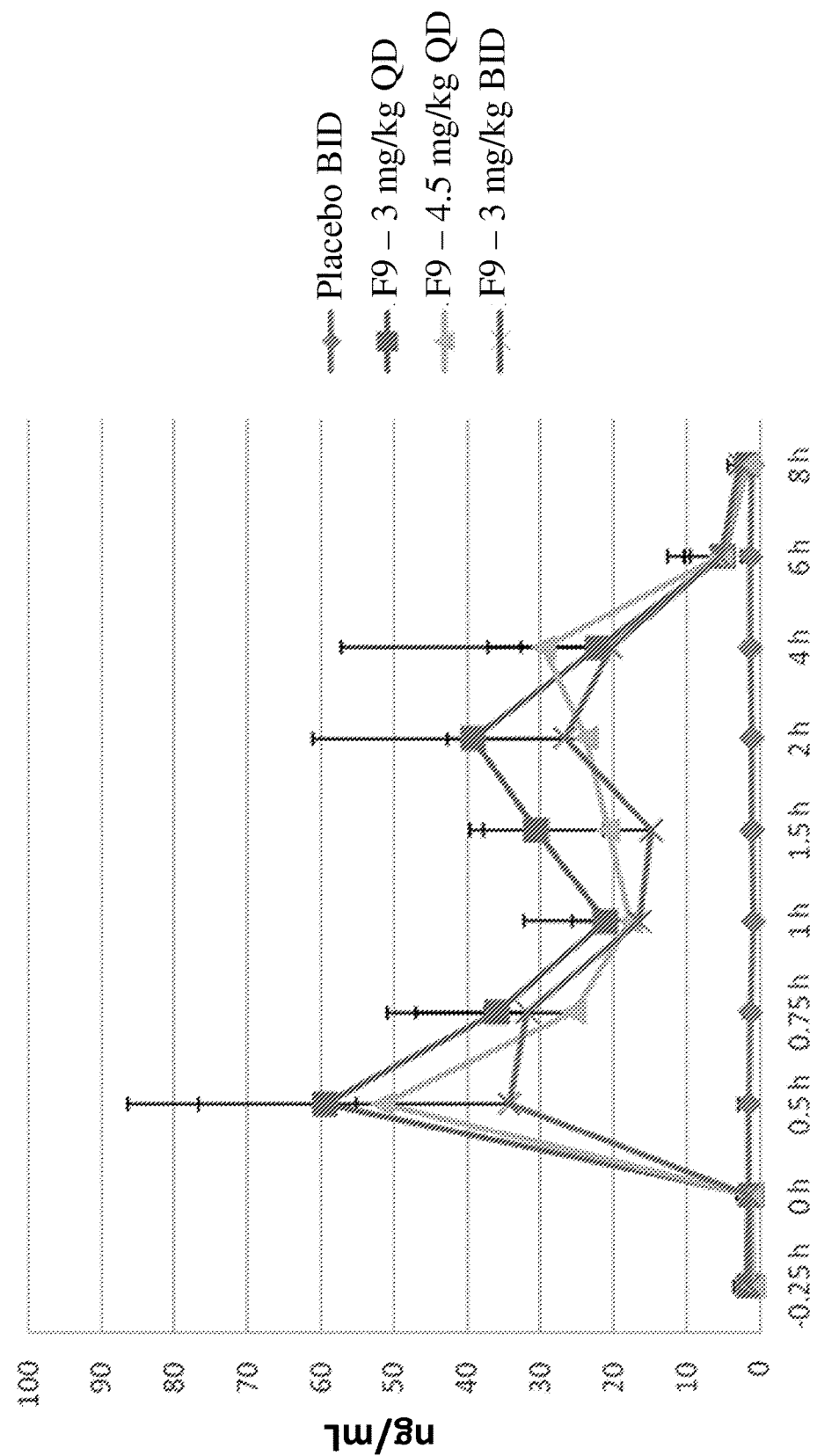
FIG. 67 is a line graph depicting serum concentrations of growth hormone in animals on Day 1 after being treated with different concentrations and treatment regimens of a capromorelin composition.
Figure 68:
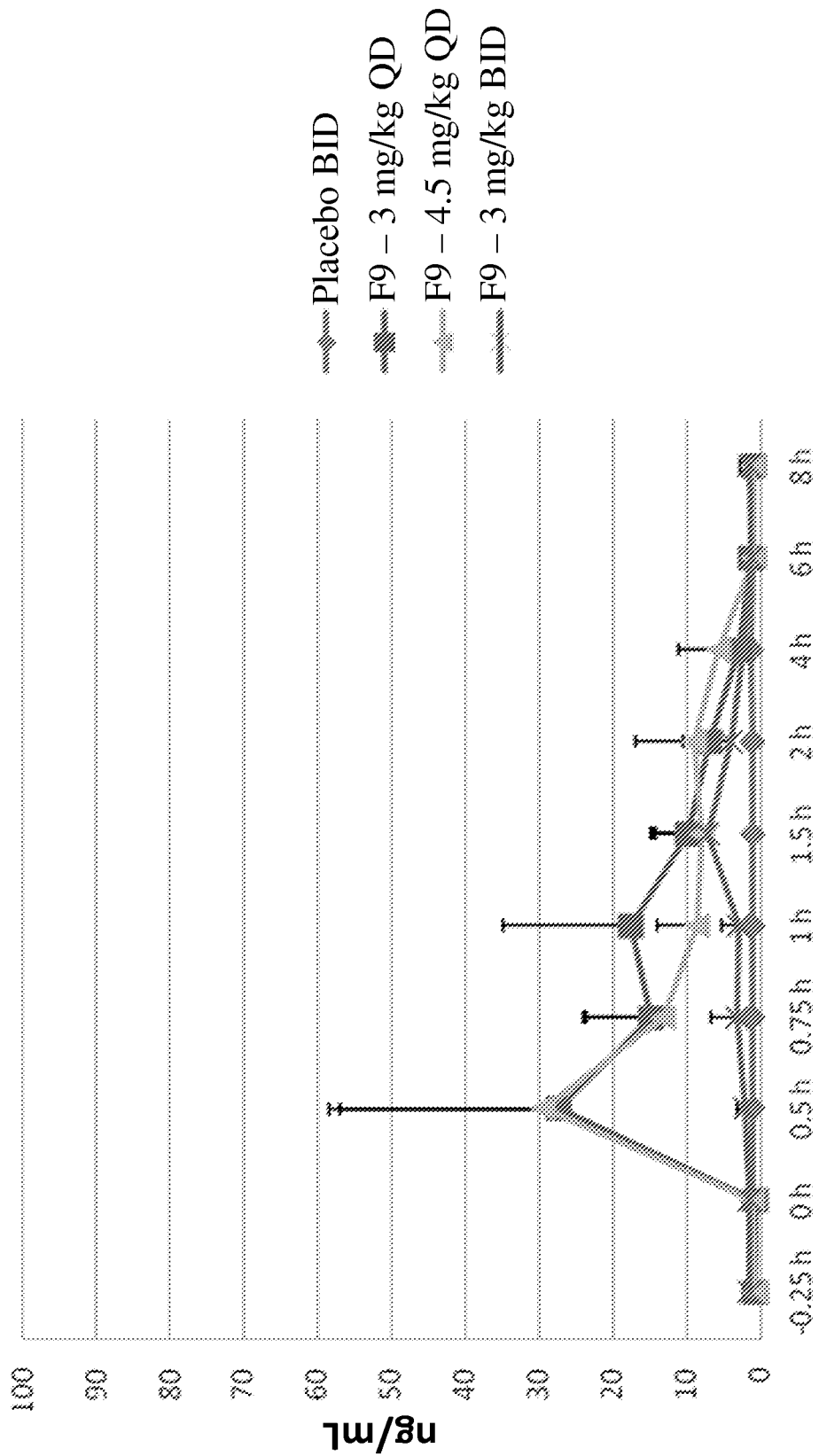
FIG. 68 is a line graph depicting serum concentrations of growth hormone in animals on Day 4 after being treated with different concentrations and treatment regimens of a capromorelin composition.
Figure 69:
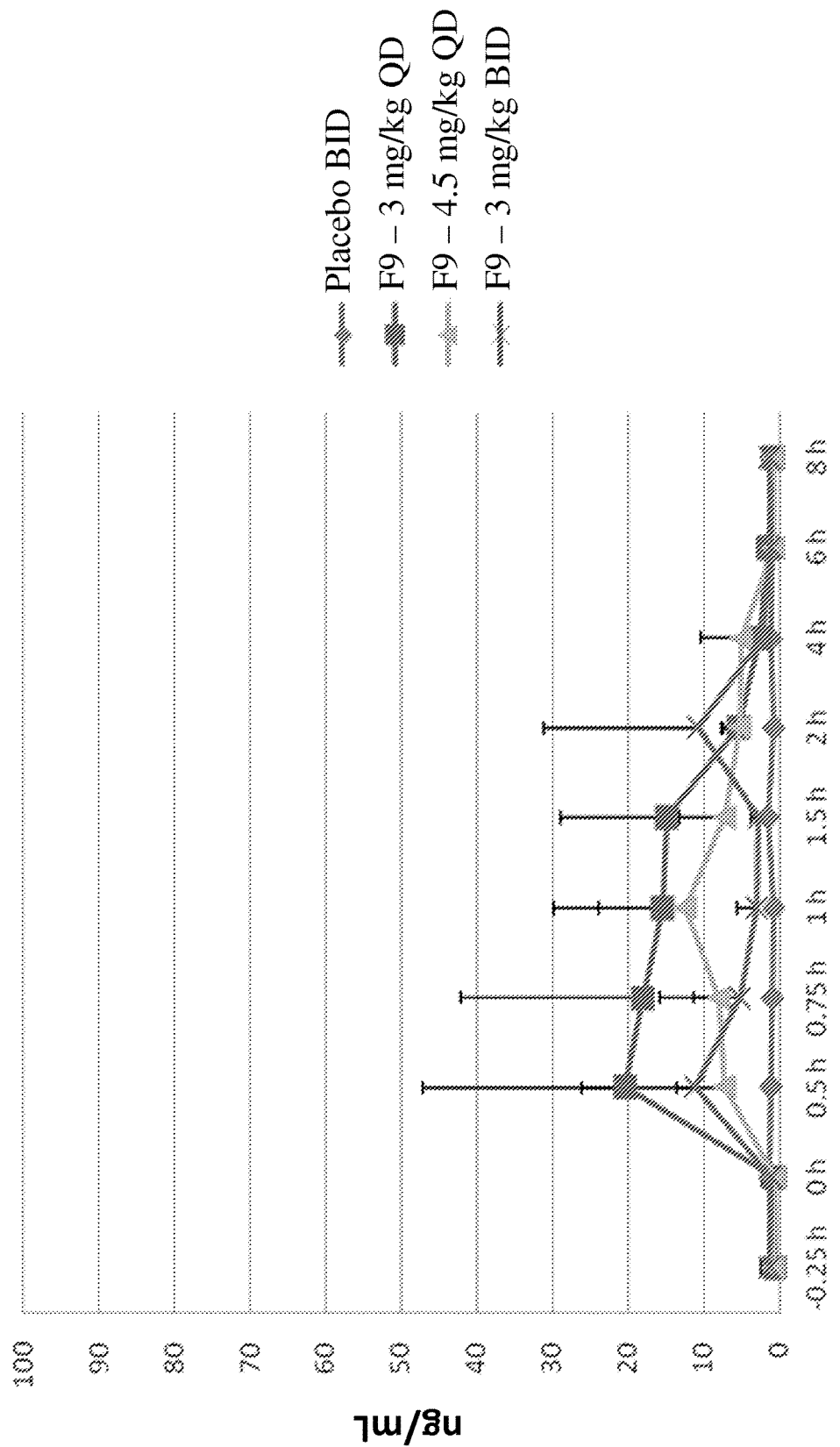
FIG. 69 is a line graph depicting serum concentrations of growth hormone in animals on Day 7 after being treated with different concentrations and treatment regimens of a capromorelin composition.

Similarly, as shown in FIGS. 64A-74, the levels of IGF-1, growth hormone, and cortisol increased as a result of capromorelin administration. In particular, as shown in FIGS. 64A-66, the IGF-1 levels in the control animals remained near baseline throughout the study. However, the animals in Groups 2-4 experienced increases in the amounts of IGF-1 present in the serum on Days 1, 4, and 7. Moreover, the IGF-1 levels exhibited a sustained increase over a twenty-four hour period in the treated animals by Day 4 (FIG. 64B) and remained elevated on Day 7. Furthermore, the animals receiving the twice-daily administrations (Group 4) exhibited the highest sustained increase, but it appeared that there was little difference in the sustained levels of IGF-1 between Groups 2 and 3. Finally, the data in FIG. 66 shows that the IGF-1 levels remained slightly elevated after the treatment had been ceased for 2 days (i.e., on Day 9).

Figure 70:
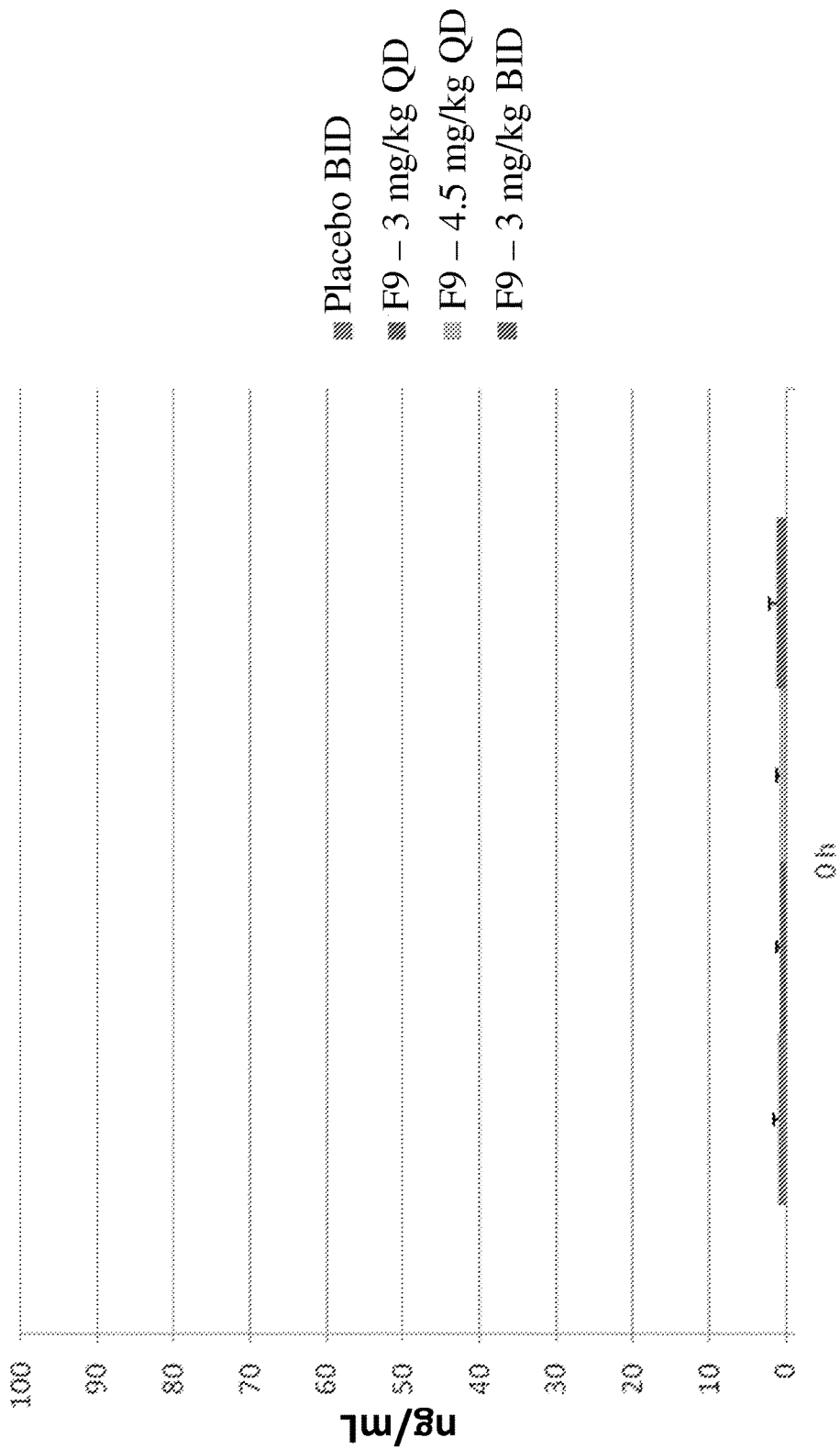
FIG. 70 is a bar graph depicting serum concentrations of growth hormone in animals after seven days of treatment with treatment regimens of a capromorelin composition and two days without treatment (i.e., day 9).
Figure 71:
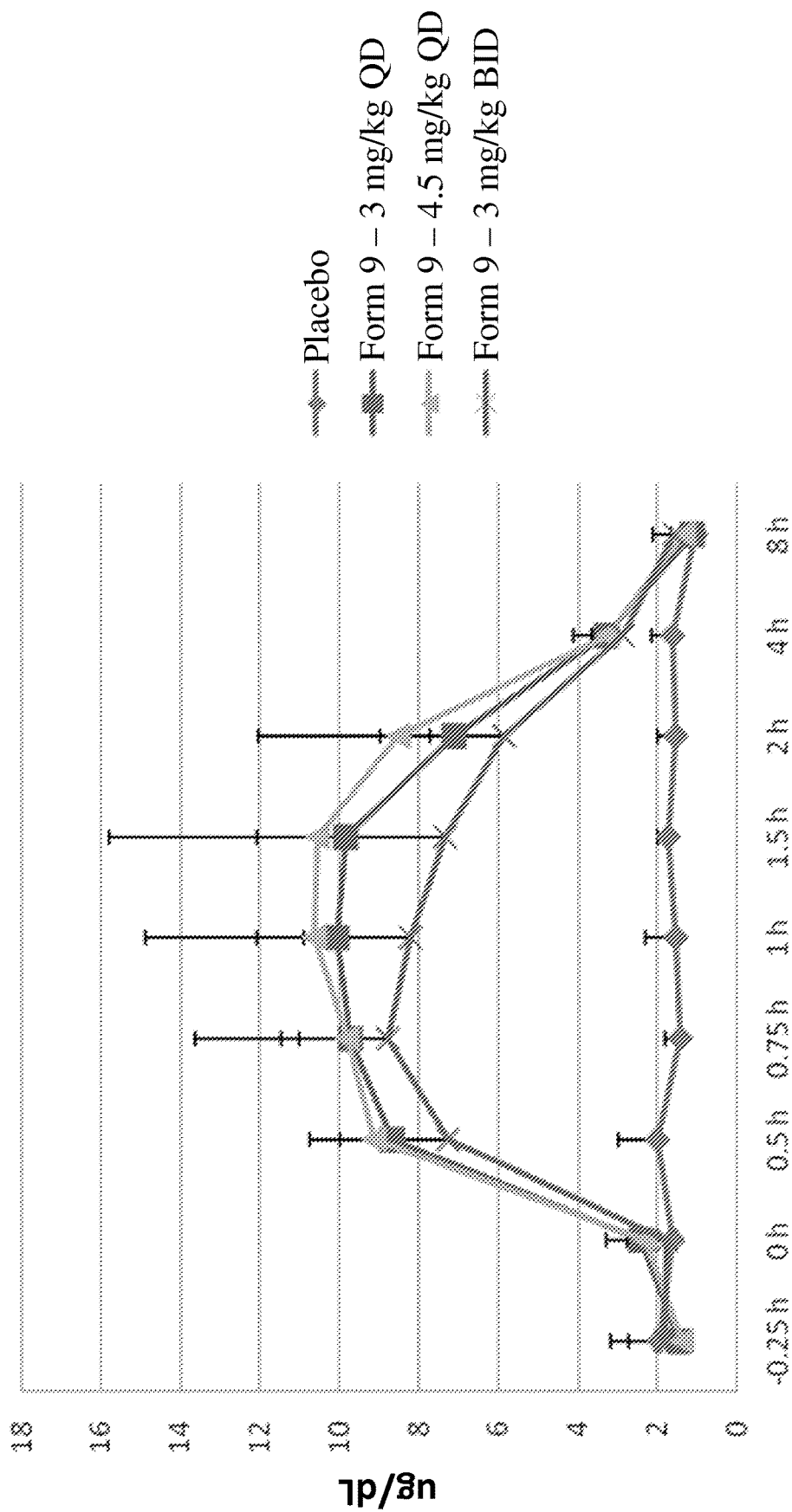
FIG. 71 is a line graph depicting serum concentrations of cortisol in animals on Day 1 after being treated with different concentrations and treatment regimens of a capromorelin composition.
Figure 72:
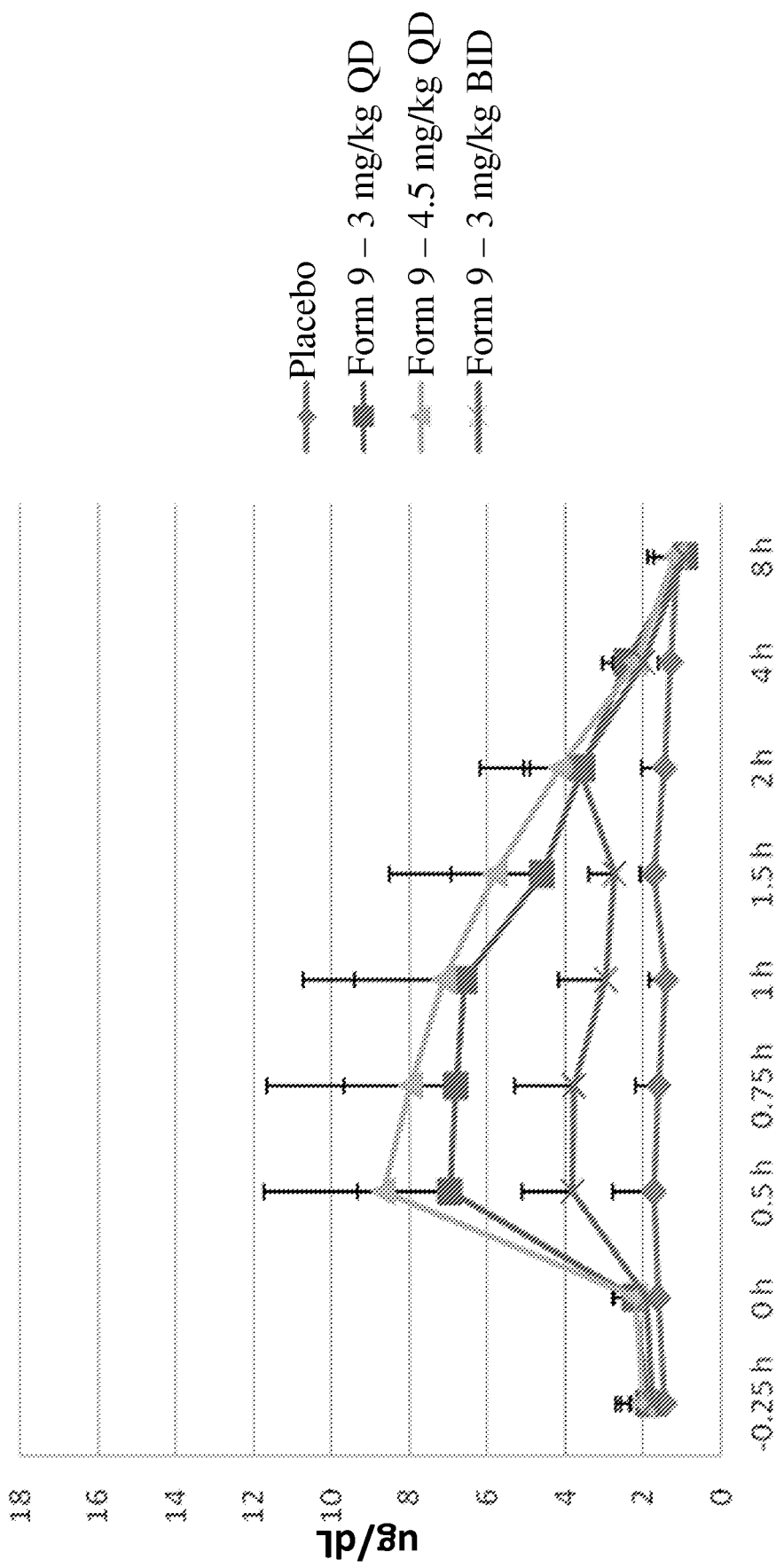
FIG. 72 is a line graph depicting serum concentrations of cortisol in animals on Day 4 after being treated with different concentrations and treatment regimens of a capromorelin composition.
Figure 73:
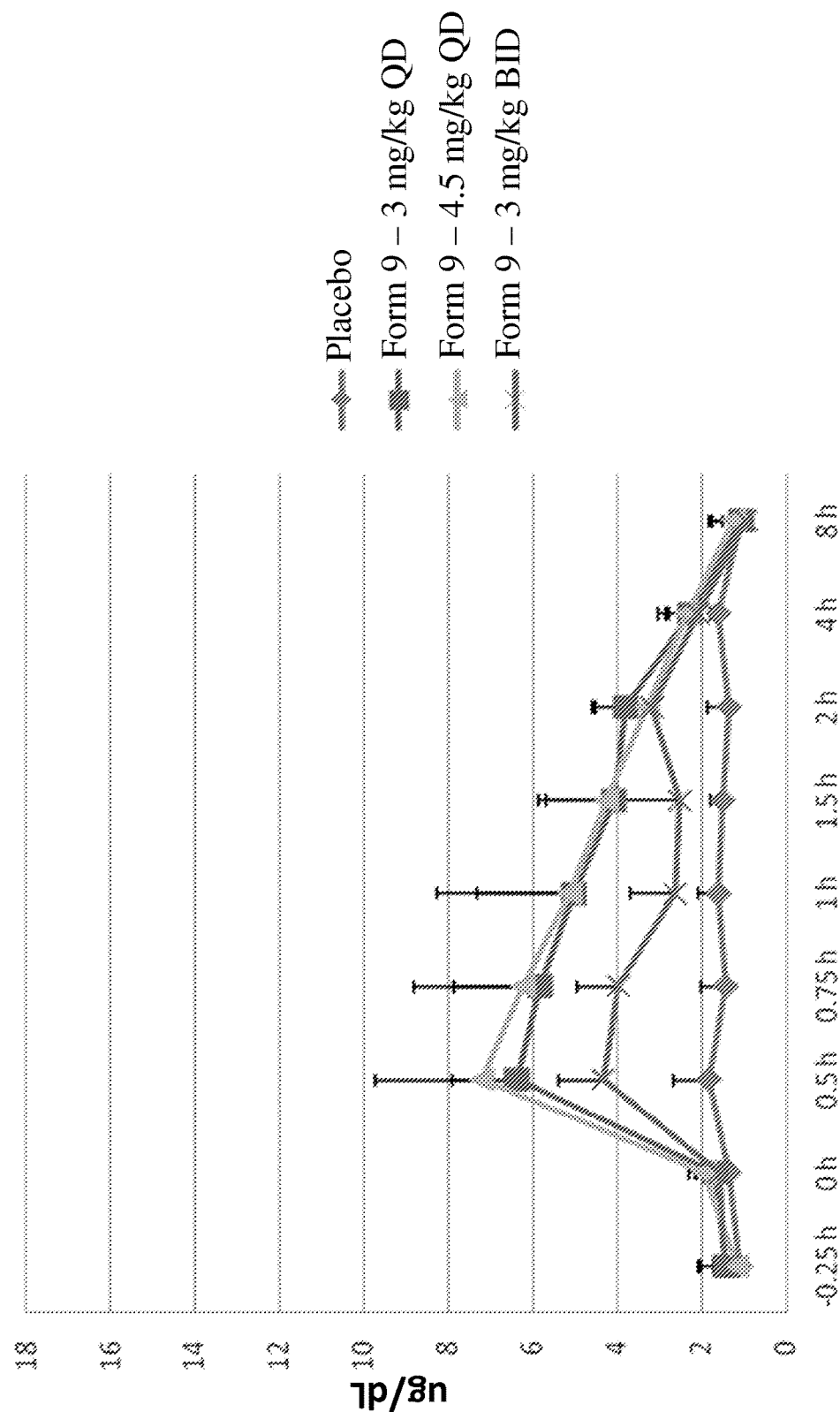
FIG. 73 is a line graph depicting serum concentrations of cortisol in animals on Day 7 after being treated with different concentrations and treatment regimens of a capromorelin composition.

As shown in FIGS. 67-70, Groups 2-4 experienced initial increases in the serum concentration of growth hormone. In particular, the level of growth hormone in the Group 1 animals remained near baseline for the duration of the experiment. However, the animals that received capromorelin experienced an increase in growth hormone in the serum on Day 1 (FIG. 67), which was mitigated by Day 4 (FIG. 68), further reduced by Day 7 (FIG. 69), and not detected after the conclusion of the experiment (Day 9; FIG. 70).

Figure 74:
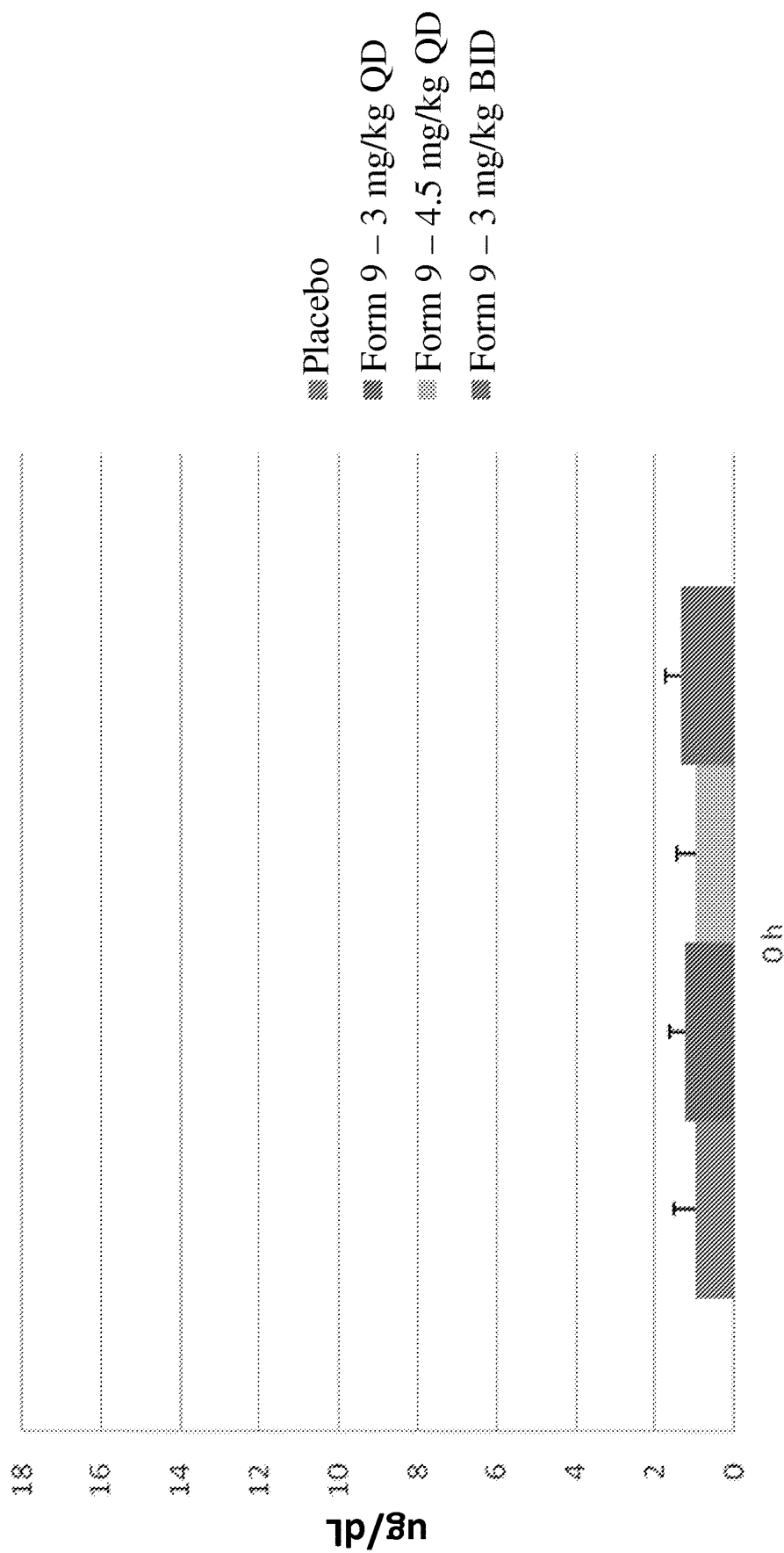
FIG. 74 is a bar graph depicting serum concentrations of cortisol in animals after seven days of treatment with treatment regimens of a capromorelin composition and two days without treatment (i.e., day 9).

Finally, as shown in FIGS. 71-74, treatment with capromorelin also resulted in initially increased levels of cortisol. In particular, the level of cortisol in the Group 1 animals remained near baseline for the duration of the experiment. However, the animals that received capromorelin experienced an initial increase in cortisol in the serum on Day 1 (FIG. 71), which was mitigated by Day 4 (FIG. 72), further reduced by Day 7 (FIG. 73), and not detected after the conclusion of the experiment (Day 9; FIG. 74). Interestingly, it appears that the cortisol profile was best mitigated in the Group 4 animals, but there was no significant difference between the Group 2 and Group 3 animals.

Overall, based on the results discussed above, the experimental formulations were well-accepted by the animals. These results demonstrate that administration of the capromorelin-containing compositions in dogs resulted in a measurable serum profile of capromorelin at all doses tested. Moreover, although the number of animals was small and the duration was short, there was a trend in Groups 2-4 of increased body weight and food intake. In addition, there did not appear to be differences in groups dosed once or twice per day in Groups 2-4. Accordingly, based on these experiments and the data presented in prior examples, it appears that a single dose of capromorelin between about 3 and about 4 mg per kg of body weight could be an effective dosage.

EXAMPLE 6

Refining Dog Acceptability/Palatability of the Capromorelin Composition

After some of the aforementioned experiments and data not shown, additional experiments were conducted to further refine the formulation based on animal acceptability/palatability. In particular, experiments were conducted using the following formulations:

| Formulation 2 | |
|---|---|
| Ingredient | % weight per volume |
| Capromorelin | 3.10 |
| Citric Acid (Anhydrous) | 0.70 |
| Sodium Citrate | 0.50 |
| Sodium Chloride | 0.70 |
| Methyl 4-Hydroxybenzoate Salt | 0.045 |
| Propyl 4-Hydroxybenzoate Salt | 0.005 |
| Sucralose | 0.70 |
| MagnaSweet Plus Liquid | 0.50 |
| Vanillin | 0.10 |
| Neosorb Sorbitol 70% | 30.00 |
| Maltitol Solution (Lycasin 80/55) | 25.00 |
| Glycerol Anhydrous | 20.50 |
| Kollidon 90F (PVP) | 1.5 |
| Purified Water | q.s. |

| Formulation 9 | |
|---|---|
| Ingredient | % weight per volume |
| Capromorelin | 3.10 |
| Citric Acid (Anhydrous) | 0.70 |
| Sodium Citrate | 0.50 |
| Sodium Chloride | 0.70 |
| Methyl 4-Hydroxybenzoate Salt | 0.045 |
| Propyl 4-Hydroxybenzoate Salt | 0.005 |
| Thaumatin T200X | 0.60 |
| *Stevia* Extract Rebaudioside A 99% | 0.70 |
| MagnaSweet Plus Liquid | 0.50 |
| Vanillin | 0.20 |
| Neosorb Sorbitol 70% | 30.30 |
| Maltitol Solution (Lycasin 80/55) | 25.00 |
| Glycerol Anhydrous | 20.20 |
| Kollidon 90F (PVP) | 1.5 |
| Ethanol (ABS) | 0.50 |
| Purified Water | q.s. |

In these experiments, testing was conducted to evaluate Formulation 2 versus Formulation 9 at a 4 mg/kg of body weight, once-per-day treatment regimen. In particular, this study was conducted to measure capromorelin concentrations in the serum, as well as measurements of food intake and weight change. In these experiments, sixteen adult (male and female) Beagle dogs weighing approximately 9 to 13 kgs were randomly divided into two treatment groups, Group 1 received Formulation 9 once per day and Group 2 received Formulation 2 once per day.

In these experiments, the animals were orally administered the different formulations at approximately 8:00 AM. The animals were fed at 10:00 AM beginning seven days prior to Day 1 and continuing for the duration of the study (5 days). The animals were offered twice the normal amount of food. Approximately two hours after the food offering, the remainder was removed and weighed to assess food intake. This restricted feeding regime was started at Day −7 to allow the animals to transition to a normal feed intake before the study was initiated. Food consumption was calculated and recorded on Days −7 through Day 5. Baseline food consumption was calculated for each individual dog as the average number of grams of food consumed on Days −3, −2, and −1. The study period food consumption was calculated for each individual dog as the average of Days 1 through 5. Body weights were collected on Days −1 and 5. Blood was collected for measurements of capromorelin and IGF-1 concentrations on Day 5 at about 15 minutes pre-administration, immediately prior to dosing (0 minutes), 30, 60, 120, 240, and/or 480 minutes post dosing. As reflected by the data in FIGS. 75-78, the animals' response showed positive signs when administered both compositions.

Figure 75:
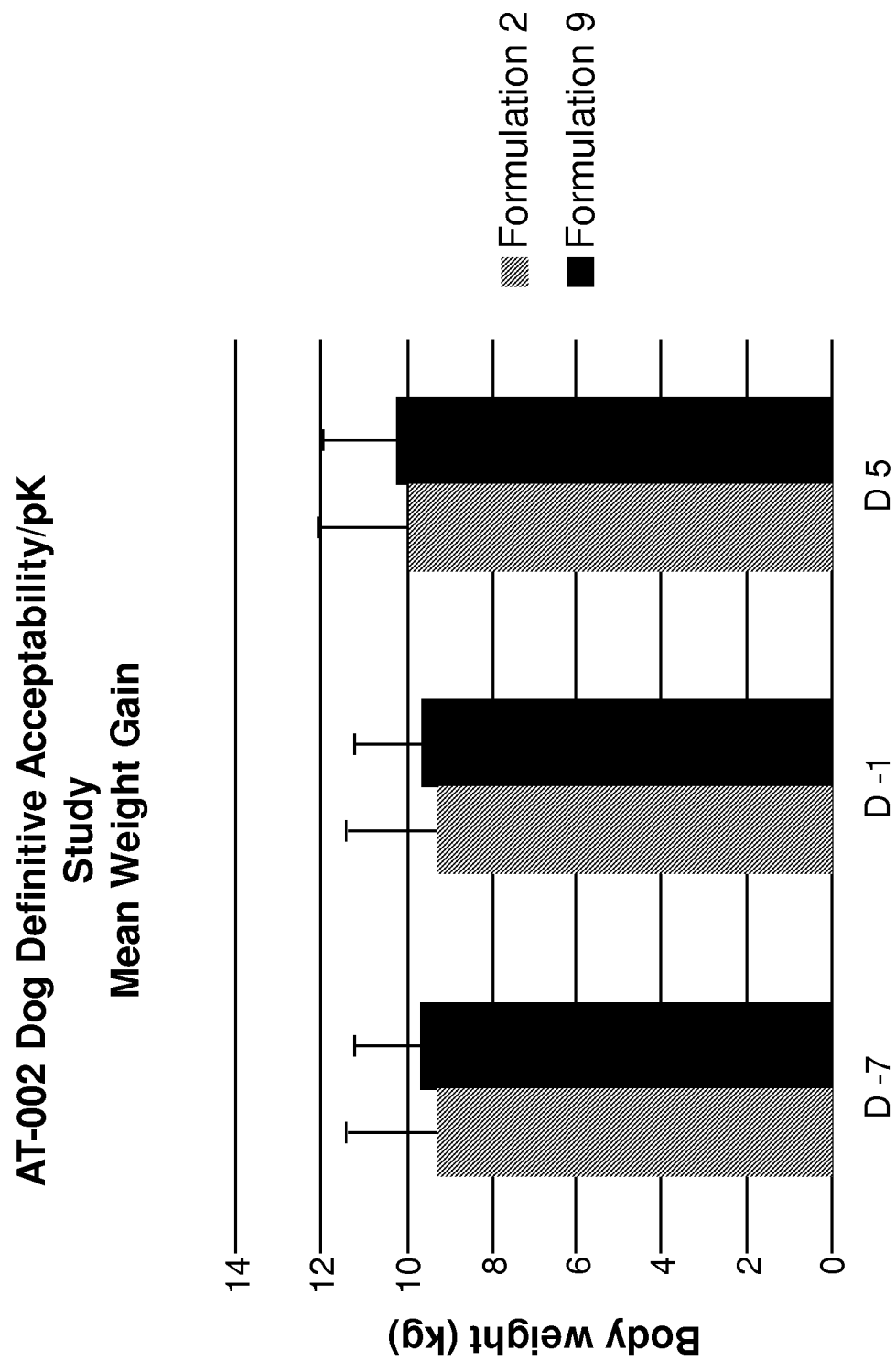
FIG. 75 is a bar graph depicting mean weight gain in animals during a five-day study comparing two formulations of a capromorelin-containing composition.
Figure 76:
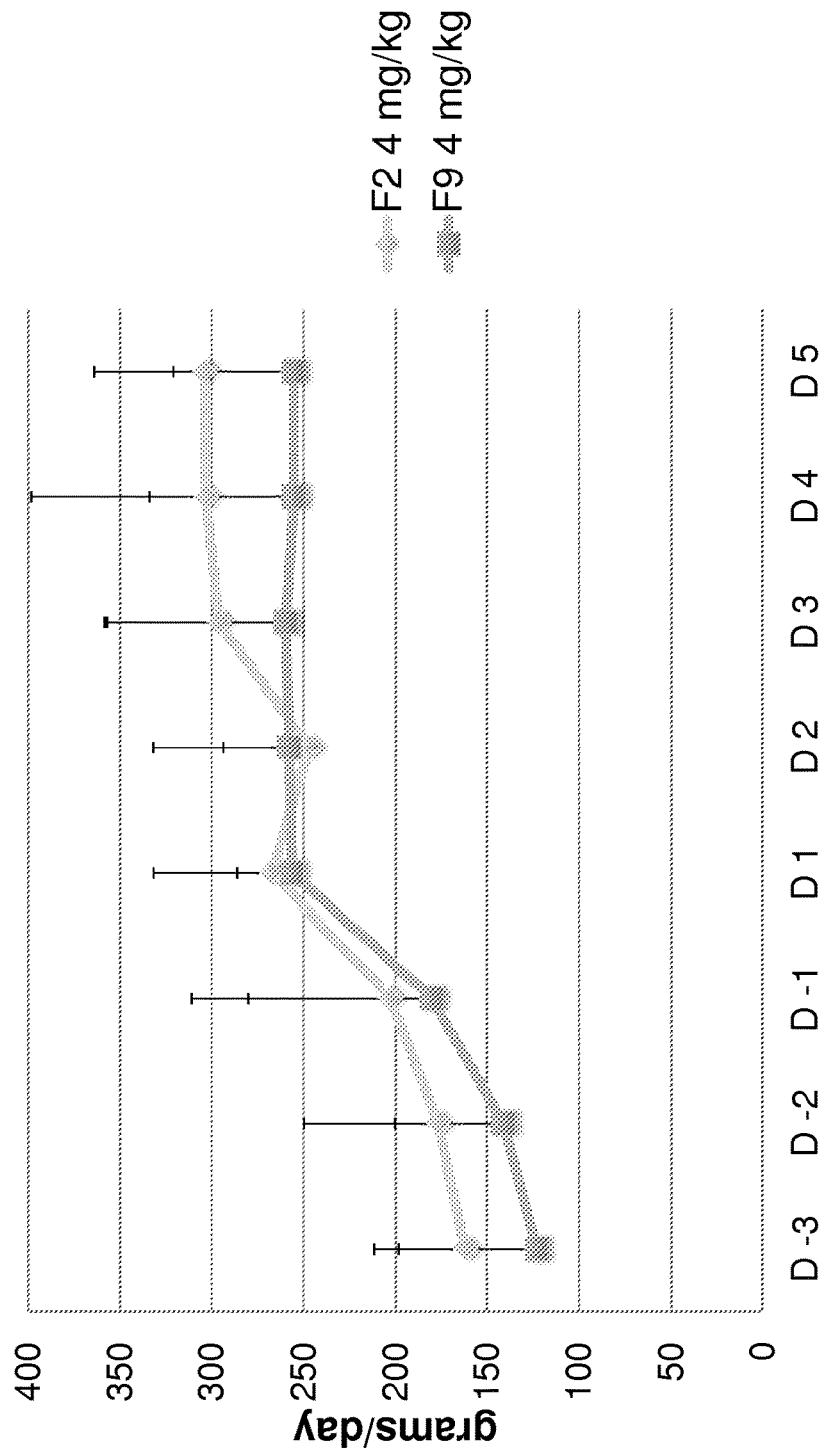
FIG. 76 is a line graph depicting food consumption by animals during a five-day study comparing two formulations of a capromorelin-containing composition.
Figure 77:
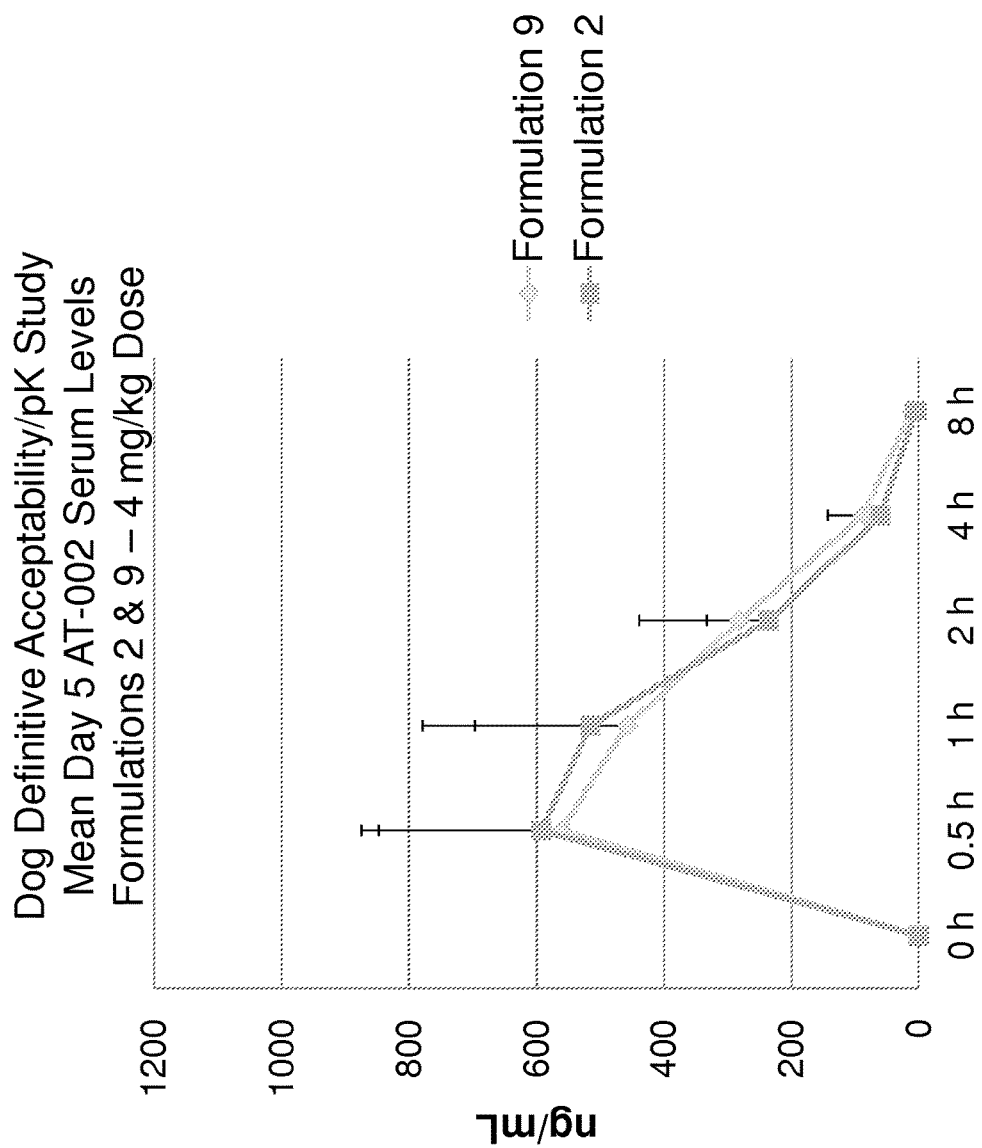
FIG. 77 a line graph depicting mean serum concentrations of capromorelin in animals on Day 5 after being treated with two formulations of a capromorelin-containing composition.
Figure 78:
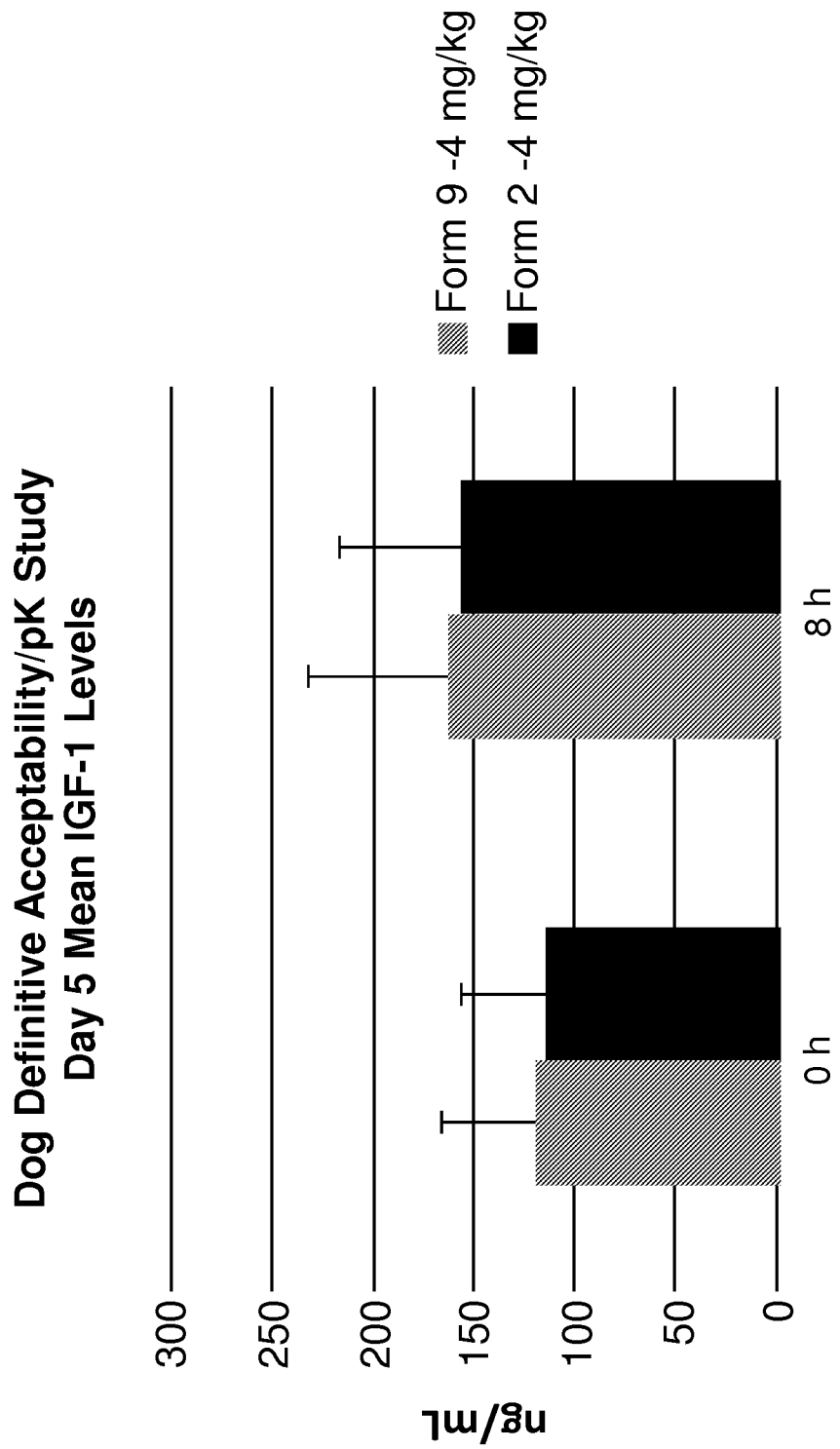
FIG. 78 is a bar graph depicting mean serum IGF-1 concentrations in animals on Day 5 after being treated with two formulations of a capromorelin-containing composition.

In particular, as shown in FIGS. 75 and 76, both formulations induced weight gain and increased food consumption over the course of the study. First, as shown in FIG. 75, although throughout the experiment the body weights of the animals were greater in the group receiving Formulation 9, a greater increase in body weight was seen in animals receiving Formulation 2. Specifically, animals receiving Formulation 2 exhibited an approximately 7.84% increase in body weight on Day 5, relative to Day −1, while animals receiving Formulation 9 exhibited an approximately 6.5% increase in body weight over the same time period. Similarly, as shown in FIG. 76, both groups of animals also consumed increased amounts of food over the course of the five-day experiment. In particular, relative to Days −3 to −1, over the course of the five day experiment, the dogs that received Formulation 9 consumed 73.5% more food and the dogs that received Formulation 2 consumed 56.9% more food. In addition, as shown in FIGS. 77 and 78, capromorelin and increased IGF-1 concentrations were detectable in the sera of the animals. Overall, based on the data discussed above, it appears that either Formulation 2 or 9 could function as vehicle to deliver the capromorelin-containing composition.

EXAMPLE 7

Dog Dose Titration Study

Additional experiments were performed in order to further refine the dosage administered to the dogs to provide the desired response (i.e., increased body weight and increased food consumption). In particular, the dogs received either Formulation 2 from Example 6 above or a placebo form of the same Formulation. In these experiments, the dogs were divided into five groups, with each group having three males and three females. The groups were divided by dosing concentration. Specifically, the first group received the placebo formulation once per day, the second group received Formulation 2 that was administered at a dose of 0.33 mg/kg once per day, the third group received Formulation 2 that was administered at a dose of 2.0 mg/kg once per day, the fourth group received Formulation 2 that was administered at a dose of 3.0 mg/kg once per day, and the fifth group received Formulation 2 that was administered at a dose of 4.0 mg/kg once per day.

In these experiments, the animals were orally administered the formulation at approximately 8:00 AM. The animals were fed at 10:00 AM beginning 10 days prior to Day 1 and continuing for the duration of the study (7 days). Approximately two hours after the food offering, the remainder was removed and weighed to assess food intake. This feeding regime was started at Day −10 to allow the animals to transition to a normal feed intake before the study was initiated. Food consumption was calculated and recorded on Days −3 through Day 7. Baseline food consumption was calculated for each group of dogs as the average number of grams of food consumed on Days −3, −2, and −1. The study period food consumption was calculated for each group of dogs as the average of study Days 1 through 7. Body weights were collected on Days 1 (immediately prior to dosing) and 8 (following an overnight fast). No blood was collected for during this experiment.

Figure 89:
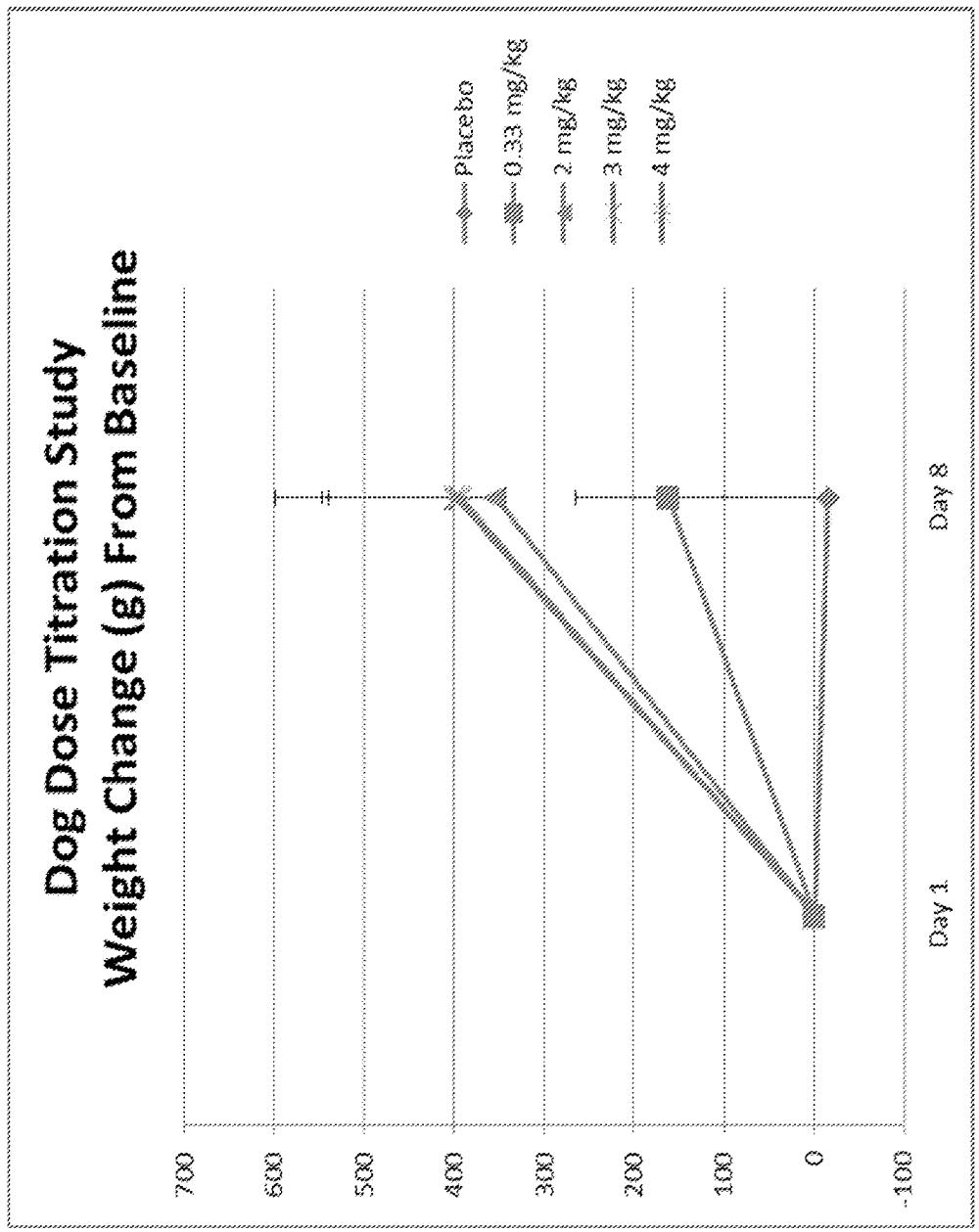
FIG. 89 is a line graph depicting body weight measurement of animals over the on Days 1 and 8 of an experiment in which the animals were treated with different doses of a formulation of a capromorelin composition.
Figure 90:
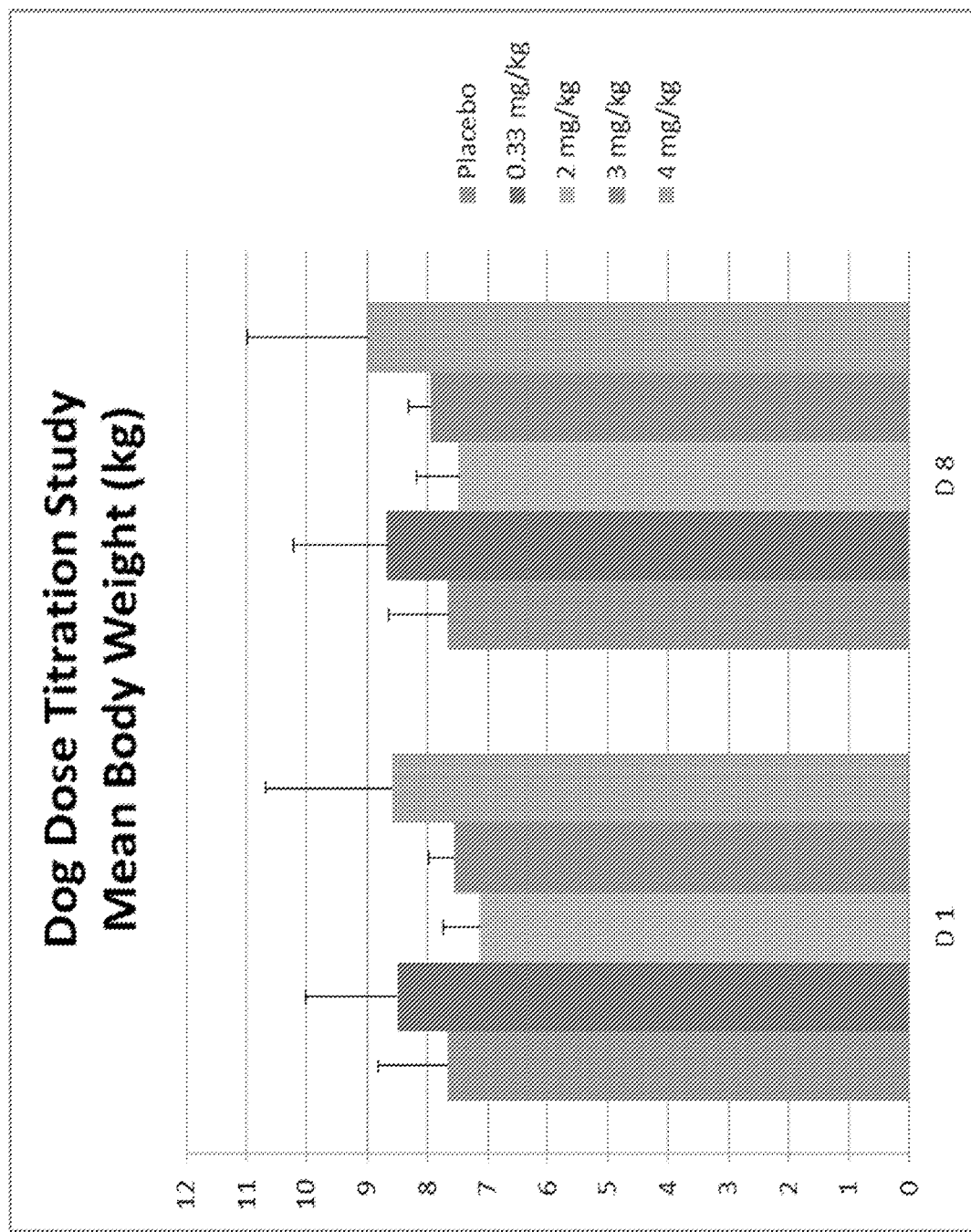
FIG. 90 is a bar graph depicting body weight measurement of animals over the on Days 1 and 8 of an experiment in which the animals were treated with different doses of a formulation of a capromorelin composition.

As reflected by the data in FIGS. 89 and 90, the animals' response showed positive signs when administered nearly all of the doses. In particular, as best seen in FIG. 89, the body weights increased in all of groups of dogs that received Formulation 2. Interestingly, the body weights of the animals in the placebo group slightly decreased. As viewed a different way, the percent change in body weights went up in all animals that received Formulation 2, as seen in Table 2. In addition, using statistical analyses, it was shown that, relative to placebo, all treatments except for the 0.33 mg/kg, produced statistically significant increases in body weight values.

TABLE 2

Weight Change

| Treatment | Comparison of Weight on Day 1 to Weight on Day 8 |
| --- | --- |
| Placebo - 1x per day | −0.26% |
| Formulation 2 - 0.33 mg/kg 1x per day | 1.88% |
| Formulation 2 - 2.0 mg/kg 1x per day | 4.91% |

TABLE 2-continued

Weight Change

| Treatment | Comparison of Weight on Day 1 to Weight on Day 8 |
| --- | --- |
| Formulation 2 - 3 mg/kg 1x per day | 5.29% |
| Formulation 2 - 4 mg/kg 1x per day | 4.54% |

Figure 91:
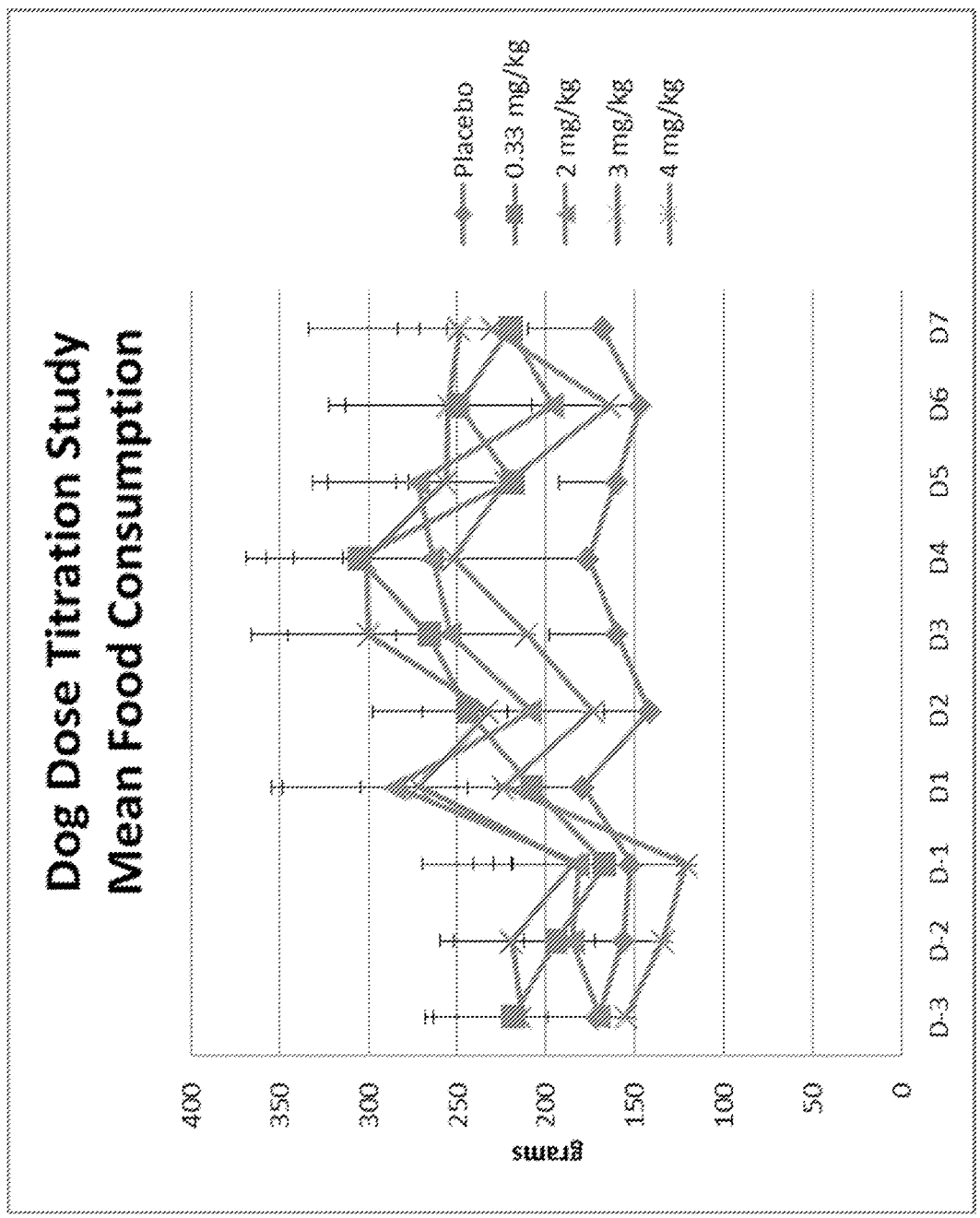
FIG. 91 is a line graph depicting measurements of food consumed by animals over the course of an experiment in which the animals were treated with different doses of a formulation of a capromorelin composition.
Figure 92:
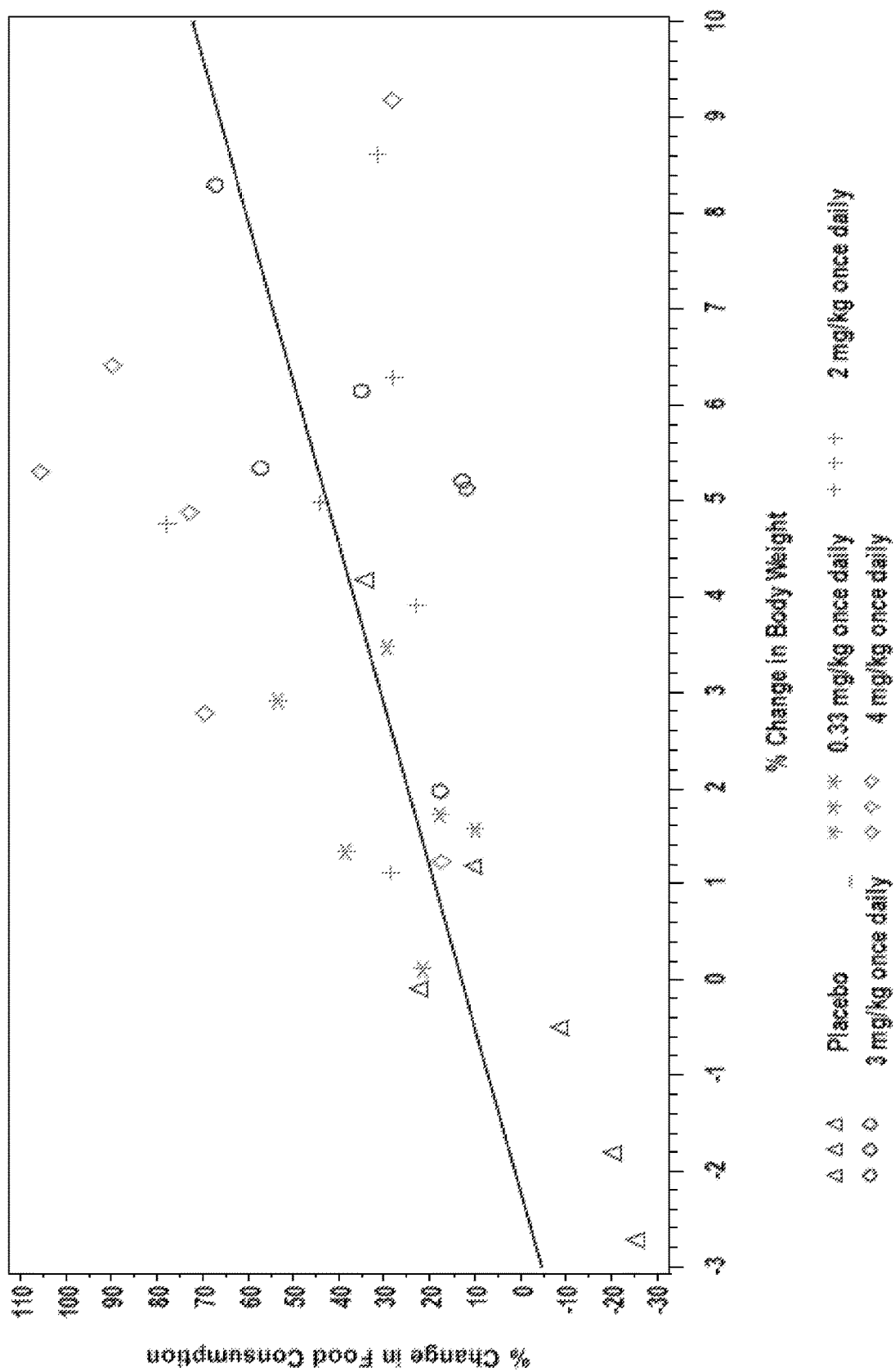
FIG. 92 is a line graph depicting the correlation between changes in food consumption versus changes in body weight for the experiments of FIGS. 89-91.

In addition, as shown in FIG. 91 and in Table 3 below, the average food consumption increased in the non-placebo groups when compared to baseline. Specifically, the baseline average was calculated by averaging the food consumed by the dogs on each of Days −3 to −1. Then, the food consumption average was calculated by taking the daily food consumption during the study period on Days 1 to 7. In particular, FIG. 91 generally shows an increase in the amount of food consumed by the animals receiving the non-placebo formulation. In addition, using statistical analyses, it was shown that, relative to placebo, the 4 mg/kg group consumed significantly more food. Moreover, referring to FIG. 92, the Pearson correlation coefficient for the percent change in food consumption versus the percent change in body weight was 0.585, which corresponds to a slope of 5.9%. As such, the increase in body weight was directly proportional to the increased food intake.

TABLE 3

Food Intake Change

| Treatment | Day −3 to −1 (Baseline Period) Average Food Consumption (Grams) | Day 1 to Day 7 (Study Period) Average Food Consumption (Grams) | Difference | % Food Consumption Change over Baseline |
| --- | --- | --- | --- | --- |
| Placebo - 1x per day | 159.89 | 161.76 | 1.87 | 1.17 |
| Formulation 2 - 0.33 mg/kg 1x per day | 193.33 | 244.55 | 51.22 | 26.49 |
| Formulation 2 - 2.0 mg/kg 1x per day | 178.89 | 242.83 | 63.94 | 35.74 |
| Formulation 2 - 3 mg/kg 1x per day | 205.83 | 266.48 | 60.65 | 29.47 |
| Formulation 2 - 4 mg/kg 1x per day | 136.72 | 210.93 | 74.21 | 54.28 |

EXAMPLE 8

Probe Formulation Study

Similar to the previously mentioned pharmacokinetic analysis conducted in dogs, a pharmacokinetic study was conducted in cats to assess capromorelin and IGF-1 concentrations in the serum after administration of different formulations. Briefly, twelve cats were randomized into Group A (six cats) and Group B (six cats). Group A received an IV formulation that included 0.75 mg/kg of capromorelin and Group B received the previously tested formulation 4 via oral gavage. Formulation 4 includes capromorelin at a concentration of 3 mg/kg. Serum samples were taken after administration of the two test formulations to assess capromorelin and IGF-1 concentrations. Samples were taken a time 0 (pre-administration) and 5 minutes, 10 minutes, 30 minutes, 1 h, 2 h, 4 h, 6 h, 8 h, and 12 h post administration.

Figure 47:
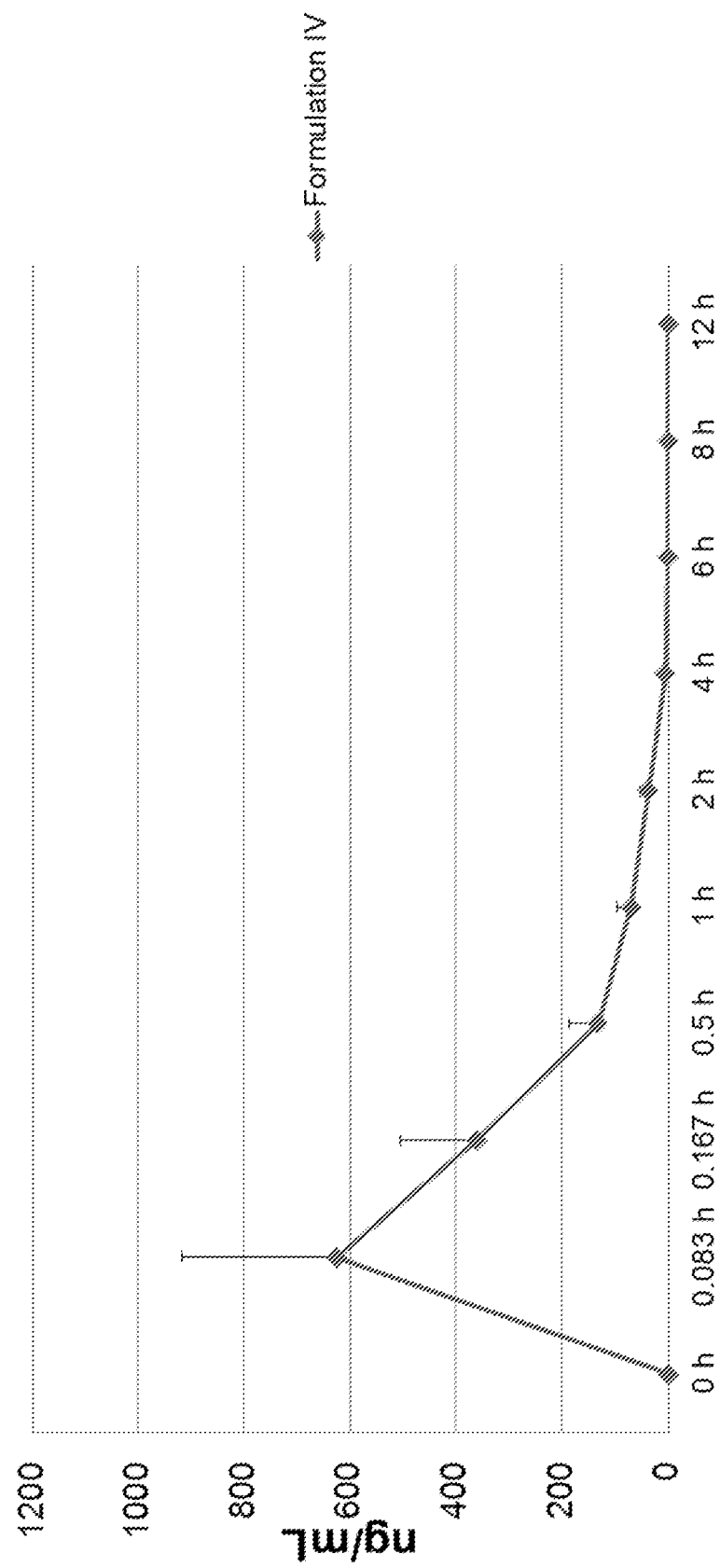
FIG. 47 is a line graph depicting serum concentrations of capromorelin over twelve hours in cats that have received an intravenous injection of 0.75 milligrams of capromorelin per kilogram of body weight.
Figure 48:
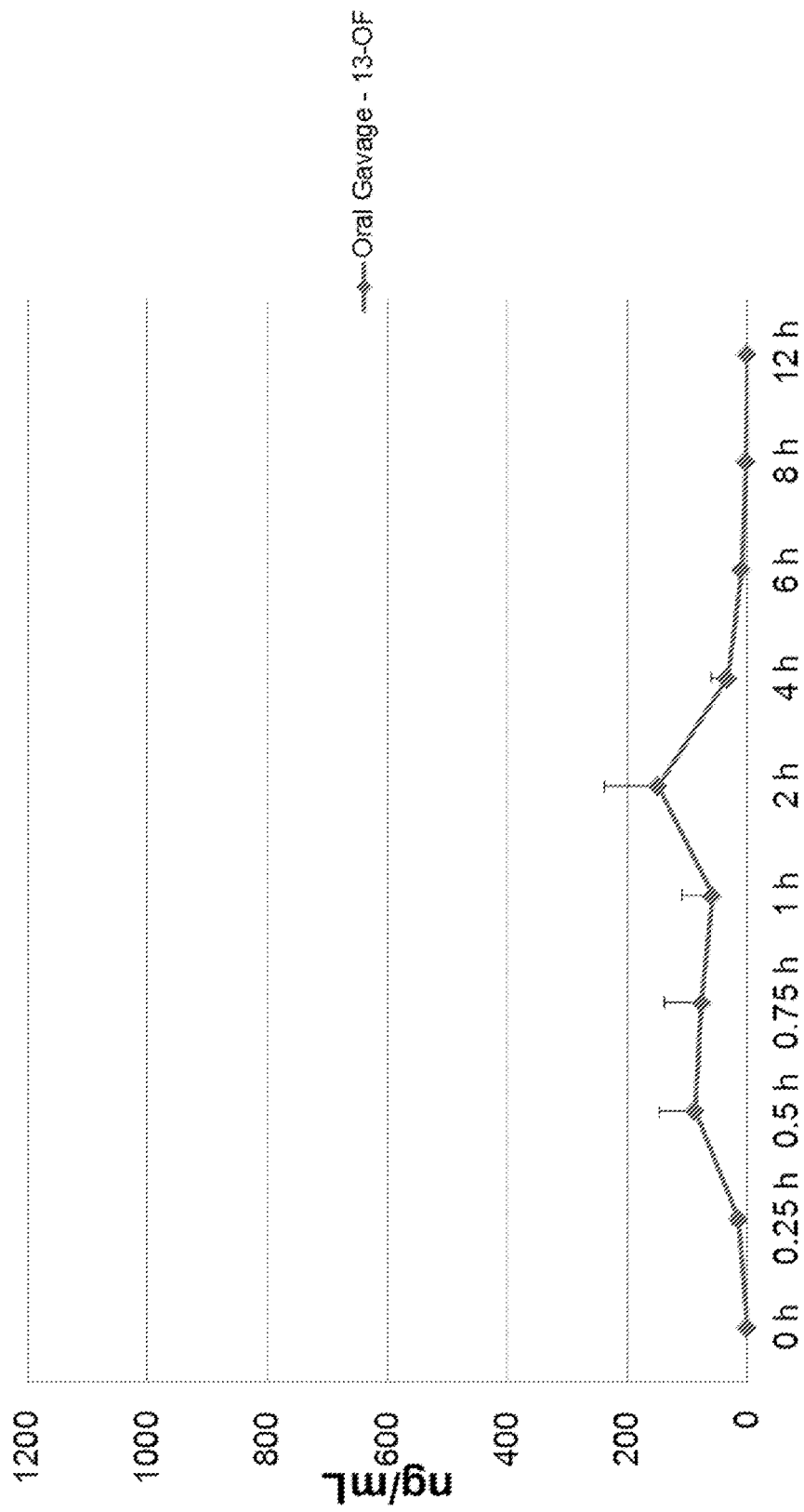
FIG. 48 is a line graph depicting serum concentrations of capromorelin over twelve hours in cats that have received an oral administration of 3 milligrams of capromorelin per kilogram of body weight.
Figure 49:
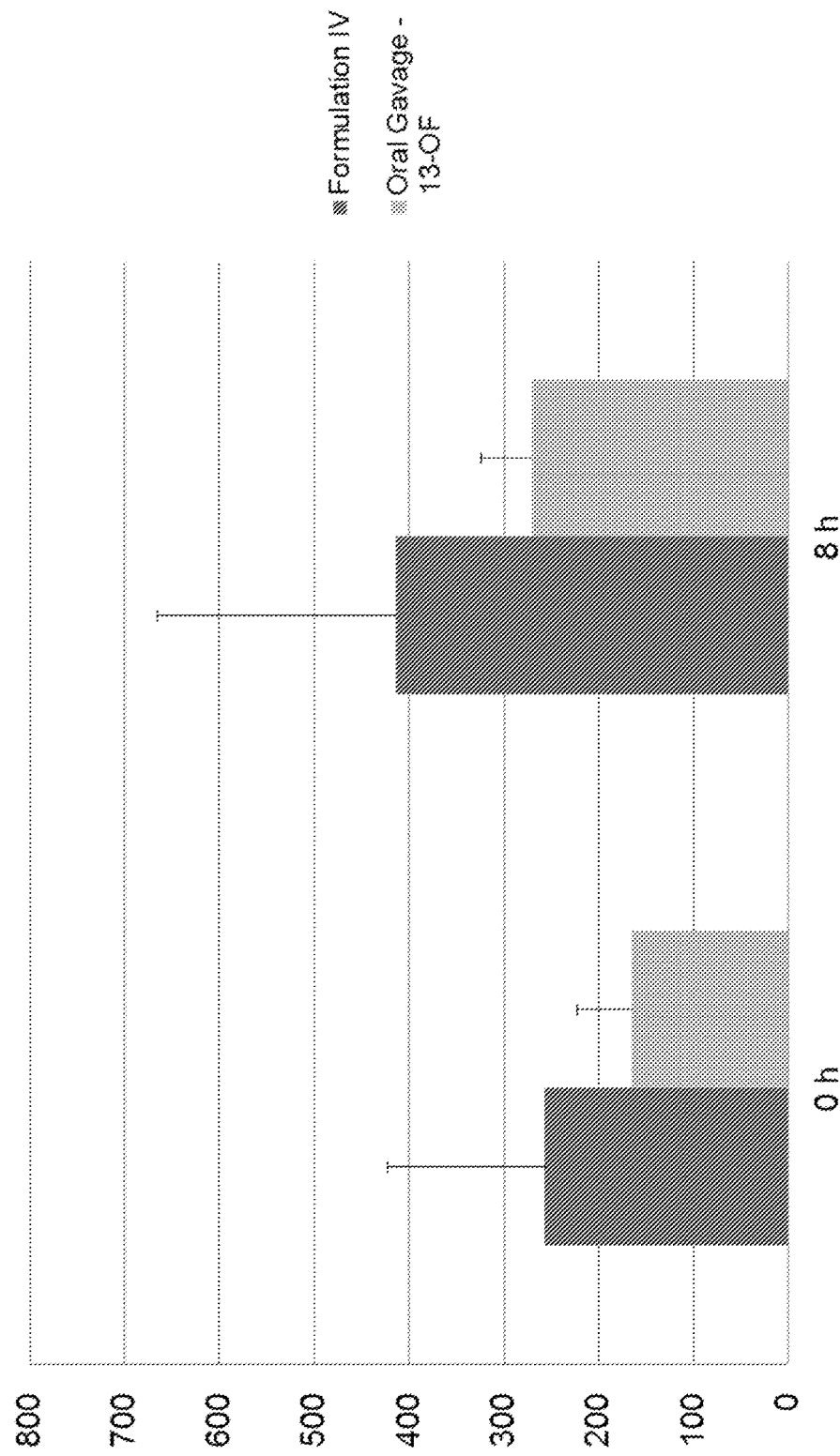
FIG. 49 is a bar graph depicting serum concentrations of insulin-like growth factor-1 in cats that have received the intravenous and oral administrations of capromorelin.

As shown in FIGS. 47 and 48, capromorelin compositions in cats do not exhibit the same pharmacokinetic profile as these compositions exhibit in dogs. In particular, as shown in FIG. 48, formulation 4, which was administered via oral gavage, produced a relatively low serum concentration of capromorelin, with the peak concentration occurring two hours after administration. The IV formulation, however, produced a serum concentration of capromorelin similar to what was observed in dogs. Specifically, the serum concentration of capromorelin increased relatively soon after administration (i.e., 5 minutes) and proceeded to decrease until the final samples were taken twelve hours after administration. In spite of the relatively low levels of oral bioavailability (formulation 4), IGF-1 is still induced eight hours after administration, as shown in FIG. 49. This disparity in bioavailability and IGF-1 expression could indicate a relatively large efficacy window for capromorelin to trigger an IGF-1-induced lean muscle response.

EXAMPLE 9

Refining the Dosing Regimen of the Inappetance-Controlling Compound Containing Capromorelin for Cats A four-day study was performed to further assess the pharmacokinetics of formulation 8 from Example 3 (i.e., the most "well-accepted" formulation) in cats. Moreover, the administration of formulation 8 was also analyzed to determine if administration of this formulation could induce sustained production of IGF-1 and relatively depressed, mitigated, or lower levels of cortisol. The different capromorelin-dosing regimens were also assessed for the impact on food intake and changes in body mass.

Twenty-four adult cats were divided into one of four treatment groups, with all four groups as active treatment groups. Each of the active treatment groups included 6 cats. The first group received a sterile injection of a capromorelin composition containing a 0.75 mg/kg concentration of capromorelin once per day during the four-day experiment. The second group received a once-daily sterile injection of a capromorelin composition at a concentration of 2 mg/kg. The third group received a once-daily dose of a capromorelin composition at a concentration of 2 mg/kg, via oral gavage. The fourth group received a once-daily dose of a capromorelin composition containing capromorelin at a concentration of 4 mg/kg, via oral gavage.

During the seven day study period, on an at least once-daily basis, each of the cats was monitored for clinical observations, mortality, moribundity, body mass, acceptability/palatability, and food consumption. Serum samples were taken to measure capromorelin concentration, IGF-1 concentration, and cortisol concentration. Serum samples were taken on days 1 and 4 immediately prior to dosing (0 minutes) and 30, 60, 90, 120, 240, 360, and/or 480 minutes post dosing. Additional serum samples were taken at 8 AM on Day 7 of the study to assess long-term impact of the active treatments.

Figure 50:
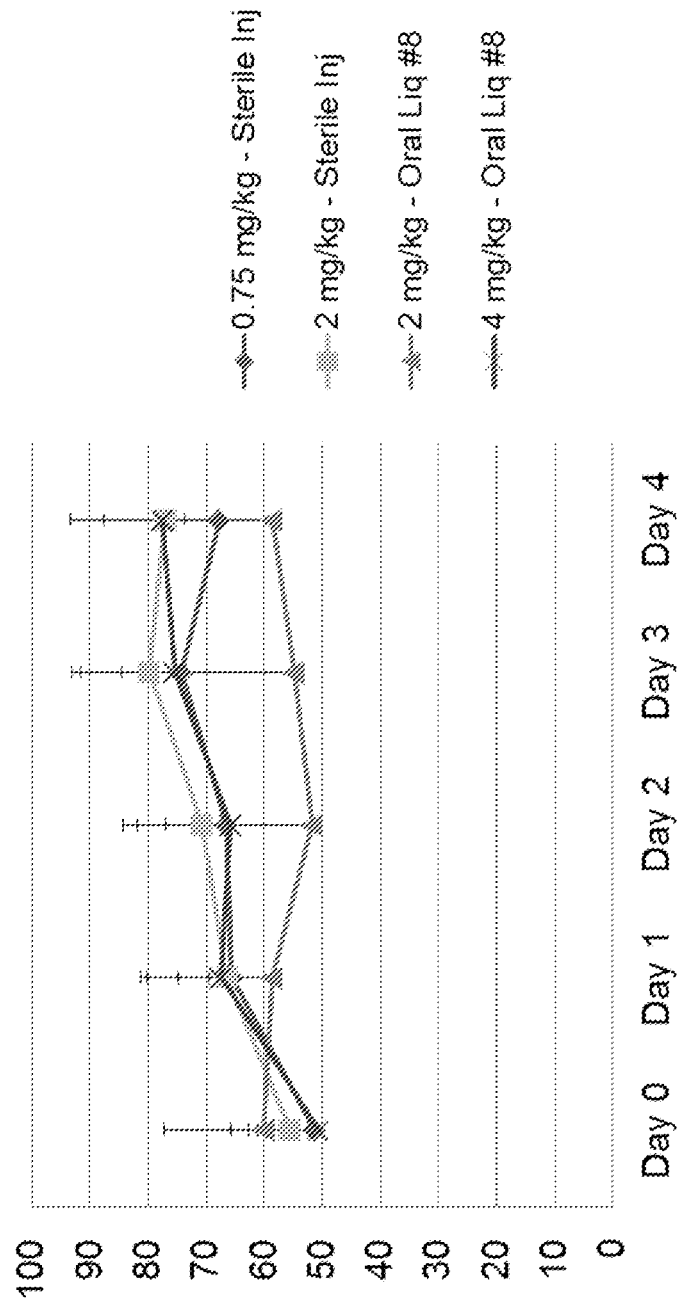
FIG. 50 is a line graph depicting the daily average food consumption by cats in response to receiving different concentrations and treatment regimens of a capromorelin composition.
Figure 51:
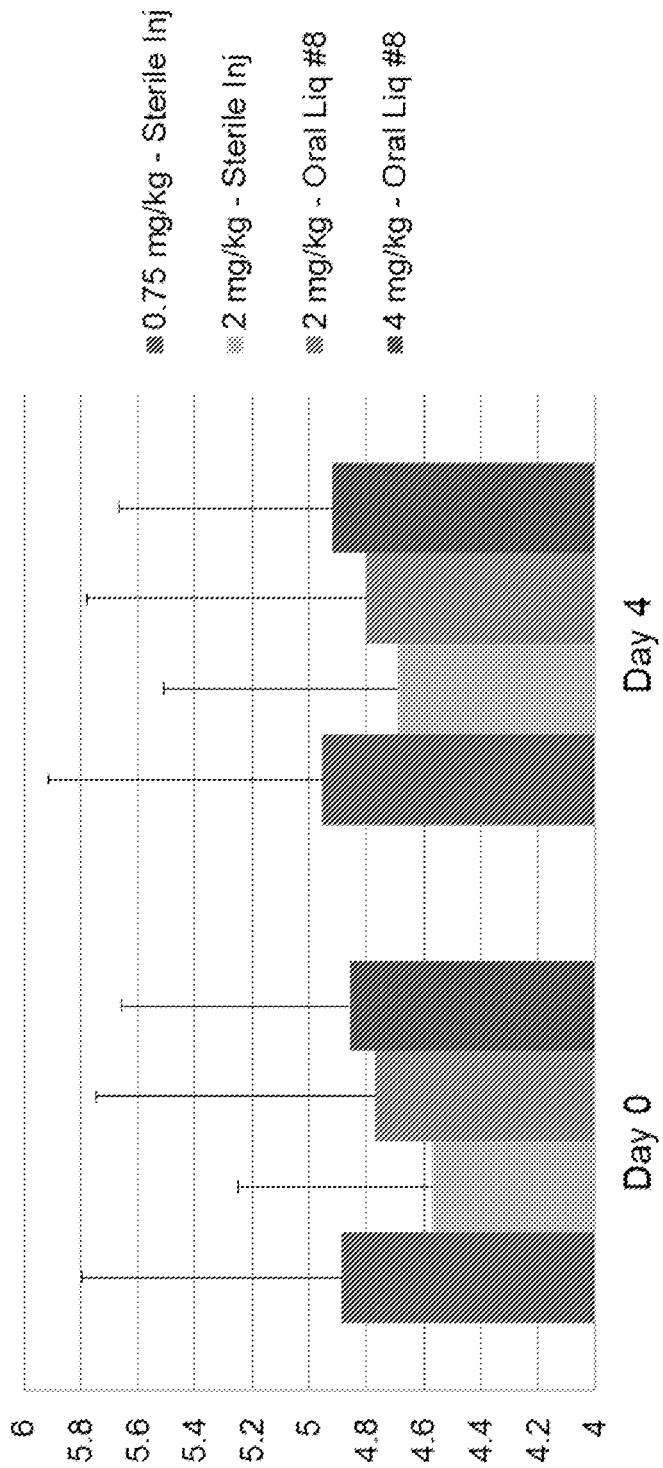
FIG. 51 is a bar graph depicting the average body weight of cats that have received different concentrations and treatment regimens of a capromorelin composition.

As indicated in FIGS. 50 and 51, over the course of the experiment, most of the cats consumed greater amounts of food and did not lose weight during the experiment. Specifically, as shown in FIG. 50, cats receiving the sterile injectable formulations or the 4 mg/kg oral gavage administration, consumed more food on day 4 of the experiment relative to prior days of the experiment. Similarly, as shown in FIG. 51, in general, the cats gained weight during the course of the experiment. For example, cats receiving the 0.75 mg/kg and the 2 mg/kg sterile injections of capromorelin exhibited a 1.33% and a 2.37% increase in body weight, respectively, relative to baseline measurements. Similarly, cats receiving the 2 mg/kg and 4 mg/kg oral administrations of capromorelin exhibited a 0.70% and a 1.47% increase in body weight, respectively, relative to baseline measurements.

Figure 52:
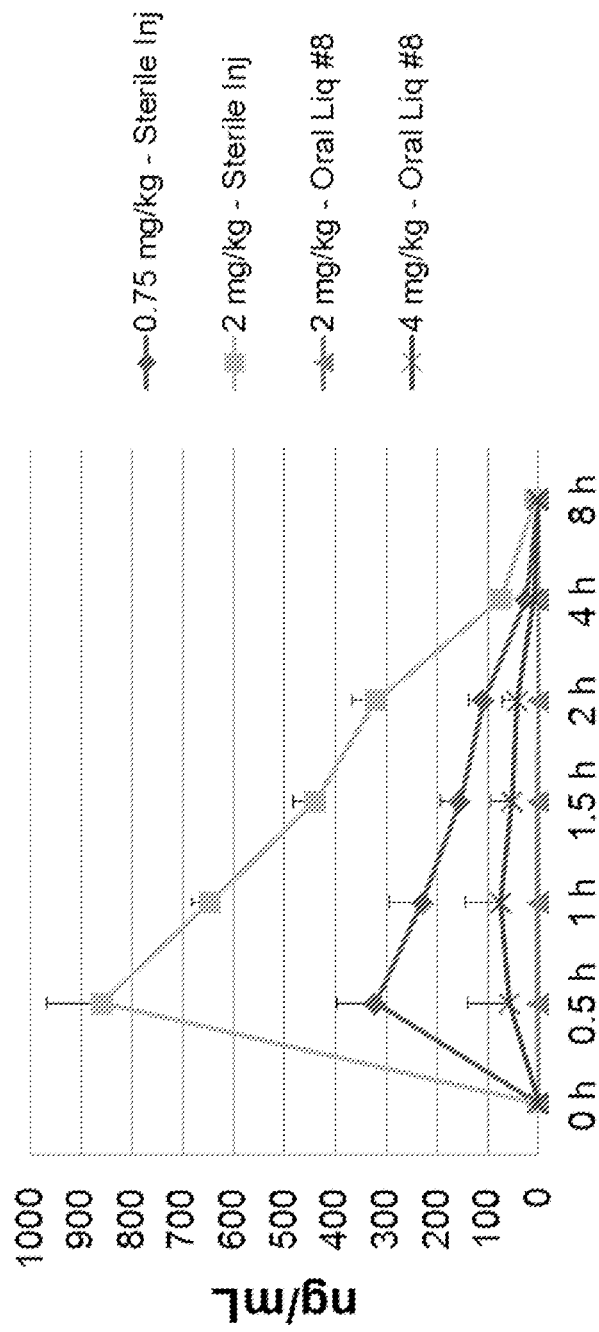
FIG. 52 is a line graph depicting measurements of capromorelin concentration in the serum of cats on day 1 after being treated with different concentrations and treatment regimens of a capromorelin composition.
Figure 53:
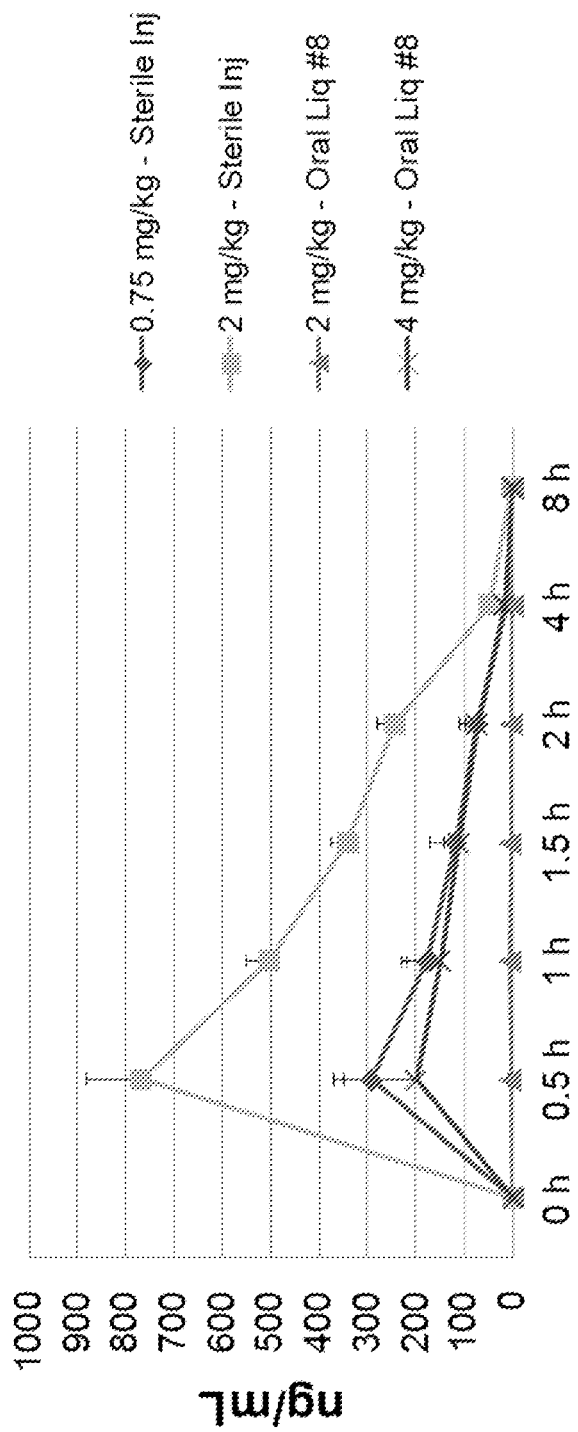
FIG. 53 is a line graph depicting measurements of capromorelin concentration in the serum of cats on day 4 after being treated with different concentrations and treatment regimens of a capromorelin composition.
Figure 54:
FIG. 54 is a bar graph depicting serum concentrations of capromorelin in cats three days after being treated with different concentrations and treatment regimens of a capromorelin composition.

Referring now to FIGS. 52-54, cats receiving the sterile injectable formulations exhibited a different pharmacokinetic profile, relative to the cats receiving the oral formulation. The cats receiving sterile injectable formulation displayed a pharmacokinetic profile similar to the previous examples with dogs. Specifically, the capromorelin concentration in the serum peaked at about 0.5 h post administration and decreased until reaching near undetectable levels by around eight hours after administration. Additionally, the serum concentrations of capromorelin in the groups receiving the sterile injectable formulation appear to correspond to the concentration of capromorelin administered, as shown in FIGS. 51-53. More specifically, the maximum concentrations of capromorelin in the serum are approximately 2.5 to 3 times greater in the group of cats receiving the 2 mg/kg sterile injection relative to the cats receiving the 0.75 mg/kg dose.

Conversely, cats receiving the oral formulations exhibited relatively low levels of capromorelin in the serum. Specifically, the 2 mg/kg oral formulation in the active treatment groups exhibited elevated concentrations of capromorelin in their serum, but lower than the cats receiving the sterile injectable formulations. Using data from serum samples taken on days 1 and 4 of the study, capromorelin concentrations tended to begin rising at approximately 0.5 h after dosing and, in general, decreased to near undetectable levels by eight hours after administration. These results confirm that the capromorelin composition was correctly administered.

As reflected in FIGS. 55-60, cats receiving both the sterile injectable and the oral formulations experienced changes in serum concentrations of IGF-1 and cortisol, which are likely attributable to the capromorelin administration.

Figure 55:
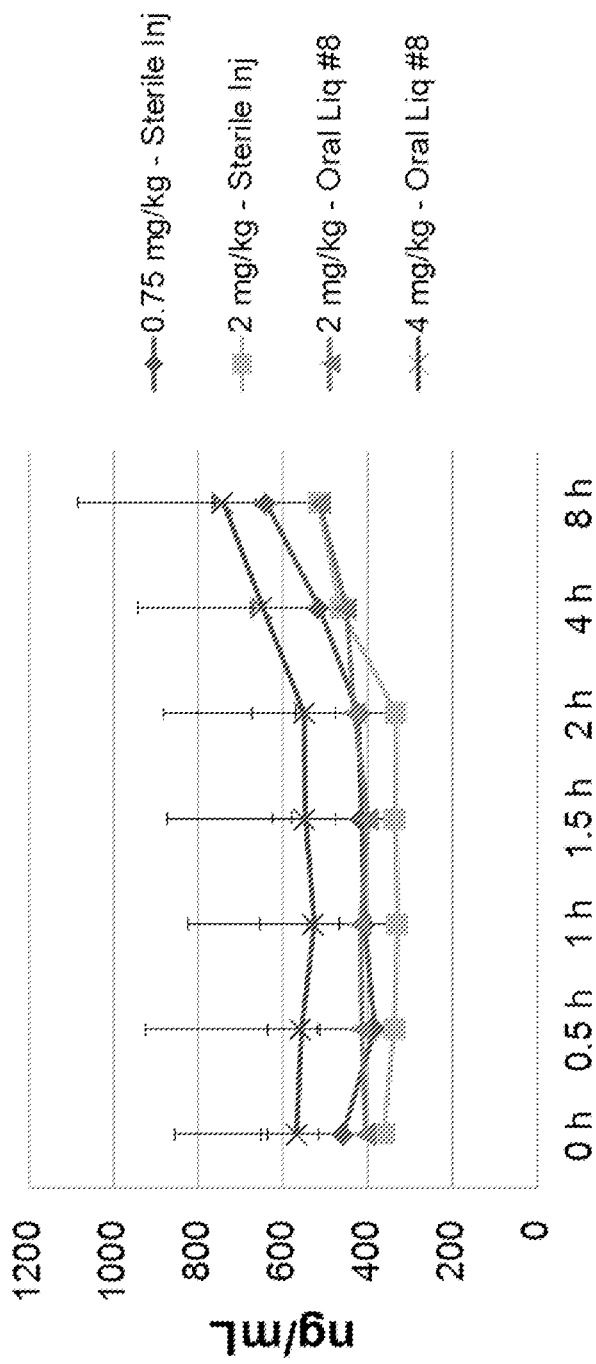
FIG. 55 is a line graph depicting measurements of insulin-like growth factor-1 concentration in the serum of cats on day 1 after being treated with different concentrations and treatment regimens of a capromorelin composition.
Figure 56:
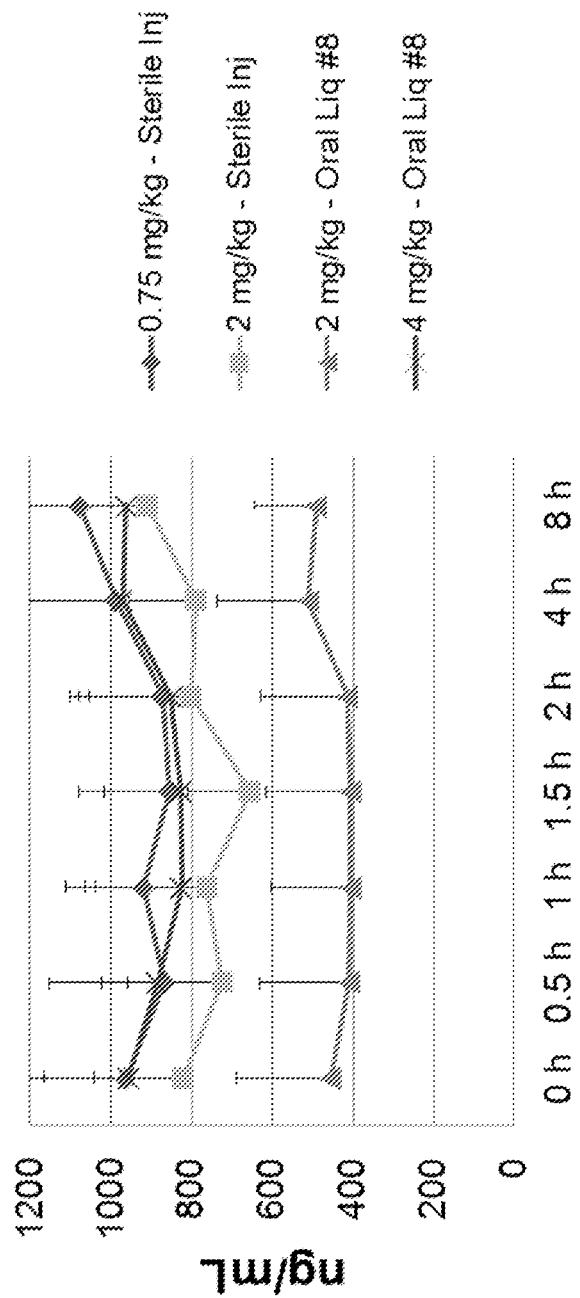
FIG. 56 is a line graph depicting measurements of insulin-like growth factor-1 concentration in the serum of cats on day 4 after being treated with different concentrations and treatment regimens of a capromorelin composition.
Figure 57:
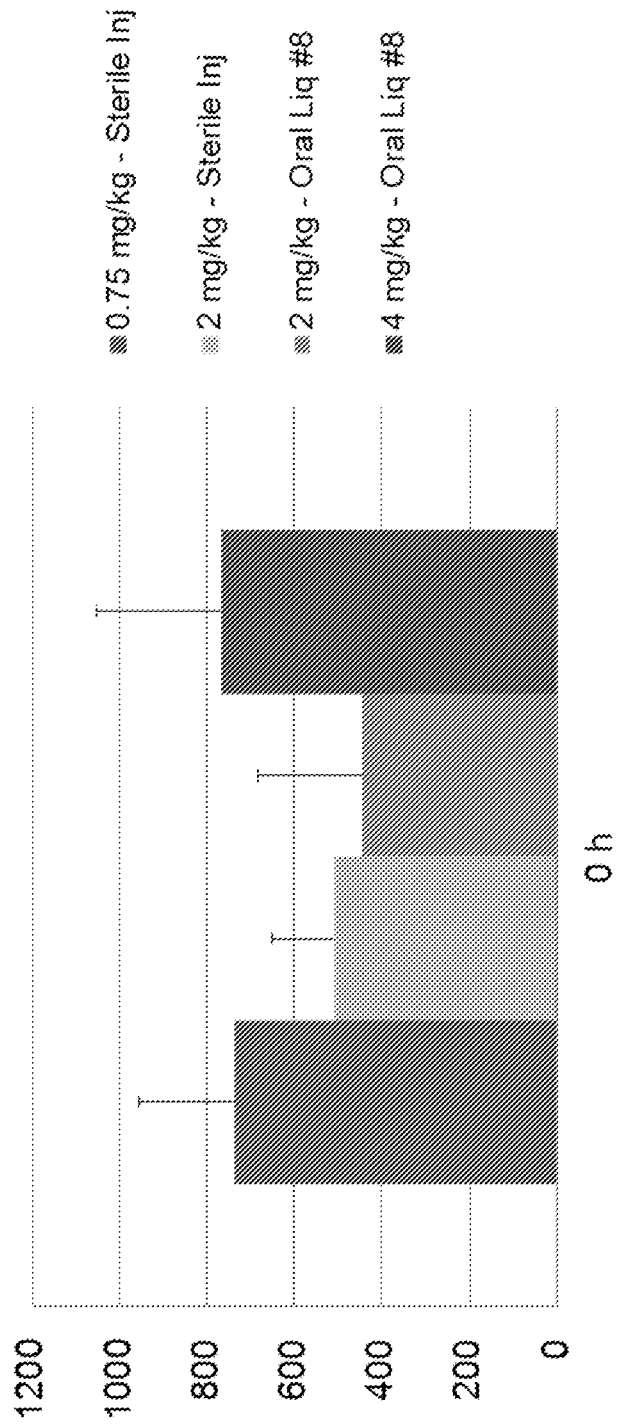
FIG. 57 is a bar graph depicting serum concentrations of insulin-like growth factor-1 in cats after seven days of treatment with different concentrations and treatment regimens of a capromorelin composition and three days without treatment (i.e., day 10).

First, as shown in FIGS. 55-57, treatment with capromorelin induced IGF-1 levels within the serum of the cats. Specifically, as shown in FIG. 55, approximately two to four hours after initially dosing the cats with most of the capromorelin formulations, IGF-1 levels exhibited an increase in the serum. However, one treatment group, the cats receiving the 2 mg/kg oral formulation, experienced only moderately increased concentrations of IGF-1 at eight hours post administration, relative to pre-treatment levels. Similarly, on day 4, cats receiving the sterile injectable formulations and the 4 mg/kg oral formulation exhibited sustained increased IGF-1 levels, similar to the IGF-1 profile observed in dogs. On day 4, the cats dosed with the 2 mg/kg oral formulation did not exhibit further increases of IGF-1, as shown in FIG. 56. As shown in FIG. 57, three days after terminating treatment (Day 7), levels of serum IGF-1 in the cats receiving capromorelin treatment were similar in all treatment groups.

More specifically, in data not shown, relative to time 0 (i.e., prior to administration of the capromorelin composition), the cats in at least some of the treatment groups exhibit increased IGF-1 levels in the serum. For example, on day 1, at eight hours post administration, the cats receiving the 0.75 mg/kg and 2 mg/kg sterile injectable formulations exhibit approximately 39.8% and 43.1% increases in serum IGF-1 concentration, respectively, relative to time 0 on day 1. The cats receiving the 2 mg/kg and 4 mg/kg oral formulations exhibit approximately 26.6% and 30.8% increases in serum IGF-1 concentration, respectively, relative to time 0 on day 1. On day 4, at eight hours post administration, the 0.75 mg/kg and 2 mg/kg sterile injectable formulations induce approximately 12.2% and 10.8% increases in serum IGF-1 concentration, relatively to time 0 on day 4, respectively. Similarly, on day 4, at eight hours post administration, the 2 mg/kg and 4 mg/kg oral formulations induce approximately 7.6% and 0.7% increases in serum IGF-1 concentration, relatively to time 0 on day 4, respectively. It is possible that the cats receiving the sterile injectable and 4 mg/kg oral formulations exhibit increases of a lesser magnitude because serum concentrations of IGF-1 are already at a higher level than are IGF-1 levels in cats receiving theses dosing regimens of capromorelin.

Figure 58:
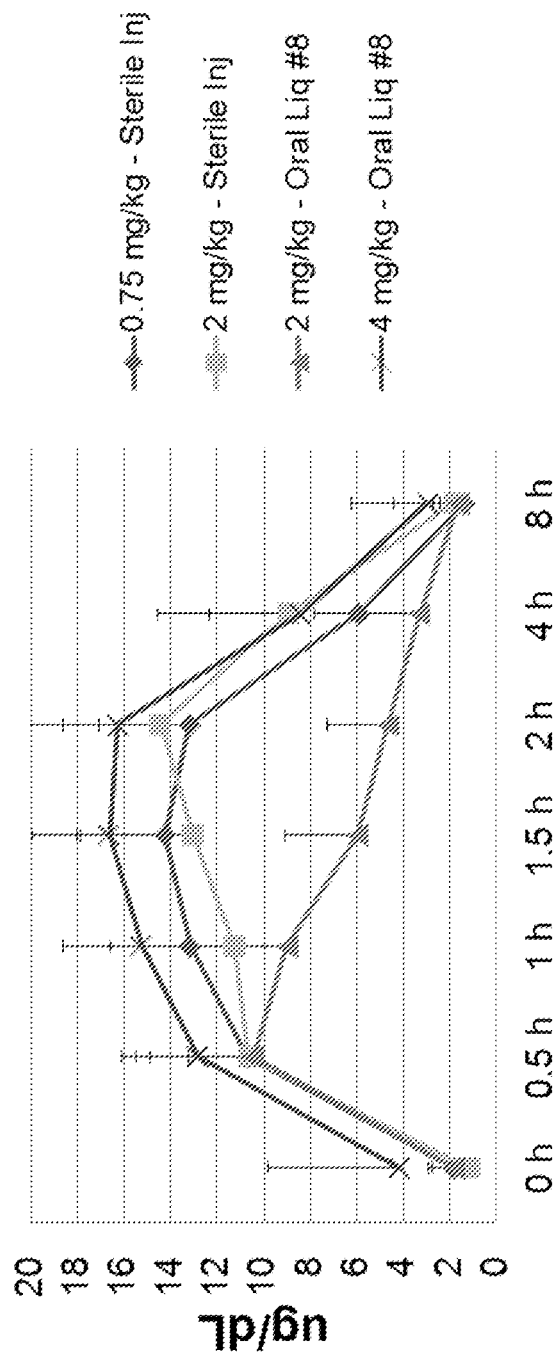
FIG. 58 is a line graph depicting measurements of cortisol concentration in the serum of cats on day 1 after being treated with different concentrations and treatment regimens of a capromorelin composition.
Figure 59:
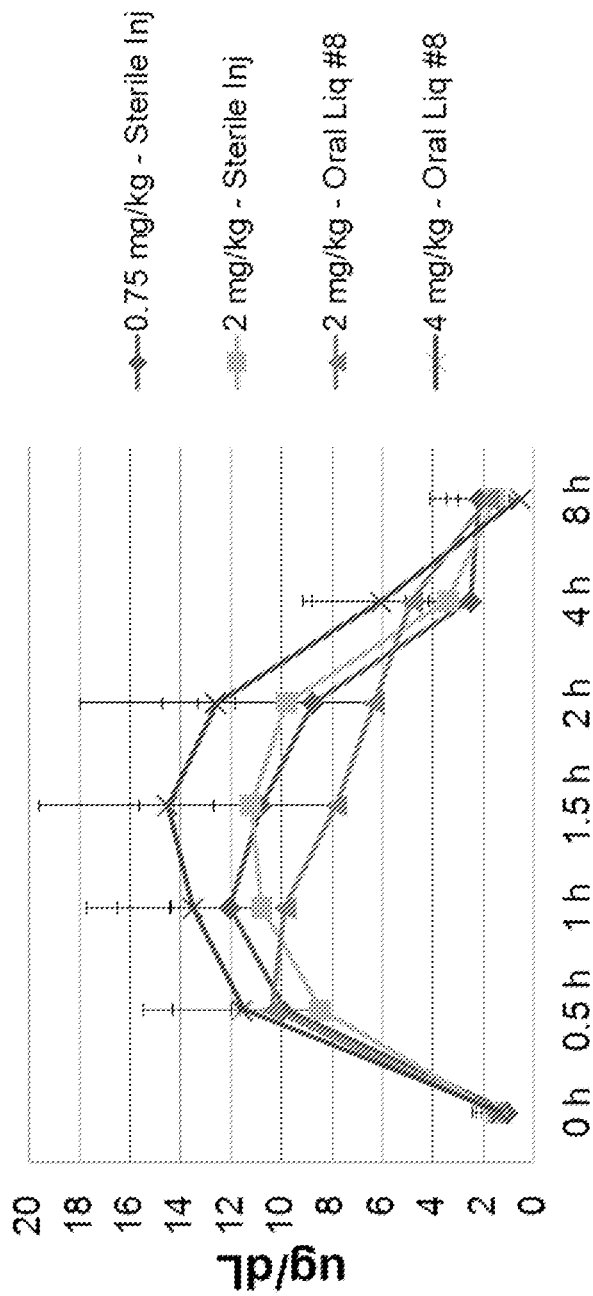
FIG. 59 is a line graph depicting measurements of cortisol concentration in the serum of cats on day 4 after being treated with different concentrations and treatment regimens of a capromorelin composition.
Figure 60:
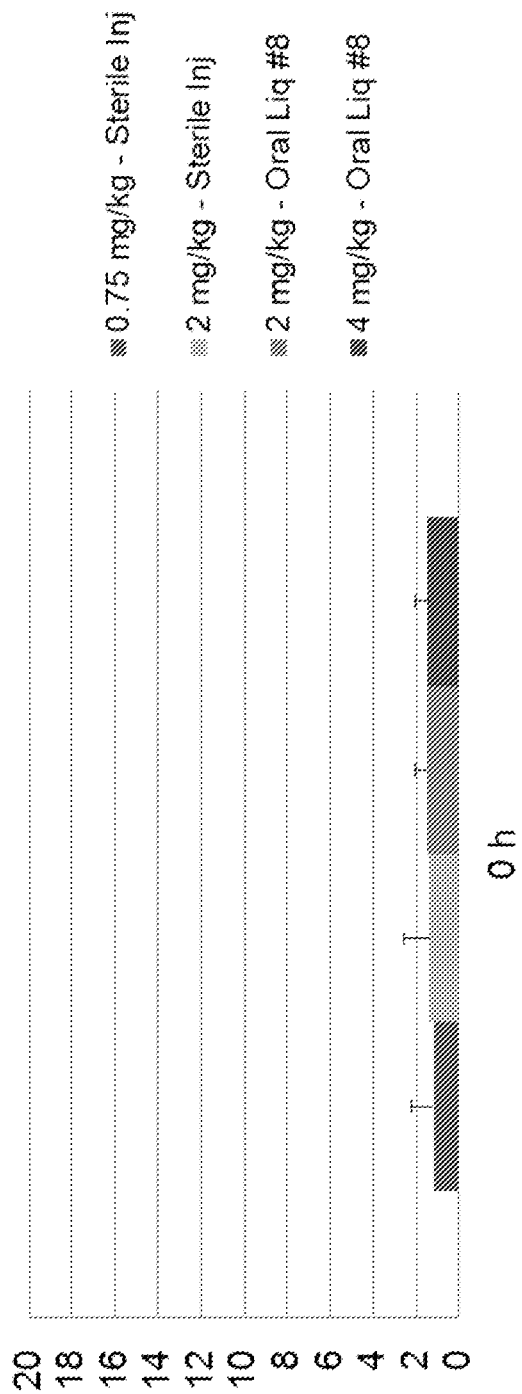
FIG. 60 is a bar graph depicting serum concentrations of cortisol in cats three days after seven days of treatment with different concentrations and treatment regimens of a capromorelin composition and three days without treatment (i.e., day 10).

Referring now to FIGS. 58-60, cortisol concentrations in the serum appear to correlate with administration of capromorelin. Specifically, on days 1 and 4 (FIGS. 58 and 59, respectively), at approximately 0.5 h post treatment, cortisol concentrations in the serum of dogs treated with capromorelin begin increasing. Moreover, in all treatment groups other than the 2 mg/kg oral formulation group, the cortisol concentrations continued to increase until between 90 and 120 minutes, where the concentrations began to decrease until reaching near undetectable levels at 480 minutes. In addition, increases in cortisol serum levels were mitigated on day 4, relative to the levels detected during day 1. Moreover, as shown in FIG. 60, three days after terminating treatment (Day 7), levels of serum cortisol in the cats receiving capromorelin treatment were similar in all treatment groups.

Overall, most of the dosing regimens produced discernible impacts on the cats. Moreover, no toxicological responses were noted. Pharmacological effects were noted, including no increases in body weight and food consumption, as well as increased levels of serum IGF-1, cortisol, and capromorelin. In general, it appeared as through the sterile injectable formulation induced more desirable profiles of serum IGF-1, cortisol, and capromorelin.

EXAMPLE 10

Further Refinement of the Dosing Regimen of the Inappetance-Controlling Compound Containing Capromorelin for Cats Next, additional experiments were conducted to further refine the formulation intended for use with the inappetance-controlling compound containing capromorelin, to confirm the capromorelin serum profile and the IGF-1 response, and to confirm that treatment with a capromorelin-containing composition results in weight gain and increased food consumption. In particular, following an acclimation period of seven days, a total of 20 cats (10 neutered males and 10 intact females) were randomly divided between four treatment groups, with five animals assigned to each group. Specifically, Group 1 received Formulation 1 (referred to as PRT2-81 in corresponding Figures; described below) once per day at a dose of 4 mg/kg of body weight of capromorelin; Group 2 received Formulation 2 (referred to as New Form in corresponding Figures; described below) once per day at a dose of 4 mg/kg of body weight of capromorelin; Group 3 received Formulation 3 (referred to as PERT2-86 in corresponding Figures; described below) once per day at a dose of 4 mg/kg of body weight of capromorelin; and Group 4 received Formulation 4 (referred to as PRT3-99I in corresponding Figures; described below) once per day at a dose of 4 mg/kg of body weight of capromorelin.

| Formulation 1 - PRT2-81 | |
|---|---|
| Ingredient | % weight per volume |
| Capromorelin | 2.10 |
| Citric Acid | 0.70 |
| Sodium Citrate | 0.50 |
| Sodium Chloride | 0.70 |
| Methyl 4-Hydroxybenzoate Salt | 0.112 |
| Propyl 4-Hydroxybenzoate Salt | 0.013 |
| Thaumatin T200X | 0.40 |
| S Rebaudioside A | 0.40 |
| MagnaSweet Plus Liquid | 0.50 |
| Ethyl Vanillin | 0.10 |
| Ethanol | 0.25 |
| Neosorb Sorbitol 70% | 30.00 |
| Maltitol Solution (Lycasin 80/55) | 25.00 |
| Glycerin | 20.00 |
| Kollidon 90F (PVP) | 1.5 |
| Purified Water | q.s. |

| Formulation 2 - New Form | |
|---|---|
| Ingredient | % weight per volume |
| Capromorelin | 3.10 |
| Citric Acid | 0.70 |
| Sodium Citrate | 0.50 |
| Sodium Chloride | 0.70 |
| Methyl 4-Hydroxybenzoate Salt | 0.045 |
| Propyl 4-Hydroxybenzoate Salt | 0.005 |
| Thaumatin T200X | 0.60 |
| MagnaSweet Plus Liquid | 0.50 |
| S Rebaudioside A | 0.7 |
| Vanillin | 0.20 |
| Neosorb Sorbitol 70% | 30.00 |
| Maltitol Solution (Lycasin 80/55) | 25.00 |
| Glycerol Anhydrous | 20.00 |
| Kollidon 90F (PVP) | 1.5 |
| Purified Water | q.s. |

| Formulation 3 - PERT2-86 | |
|---|---|
| Ingredient | % weight per volume |
| Capromorelin | 2.10 |
| Citric Acid | 0.70 |
| Sodium Citrate | 0.50 |
| Sodium Chloride | 0.70 |
| Methyl 4-Hydroxybenzoate Salt | 0.112 |
| Propyl 4-Hydroxybenzoate Salt | 0.013 |
| Thaumatin T200X | 0.40 |
| S Rebaudioside A | 0.40 |
| MagnaSweet Plus Liquid | 0.50 |
| Ethyl Vanillin | 0.13 |
| Ethanol | 0.30 |
| Neosorb Sorbitol 70% | 30.00 |
| Maltitol Solution (Lycasin 80/55) | 25.00 |
| Glycerol Anhydrous | 20.50 |
| Pluriol-E3350 (PEG) | 7.5 |
| Purified Water | q.s. |

| Formulation 4- PRT3-99I | |
|---|---|
| Ingredient | % weight per volume |
| Capromorelin | 3.10 |
| Citric Acid (Anhydrous) | 0.70 |
| Sodium Citrate | 0.50 |
| Sodium Chloride | 0.70 |
| Methyl 4-Hydroxybenzoate Salt | 0.045 |

-continued

| Formulation 4- PRT3-99I | |
|---|---|
| Ingredient | % weight per volume |
| Propyl 4-Hydroxybenzoate Salt | 0.005 |
| Thaumatin T200X | 0.60 |
| *Stevia* Extract Rebaudioside A 99% | 0.70 |
| MagnaSweet Plus Liquid | 0.50 |
| Vanillin | 0.20 |
| Neosorb Sorbitol 70% | 30.30 |
| Maltitol Solution (Lycasin 80/55) | 25.00 |
| Glycerol Anhydrous | 20.20 |
| Kollidon 90F (PVP) | 1.5 |
| Ethanol (ABS) | 0.50 |
| Purified Water | q.s. |

In these experiments, on Days 1 through 6, all animals were orally administered the appropriate formulation of capromorelin by syringe in the corner of the right side of the mouth. On Day 6, blood samples were taken from each cat at multiple time points for measurements of capromorelin and IGF-1 in the serum. In particular, blood samples were taken at pre-dose (0 minutes), 30, 60, 90, 120, 240, and 480 minutes post dose. Moreover, IGF-1 was measured at 0 minutes and 480 minutes, and capromorelin was measured at each time period. In addition, on Days 1, 2, 3, 4, and 5, dose acceptability and palatability observations were performed.

As summarized in FIGS. 79-82, the cats did not appear to have significant issues with any of the formulations, although the cats appeared to generally dislike the dosing procedure. In general, none of the formulations were "well accepted" by the cats; however most of the formulations were still accepted with some adverse clinical observation projected by some of the cats (i.e., licking, smacking of the mouth/lips, and salivation). Overall, the formulations were generally accepted at similar levels by the cats.

Figure 83:
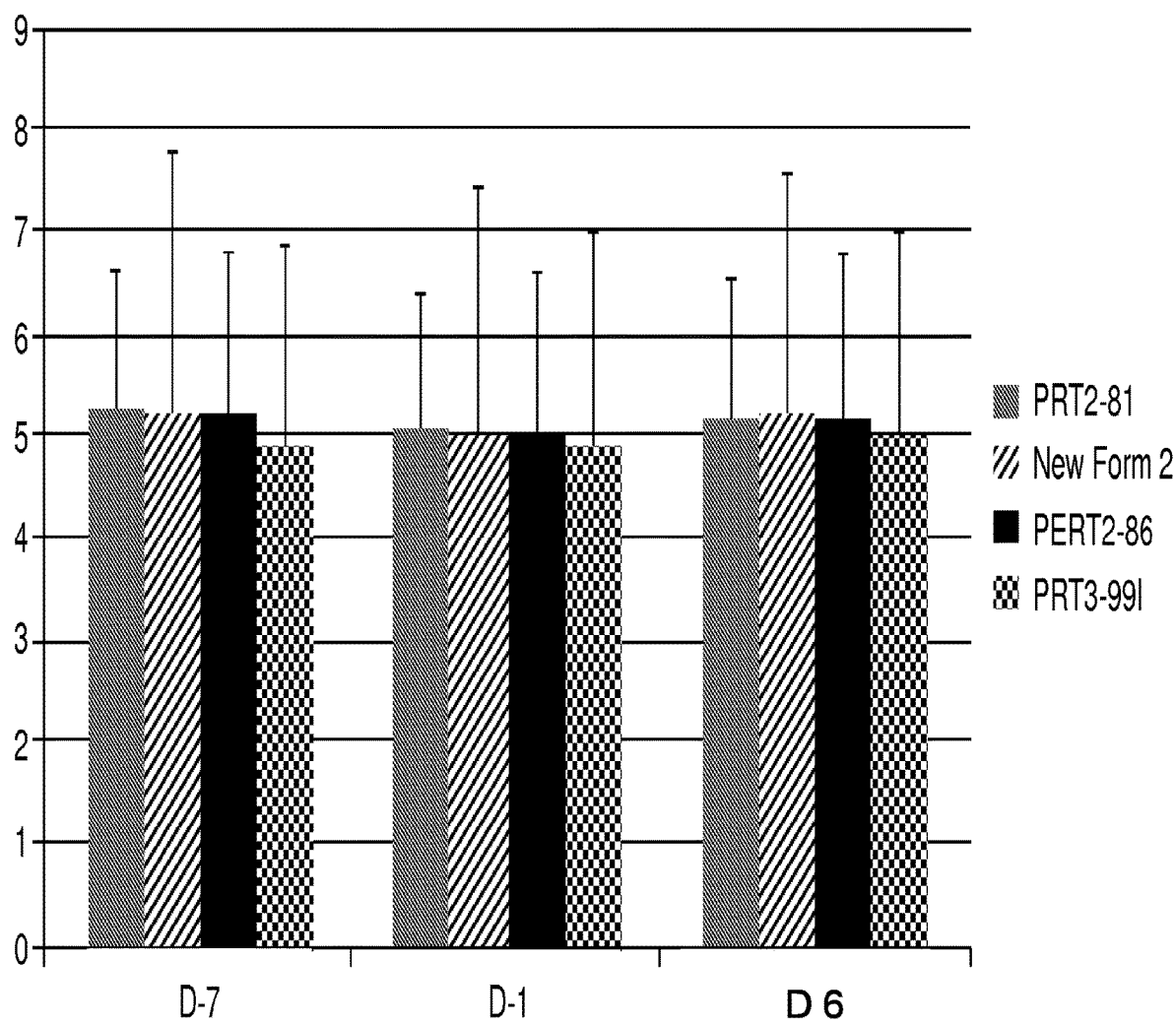
FIG. 83 is a bar graph depicting body weight measurement of animals over the course of an experiment in which the animals were treated with different formulations of a capromorelin composition.

Next, as shown in FIG. 83 and Table 4 below, the cats all gained weight as a result of receiving the test formulations. On average, all of the groups experienced between a 2% and 4% increase in weight.

TABLE 4

Weight Change

| Group | Day −1 Weights (mean ± SD, kg) | Day 6 Weights (mean ± SD, kg) | Average Increase in Weight on Day 6 v. Day −1 |
|---|---|---|---|
| 1 - PRT2-81 | 5.1 ± 1.4 | 5.2 ± 1.4 | 2.0% |
| 2 - New Form | 5.0 ± 2.5 | 5.2 ± 2.4 | 4.0% |
| 3 - PERT2-86 | 5.0 ± 1.6 | 5.2 ± 1.6 | 4.0% |
| 4 - PRT3-99I | 4.9 ± 2.1 | 5.0 ± 2.0 | 2.0% |

Figure 86:
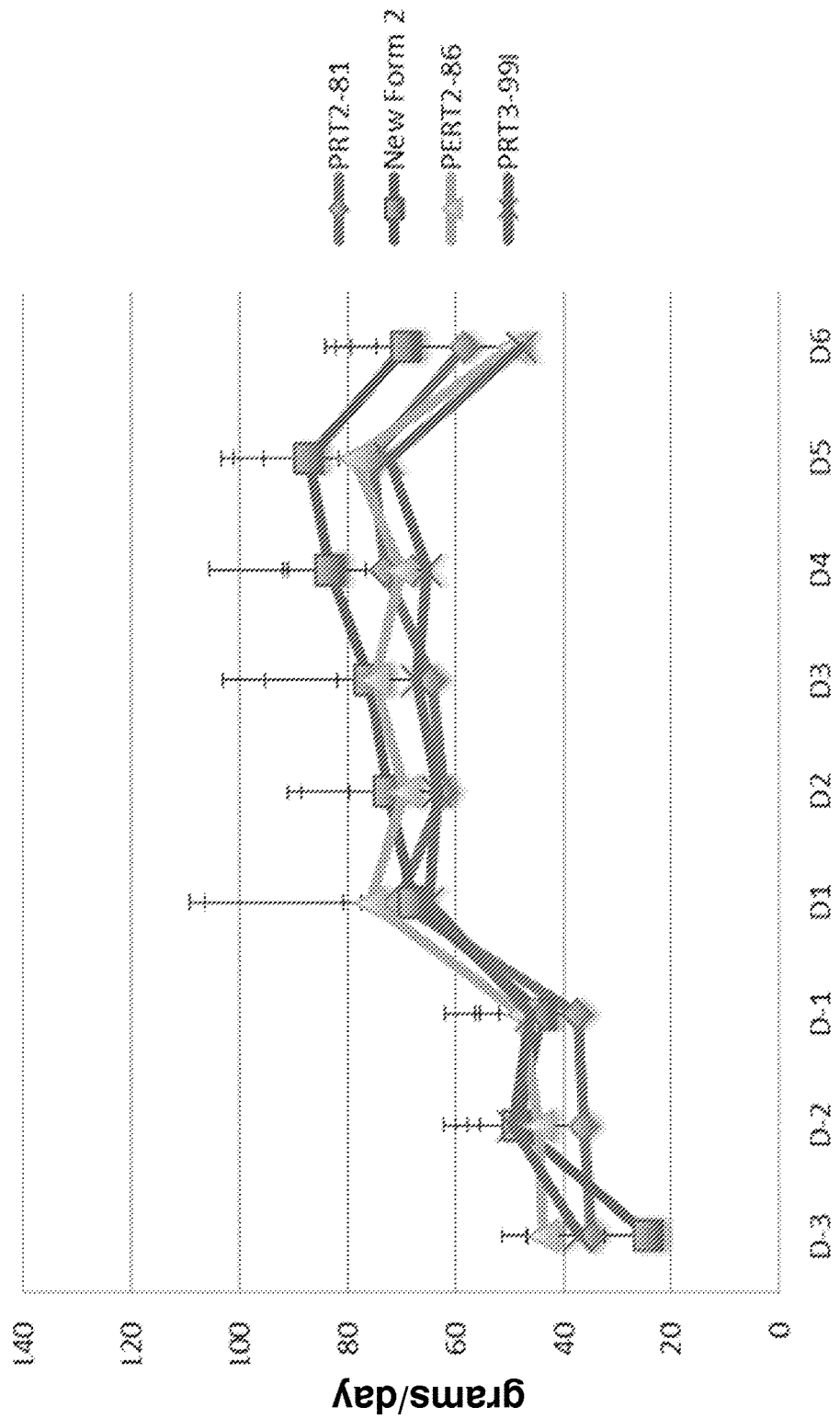
FIG. 86 is a line graph depicting measurements of food consumed by animals over the course of an experiment in which the animals were treated with different formulations of a capromorelin composition.

As illustrated in FIGS. 84-6 and Table 5 below, the increase seen in the weights of the cats was due, at least in part, to an increase in food consumption. In particular, during the experiment, food consumption was calculated for all animals, including during the acclimation period during Days −3 to −1. Specifically, during the acclimation period, mean individual food consumption ranged from 19 to 60 grams per day for all male study cats and 23 to 50 grams per day for all female study cats. The acclimation mean individual daily food consumed, based on Day −1 body weight, was calculated to be 3.6 to 8.8 g/kg for all male study animals and 6.1 to 14.0 g/kg for all female study animals. As shown in FIGS. 84-86, all study animals were observed with an increased appetite, which resulted in increased mean food consumption, when comparing the acclimation period to the post-dosing period. Significantly, food consumption likely decreased on Day 6 due to the numerous blood samples collected that day. As highlighted in Table 5, each of the different formulations induced large increases in food consumption.

TABLE 5

Food Intake Increase

| Group | Day −3 to −1 Mean (g) | Day 1 to 6 Mean (g) | Difference (g) | Percent Food Intake Increase |
|---|---|---|---|---|
| 1 - PRT2-81 | 36.20 | 67.23 | 31.03 | 85.72 |
| 2 - New Form | 38.21 | 75.93 | 37.72 | 98.72 |
| 3 - PERT2-86 | 45.33 | 69.73 | 24.40 | 53.83 |
| 4 - PRT3-99I | 44.13 | 63.33 | 19.20 | 43.51 |

Figure 87:
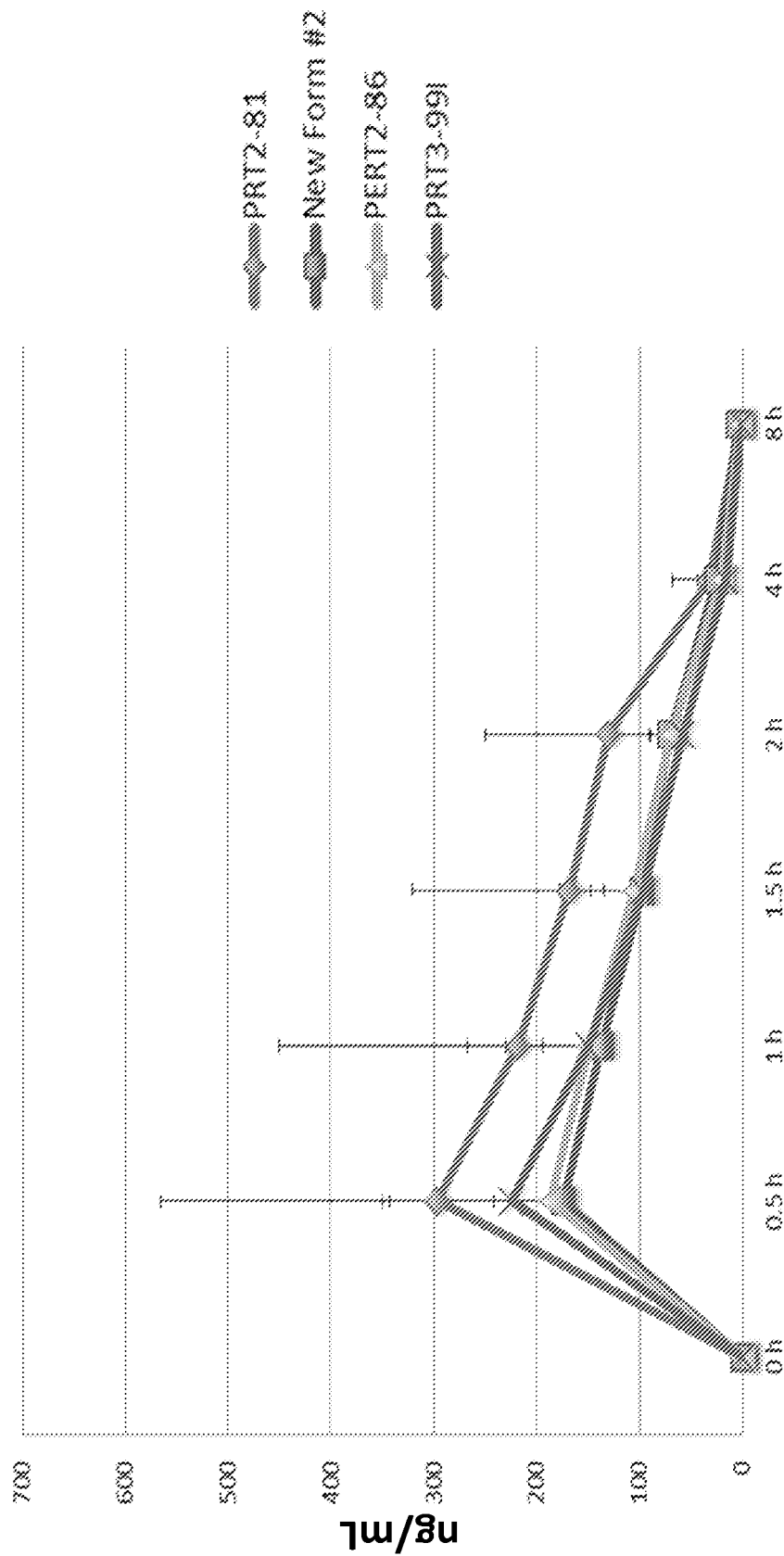
FIG. 87 is a line graph depicting serum concentrations of capromorelin in animals on Day 6 after being treated with different formulations a capromorelin composition.
Figure 88:
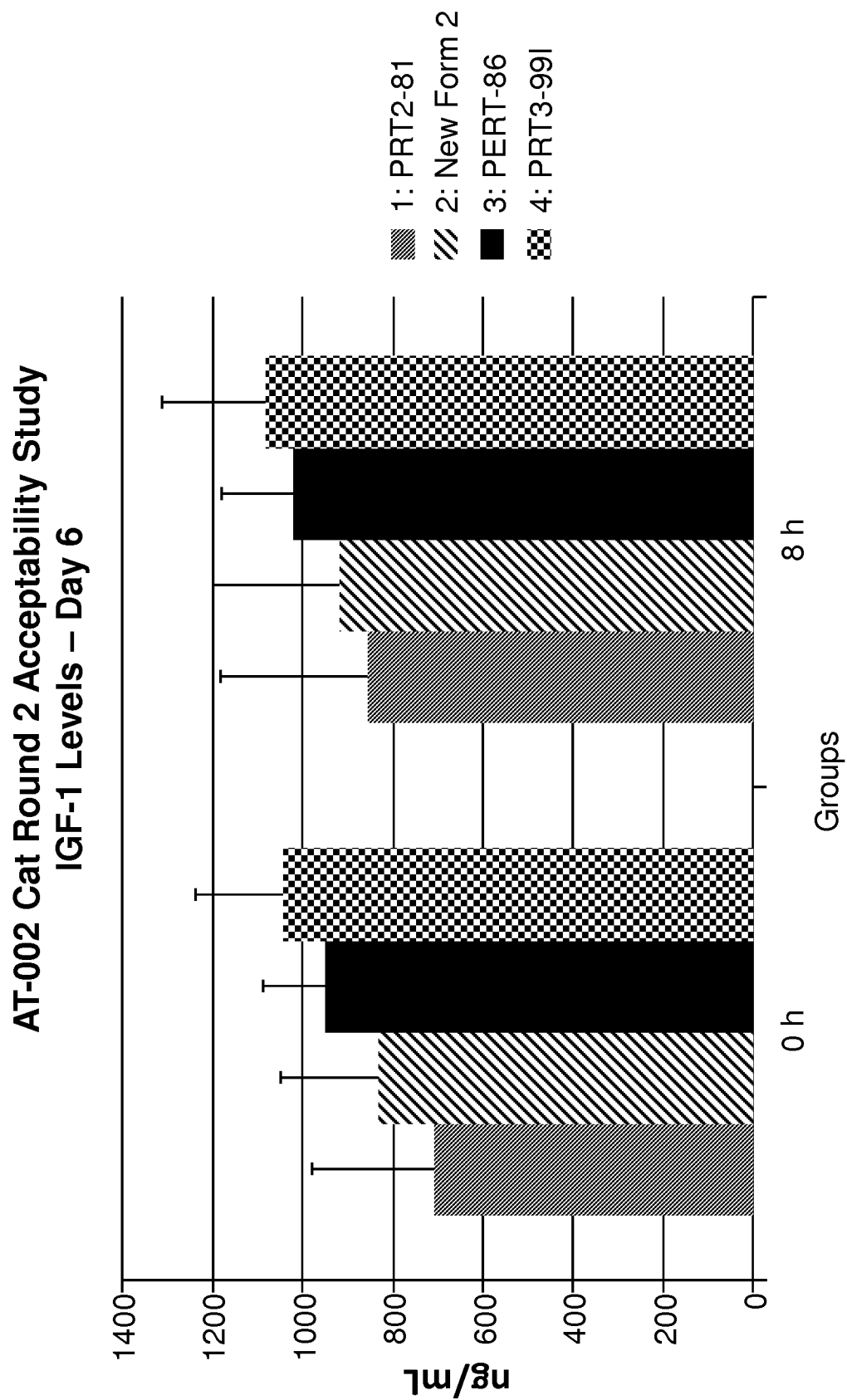
FIG. 88 is a bar graph depicting serum concentrations of IGF-1 in animals on Day 6 after being treated with different formulations of a capromorelin composition.

Next, as shown in FIG. 87, similar to prior results in both cats and dogs, each of the test formulations induced an initial spike in capromorelin concentration in the test animals within 30 minutes of administration. After the initial spike and over the course of the next eight hours, the serum concentrations of capromorelin decreased to levels below detection limitations of the assay. Interestingly, animals in Group 1, on average, exhibited a higher initial spike in capromorelin concentration in the serum, but eventually cleared the composition by eight hours post dosing. In addition, as shown in FIG. 88 and Table 6 below, all four tested formulations induced some level of increase in serum concentration of IGF-1. As discussed in previous experiments, these daily increases may not be as significant as expected due to the fact that by Day 6, it would be expected to have sustained amounts of IGF-1 circulating through the animals as a result of treatment with a capromorelin-containing composition.

TABLE 6

Percent Increase of Serum IGF-1 levels on Day 6

| Group | Serum IFG-1 levels at T = 0 min (ng/mL) | Serum IFG-1 levels at T = 480 min (ng/mL) | Percent Food Intake Increase |
|---|---|---|---|
| 1 - PRT2-81 | 714.0 | 859.1 | 20.3 |
| 2 - New Form | 833.7 | 922.6 | 10.7 |
| 3 - PERT2-86 | 952.7 | 1023.9 | 7.5 |
| 4 - PRT3-99I | 1047.6 | 1085.4 | 3.6 |

EXAMPLE 11

Additional Refinement of the Dosing Regimen of the Inappetance-Controlling Compound Comprising Capromorelin for Cats In order to determine a dosing scheme for cats that provides the desired profile of IGF-1 and cortisol levels to support the positive effects associated with the inappetance-controlling composition (i.e., increased appetite and muscle mass), additional experiments were conducted. In particular, all of the cats in this experiment received different doses of Formulation 4 from Example 10 discussed above. In particular, a total of 30 cats were divided into five groups, with three males and three females included in each group: Group 1 received the placebo formulation once per day; Group 2 received Formulation 4 at a dose of 1 mg/kg once per day; Group 3 received Formulation 4 at a dose of 2 mg/kg once per day; Group 4 received Formulation 4 at a dose of 3 mg/kg once per day; and Group 5 received Formulation 4 at a dose of 4 mg/kg once per day. All animals were orally dosed.

The experiment proceeded after an acclimation period of seven days, with this period intended to allow the cats to adapt to the feeding regimen associated with the experiments. Starting with Day −7, 300 grams of food was offered to each of the animals for a period of approximately 4 hours, starting at 11:00 AM and ending at 3:00 PM. After removal, the food was weighed each day to assess consumption. In these experiments, on Days 1 through 10, all animals were orally administered in the corner of the mouth with the appropriate dose of Formulation 4. On Days 1 and 10, blood samples were taken from each cat at multiple time points for measurements of capromorelin, IGF-1, and/or cortisol in the serum. In particular, blood samples were taken at pre-dose (0 minutes), 30, 60, 90, 120, 240, and 480 minutes post dose. Blood samples were also taken on Days 12 and 15 to assess "washout" of the capromorelin composition. Moreover, body weights of the individual animals were measured on Days −7, −1, 5, and 10. In addition, appropriate dosing of Formulation 4 was based on the weight data gathered on Day −1.

Figure 93:
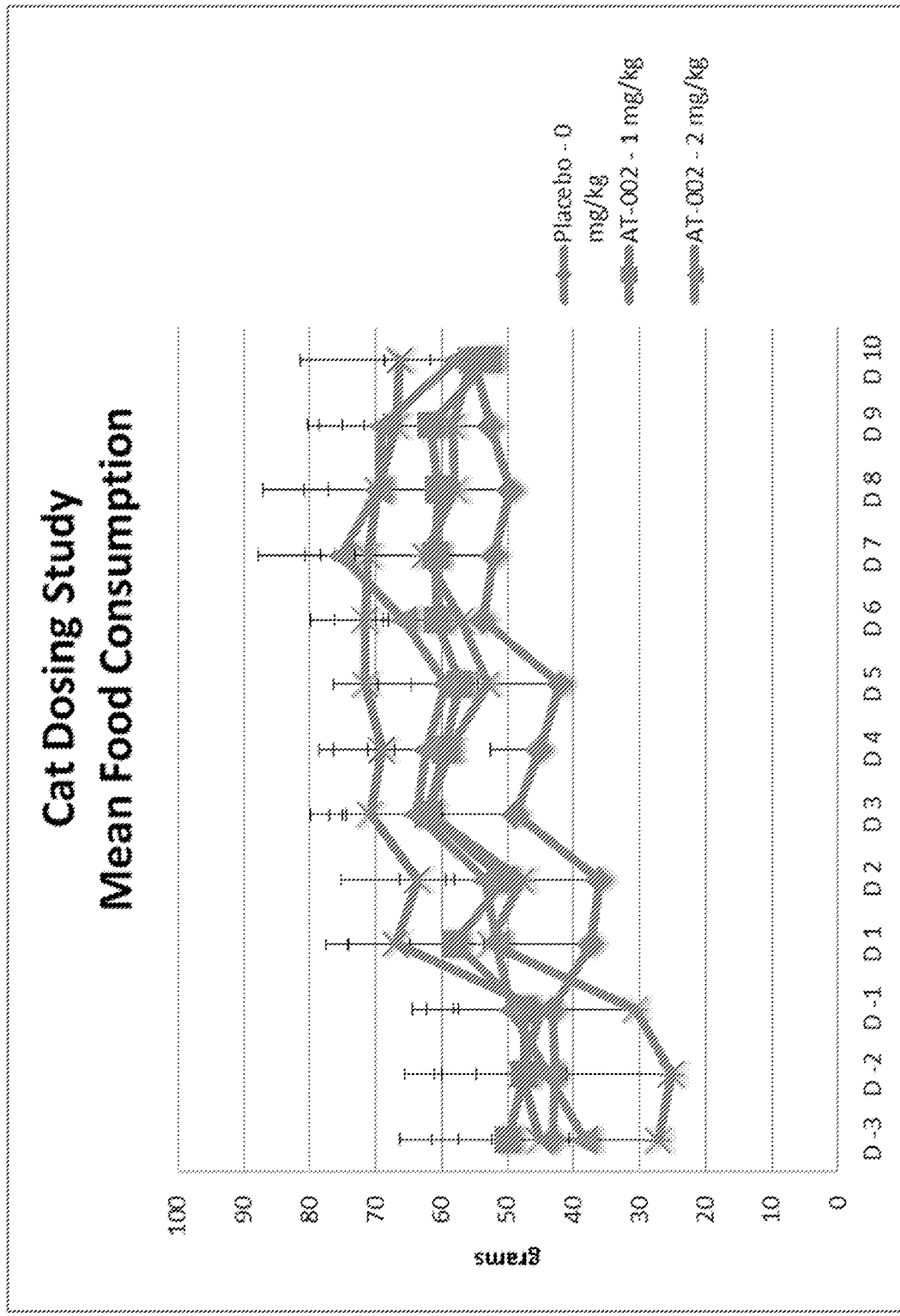
FIG. 93 a line graph depicting the daily average food consumption by cats in response to receiving different concentrations of a capromorelin composition.

As shown in FIG. 93 and Table 7, administration of the inappetance-controlling composition resulted in an overall daily increase in food consumption, relative to the baseline amounts. In particular, the baseline values were calculated by averaging the food consumed for each group on Days −3 to −1 and the study period average was calculated for Days 1 through 10. Although food consumption generally increased during the study, on Day 10, one of the two days on which there was extensive blood sampling, the amount of food consumed was slightly reduced, which is likely attributable to the stress induced by the blood sampling. As shown in Table 7 and generally illustrated in FIG. 93, treatment with all different doses of Formulation 4 resulted in increased food consumption.

TABLE 7

Food Intake Increase

| Group | Day −3 to −1 (Baseline) (g) | Day 1 to 10 (Study Period) (g) | Difference (g) | Percent Food Consumption Change Over Baseline |
|---|---|---|---|---|
| 1 - Placebo | 43.06 | 47.25 | 4.20 | 9.75 |
| 2 - 1 mg/kg | 48.33 | 58.43 | 10.10 | 20.90 |
| 3 - 2 mg/kg | 43.89 | 62.83 | 18.95 | 43.17 |
| 4 - 3 mg/kg | 45.94 | 68.78 | 22.84 | 49.71 |
| 5 - 4 mg/kg | 27.67 | 56.62 | 28.95 | 104.62 |

Figure 94:
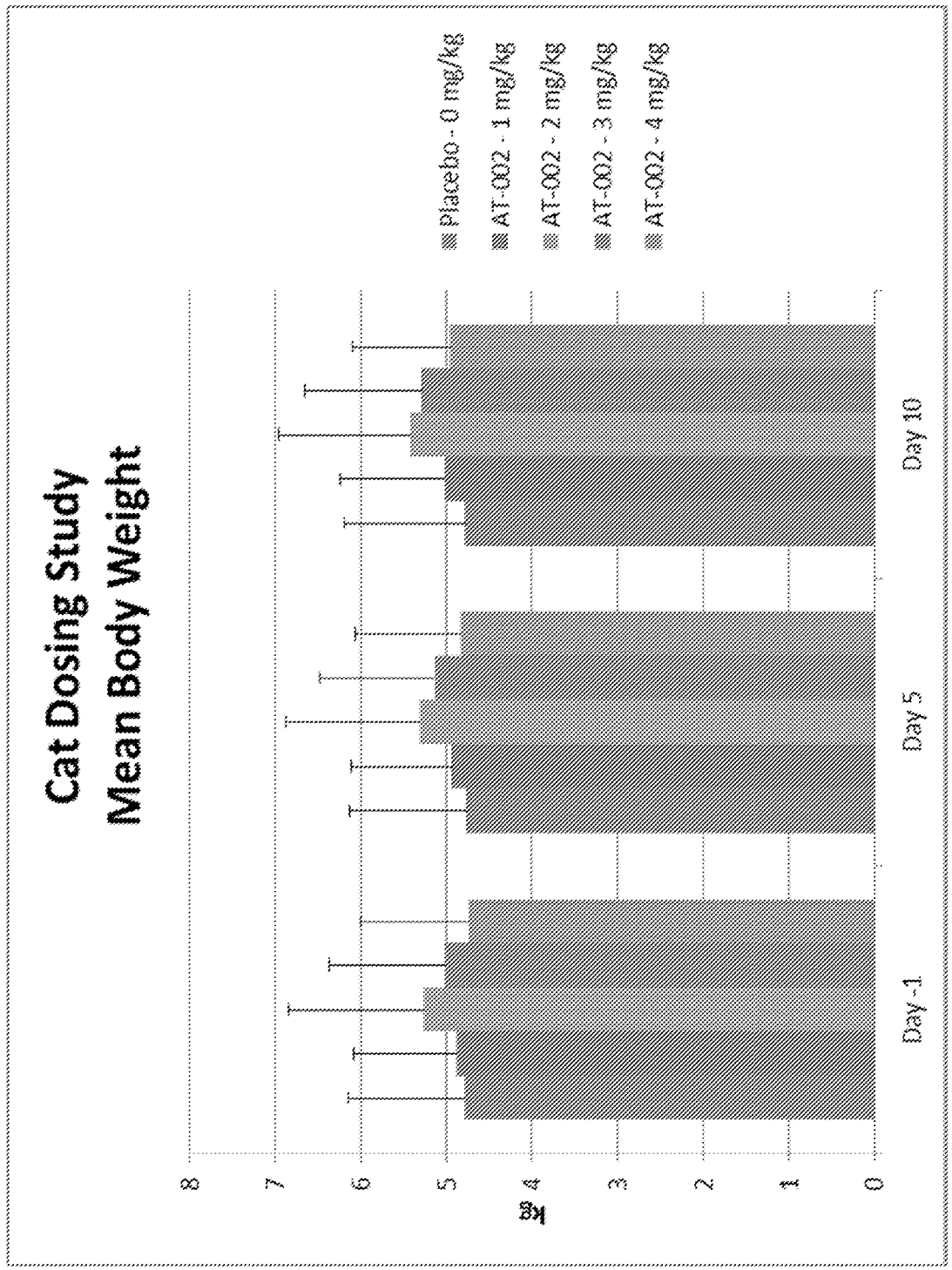
FIG. 94 is a bar graph depicting the average body weight of cats that have received different concentrations of a capromorelin composition.

Next, as shown in FIG. 94 and Table 8 below, treatment with different doses of Formulation 4 of the inappetance-controlling composition also resulted in generally increased body weights of the cats. In addition, the animals that received the placebo formulation did not have any change in body weight between Days −1 and 10. Overall, the cats in all of the experimental groups gained weight as a result of the treatment, with the animals that received the 3 mg/kg and 4 mg/kg doses exhibiting significant increases in body weight, relative to the placebo control animals.

TABLE 8

Change in Body Weight

| Group | Mean - Change from Baseline to Day 10 (kg) | Mean - Change from Baseline to Day 10 (%) |
|---|---|---|
| 1 - Placebo | 0.00 | 0.00 |
| 2 - 1 mg/kg | 0.15 | 3.07 |
| 3 - 2 mg/kg | 0.16 | 3.04 |
| 4 - 3 mg/kg | 0.27 | 5.38 |
| 5 - 4 mg/kg | 0.21 | 4.43 |

Figure 95:
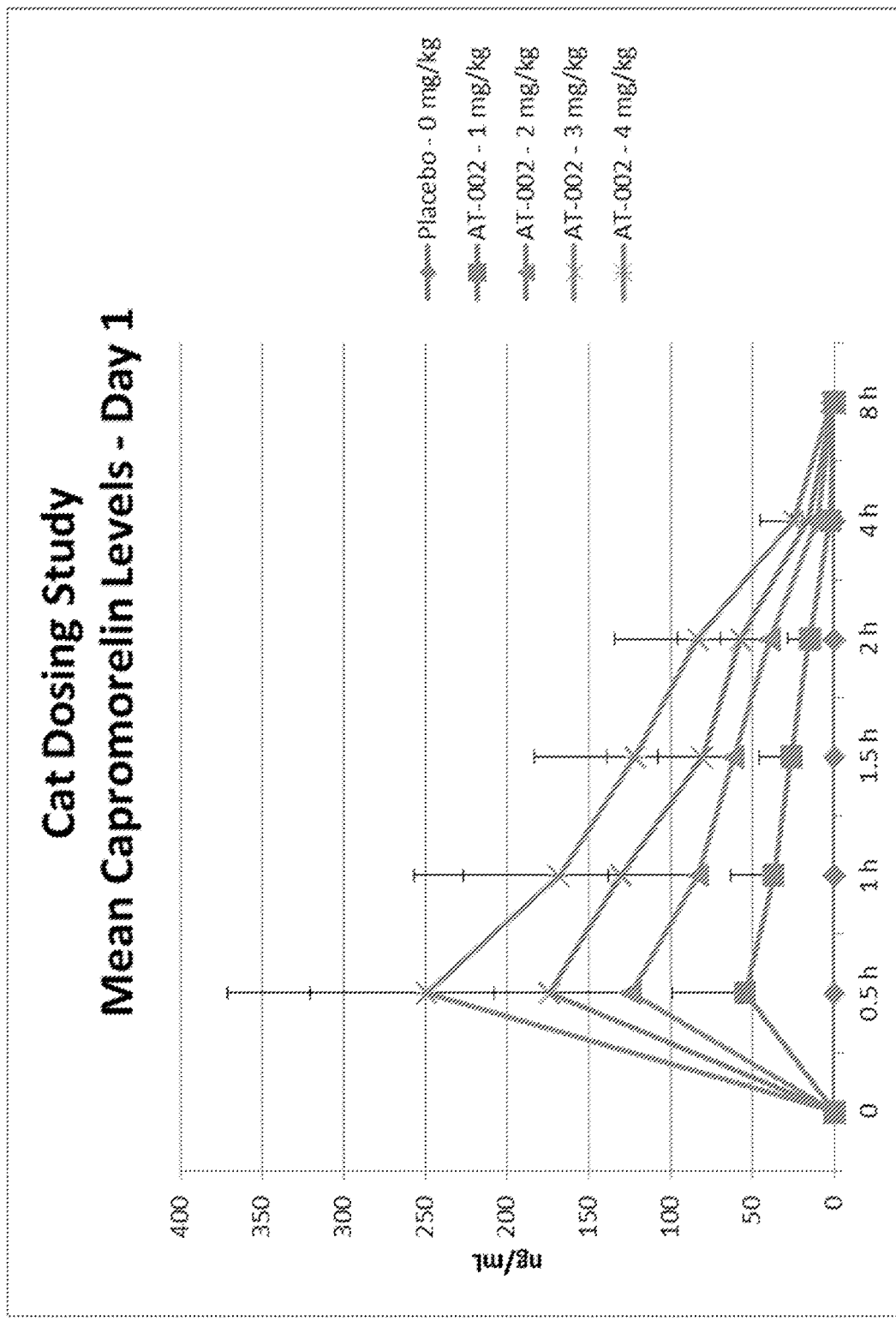
FIG. 95 is a line graph depicting measurements of capromorelin concentration in the serum of cats on day 1 after being treated with different concentrations of a capromorelin composition.
Figure 96:
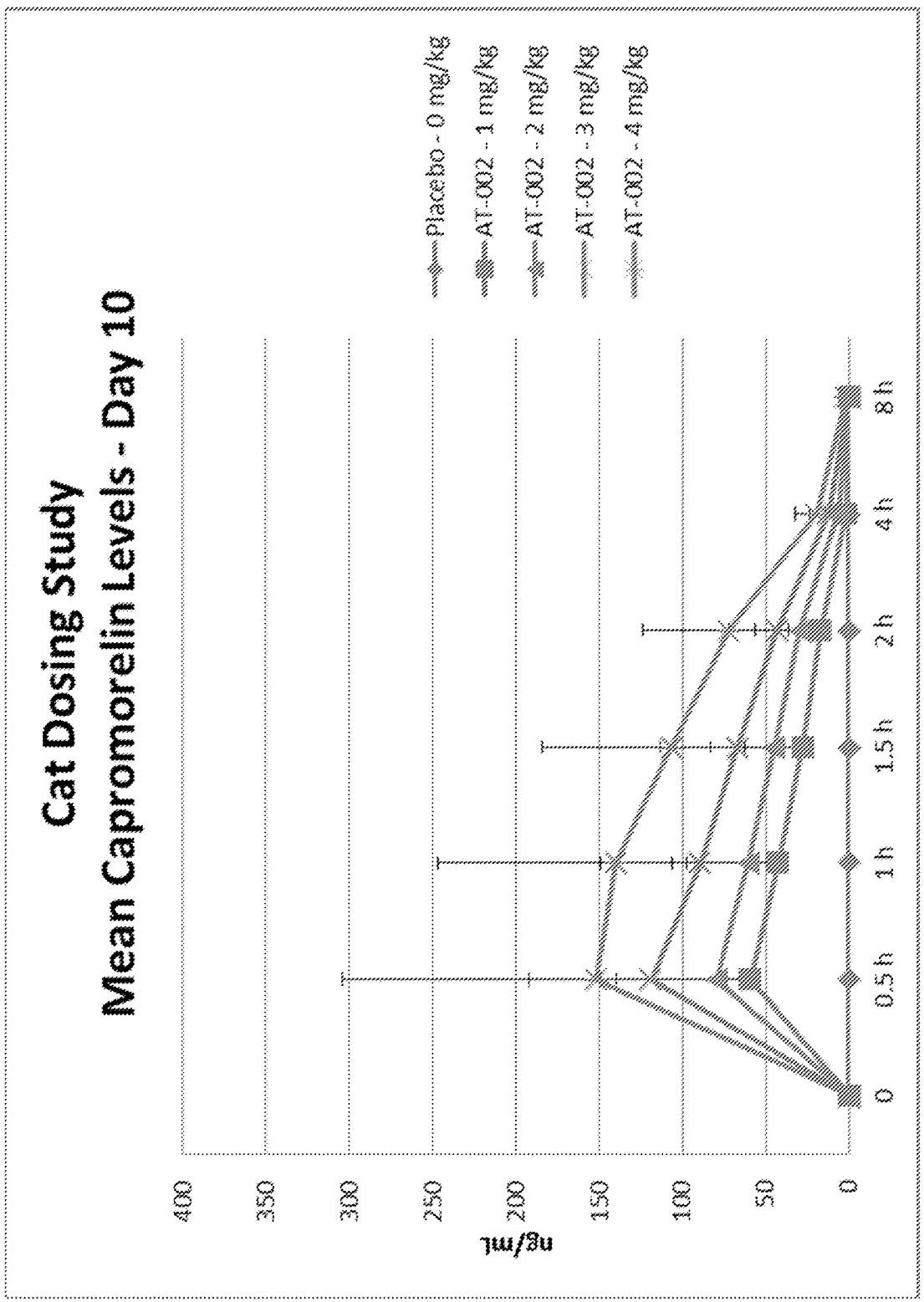
FIG. 96 is a line graph depicting measurements of capromorelin concentration in the serum of cats on day 10 after being treated with different concentrations of a capromorelin composition.

Referring now to FIGS. 95 and 96, treatment with different doses of Formulation 4 of the inappetance-controlling composition resulted in corresponding increases in capromorelin concentration in the serum. In particular, the greater doses of capromorelin administered to the cats were correlated with greater concentrations of capromorelin detected in the serum during the eight hours after administration on both Days 1 and 10. Moreover, there was no evidence of capromorelin accumulation within the animals, as the concentration of capromorelin returned to undetectable levels by eight hours after administration on both Days 1 and 10.

Figure 97:
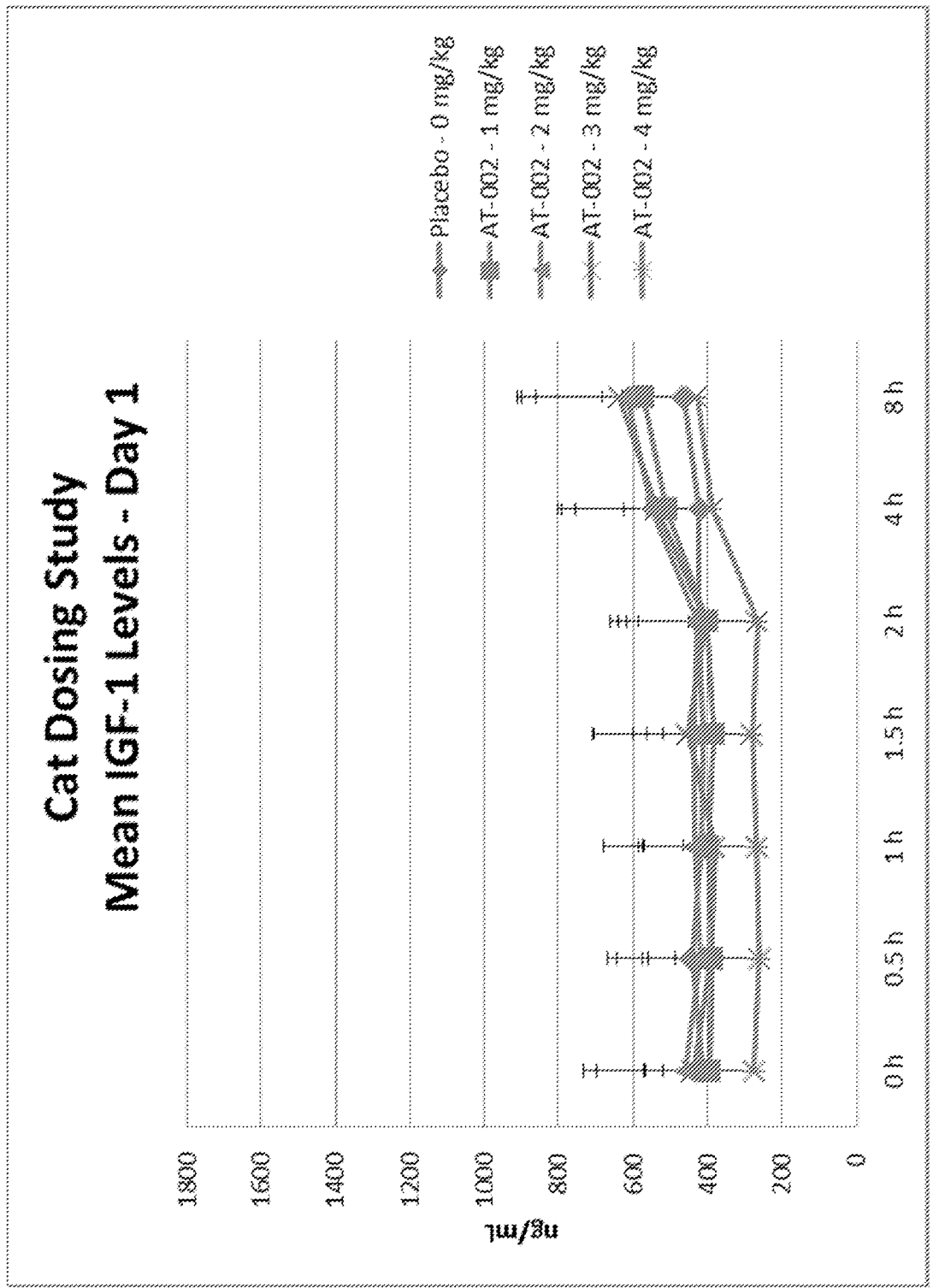
FIG. 97 is a line graph depicting measurements of IGF-1 concentration in the serum of cats on day 1 after being treated with different concentrations of a capromorelin composition.
Figure 98:
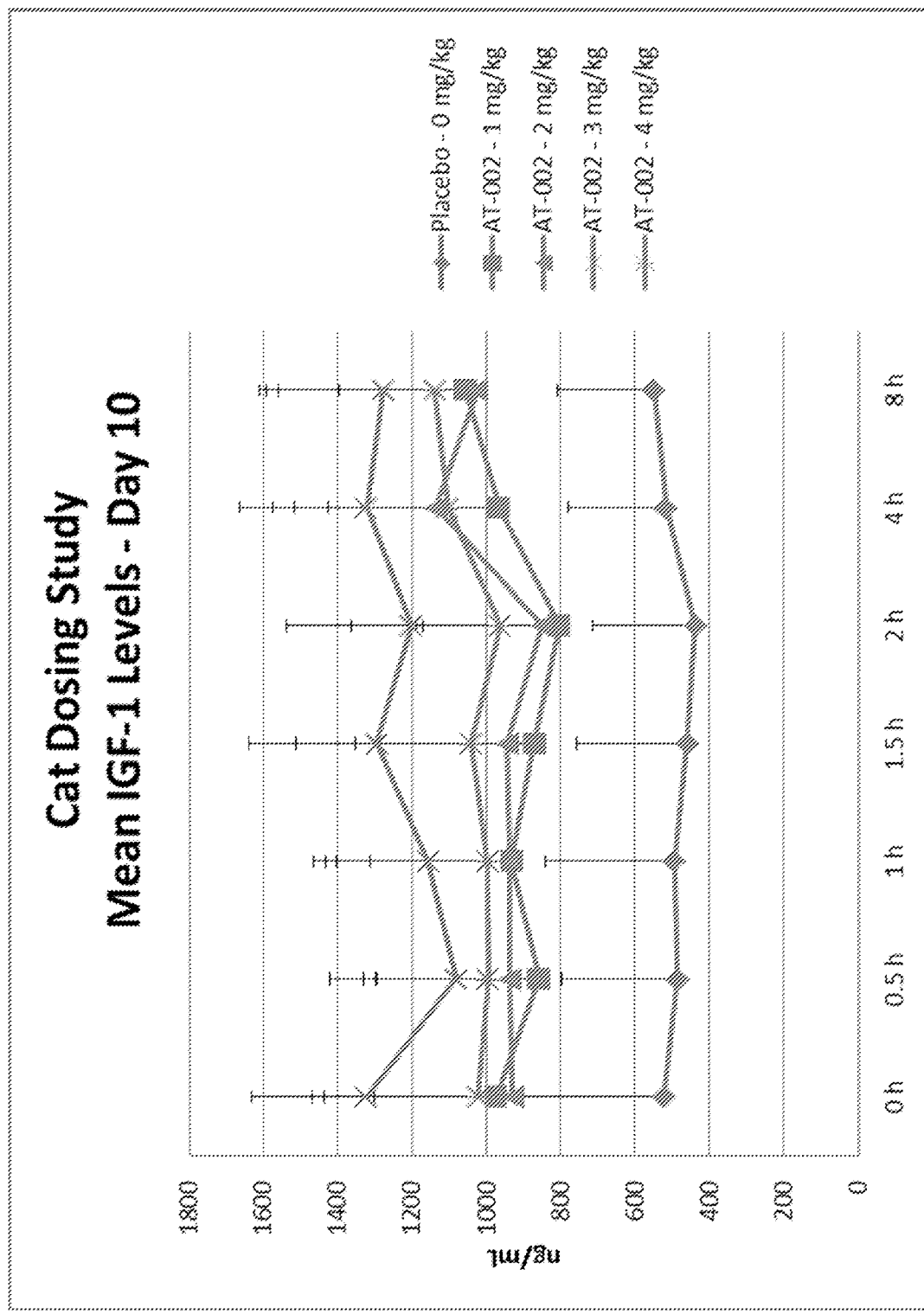
FIG. 98 is a line graph depicting measurements of IGF-1 concentration in the serum of cats on day 10 after being treated with different concentrations of a capromorelin composition.
Figure 99:
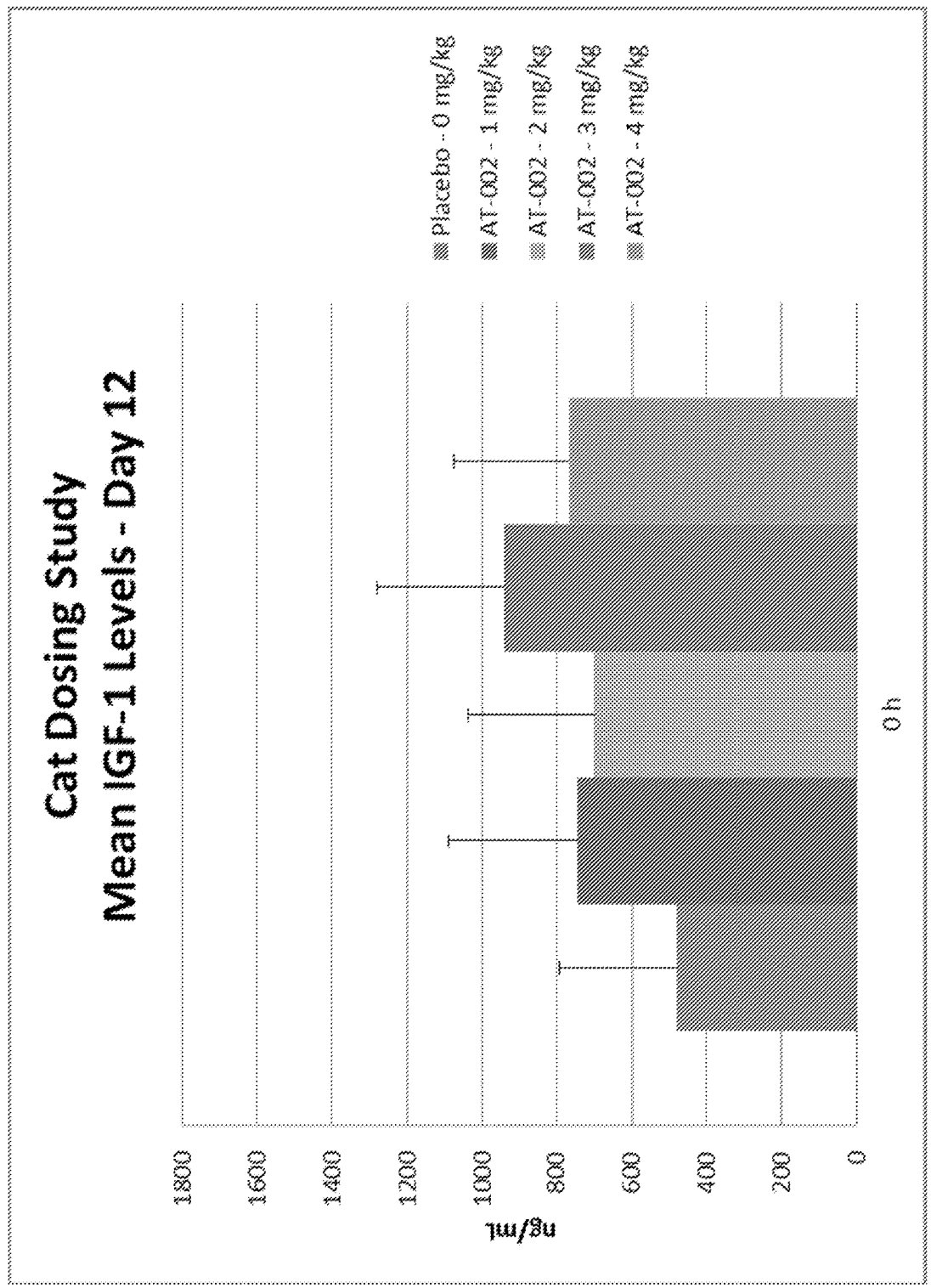
FIG. 99 is a bar graph depicting measurements of IGF-1 concentration in the serum of cats after ten days of treatment with different concentrations of a capromorelin composition and two days without treatment (i.e., day 12).
Figure 100:
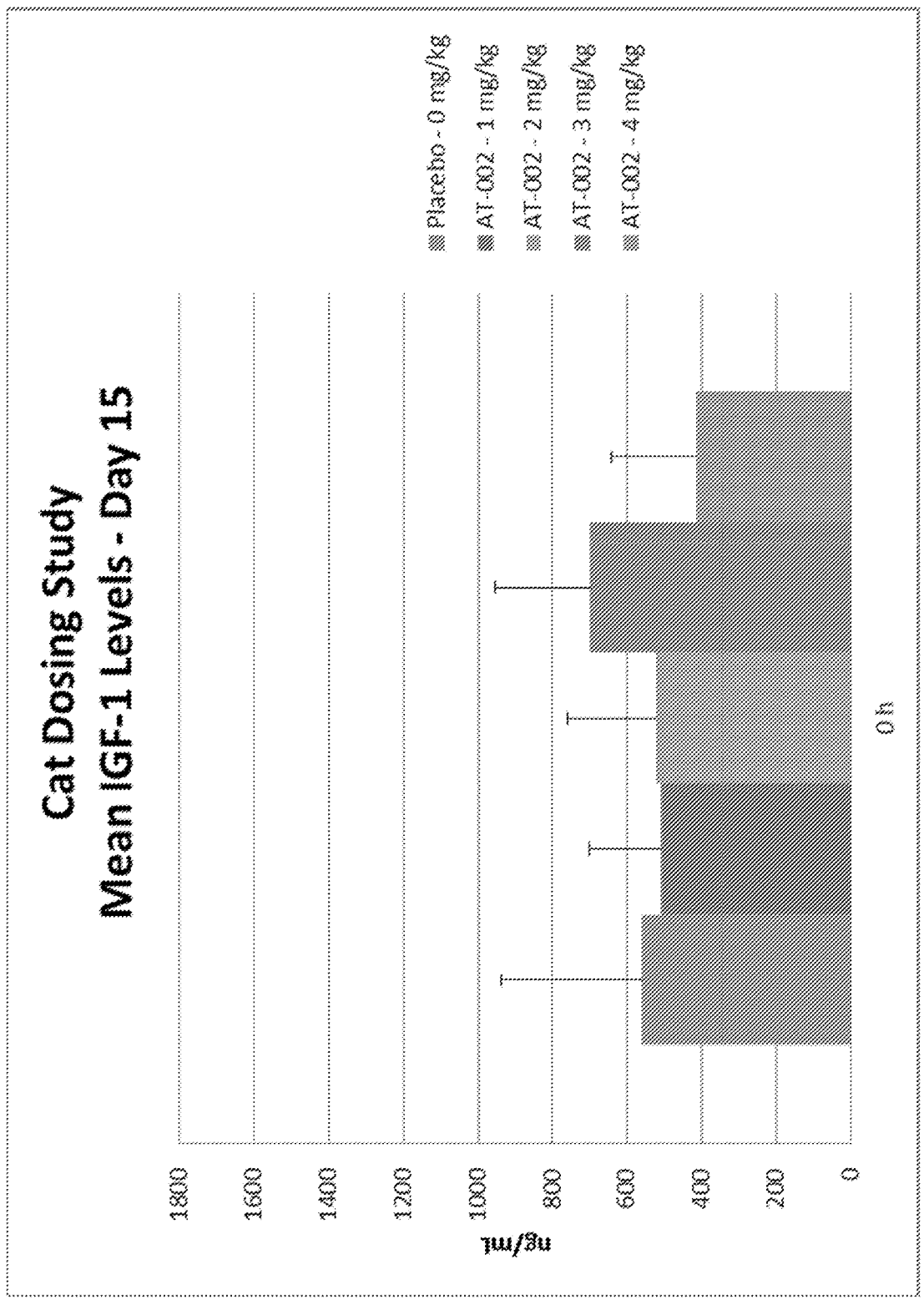
FIG. 100 is a bar graph depicting measurements of IGF-1 concentration in the serum of cats after ten days of treatment with different concentrations of a capromorelin composition and five days without treatment (i.e., day 15).

As illustrated in FIGS. 97-100 and Tables 9 and 10 below, treatment with different doses of Formulation 4 of the inappetance-controlling composition resulted in initial increases in IGF-1 levels in the serum of the cats. Initially, as shown in FIG. 97 and Table 9, after administration on Day 1, the serum levels of IGF-1 began to rise in the experimental groups around 120 minute post administration and were all higher by 480 minutes post administration, relative to the pre-dose time point. Moreover, as shown in FIG. 98 and Table 10, by Day 10, the animals receiving the non-placebo formulation all exhibited sustained increases in IGF-1 concentration in the serum over the entire sampling time frame. This sustained increase in IGF-1 after receiving multiple consecutive daily or twice daily doses of a capromorelin-comprising composition is consistent with the previously discussed examples. Overall, based on a review of the data, it appears that the animals in Group 4 (3 mg/kg) exhibited the highest sustained increase of IGF-1 over the study period. In particular, as shown in Table 10, the percent increase in IGF-1 for Group 4 at the 480 minute time point relative to the pre-dose time point was actually negative because of the highly sustained IGF-1 levels over the previous 24 hours. Further, as shown in FIGS. 99 and 100, two days after ceasing treatments (Day 12—FIG. 99), the serum IGF-1 levels began to decrease, and by five days after treatments (Day 15—FIG. 100), the serum IGF-1 levels had returned to baseline.

TABLE 9

IGF-1 Serum Concentrations: Day 1

| Group | Percent Increase in IGF-1 at 480 Minutes relative to Pre-Dose Levels (0 Minutes) |
|---|---|
| 1 - Placebo | 12.79 |
| 2 - 1 mg/kg | 44.69 |
| 3 - 2 mg/kg | 34.35 |
| 4 - 3 mg/kg | 45.02 |
| 5 - 4 mg/kg | 56.83 |

TABLE 10

IGF-1 Serum Concentrations: Day 10

| Group | Percent Increase in IGF-1 at 480 Minutes relative to Pre-Dose Levels (0 Minutes) |
|---|---|
| 1 - Placebo | 5.23 |
| 2 - 1 mg/kg | 8.51 |
| 3 - 2 mg/kg | 10.41 |
| 4 - 3 mg/kg | −3.45 |
| 5 - 4 mg/kg | 11.26 |

Figure 101:
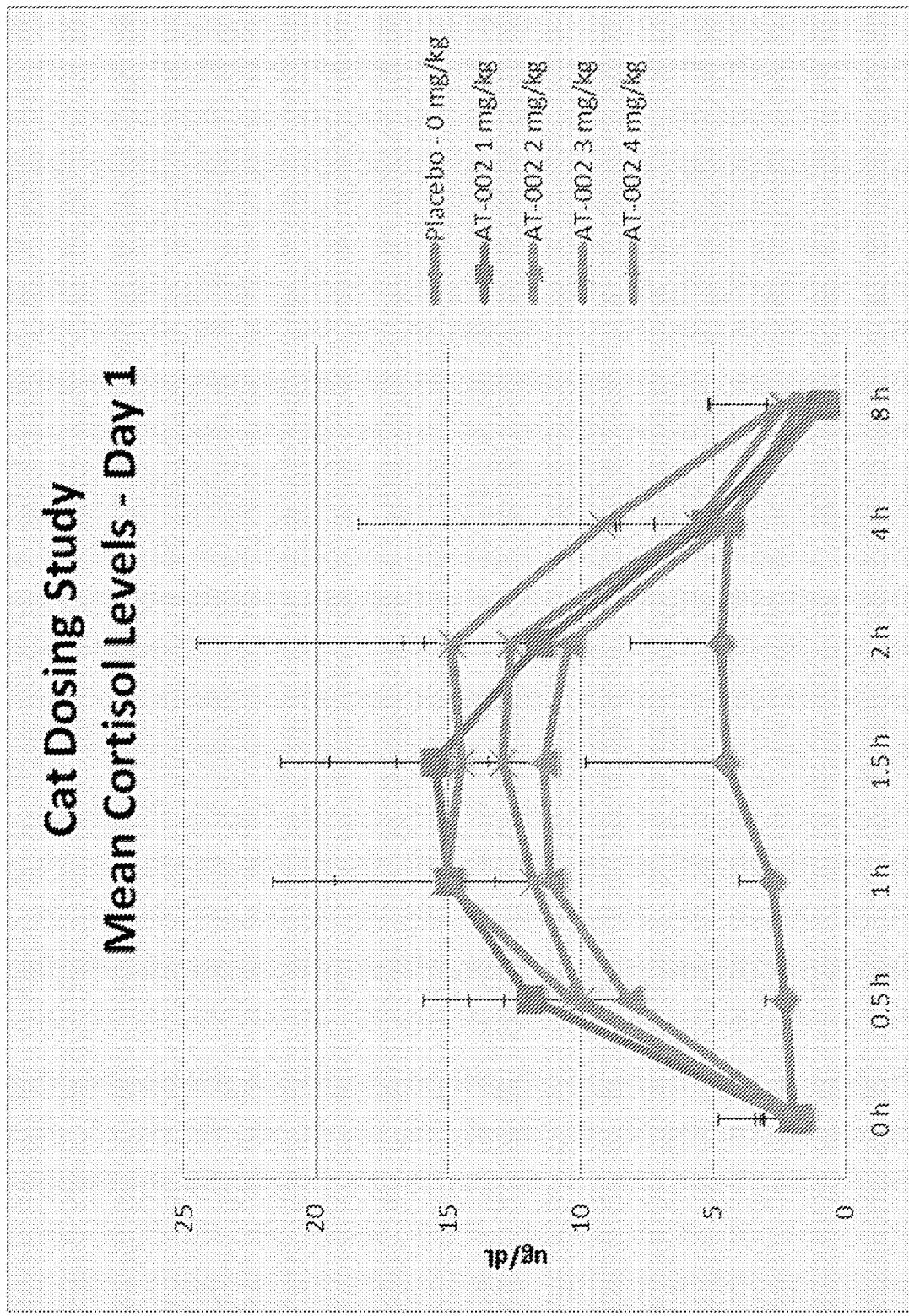
FIG. 101 is a line graph depicting measurements of cortisol concentration in the serum of cats on day 1 after being treated with different concentrations of a capromorelin composition.
Figure 102:
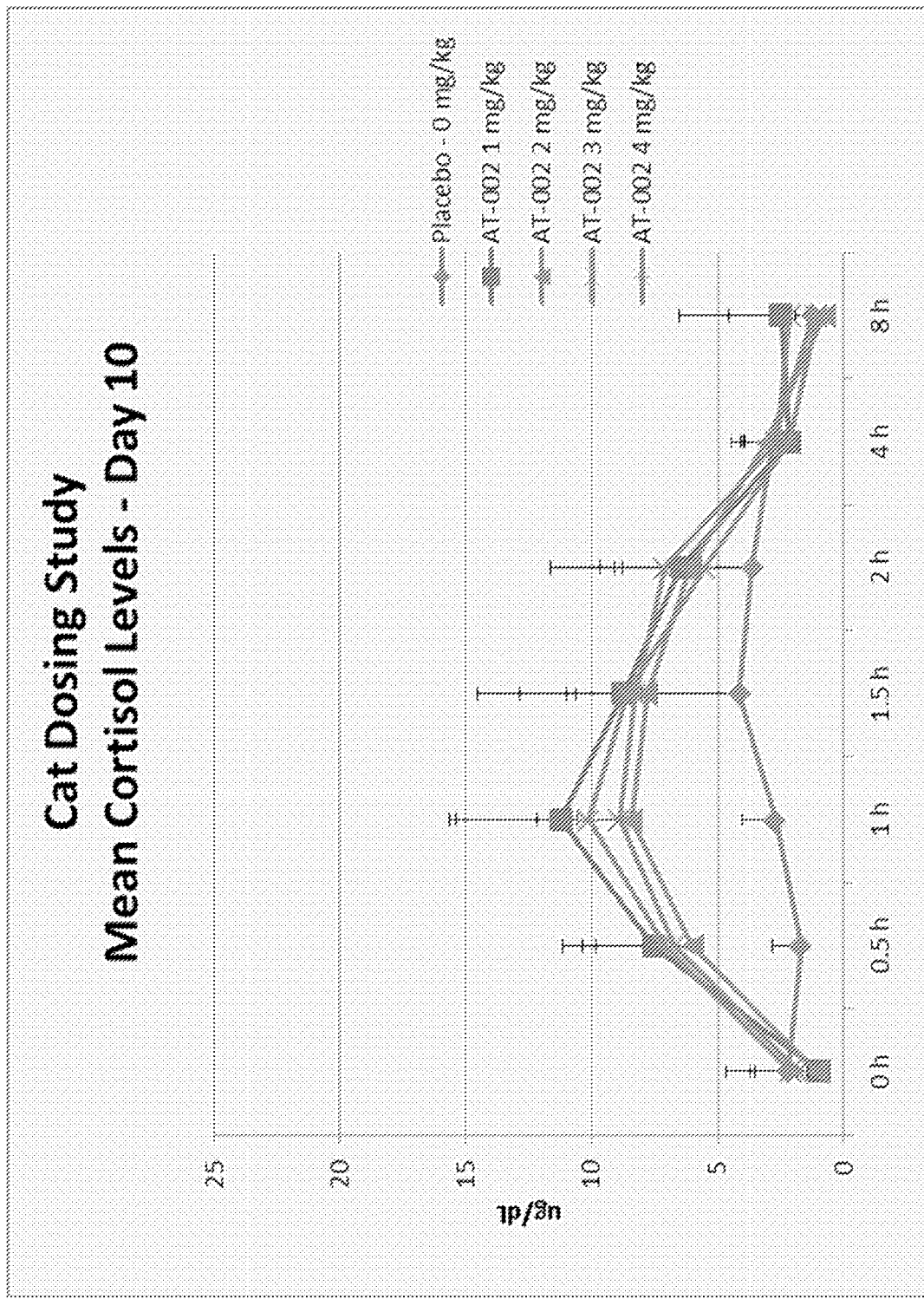
FIG. 102 is a line graph depicting measurements of cortisol concentration in the serum of cats on day 10 after being treated with different concentrations of a capromorelin composition.
Figure 103:
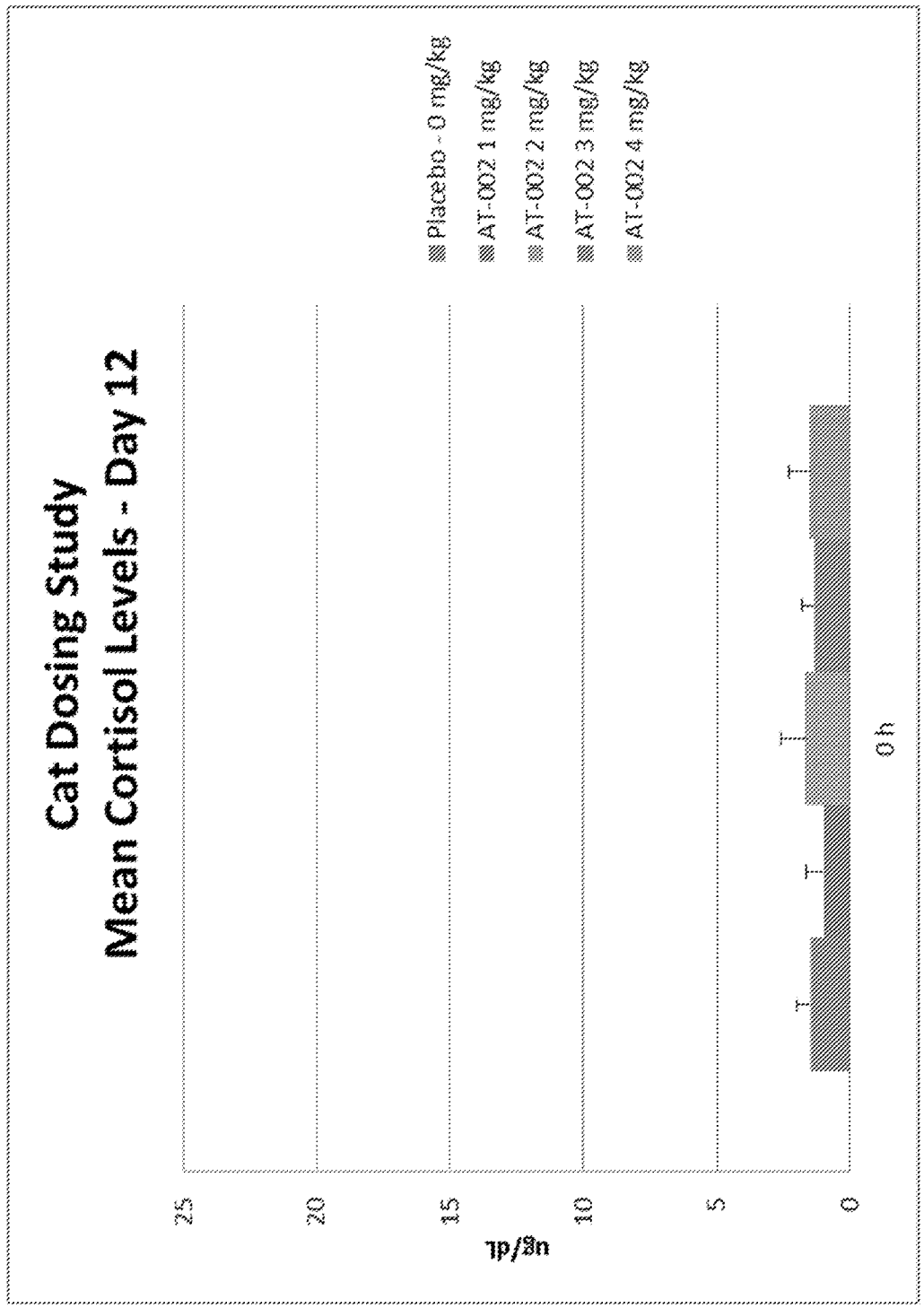
FIG. 103 is a bar graph depicting measurements of cortisol concentration in the serum of cats after ten days of treatment with different concentrations of a capromorelin composition and two days without treatment (i.e., day 12).
Figure 104:
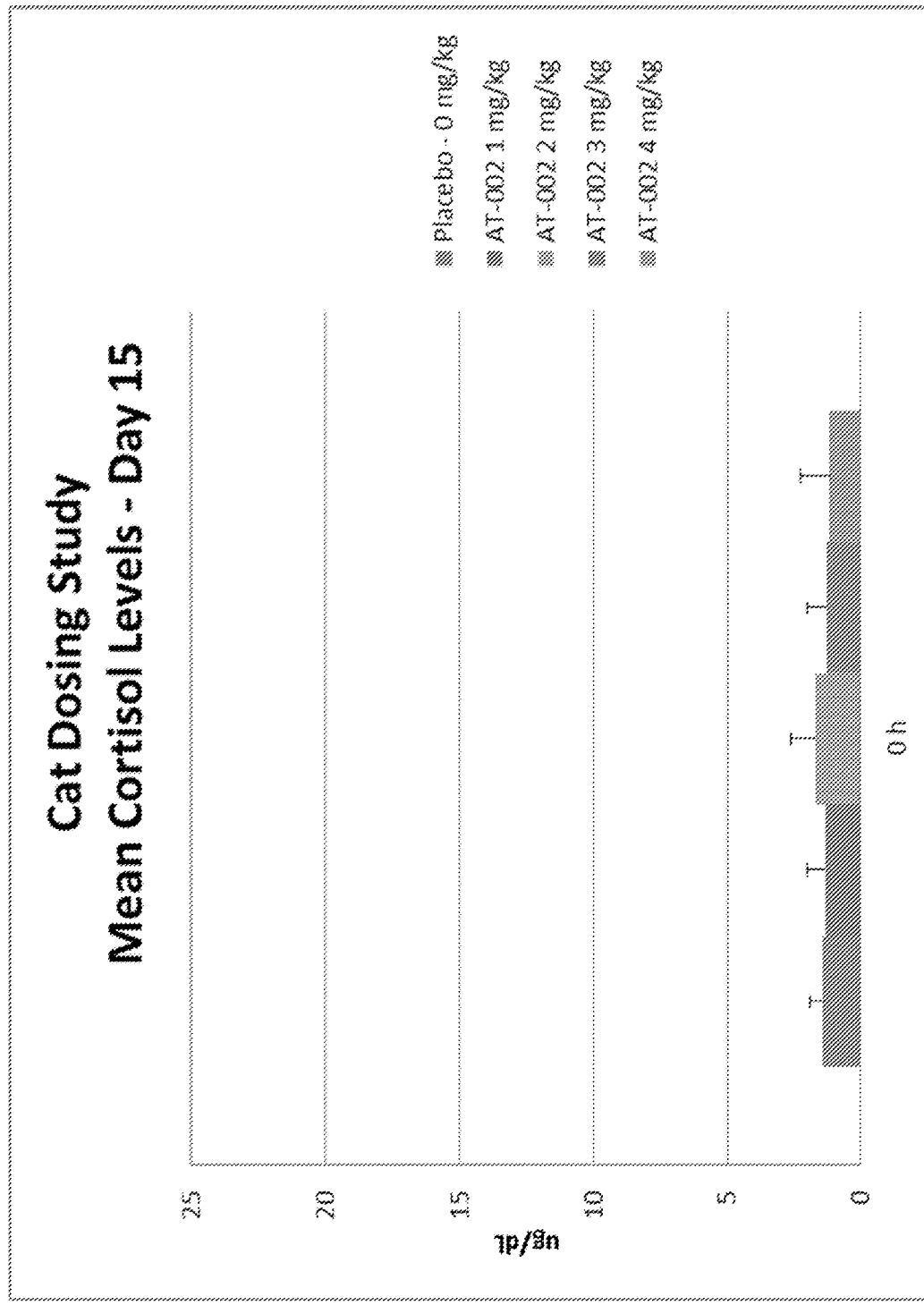
FIG. 104 is a bar graph depicting measurements of cortisol concentration in the serum of cats after ten days of treatment with different concentrations of a capromorelin composition and five days without treatment (i.e., day 15).

As illustrated in FIGS. 101 and 102, treatment with different doses of Formulation 4 of the inappetance-controlling composition resulted in initial increases in cortisol levels in the serum of the cats. In particular, as shown in FIG. 101, on Day 1, each of the animals in the experimental groups showed an initial increase in serum cortisol concentration, which eventually returned to baseline levels by 480 minutes after administration. Moreover, this increase seen on Day 1 in the experimental groups was mitigated by Day 10. Specifically, as shown in FIG. 102, the increase in serum cortisol concentration was abrogated, relative to the serum concentrations spikes detected on Day 1, which is consistent with the other Examples discussed above. In addition, as shown in FIGS. 103 and 104, after the experimental period, on Days 12 and 15, there was no sustained increase in serum cortisol concentrations detected in the experimental or control animals.

EXAMPLE 12

Cat Probe Formulation Study and Pharmacokinetic Analysis

Similar to some of the other pharmacokinetic analyses conducted in dogs and cats, an additional pharmacokinetic study was conducted in cats to assess capromorelin formulations that allow sufficient drug to circulate to produce appetite stimulation and to define the capromorelin pharmacokinetic profile in cats. Briefly, twelve cats were randomized into Group 1 (six cats) and Group 2 (six cats). Group 1 received an intravenous formulation that included 0.75 mg/kg of capromorelin dissolved in sterile water and Group 2 received a previously tested formulation via oral gavage. Food consumption was determined daily for all cats. Specifically, animals were offered feed at approximately 11:00 AM, with the removal of feed at approximately 3:00 PM. Upon removal of feed, the amount consumed was calculated. As an initial matter, the observed food consumption did not reveal any significant increases in food consumption (data not shown), but the length of the treatment regimen was shorter than traditional treatment regimens.

Initially, the cats were given a seven day acclimation period to adjust to the experimental conditions and feed provided. After the acclimation period, on Day 0, all animals in Group 1 received an intravenous injection of the composition containing a dose of 0.75 mg/kg of capromorelin. On Day 0, the animals in Group 2 received an oral administration of the formulation via gavage at a dose of 3 mg/kg of capromorelin. On Day 0, serum samples were taken from the Group 1 animals at time 0 (pre-administration) and 5 minutes, 10 minutes, 30 minutes, 1 h, 2 h, 4 h, 6 h, 8 h, and 12 h post administration and serum samples were also taken from the Group 2 animals at time 0 (per-administration) and 15 minutes, 30 minutes, 45 minutes, 1 h, 2 h, 4 h, 6 h, 8 h, and 12 h post administration. Thereafter, on Day 1, the animals in Group 2 received a second dose of the test formulation at a dose of 1 mg/kg to assess palatability and acceptability, which revealed general acceptability and palatability of the formulation (data now shown).

Figure 105:
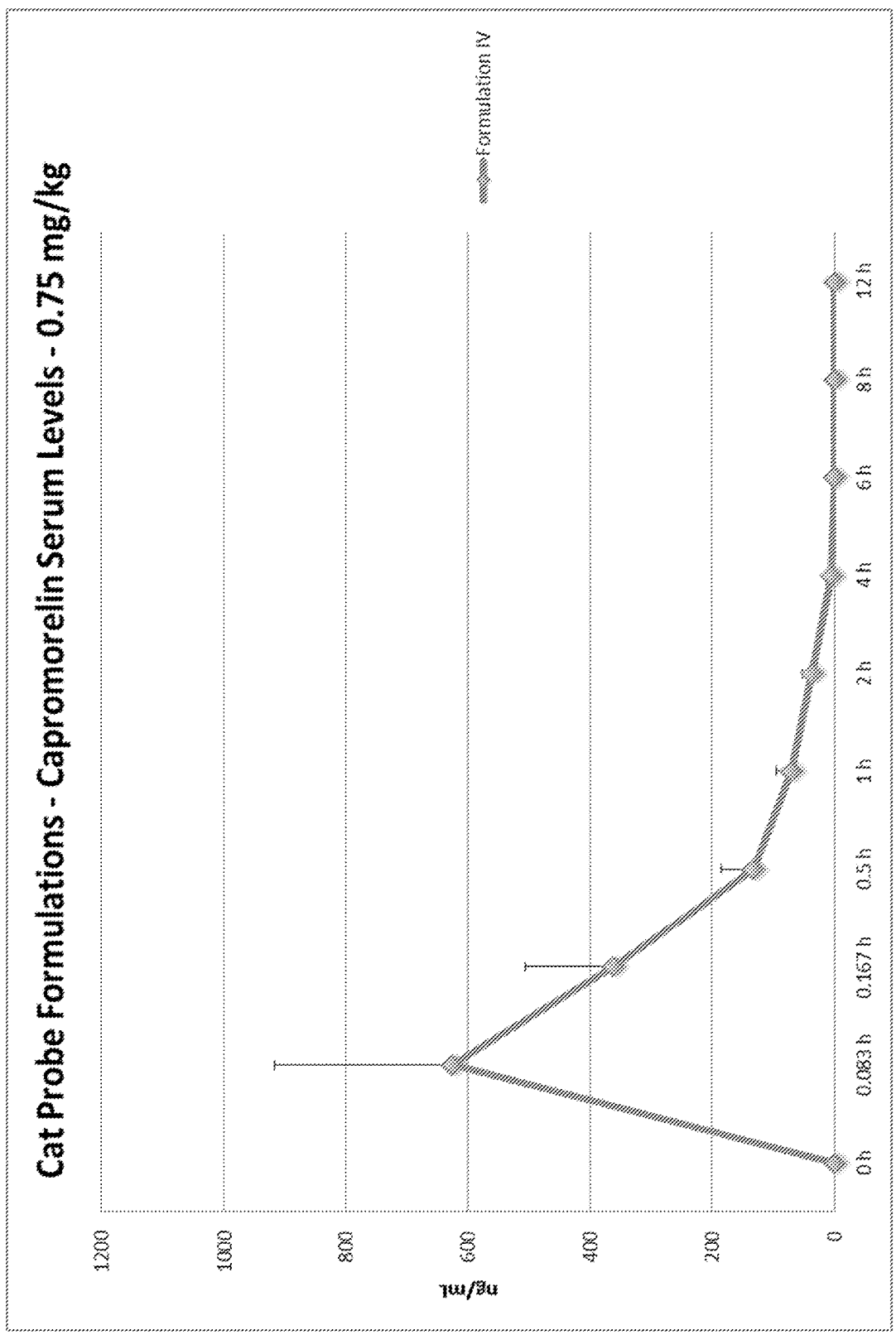
FIG. 105 is a line graph depicting measurements of capromorelin concentration in the serum of cats on day 0 (i.e., the first day of experimentation) after receiving an intravenous administration of capromorelin at a concentration of 0.75 mg/kg.
Figure 106:
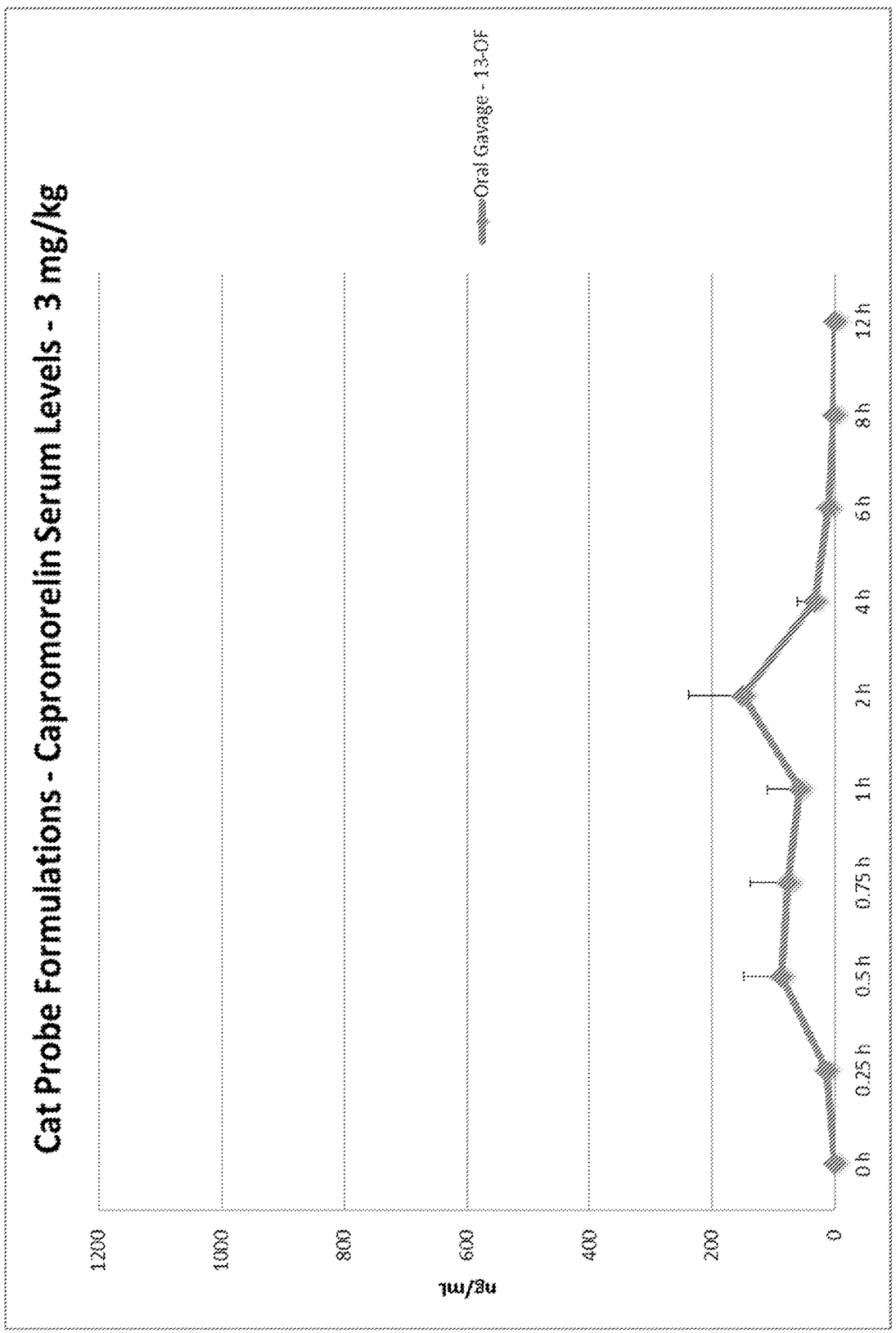
FIG. 106 is a line graph depicting measurements of capromorelin concentration in the serum of cats on day 0 (i.e., the first day of experimentation) after receiving an oral administration of capromorelin at a concentration of 3.0 mg/kg.
Figure 107:
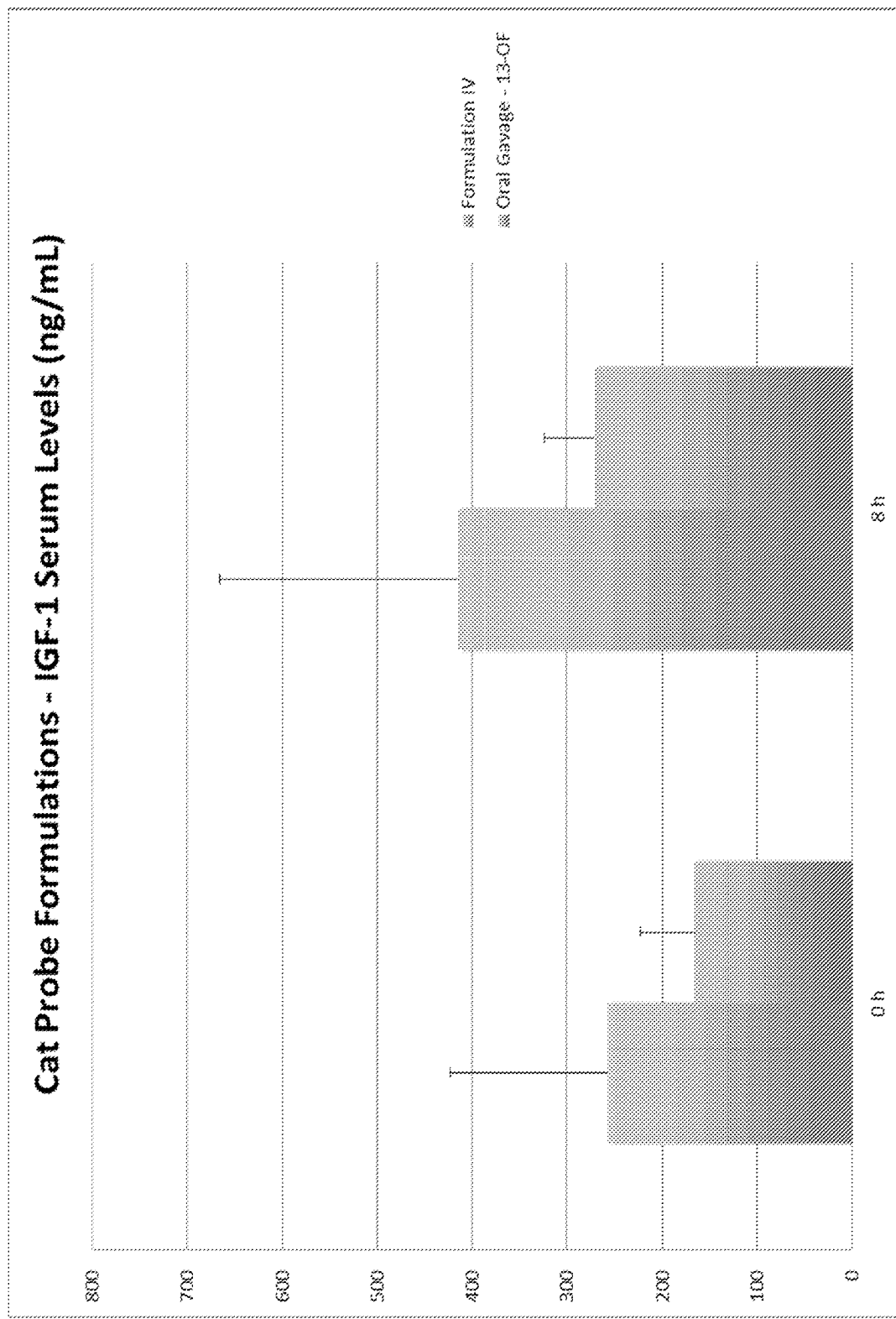
FIG. 107 is a bar graph depicting measurements of IGF-1 concentration in the serum of cats on day 0 (i.e., the first day of experimentation) after receiving different treatments of a capromorelin composition.

Referring to FIGS. 105 and 106, the serum profile of the concentration of capromorelin differed between Groups 1 and 2. In particular, as one would expect, the serum concentration of the Group 1 animals increased at a much faster rate and reached a much greater level, compared to the Group 2. Specifically, the Group 2 animals, which received an oral administration of the capromorelin composition, experienced a small peak in serum concentration at around 2 hours post administration of around 150 ng/mL. Conversely, the Group 1 animals, which received an intravenous injection of the composition, experienced a greater peak (around 625 ng/mL) at around 5 minutes post administration. Referring now to FIG. 107, the animals in Group 1 also experienced a greater increased in IGF-1 levels in the serum compared to the animals in Group 2.

In addition to testing the aforementioned plasma levels of capromorelin and IGF-1, additional pharmacokinetic analysis was also completed. In particular, it was determined that the plasma profile of the capromorelin in the Group 1 animals was biphasic, which included both a distribution and an elimination component. Moreover, this analysis also revealed that the clearance of capromorelin in the Group 1 animals was rapid, (approximately 30 mL/min/kg), which is substantially similar to hepatic blood flow in cats. As a result of this relatively rapid clearance rate, it is suggestive that the oral bioavailability will be generally low and variable in cats. In addition, the pharmacokinetic data also suggests that the terminal half-life of capromorelin in cats is about 0.9 hours. The overall pharmacokinetic data for the Group 1 animals is illustrated in FIG. 108.

The plasma profile of the Group 2 animals consisted of an absorption phase, plateau or double peak at the $T_{max}$, and a rapid terminal phase. In particular, the pharmacokinetic data for the Group 2 animals is illustrated in FIG. 109. For example, the mean $C_{max}$ was 148.9 ng/mL and occurred at 2 hours. The plateau or double peak of the profile could be due to the enterohepatic recycling, which occurs when a drug is eliminated as a drug-conjugate complex in the bile such that the complex is broken down in the distal intestinal track so that the drug is reabsorbed. The plateau or double peak could also be due to absorption at different points in the intestinal track. In addition, the mean-terminal half-life was 1.04 hours.

EXAMPLE 13

Cat Compromised Kidney Study

The following study was undertaken to assess multiple points. First, the following experiments were conducted to determine if a formulation of capromorelin, when administered either intravenously or subcutaneously, can stimulate appetite in cats with compromised kidney function. Second, the following experiments were conducted to assess the pharmacokinetic profile of capromorelin in the serum of cats with compromised kidney function. Finally, the following experiments were conducted to determine if capromorelin accumulates in the serum after 14 days of treatment that is subcutaneously administered.

Sixteen cats with compromised kidney function were acclimatized for the following study. Animals assigned to Group 1 (n=6) received an intravenous administration of a capromorelin formulation (i.e., capromorelin in sterile water) at a dose of 0.75 mg/kg on Day 0 of the experiment. Animals assigned to Group 2 (n=6) received a subcutaneous administration of a capromorelin formulation (2.1% w/v capromorelin, 1% w/v benzyl alcohol, and citrate buffer) daily for 14 days at a dose of 2 mg/kg. Animals assigned to Group 3 (n=4) served as untreated controls. During the study, blood samples were taken from the Group 1 animals at time points 0 (pre-administration), 5 minutes, 10 minutes, 30 minutes, 1 h, 2 h, 4 h, 6 h, 8 h, and 12 h post administration on Day 0. Blood samples were taken from the Group 2 animals at time points 0 (pre-administration), 15 minutes, 30 minutes, 45 minutes, 1 h, 2 h, 4 h, 6 h, 8 h, and 12 h post administration on Day 0 and time points 0, 30 minutes, 1 h, 2 h, 4 h, and 8 h post administration on Day 13. In addition, body weights were collected on study days −7, −1, and 13 (for Groups 2 and 3 only). Diet consumption was also monitored on study days −7 until day 13 for the animals in Groups 2 and 3 only.

Figure 110:
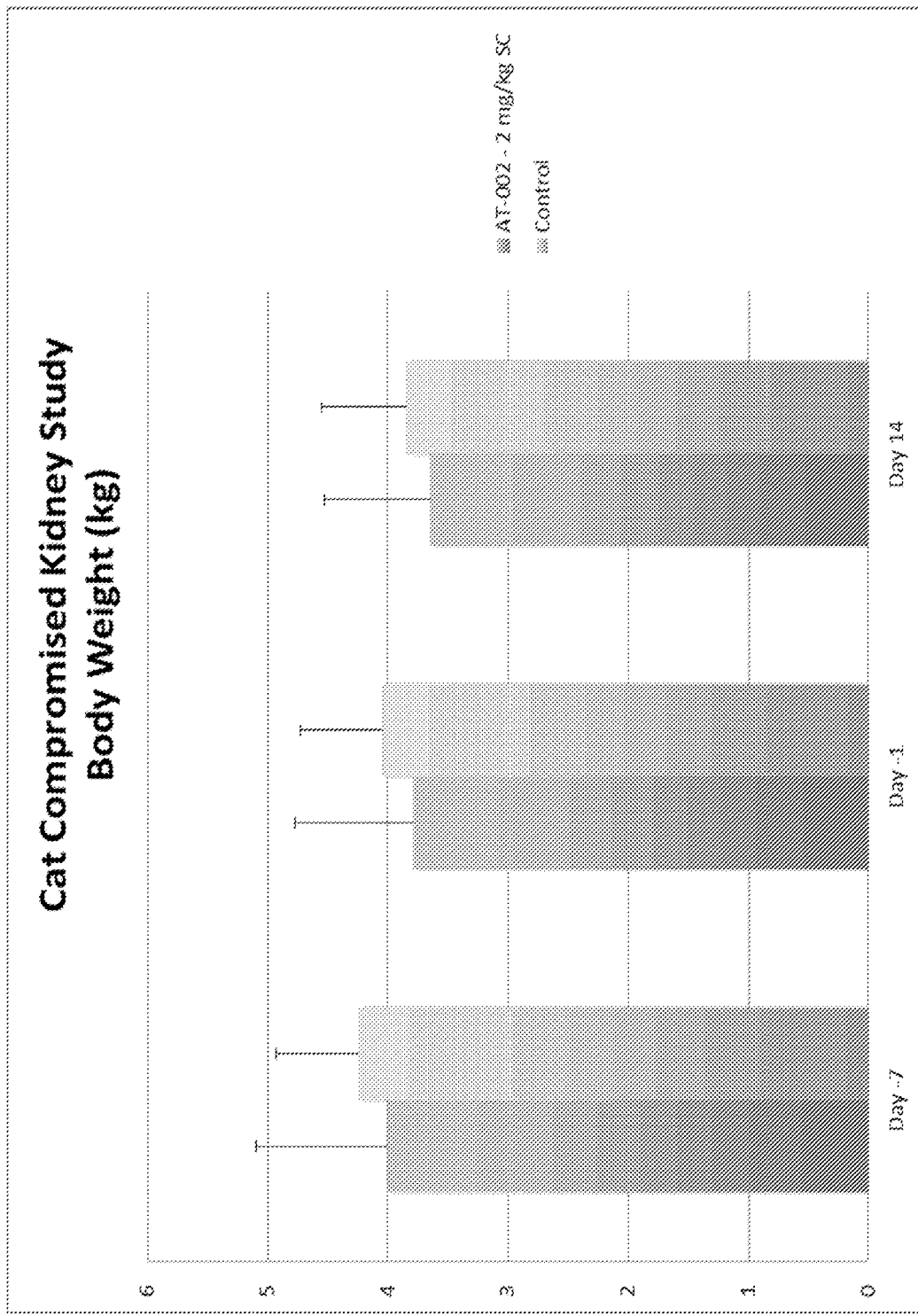
FIG. 110 is a bar graph depicting body weight measurements of cats that have been exposed to different treatments using a capromorelin composition over the course of a fourteen day experiment.
Figure 111:
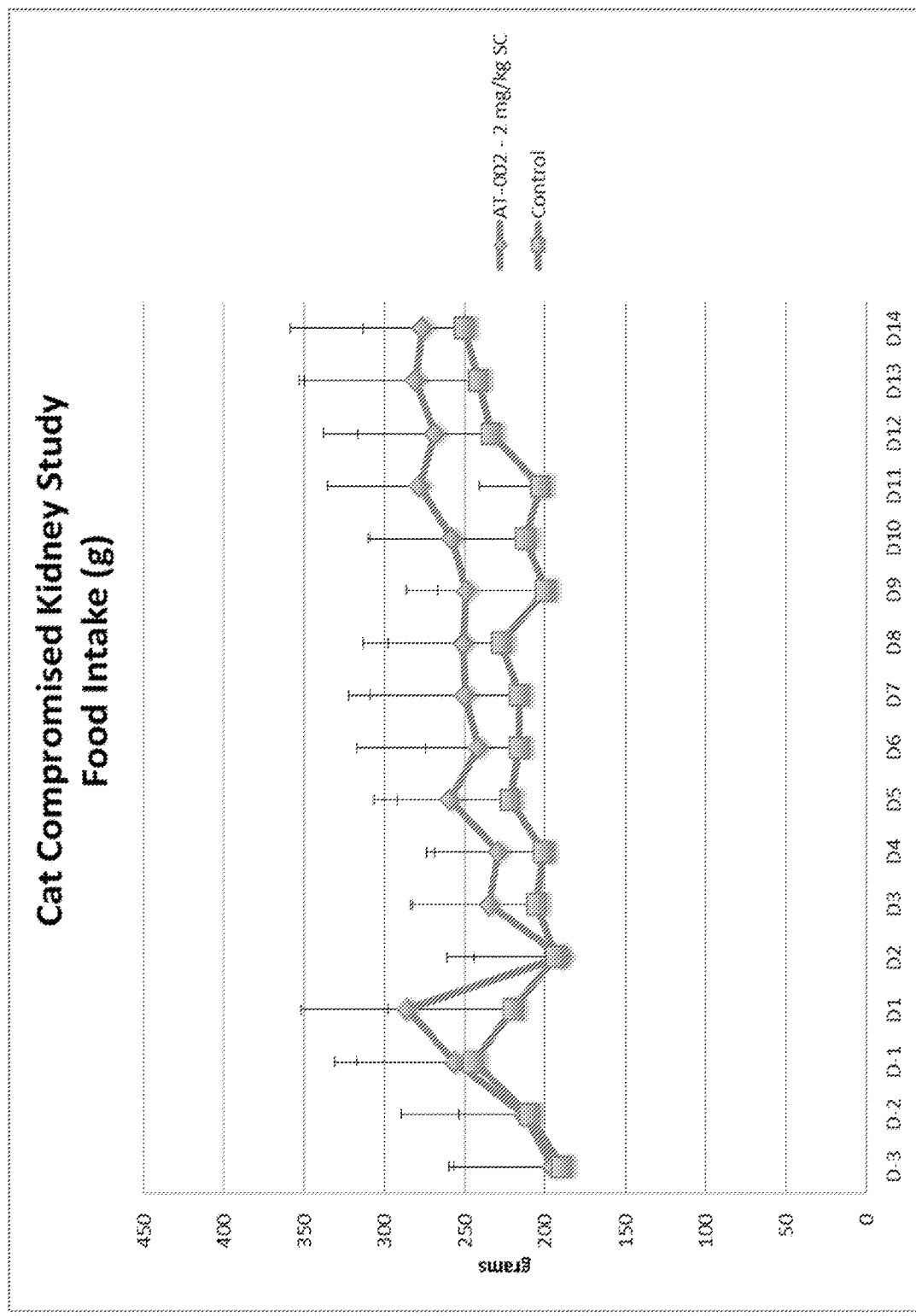
FIG. 111 is a line graph depicting food intake measurements over the course of a fourteen day experiment.

Referring to FIG. 110, there were no significant differences found in the body weights of animals in Groups 2 and 3 over the course of the study. In particular, during the study, animals in both Groups 2 and 3 lost weight, which suggests that the loss of weight in the Group 2 animals is likely not due to the treatment. Similarly, as shown in FIG. 111, there is no significant difference in the amount of food consumed between the animals in Groups 2 and 3, although it appears that the raw means of food consumed by the Group 2 animals are greater than the means of the amount of food consumed by the Group 3 animals.

Figure 112:
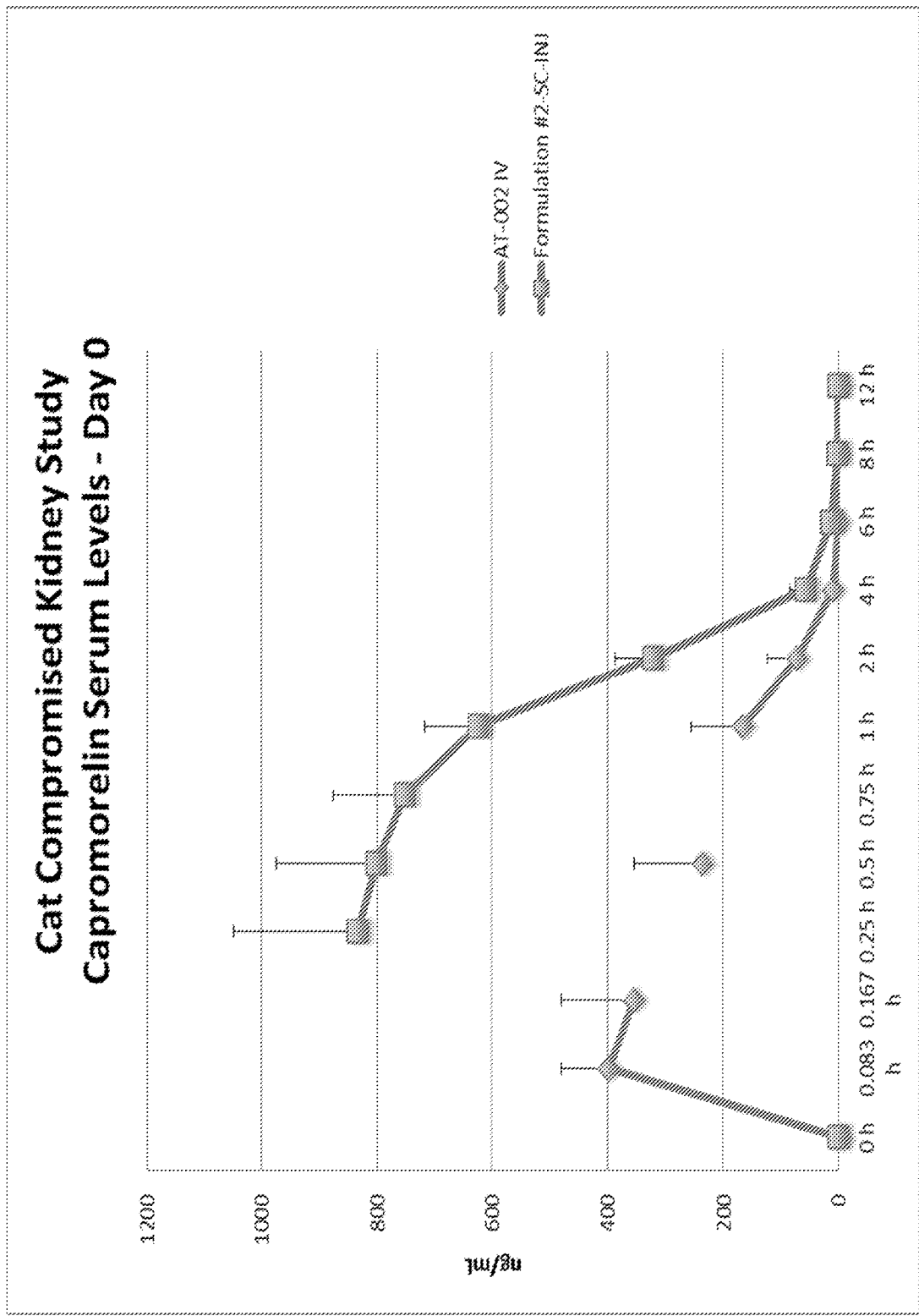
FIG. 112 is a line graph depicting measurements of capromorelin concentration in the serum of cats on day 0 (i.e., the first day of experimentation) after receiving either an intravenous administration of capromorelin at a dose of 0.75 mg/kg or a subcutaneous administration of capromorelin at a dose of 2 mg/kg.
Figure 113:
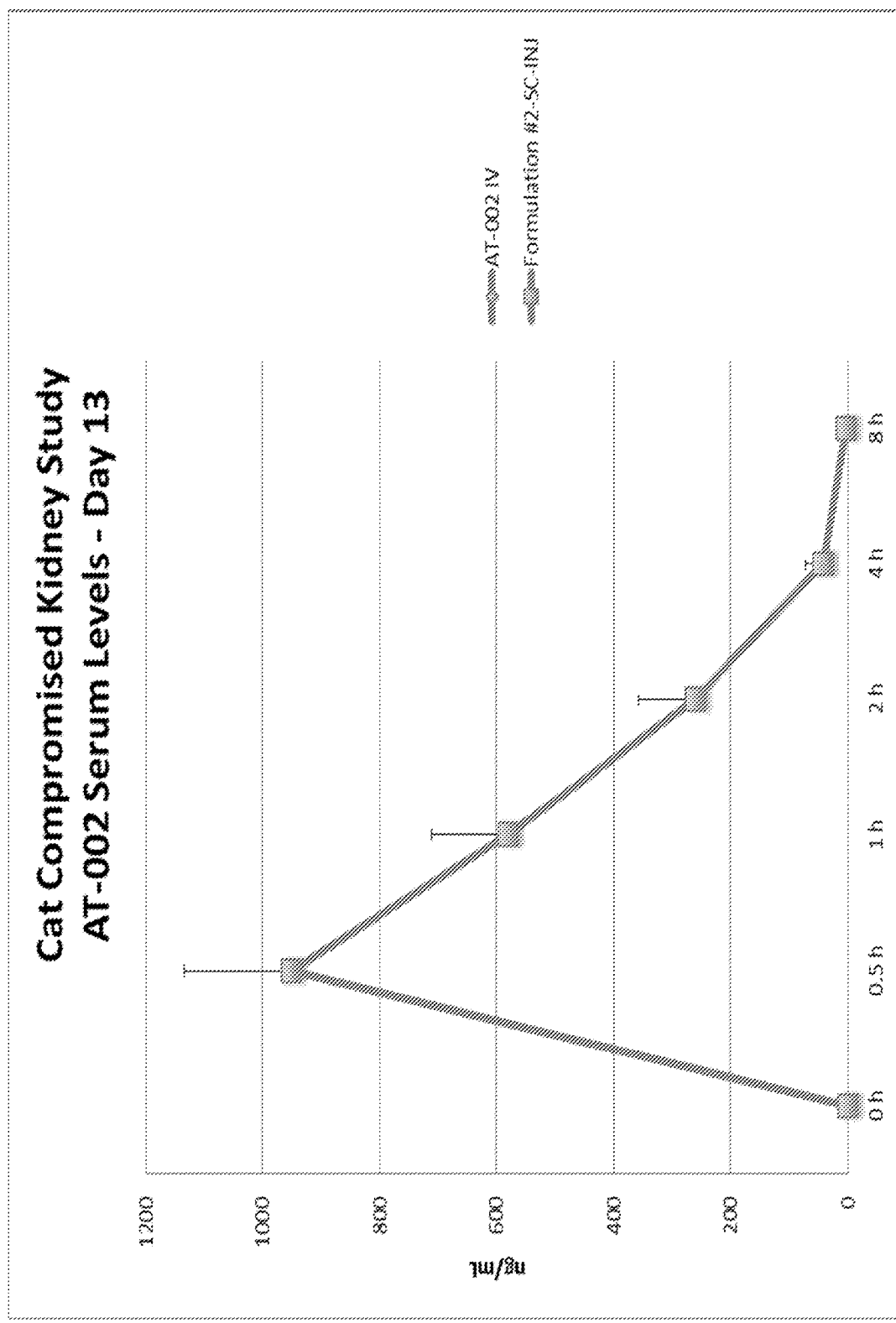
FIG. 113 is a line graph depicting measurements of capromorelin concentration in the serum of cats on day 13 (i.e., the fourteenth day of experimentation) after receiving subcutaneous administrations of capromorelin at a dose of 2 mg/kg for 14 days.

Referring to FIG. 112, after administration of the capromorelin compositions to the animals in Groups 1 and 2, an initial increase was immediately seen in the serum concentration of capromorelin. In particular, in the Group 1 animals that received an intravenous administration of the composition, the serum concentration of capromorelin initially spiked at about 5 minutes post-administration (about 397 ng/mL) and then gradually returned to baseline by about 8 hours after administration. Similarly, on Day 0 in the Group 2 animals that received a subcutaneous injection of the composition, the serum concentration of capromorelin also initially spiked at about 15 minutes post-administration (about 833 ng/mL) and then returned to baseline levels by about 8 hours after administration. Moreover, as shown in FIG. 113, on Day 13 of the study (i.e., after having received 13 previous administrations), the animals in Group 2 exhibited a spike in serum capromorelin concentration at 30 minutes post administration (about 950 ng/mL) and then returned to baseline levels by about 8 hours post administration. As such, it appears that capromorelin does not accumulate in the serum of animals after 14 days of treatment because the levels of capromorelin in the Group 2 animals were at a baseline at both times 0 and 8 hours post administration on Day 13.

Figure 114:
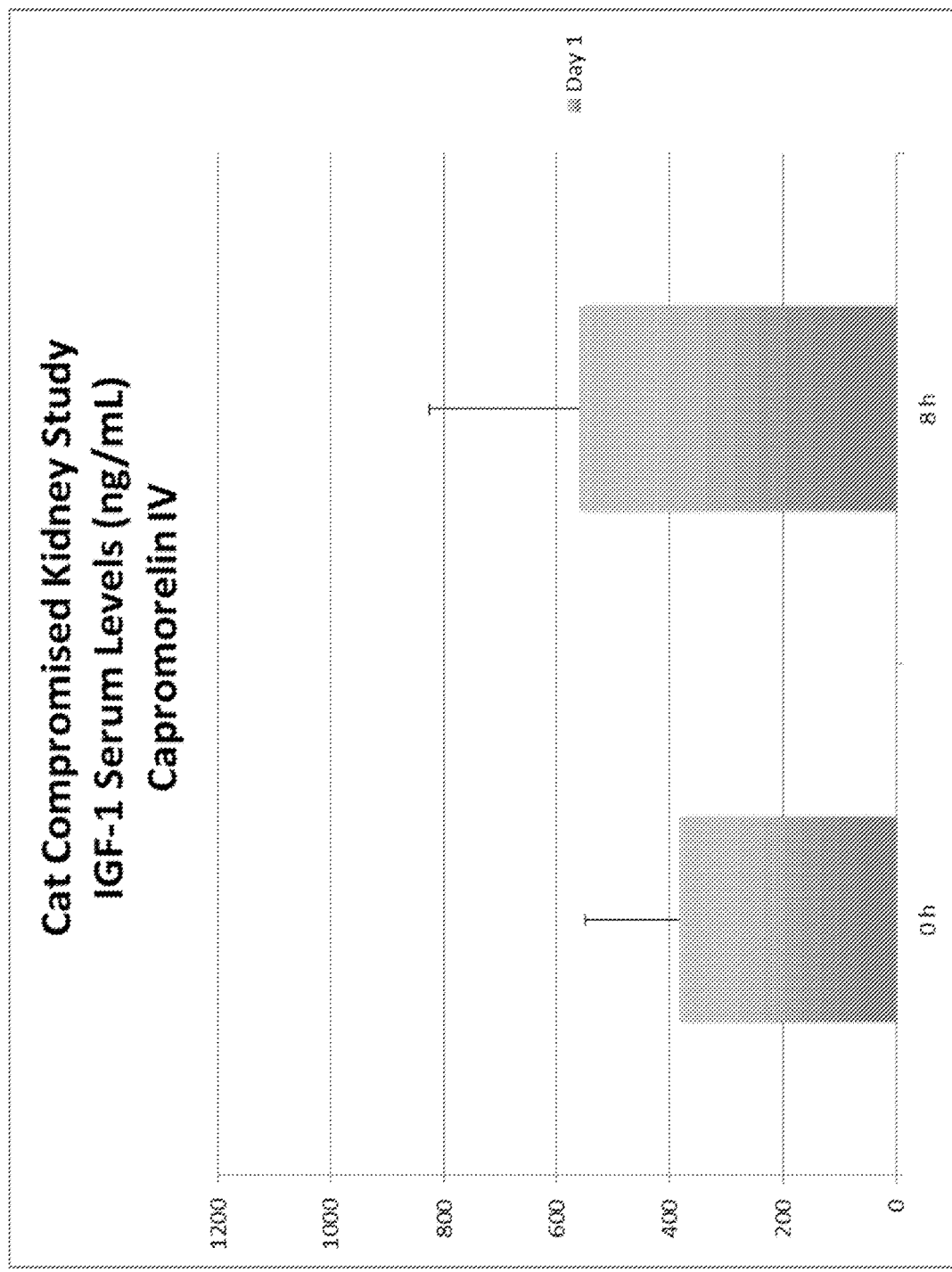
FIG. 114 is a bar graph depicting measurements of IGF-1 concentration in the serum of cats on day 0 (i.e., the first day of experimentation) after receiving an intravenous administration of a capromorelin composition.
Figure 115:
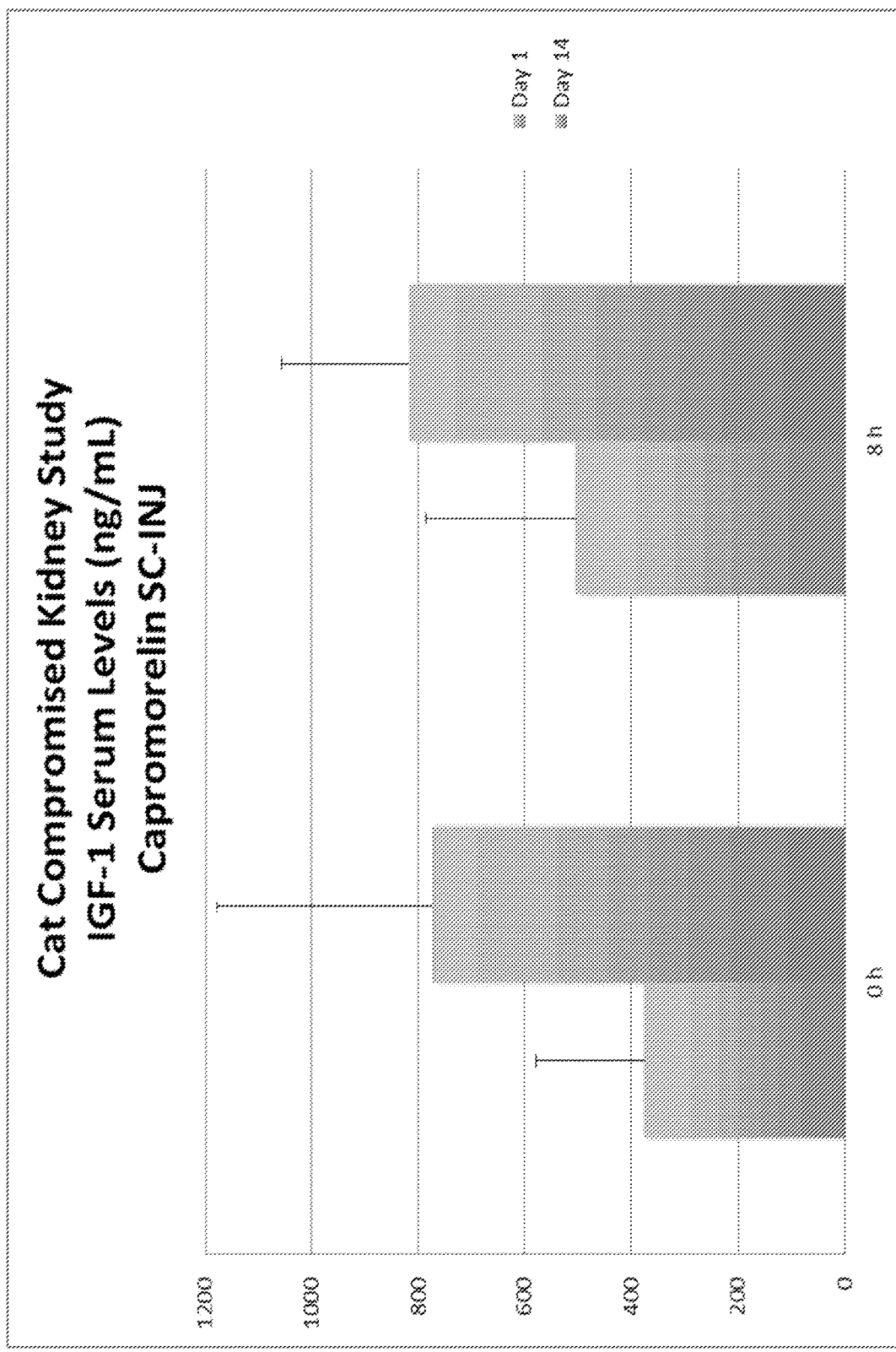
FIG. 115 is a bar graph depicting measurements of IGF-1 concentration in the serum of cats on days 0 (i.e., the first day of experimentation) and 13 (i.e., the fourteenth day of experimental) after receiving a subcutaneously administered capromorelin treatment regimen.

Referring now to FIGS. 114 and 115, the animals in Groups 1 and 2 both experienced an increased in serum concentration of IGF-1 as a result of the treatment with capromorelin. In particular, after 8 hours post administration on Day 0, the animals in Group 1 experienced an increase in IGF-1 (FIG. 114), which was also seen on Days 0 and 13 in the Group 2 animals (FIG. 115).

Figure 116:
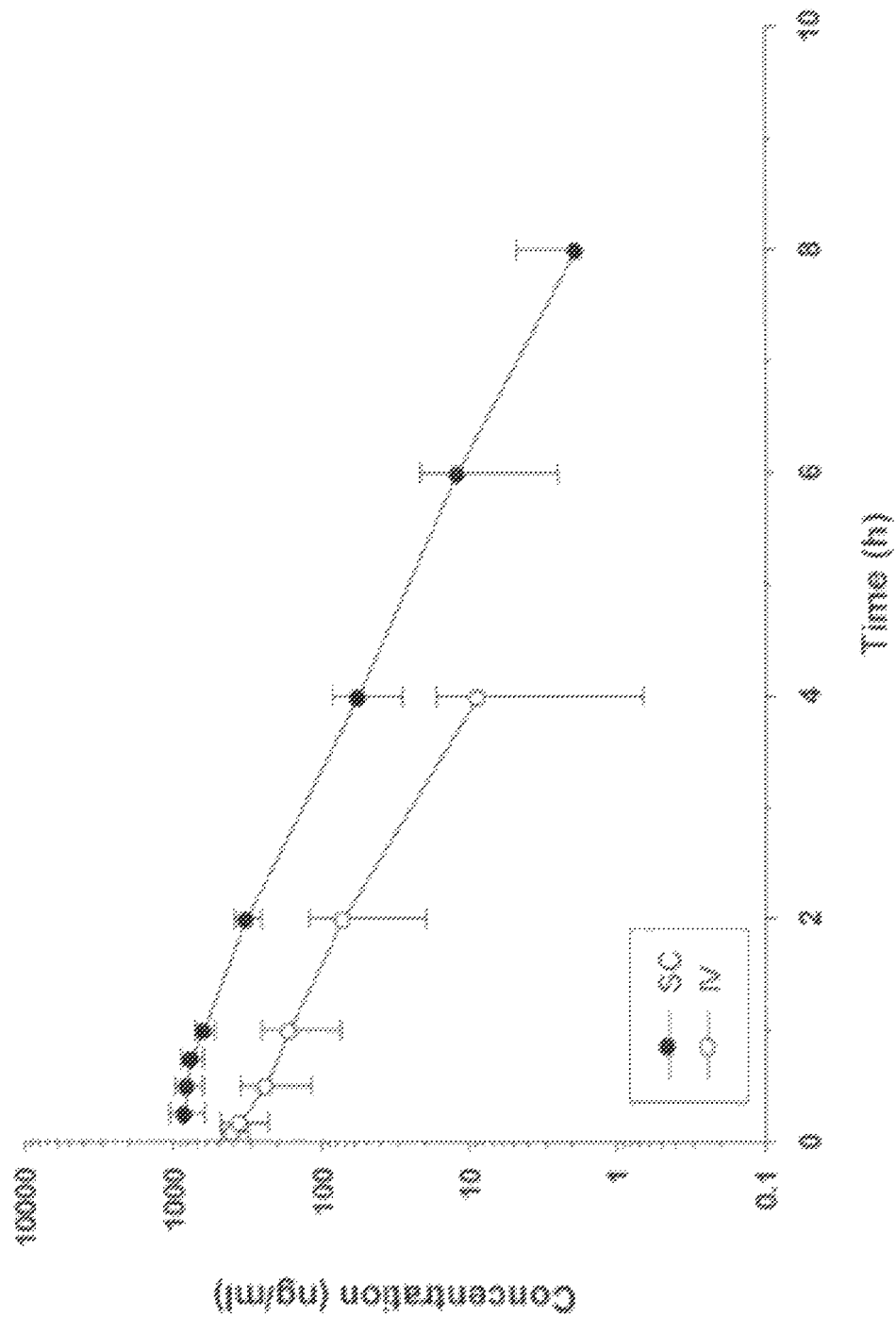
FIG. 116 is a line graph depicting measurements of capromorelin concentration in the serum of cats on day 0 (i.e., the first day of experimentation) after receiving either an intravenous administration of capromorelin at a dose of 0.75 mg/kg or a subcutaneous administration of capromorelin at a dose of 2 mg/kg.

Furthermore, additional pharmacokinetic analyses were also conducted on the serum samples from the Groups 1 and 2 animals. Referring to FIGS. 116 and 117, the pharmacokinetics of capromorelin in the Group 1 animals was similar to what was previously observed regarding a rapid clearance (20 mL/min/kg) in several of the test animals. Moreover, the terminal half-life of the capromorelin was estimated to be between 0.67 and 0.9 hours. All together, the pharmacokinetics are substantially similar to non-kidney compromised cats, with respect to administration via intravenous injection.

Referring to FIGS. 116 and 118, the pharmacokinetics of subcutaneously administered capromorelin were also determined. In particular, the geometric Cmax was 893 ng/mL and was noted at 0.42 hours. In addition, the mean fraction of the dose absorbed was determined by dividing the mean area under the curve (AUC)/dose of the animals in Group 2, which was divided by AUC/dose of the animals in Group 1. In this case, the mean fraction of the dose (F) absorbed is 1.37. The mean absorption time was rapid (0.4 hr), which suggests rapid absorption of capromorelin via subcutaneous administration, which is shorter than oral administration times of absorption. Taken together, this pharmacokinetic data suggests that capromorelin that is subcutaneously administered to cats is well absorbed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A method of treating inappetence in a companion animal,
the method comprising the step of administering at least once per day a therapeutically effective amount of a capromorelin-containing composition to the companion animal for at least five days, which therapeutically effective amount comprises from 3 milligrams to 4.5 milligrams of capromorelin per kilogram of body weight of the companion animal, wherein after the administrating the companion animal increases food intake by at least 50% relative to food intake prior to the administrating, and wherein lean muscle mass in the companion animal is increased by at least 5% relative to the lean muscle mass of the companion animal prior to the administrating;
wherein the companion animal is a cat or a dog.

2. The method of claim 1, wherein the therapeutically effective amount of the capromorelin-containing composition comprises a sufficient amount of capromorelin to achieve a $C_{max}$ of 150 nanograms of capromorelin or a metabolite thereof per milliliter of plasma at a $T_{max}$ of about two hours.

3. The method of claim 1, wherein the capromorelin-containing composition further comprises a sweetening agent selected from the group consisting of thaumatin, maltodextrin, Stevia extract Rebaudioside A, glycyrrhizic acid, monoammonium glycyrrhizinate, sucralose, sodium saccharin, neohesperidin dihydrochalcone, a vanilla-comprising composition, and combinations thereof.

4. The method of claim 1, wherein the therapeutically effective amount of the capromorelin-containing composition is administered using a dosage form selected from the group consisting of a spray, a syringe, a pill, a tablet, an implant, a patch, and a film.

5. The method of claim 1, wherein the therapeutically effective amount of the capromorelin-containing composition is administered to the companion animal at least twice per day.

6. The method of claim 1, wherein the therapeutically effective amount of the capromorelin-containing composition is administered for a treatment period of at least one week.

7. The method of claim 6, wherein the therapeutically effective amount of the capromorelin-containing composition is administered for a treatment period of at least two weeks.

8. The method of claim 7, wherein the therapeutically effective amount of the capromorelin-containing composition is administered for a treatment period of at least one month.

9. The method of claim 1, wherein the companion animal is a cat.

10. The method of claim 1, wherein the companion animal is a dog.

11. The method of claim 1, wherein the therapeutically effective dose of the capromorelin-containing composition is administered with a chemotherapeutic regimen.

12. The method of claim 1, wherein the administration of the capromorelin-containing composition is selected from the group consisting of oral administration, intramuscular administration, and subcutaneous administration.

13. The method of claim 1, wherein the capromorelin-containing composition is in an oral liquid dose form.

14. The method of claim 13, wherein the oral liquid dose form is either sprayed onto a food product or administered using a syringe.

15. The method of claim 1, wherein the capromorelin-containing composition is incorporated into a food product, a treat, or a chew.

16. The method of claim 1, wherein lean muscle mass in the companion animal is increased by at least 10%.

17. The method of claim 1, wherein the companion animal increases food intake by at least 85% relative to food intake prior to the administrating.

18. A method of increasing lean muscle mass and treating inappetence,
the method comprising orally administering at least once per day a therapeutically effective dose of an oral capromorelin composition to the non-human animal for at least five days, which therapeutically effective dose comprises from 3 milligrams to 4.5 milligrams of capromorelin per kilogram of body weight of the non-human animal, wherein after the administrating the non-human animal increases food intake by at least 50% relative to food intake prior to the administrating, and wherein lean muscle mass in the non-human animal is increased by at least 5% relative to the lean muscle mass of the non-human animal prior to the administrating;
wherein the non-human animal is a cat or a dog.

19. The method of claim 18, wherein the therapeutically effective dose of a capromorelin composition consists of a sufficient amount of capromorelin to achieve a $C_{max}$ of 150 nanograms of capromorelin or a metabolite thereof per milliliter of plasma at a $T_{max}$ of about two hours.

20. The method of claim 18, wherein lean muscle mass is increased by at least 10% after the oral capromorelin composition is administered to the non-human animal.

21. The method of claim 18, wherein the therapeutically effective dose of the oral capromorelin composition is administered with a chemotherapeutic regimen.

22. The method of claim 18, wherein the non-human animal's food consumption is increased by at least 85% relative to food intake prior to the administrating.

23. The method of claim 18, wherein the oral capromorelin composition further comprises a sweetening agent selected from the group consisting of thaumatin, maltodextrin, Stevia extract Rebaudioside A, glycyrrhizic acid, mono-ammonium glycyrrhizinate, sucralose, sodium saccharin, neohesperidin dihydrochalcone, and a vanilla-comprising composition.

24. The method of claim 18, wherein the oral capromorelin composition further comprises at least one emulsifying agent.

25. The method of claim 18, wherein the oral administration of the capromorelin composition is selected from the group consisting of use of a syringe, a pill, an implant, a spray, an oral solution, a tablet, and a film.

26. The method of claim 18, wherein the capromorelin composition is administered at least twice per day.

27. The method of claim 18, wherein the capromorelin composition is administered for at least one week.

28. The method of claim 27, wherein the capromorelin composition is administered for at least two weeks.

29. A method of treating inappetence in a companion animal,
the method comprising the step of administering at least once a day a therapeutically effective amount of a capromorelin-containing composition to the companion animal for at least five days, which therapeutically effective amount consists of from 3 milligrams to 4.5 milligrams of capromorelin per kilogram of body weight of the companion animal,
wherein capromorelin is the only therapeutic used in the method,
wherein after the administrating the companion animal increases food intake by at least 50% relative to food intake prior to the administrating, and
wherein lean muscle mass of the companion animal is increased by at least 5% relative to the lean muscle mass of the companion animal prior to the administrating;
wherein the companion animal is a cat or a dog.

30. The method of claim 29, wherein the therapeutically effective amount of the capromorelin-containing composition is orally administered to the companion animal.

31. The method of claim 30, wherein the therapeutically effective amount of the capromorelin-containing composition comprises a sufficient amount of capromorelin to achieve a $C_{max}$ of 150 nanograms of capromorelin or a metabolite thereof per milliliter of plasma at a $T_{max}$ of about two hours.

32. The method of claim 29, wherein the therapeutically effective amount of the capromorelin-containing composition is administered for a treatment period of at least one week.

33. The method of claim 32, wherein the therapeutically effective amount of the capromorelin-containing composition is administered for a treatment period of at least two weeks.

34. The method of claim 29, wherein the companion animal is a dog.

35. The method of claim 29, wherein the administration of the capromorelin-containing composition is selected from the group consisting of oral administration, intramuscular administration, and subcutaneous administration.

36. The method of claim 29, wherein the composition is in an oral liquid dose form.

37. The method of claim 29, wherein lean muscle mass in the companion animal is increased by at least 10%.

38. The method of claim 29, wherein the companion animal increases food intake by at least 85% relative to food intake prior to the administrating.

39. A method of increasing lean muscle mass and treating inappetence of a non-human animal,
the method comprising orally administering at least once a day a therapeutically effective dose of an oral capromorelin composition to the non-human animal for at least five days, which therapeutically effective amount consists of from 3 milligrams to 4.5 milligrams of capromorelin per kilogram of body weight of the non-human animal,
wherein capromorelin is the only therapeutic used in the method,
wherein after the administrating the non-human animal increases food intake by at least 50% relative to food intake prior to the administrating, and
wherein lean muscle mass of the non-human animal is increased by at least 5% relative to the lean muscle mass of the non-human animal prior to the administrating;
wherein the non-human animal is a cat or a dog.

40. The method of claim 39, wherein the therapeutically effective dose of the oral capromorelin composition comprises a sufficient amount of capromorelin to achieve a $C_{max}$ of 150 nanograms of capromorelin or a metabolite thereof per milliliter of plasma at a $T_{max}$ of about two hours.

41. The method of claim 39, wherein lean muscle mass is increased by at least 10% after the oral capromorelin composition is administered to the non-human animal.

42. The method of claim 39, wherein the non-human animal's food consumption is increased by at least 85% relative to food intake prior to the administrating.

43. The method of claim 39, wherein the oral administration of the oral capromorelin composition is selected from the group consisting of use of a syringe, a pill, an implant, a spray, an oral solution, a tablet, and a film.

44. The method of claim 39, wherein the oral capromorelin composition is administered for at least one week.

45. The method of claim 44, wherein the oral capromorelin composition is administered for at least two weeks.

46. A method using capromorelin to treat inappetence in a companion animal in need thereof, the method comprising:
administering at least once a day a therapeutically effective amount of a capromorelin-containing composition to a companion animal in need thereof for at least five days, which therapeutically effective amount consists of from 3 milligrams to 4.5 milligrams of capromorelin per kilogram of body weight of the companion animal, wherein capromorelin is the only therapeutic used in the method;
wherein after the administrating the companion animal increases food intake by at least 50% relative to food intake prior to the administrating, and
wherein lean muscle mass of the companion animal is increased by at least 5% relative to the lean muscle mass of the companion animal prior to the administrating; and
wherein the companion animal is a cat or a dog.

* * * * *